United States Patent
Fox et al.

(10) Patent No.: US 6,455,277 B1
(45) Date of Patent: Sep. 24, 2002

(54) POLYNUCLEOTIDES ENCODING HUMAN GLIAL CELL LINE-DERIVED NEUROTROPHIC FACTOR RECEPTOR POLYPEPTIDES

(75) Inventors: Gary M. Fox, Newbury Park; Shuqian Jing; Duanzhi Wen, both of Thousand Oaks, all of CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 08/837,199

(22) Filed: Apr. 14, 1997

Related U.S. Application Data

(60) Provisional application No. 60/015,907, filed on Apr. 22, 1996, and provisional application No. 60/017,221, filed on May 9, 1996.

(51) Int. Cl.$^7$ .................. C12N 15/12; C12N 15/85; C12N 15/63
(52) U.S. Cl. ............. 435/69.1; 435/325; 435/320.1; 435/252.3; 536/23.5
(58) Field of Search ...................... 435/69.1, 325, 435/320.1, 252.3; 536/23.5

(56) References Cited

U.S. PATENT DOCUMENTS

| | | | |
|---|---|---|---|
| 4,518,584 A | 5/1985 | Mark et al. | 424/85 |
| 4,892,538 A | 1/1990 | Aebischer et al. | 604/891.1 |
| 5,011,472 A | 4/1991 | Aebischer et al. | 604/50 |
| 5,106,627 A | 4/1992 | Aebischer et al. | 424/424 |

FOREIGN PATENT DOCUMENTS

| | | |
|---|---|---|
| EP | 398753 | 5/1990 |
| EP | 401384 | 12/1990 |
| WO | WO 90/14363 | 5/1990 |
| WO | WO 93/06116 | 9/1992 |
| WO | WO 95/34670 | 12/1995 |

OTHER PUBLICATIONS

Radinger In "Peptide Hormones" (Jun. 1976) ed. J.A. Parsons, University Park Press, Baltimore, pp 1–7.*
Angrist et al. (1995), 'Mutation analysis of the RET receptor tyrosine kinase in Hirschsprung disease', *Human Mol. Gen.* 4:821–830.
Choi–Lundberg et al. (1995), 'Ontegeny and distribution of glial cell line–derived neurotrophic factor (GDNF) mRNA in rat', *Dev Brain Res* 85:80–88.
Cunningham and Wells (1989), 'High–Resolution Epitope Mapping of hGH–Receptor Interactions by Alanine–scanning Mutagenesis', *Science* 244: 1081–1085.
Davis, et al. (1993), 'LIFRβ and gp130 as Heterodimerizing Signal Transducers of the Tripartite CNTF Receptor', *Science* 270:1805–1807.
Economides, et al. (1995), 'Designer cytokines: targeting actions to cells of choice', *Science* 270:1351–1353.
Edery, et al. (1994), 'Mutations of the RET proto–oncogene in Hirschsprung's disease', *Nature* 367:378–380.

Hefti (1994), 'Neurotrophic Factor Therapy for Nervous System Degenerative Diseases', *J. Neurobiol.* 25:1418–1435.
Henderson et al. (1994), 'GDNF: A Potent Survival Factor for Motoneurons Present in Peripheral Nerve and Muscle', *Science* 266:1062–1064.
Ikeda, et al. (1990), 'Specific expression of the *ret* proto–oncogene in human neuroblastoma cell lines', *Oncogene* 5:1291–1296.
Iwamoto, et al. (1993), 'cDNA cloning of mouse *ret* proto–oncogene and its sequence similarity to the cadherin superfamily', *Oncogene* 8:1087–1091.
Jing, et al. (1990), 'Role of the human transferrin receptor cytoplasmic domain in endocytosis: localization of a specific signal sequence for internalization', *J. Cell Bio.* 110:283–294.
Kohler, et al. (1975), 'Continuous cultures of fused cells secreting antibody of predefined specificity', *Nature* 256:495–497.
Li et al. (1995), 'Rescue of adult mouse motoneurons from injury–induced cell death by glial cell line–derived neurotrophic factor', *Proc. Natl. Acad. Sci.* 92:9771–9775.
Lin et al. (1993), 'GDNF: A Glial Cell Line–Derived Neurotrophic Factor for Midbrain Dopaminergic Neurons', *Science* 260: 1130–1132.
Malik et al. (1992), 'Polyethylene Glycol (PEG)–modified Granulocyte–Macrophage Colony–stimulating Factor (GM–CSF) with Conserved Biological Activity', *Exp. Hematol.* 20:1028–1035.
Oppenheim et al. (1995), 'Developing motor neurons rescued from programmed and axotomy–induced cell death by GDNF', *Nature* 373:344–346.
Pachnis et al. (1993), 'Expression of the *c–ret* proton–oncogene during mouse embryogenesis', *Development* 119:1005–1017.

(List continued on next page.)

*Primary Examiner*—Gary L. Kunz
*Assistant Examiner*—Robert C. Hayes
(74) *Attorney, Agent, or Firm*—Robert L. Sharp; Ron K. Levy; Steven M. Odre

(57) ABSTRACT

The present invention relates to glial cell line-derived neurotophic factor (GDNF), a potent neurotrophin that exhibits a broad spectrum of biological activities on a variety of cell types from both the central and peripheral nervous systems. The present invention involves the cloning and characterization of a high affinity receptor for GDNF. This molecule has been named GDNF receptor (GDNFR) since it is the first known component of a receptor system. Nucleic acid and amino acid sequences are described for GDNFR protein products. A hydrophobic domain with the features of a signal peptide is found at the amino terminus, while a second hydrophobic domain at the carboxy terminus is involved in the linkage of the receptor to the cell membrane. The lack of a transmembrane domain and cytoplasmic region indicates that GDNFR requires one or more accessory molecules in order to mediate transmembrane signaling. GDNFR mRNA is widely distributed in both nervous system and non-neural tissues, consistent with the similar distribution found for GDNF.

11 Claims, 40 Drawing Sheets

OTHER PUBLICATIONS

Romeo et al. (1994), 'Point mutations affecting the tyrosine kinase domain of the *RET* proto–oncogene in Hirschsprung's disease', *Nature* 367:377–378.

Schlessinger et al. (1992), 'Growth Factor Signaling by Receptor Tyrosine Kinases', *Neuron* 9:383–391.

Schuchardt et al. (1994), 'Defects in the kidney and enteric nervous system of mice lacking the tyrosine kinase receptor Ret', *Nature* 367:380–383.

Takebe et al. (1988), 'SRα Promoter: an Efficient and Versatile Mammalian cDNA Expression System Composed of the Simian Virus 40 Early Promoter and the R–U5 Segment of Human T–Cell Leukemia Virus Type 1 Long Terminal Repeat', *Mol and Cell Bio* 8:466–472.

Urlaub et al. (1980), 'Isolation of Chinese hamster cell mutants deficient in dihydrofolate reductase activity', *Proc. Natl. Acad. Sci* 77:4216–4220.

Van Heyningen (1994), 'One gene—four syndromes', *Nature* 367:319–320.

Von Heijne (1987), 'SIGPEP: a sequence data base for secretory signal peptides', *Protein Seq Data Anal* 1:41–42.

Von Heijne (1986), 'A new method for predicting signal sequence cleavage sites', *Nucleic Acids Res.* 14:4683–4690.

Wells et al. (1985), 'Cassette mutagenesis: an efficient method for generation of multiple mutations at defined sites', *Gene* 34:315–323.

Yan et al. (1995), 'In vivo neurotrophic effects of GDNF on neonatal and adult facial motor neurons', *Nature* 373:341–344.

Zurn et al. (1994), 'Glial cell line0derived neurotrophic factor (GDNF), a new neurotrophic factor for motoneurones', *NeuroReport* 6:113–118.

\* cited by examiner

FIG. 1A

Human Glial Cell Line-Derived
Neurotrophic Factor Receptor Protein

```
             10                     30                    50
  AATCTGGCCTCGGAACACGCCATTCTCCGCGCCGCTTCCAATAACCACTAACATCCCTA 70                     90                   110
  ACGAGCATCCGAGCCGAGGGCTCTGCTCGGAAATCGTCCTGGCCCAACTCGGCCCTTCGA 130                    150                   170
  GCTCTCGAAGATTACCGCATCTATTTTTTTTTTCTTTTTTTTCTTTTCCTAGCGCAGATA 190                    210                   230
  AAGTGAGCCCGGAAAGGGAAGGAGGGGGCGGGGACACCATTGCCCTGAAAGAATAAATAA 250                    270                   290
  GTAAATAAACAAACTGGCTCCTCGCCGCAGCTGGACGCGGTCGGTTGAGTCCAGGTTGGG 310                    330                   350
  TCGGACCTGAACCCCTAAAAGCGGAACCGCCTCCCGCCCTCGCCATCCCGGAGCTGAGTC 370                    390                   410
  GCCGGCGGCGGTGGCTGCTGCCAGACCCGGAGTTTCCTCTTTCACTGGATGGAGCTGAAC 430                    450                   470
  TTTGGGCGGCCAGAGCAGCACAGCTGTCCGGGGATCGCTGCACGCTGAGCTCCCTCGGCA 490                    510                   530
  AGACCCAGCGGCGGCTCGGGATTTTTTTGGGGGGCGGGGACCAGCCCCGCGCCGGCACC 550                    570                   590
  ATGTTCCTGGCGACCCTGTACTTCGCGCTGCCGCTCTTGGACTTGCTCCTGTCGGCCGAA
   M   F   L   A   T   L   Y   F   A   L   P   L   L   D   L   L   L   S   A   E
```

FIG. 1B

```
            610                 630                 650
GTGAGCGGCGGAGACCGCCTGGATTGCGTGAAAGCCAGTGATCAGTGCCTGAAGGAGCAG
 V   S   G   G   D   R   L   D   C   V   K   A   S   D   Q   C   L   K   E   Q 670                 690                 710
AGCTGCAGCACCAAGTACCGCACGCTAAGGCAGTGCGTGGCGGGCAAGGAGACCAACTTC
 S   C   S   T   K   Y   R   T   L   R   Q   C   V   A   G   K   E   T   N   F 730                 750                 770
AGCCTGGCATCCGGCCTGGAGGCCAAGGATGAGTGCCGCAGCGCCATGGAGGCCCTGAAG
 S   L   A   S   G   L   E   A   K   D   E   C   R   S   A   M   E   A   L   K 790                 810                 830
CAGAAGTCGCTCTACAACTGCCGCTGCAAGCGGGGTATGAAGAAGGAGAAGAACTGCCTG
 Q   K   S   L   Y   N   C   R   C   K   R   G   M   K   K   E   K   N   C   L 850                 870                 890
CGCATTTACTGGAGCATGTACCAGAGCCTGCAGGGAAATGATCTGCTGGAGGATTCCCCA
 R   I   Y   W   S   M   Y   Q   S   L   Q   G   N   D   L   L   E   D   S   P 910                 930                 950
TATGAACCAGTTAACAGCAGATTGTCAGATATATTCCGGGTGGTCCCATTCATATCAGAT
 Y   E   P   V   N   S   R   L   S   D   I   F   R   V   V   P   F   I   S   D 970                 990                1010
GTTTTTCAGCAAGTGGAGCACATTCCCAAAGGGAACAACTGCCTGGATGCAGCGAAGGCC
 V   F   Q   Q   V   E   H   I   P   K   G   N   N   C   L   D   A   A   K   A 1030                1050                1070
TGCAACCTCGACGACATTTGCAAGAAGTACAGGTCGGCGTACATCACCCCGTGCACCACC
 C   N   L   D   D   I   C   K   K   Y   R   S   A   Y   I   T   P   C   T   T 1090                1110                1130
AGCGTGTCCAACGATGTCTGCAACCGCCGCAAGTGCCACAAGGCCCTCCGGCAGTTCTTT
 S   V   S   N   D   V   C   N   R   R   K   C   H   K   A   L   R   Q   F   F
```

FIG. 1C

```
          1150                1170                1190
GACAAGGTCCCGGCCAAGCACAGCTACGGAATGCTCTTCTGCTCCTGCCGGGACATCGCC
 D   K   V   P   A   K   H   S   Y   C   M   L   F   C   S   C   R   D   I   A 1210                1230                1250
TGCACAGAGCGGAGCCGACACACCATCGTGCCTGTGTGCTCCTATCAAGAGACGGAGAAG
 C   T   E   R   R   R   Q   T   I   V   P   V   C   S   Y   E   E   R   E   K 1270                1290                1310
CCCAACTGTTTGAATTTGCAGGACTCCTCCAAGACGAATTACATCTGCAGATCTCGCCTT
 P   N   C   L   N   L   Q   D   S   C   K   T   N   Y   I   C   R   S   R   L 1330                1350                1370
GCGGATTTTTTTACCAACTGCCAGCCAGAGTCAAGGTCTGTCAGCAGCTGTCTAAAGGAA
 A   D   F   F   T   N   C   Q   P   E   S   R   S   V   S   S   C   L   K   E 1390                1410                1430
AACTACGCTGACTGCCTCCTCGCCTACTCGGGGCTTATTGGCACAGTCATGACCCCCAAC
 N   Y   A   D   C   L   L   A   Y   S   G   L   I   G   T   V   M   T   P   N 1450                1470                1490
TACATAGACTCCAGTAGCCTCAGTGTGGCCCCATGCTCTGACTGCAGCAACAGTGGGAAC
 Y   I   D   S   S   S   L   S   V   A   P   W   C   D   C   S   N   S   G   N 1510                1530                1550
GACCTAGAAGAGTGCTTGAAATTTTTGAATTTCTTCAAGGACAATACATGTCTTAAAAAT
 D   L   E   E   C   L   K   F   L   N   F   F   K   D   N   T   C   L   K   N 1570                1590                1610
GCAATTCAAGCCTTTGGCAATGGCTCCGATGTGACCGTGTGGCAGCCAGCCTTCCCAGTA
 A   I   Q   A   F   G   N   G   S   D   V   T   V   W   Q   P   A   F   P   V 1630                1650                1670
CAGACCACCACTGCCACTACCACCACTGCCCTCCGGGTTAAGAACAAGCCCCTGGGGCCA
 Q   T   T   T   A   T   T   T   A   L   R   V   K   N   K   P   L   C   P
```

FIG. 1D

```
        1690                1710                1730
GCAGGGTCTGAGAATGAAATTCCCACTCATGTTTTGCCACCGTGTGCAAATTTACAGGCA
 A  C  S  E  N  E  I  P  T  H  V  L  P  P  C  A  N  L  Q  A 1750                1770                1790
CAGAAGCTGAAATCCAATGTGTCGGGCAATACACACCTCTGTATTTCCAATGGTAATTAT
 Q  K  L  K  S  N  V  S  G  N  T  H  L  C  I  S  N  G  N  Y 1810                1830                1850
GAAAAAGAAGGTCTCGGTGCTTCCAGCCACATAACCACAAAATCAATGGCTGCTCCTCCA
 E  K  E  G  L  G  A  S  S  H  I  T  T  K  S  M  A  A  P  P 1870                1890                1910
AGCTGTGGTCTGAGCCCACTGCTGGTCCTGGTGGTAACCGCTCTGTCCACCCTATTATCT
 S  C  G  L  S  P  L  L  V  L  V  V  T  A  L  S  T  L  L  S 1930                1950                1970
TTAACAGAAACATCATAGCTGCATTAAAAAAATACAATATGGACATGTAAAAAGACAAAA
 L  T  E  T  S  *

1990                2010                2030
ACCAAGTTATCTGTTTCCTGTTCTCTTGTATAGCTGAAATTCCAGTTTAGGAGCTCAGTT 2050                2070                2090
GAGAAACAGTTCCATTCAACTGGAACATTTTTTTTTTT.CCTTTTAAGAAAGCTTCTTGT 2110                2130                2150
GATCCTT.GGGGCTTCTGTGAAAAACCTGATGCAGTGCTCCATCCAAACTCAGAAGGCTT 2170                2190                2210
TGGGATATGCTGTATTTTAAAGGGACAGTTTGTAACTTGGGCTGTAAAGCAAACTGGCGC 2230                2250                2270
TGTGTTTTCGATGATGATGAT.ATCATGAT.ATGAT.........................

2290                2310                2330
...............GATTTTAACAGTTTTACTTCTGGCCTTTCCTAGCTAGAGAAGGAG
```

FIG. 1E

```
          2350                2370                2390
TTAATATTTCTAAGGTAACTCCCATATCTCCTTTAATGACATTGATTTCTAATGATATAA 2410                2430                2450
ATTTCAGCCTACATTGATGCCAAGCTTTTTTGCCACAAAGAAGATTCTTACCAAGAGTGG 2470                2490                2510
GCTTTGTGGAAACAGCTGGTACTGATGTTCACCTTTATATATGTACTAGCATTTTCCACG 2530                2550
CTGATGTTTATGTACTGTAAACAGTTCTGCACTCTTGTACAAAAGAAAA
```

FIG. 2

Human Glial Cell Line-Derived
Neurotrophic Factor Receptor Protein

Rat Glial Cell Line-Derived
Neurotrophic Factor Receptor Protein

```
          10                  30                  50
AGCTCGCTCTCCCGGGGCAGTGGTGTGGATGCACCGGAGTTCGGGCGCTGGGCAAGTTGG 70                  90                 110
GTCGGAACTGAACCCCTGAAAGCGGGTCCGCCTCCCGCCCTCGCGCCCGCCCGGATCTGA 130                 150                 170
GTCGCTGGCGGCGGTGGGCGGCAGAGCGACGGGGAGTCTGCTCTCACCCTGGATGGAGCT 190                 210                 230
GAACTTTGAGTGGCCAGAGGAGCGCAGTCGCCCGGGGATCGCTGCACGCTGAGCTCTCTC 250                 270                 290
CCCGAGACCGGGCGGCGGCTTTGGATTTTGGGGGGGCGGGGACCAGCTGCGCGGCGGCAC 310                 330                 350
CATGTTCCTAGCCACTCTGTACTTCGCGCTGCCACTCCTGGATTTGCTGATGTCCGCCGA
  M  F  L  A  T  L  Y  F  A  L  P  L  L  D  L  L  M  S  A  E 370                 390                 410
GGTGAGTGGTGGAGACCGTCTGGACTGTGTGAAAGCCAGCGATCAGTGCCTGAAGGAACA
  V  S  G  G  D  R  L  D  C  V  K  A  S  D  Q  C  L  K  E  Q 430                 450                 470
GAGCTGCAGCACCAAGTACCGCACACTAAGGCAGTGCGTGGCGGGCAAGGAAACCAACTT
  S  C  S  T  K  Y  R  T  L  R  Q  C  V  A  G  K  E  T  N  F 490                 510                 530
CAGCCTGACATCCGGCCTTGAGGCCAAGGATGAGTGCCGTAGCGCCATGGAGGCCTTGAA
  S  L  T  S  G  L  E  A  K  D  E  C  R  S  A  M  E  A  L  K
```

FIG. 3B

```
          550                 570                 590
GCAGAAGTCTCTGTACAACTGCCGCTGCAAGCGGGGCATGAAGAAAGAGAAGAATTGTCT
 Q  K  S  L  Y  N  C  R  C  K  R  G  M  K  K  E  K  N  C  L 610                 630                 650
GCGTATCTACTGGAGCATGTACCAGAGCCTGCAGGGAAATGACCTCCTGGAAGATTCCCC
 R  I  Y  W  S  M  Y  Q  S  D  Q  G  N  D  L  L  E  D  S  P 670                 690                 710
GTATGAGCCGGTTAACAGCAGGTTGTCAGATATATTCCGGGCAGTCCCGTTCATATCAGA
 Y  E  P  V  N  S  R  L  S  D  I  F  R  A  V  P  F  I  S  D 730                 750                 770
TGTTTTCCAGCAAGTGGAACACATTTCCAAAGGGAACAACTGCCTGGACGCAGCCAAGGC
 V  F  Q  Q  V  E  H  I  S  K  G  N  N  C  L  D  A  A  K  A 790                 810                 830
CTGCAACCTGGACGACACCTGTAAGAAGTACAGGTCGGCCTACATCACCCCCTGCACCAC
 C  N  L  D  D  T  C  K  K  Y  R  S  A  Y  I  T  P  C  T  T 850                 870                 890
CAGCATGTCCAACGAGGTCTGCAACCGCCGTAAGTGCCACAAGGCCCTCAGGCAGTTCTT
 S  M  S  N  E  V  C  N  R  R  K  C  H  K  A  L  R  Q  F  F 910                 930                 950
CGACAAGGTTCCGGCCAAGCACAGCTACGGGATGCTCTTCTGCTCCTGCCGGGACATCGC
 D  K  V  P  A  K  H  S  Y  G  M  L  F  C  S  C  R  D  I  A 970                 990                1010
CTGCACCGAGCGGCGGCGACAGACTATCGTCCCCGTGTGCTCCTATGAAGAACGAGAGAG
 C  T  E  R  R  R  Q  T  I  V  P  V  C  S  Y  E  E  R  E  R 1030                1050                1070
GCCCAACTGCCTGAGTCTGCAAGACTCCTGCAAGACCAATTACATCTGCAGATCTCGCCT
 P  N  C  L  S  L  Q  D  S  C  K  T  N  Y  I  C  R  S  R  L
```

FIG. 3C

```
         1090                1110                1130
TGCAGATTTTTTTACCAACTGCCAGCCAGAGTCAAGGTCTGTCAGCAACTGTCTTAAGGA
 A  D  F  F  T  N  C  Q  P  E  S  R  S  V  S  N  C  L  K  E 1150                1170                1190
GAACTACGCAGACTGCCTCCTGGCCTACTCGGGACTGATTGGCACAGTCATGACTCCCAA
 N  Y  A  D  C  L  L  A  Y  S  G  L  I  G  T  V  M  T  P  N 1210                1230                1250
CTACGTAGACTCCAGCAGCCTCAGCGTGGCACCATGGTGTGACTGCAGCAACAGCGGCAA
 Y  V  D  S  S  S  L  S  V  A  P  W  C  D  C  S  N  S  G  N 1270                1290                1310
TGACCTGGAAGACTGCTTGAAATTTCTGAATTTTTTTAAGGACAATACTTGTCTCAAAAA
 D  L  E  D  C  L  K  F  L  N  F  F  K  D  N  T  C  L  K  N 1330                1350                1370
TGCAATTCAAGCCTTTGGCAATGCCTCAGATGTGACCATGTCGCAGCCAGCCCCTCCAGT
 A  I  Q  A  F  G  N  A  S  D  V  T  M  W  Q  P  A  P  P  V 1390                1410                1430
CCAGACCACCACTGCCACCACTACCACTGCCTTCCGGGTCAAGAACAAGCCTCTGGGGCC
 Q  T  T  T  A  T  T  T  T  A  F  R  V  K  N  K  P  L  G  P 1450                1470                1490
AGCAGGGTCTGAGAATGACATCCCCACACACGTTTTACCACCCTGTGCGAATTTGCAGGC
 A  G  S  E  N  D  I  P  T  H  V  L  P  P  C  A  N  L  Q  A 1510                1530                1550
TCAGAAGCTGAAATCCAATGTGTCCGGTAGCACACACCTCTGTCTTTCTGATAGTGATTT
 Q  K  L  K  S  N  V  S  G  S  T  H  L  C  L  S  D  S  D  F 1570                1590                1610
CGCAAAGGATGGTCTCGCTGGTGCCTCCAGCCACATAACCACAAAATCAATGGCTGCTCC
 G  K  D  G  L  A  G  A  S  S  H  I  T  T  K  S  M  A  A  P
```

FIG. 3D

```
          1630                1650                1670
TCCCAGCTGCAGTCTGAGCTCACTGCCGGTGCTGATGCTCACCGCCCTTGCTGCCCTGTT
  P   S   C   S   L   S   S   L   P   V   L   M   L   T   A   L   A   A   L   L 1690                1710                1730
ATCTGTATCGTTGGCAGAAACGTCGTAGCTGCATCCGGGAAAACAGTATGAAAAGACAAA
  S   V   S   L   A   E   T   S   *

1750                1770                1790
AGAGAACCAAGTATTCTGTCCCTGTCCTCTTGTATATCTGAAAATCCAGTTTTAAAAGCT 1810                1830                1850
CCGTTGAGAAGCAGTTTCACCCAACTGGAACTCTTTCCTTGTTTTTAAGAAAGCTTGTGG 1870                1890                1910
CCCTCAGGGGCTTCTGTTGAAGAACTGCTACAGGGCTAATTCCAAACCCATAAGGCTCTG 1930                1950                1970
GGGCGTGGTGCGGCTTAAGGGGACCATTTGCACCATGTAAAGCAAGCTGGGCTTATCATG 1990                2010                2030
TGTTTGATGGTGAGGATGGTAGTGGTGATGATGATGGTAATTTTAACAGCTTGAACCCTG 2050                2070                2090
TTCTCTCTACTGGTTAGGAACAGGAGATACTATTGATAAAGATTCTTCCATGTCTTACTC 2110                2130
AGCAGCATTGCCTTCTGAAGACAGGCCCGCAGCCGTCG
```

FIG. 4

Rat Glial Cell Line-Derived
Neurotrophic Factor Receptor Protein

Human GDNF receptor Clones -- Alignment to generate consensus sequence

```
                        -237                                                              -188
(SEQ ID NO: 37)  Gdnfr                                                                ATAACCACTA
(SEQ ID NO: 38)  Hsgr-21af         TCTGGCCT CGGAACACGC CATTCTCCGC GCCGCTTCCA ATAACCACTA
(SEQ ID NO: 39)  Hsgr-21bf AATCTGGCCT CGGAACACGC CATTCTCCGC GCCGCTTCCA ATAACCACTA
(SEQ ID NO: 40)  21acon    AATCTGGCCT CGGAACACGC CATTCTCCGC GCCGCTTCCA ATAACCACTA
(SEQ ID NO: 41)  21bcon    AATCTGGCCT CGGAACACGC CATTCTCCGC GCCGCTTCCA ATAACCACTA -187                                                              -138
(SEQ ID NO: 37)  Gdnfr     ACATCCCTAA CGAGCATCCG AGCCGAGGGC TCTGCTCGGA AATCGTCCTG
(SEQ ID NO: 38)  Hsgr-21af ACATCCCTAA CGAGCATCCG AGCCGAGGGC TCTGCTCGGA AATCGTCCTG
(SEQ ID NO: 39)  Hsgr-21bf ACATCCCTAA CGAGCATCCG AGCCGAGGGC TCTGCTCGGA AATCGTCCTG
(SEQ ID NO: 40)  21acon    ACATCCCTAA CGAGCATCCG AGCCGAGGGC TCTGCTCGGA AATCGTCCTG
(SEQ ID NO: 41)  21bcon    ACATCCCTAA CGAGCATCCG AGCCGAGGGC TCTGCTCGGA AATCGTCCTG -137                                                              -88
(SEQ ID NO: 37)  Gdnfr     GCCCAACTCG GCCCTTCGAG CTCTCGAAGA TTACCGCATC TATTTTTTTT
(SEQ ID NO: 38)  Hsgr-21af GCCCAACTCG GCCCTTCGAG CTCTCGAAGA TTACCGCATC TATTTTTTTT
(SEQ ID NO: 39)  Hsgr-21bf GCCCAACTCG GCCCTTCGAG CTCTCGAAGA TTACCGCATC TATTTTTTTT
(SEQ ID NO: 40)  21acon    GCCCAACTCG GCCCTTCGAG CTCTCGAAGA TTACCGCATC TATTTTTTTT
(SEQ ID NO: 41)  21bcon    GCCCAACTCG GCCCTTCGAG CTCTCGAAGA TTACCGCATC TATTTTTTTT
```

FIG. 5B

```
                         -87                                                              -38
(SEQ ID NO: 37)   Gdnfr    TTCTTTTTTT  TCTTTTCCTA  GCGCAGATAA  AGTGAGCCCG  GAAAGGGAAG
(SEQ ID NO: 38)   Hsgr-21af TTCTTTTTTT  TCTTTTCCTA  GCGCAGATAA  AGTGAGCCCG  GAAAGGGAAG
(SEQ ID NO: 39)   Hsgr-21bf TTCTTTTTTT  TCTTTTCCTA  GCGCAGATAA  AGTGAGCCCG  GAAAGGGAAG
(SEQ ID NO: 40)   21acon   TTCTTTTTTT  TCTTTTCCTA  GCGCAGATAA  AGTGAGCCCG  GAAAGGGAAG
(SEQ ID NO: 41)   21bcon   TTCTTTTTTT  TCTTTTCCTA  GCGCAGATAA  AGTGAGCCCG  GAAAGGGAAG -37                                                              12
(SEQ ID NO: 37)   Gdnfr    GAGGGGGCGG  GGACACCATT  GCCCTGAAAG  AATAAATAAG  TAAATAAACA
(SEQ ID NO: 38)   Hsgr-21af GAGGGGGCGG  GGACACCATT  GCCCTGAAAG  AATAAATAAG  TAAATAAACA
(SEQ ID NO: 39)   Hsgr-21bf GAGGGGGCGG  GGACACCATT  GCCCTGAAAG  AATAAATAAG  TAAATAAACA
(SEQ ID NO: 40)   21acon   GAGGGGGCGG  GGACACCATT  GCCCTGAAAG  AATAAATAAG  TAAATAAACA
(SEQ ID NO: 41)   21bcon   GAGGGGGCGG  GGACACCATT  GCCCTGAAAG  AATAAATAAG  TAAATAAACA 13                                                               62
(SEQ ID NO: 37)   Gdnfr    AACTGGCTCC  TCGCCGCAGC  TGGACGCGGT  CGGTTGAGTC  CAGGTTGGGT
(SEQ ID NO: 38)   Hsgr-21af AACTGGCTCC  TCGCCGCAGC  TGGACGCGGT  CGGTTGAGTC  CAGGTTGGGT
(SEQ ID NO: 39)   Hsgr-21bf AACTGGCTCC  TCGCCGCAGC  TGGACGCGGT  CGGTTGAGTC  CAGGTTGGGT
(SEQ ID NO: 40)   21acon   AACTGGCTCC  TCGCCGCAGC  TGGACGCGGT  CGGTTGAGTC  CAGGTTGGGT
(SEQ ID NO: 41)   21bcon   AACTGGCTCC  TCGCCGCAGC  TGGACGCGGT  CGGTTGAGTC  CAGGTTGGGT
```

FIG. 5C

```
                              63
(SEQ ID NO: 37)    Gdnfr     CGGACCTGAA CCCCTAAAAG CGGAACCGCC TCCCGCCCTC GCCATCCCGG
(SEQ ID NO: 38)    Hsgr-21af CGGACCTGAA CCCCTAAAAG CGGAACCGCC TCCCGCCCTC GCCATCCCGG
(SEQ ID NO: 39)    Hsgr-21bf CGGACCTGAA CCCCTAAAAG CGGAACCGCC TCCCGCCCTC GCCATCCCGG
(SEQ ID NO: 40)    21acon    CGGACCTGAA CCCCTAAAAG CGGAACCGCC TCCCGCCCTC GCCATCCCGG
(SEQ ID NO: 41)    21bcon    CGGACCTGAA CCCCTAAAAG CGGAACCGCC TCCCGCCCTC GCCATCCCGG 113                                              162
(SEQ ID NO: 37)    Gdnfr     AGCTGAGTCG CCGGCGGCGG TGGCTGCTGC CAGACCCGGA GTTTCCTCTT
(SEQ ID NO: 38)    Hsgr-21af AGCTGAGTCG CCGGCGGGCGG TGGCTGCTGC CAGACCCGGA GTTTCCTCTT
(SEQ ID NO: 39)    Hsgr-21bf AGCTGAGTCG CCGGCGGCGG TGGCTGCTGC CAGACCCGGA GTTTCCTCTT
(SEQ ID NO: 40)    21acon    AGCTGAGTCG CCGGCGGCGG TGGCTGCTGC CAGACCCGGA GTTTCCTCTT
(SEQ ID NO: 41)    21bcon    AGCTGAGTCG CCGGCGGCGG TGGCTGCTGC CAGACCCGGA GTTTCCTCTT 163                                              212
(SEQ ID NO: 37)    Gdnfr     TCACTGGATG GAGCTGAACT TTGGGCGGCC AGAGCAGCAC AGCTGTCCGG
(SEQ ID NO: 38)    Hsgr-21af TCACTGGATG GAGCTGAACT TTGGGCGGCC AGAGCAGCAC AGCTGTCCGG
(SEQ ID NO: 39)    Hsgr-21bf TCACTGGATG GAGCTGAACT TTGGGCGGCC AGAGCAGCAC AGCTGTCCGG
(SEQ ID NO: 40)    21acon    TCACTGGATG GAGCTGAACT TTGGGCGGCC AGAGCAGCAC AGCTGTCCGG
(SEQ ID NO: 41)    21bcon    TCACTGGATG GAGCTGAACT TTGGGCGGCC AGAGCAGCAC AGCTGTCCGG
```

FIG. 5D

```
                                                                                         213                                              262
(SEQ ID NO: 37)    Gdnfr       GGATCGCTGC  ACGCTGAGCT  CCCTCGGCAA  GACCCAGCGG  CGGCTCGGGA
(SEQ ID NO: 38)    Hsgr-21af   GGATCGCTGC  ACGCTGAGCT  CCCTCGGCAA  GACCCAGCGG  CGGCTCGGGA
(SEQ ID NO: 39)    Hsgr-21bf   GGATCGCTGC  ACGCTGAGCT  CCCTCGGCAA  GACCCAGCGG  CGGCTCGGGA
(SEQ ID NO: 40)    21acon      GGATCGCTGC  ACGCTGAGCT  CCCTCGGCAA  GACCCAGCGG  CGGCTCGGGA
(SEQ ID NO: 41)    21bcon      GGATCGCTGC  ACGCTGAGCT  CCCTCGGCAA  GACCCAGCGG  CGGCTCGGGA 263                                              312
(SEQ ID NO: 37)    Gdnfr       TTTTTTTGGG  GGGGCGGGGA  CCAGCCCCGC  GCCGGCACCA  TGTTCCTGGC
(SEQ ID NO: 38)    Hsgr-21af   TTTTTTTGGG
(SEQ ID NO: 39)    Hsgr-21bf   TTTTTTTGGG
(SEQ ID NO: 40)    21acon      TTTTTTTGGG  GGGGCGGGGA  CCAGCCCCGC  GCCGGCACCA  TGTTCCTGGC
(SEQ ID NO: 41)    21bcon      TTTTTTTGGG  GGGGCGGGGA  CCAGCCCCGC  GCCGGCACCA  TGTTCCTGGC 313                                              362
(SEQ ID NO: 37)    Gdnfr       GACCCTGTAC  TTCGGCGCTGC  CGCTCTTGGA  CTTGCTCCTG  TCGGCCGAAG
(SEQ ID NO: 40)    21acon      GACCCTGTAC  TTCGGCGCTGC  CGCTCTTGGA  CTTGCTCCTG  TCGGCCGAAG
(SEQ ID NO: 41)    21bcon      GACCCTGTAC  TTCGGCGCTGC  CGCTCTTGGA  CTTGCTCCTG  TCGGCCGAAG 363                                              412
(SEQ ID NO: 37)    Gdnfr       TGAGCGGCGG  AGACCGCCCTG  GATTGCGTGA  AAGCCAGTGA  TCAGTGCCTG
(SEQ ID NO: 40)    21acon      TGAGCGGCGG  AGACCGCCCTG  GATTGCGTGA  AAGCCAGTGA  TCAGTGCCTG
(SEQ ID NO: 41)    21bcon      TGAGCGGCGG  AGACCGCCCTG  GATTGCGTGA  AAGCCAGTGA  TCAGTGCCTG
```

FIG. 5E

```
              413
Gdnfr   AAGGAGCAGA  GCTGCAGCAC  CAAGTACCGC  ACGCTAAGGC  AGTGCGTGGC   462
21acon  AAGGAGCAGA  GCTGCAGCAC  CAAGTACCGC  ACGCTAAGGC  AGTGCGTGGC
21bcon  AAGGAGCAGA  GCTGCAGCAC  CAAGTACCGC  ACGCTAAGGC  AGTGCGTGGC 463
Gdnfr   GGGCAAGGAG  ACCAACTTCA  GCCTGGCATC  CGGCCTGGAG  GCCAAGGATG   512
21acon  GGGCAAGGAG  ACCAACTTCA  GCCTGGCATC  CGGCCTGGAG  GCCAAGGATG
21bcon  GGGCAAGGAG  ACCAACTTCA  GCCTGGCATC  CGGCCTGGAG  GCCAAGGATG 513
Gdnfr   AGTGCCGCAG  CGCCATGGAG  GCCCTGAAGC  AGAAGTCGCT  CTACAACTGC   562
21acon  AGTGCCGCAG  CGCCATGGAG  GCCCTGAAGC  AGAAGTCGCT  CTACAACTGC
21bcon  AGTGCCGCAG  CGCCATGGAG  GCCCTGAAGC  AGAAGTCGCT  CTACAACTGC 563
Gdnfr   CGCTGCAAGC  GGGGTATGAA  GAAGGAGAAG  AACTGCCTGC  GCATTTACTG   612
21acon  CGCTGCAAGC  GGGGTATGAA  GAAGGAGAAG  AACTGCCTGC  GCATTTACTG
21bcon  CGCTGCAAGC  GGGGTATGAA  GAAGGAGAAG  AACTGCCTGC  GCATTTACTG 613
Gdnfr   GAGCATGTAC  CAGAGCCTGC  AGGGAAATGA  TCTGCTGGAG  GATTCCCCAT   662
21acon  GAGCATGTAC  CAGAGCCTGC  AGGGAAATGA  TCTGCTGGAG  GATTCCCCAT
21bcon  GAGCATGTAC  CAGAGCCTGC  AGGGAAATGA  TCTGCTGGAG  GATTCCCCAT
```

(SEQ ID NO: 37)
(SEQ ID NO: 40)
(SEQ ID NO: 41)

FIG. 5F

```
          663
Gdnfr     ATGAACCAGT TAACAGCAGA TTGTCAGATA TATTCCGGGT GGTCCCATTC
21acon    ATGAACCAGT TAACAGCAGA TTGTCAGATA TATTCCGGGT GGTCCCATTC
21bcon    ATGAACCAGT TAACAGCAGA TTGTCAGATA TATTCCGGGT GGTCCCATTC 713                                                   712
Gdnfr     ATATCAGATG TTTTTCAGCA AGTGGAGCAC ATTCCCAAAG GGAACAACTG
21acon    ATATCAGATG TTTTTCAGCA AGTGGAGCAC ATTCCCAAAG GGAACAACTG
21bcon    ATATCAGATG TTTTTCAGCA AGTGGAGCAC ATTCCCAAAG GGAACAACTG 763                                                   762
Gdnfr     CCTGGATGCA GCGAAGGCCT GCAACCTCGA CGACATTTGC AAGAAGTACA
21acon    CCTGGATGCA GCGAAGGCCT GCAACCTCGA CGACATTTGC AAGAAGTACA
21bcon    CCTGGATGCA GCGAAGGCCT GCAACCTCGA CGACATTTGC AAGAAGTACA 813                                                   812
Gdnfr     GGTCGGCGTA CATCACCCCG TGCACCACCA GCGTGTCCAA .GATGTCTGC
Hsgr-29a   GTCGGCGTA CATCACCCCG TGCACCACCA GCGTGTCCAA TGATGTCTGC
21acon    GGTCGGCGTA CATCACCCCG TGCACCACCA GCGTGTCCAA CGATGTCTGC
21bcon    GGTCGGCGTA CATCACCCCG TGCACCACCA GCGTGTCCAA CGATGTCTGC
29brc      GTCGGCGTA CATCACCCCG TGCACCACCA GCGTGTCCAA TGATGTCTGC
                                                                862
```

(SEQ ID NO: 37)
(SEQ ID NO: 40)
(SEQ ID NO: 41)

(SEQ ID NO: 37)
(SEQ ID NO: 40)
(SEQ ID NO: 41)

(SEQ ID NO: 37)
(SEQ ID NO: 40)
(SEQ ID NO: 41)

(SEQ ID NO: 37)
(SEQ ID NO: 42)
(SEQ ID NO: 40)
(SEQ ID NO: 41)
(SEQ ID NO: 43)

FIG. 5G

```
                863
Gdnfr    AACCGCCGCA AGTGCCACAA GGCCCTCCGG CAGTTCTTTG ACAAGGTCCC
Hsgr-29a AACCGCCGCA AGTGCCACAA GGCCCTCCGG CAGTTCTTTG ACAAGGTCCC
21acon   AACCGCCGCA AGTGCCACAA GGCCCTCCGG CAGTTCTTTG ACAAGGTCCC
21bcon   AACCGCCGCA AGTGCCACAA GGCCCTCCGG CAGTTCTTTG ACAAGGTCCC
29brc    AACCGCCGCA AGTGCCACAA GGCCCTCCGG CAGTTCTTTG ACAAGGTCCC
                                                            912

913
Gdnfr    GGCCAAGCAC AGCTACGGAA TGCTCTTTCTG CTCCTGCCGG GACATCGCCT
Hsgr-29a GGCCAAGCAC AGCTACGGAA TGCTCTTTCTG CTCCTGCCGG GACATCGCCT
21acon   GGCCAAGCAC AGCTACGGAA TGCTCTTTCTG CTCCTGCCGG GACATCGCCT
21bcon   GGCCAAGCAC AGCTACGGAA TGCTCTTTCTG CTCCTGCCGG GACATCGCCT
29brc    GGCCAAGCAC AGCTACGGAA TGCTCTTTCTG CTCCTGCCGG GACATCGCCT
                                                            962

963
Gdnfr    GCACAGAGCG GAGGCGACAG ACCATCGTGC CTGTGTGCTC CTATGAAGAG
Hsgr-29a GCACAGAGCG GAGGCGACAG ACCATCGTGC CTGTGTGCTC CTATGAAGAG
21acon   GCACAGAGCG GAGGCGACAG ACCATCGTGC CTGTGTGCTC CTATGAAGAG
21bcon   GCACAGAGCG GAGGCGACAG ACCATCGTGC CTGTGTGCTC CTATGAAGAG
29brc    GCACAGAGCG GAGGCGACAG ACCATCGTGC CTGTGTGCTC CTATGAAGAG
                                                           1012
```

(SEQ ID NO: 37)
(SEQ ID NO: 42)
(SEQ ID NO: 40)
(SEQ ID NO: 41)
(SEQ ID NO: 43)

FIG. 5H

```
                                        1013                                                                      1062
Gdnfr      (SEQ ID NO: 37)    AGGGAGAAGC CCAACTGTTT GAATTTGCAG GACTCCTGCA AGACGAATTA
Hsgr-21ar  (SEQ ID NO: 44)                                     GACTCCTGCA AGACGAATTA
Hsgr-21br  (SEQ ID NO: 45)                                                         A
Hsgr-29a   (SEQ ID NO: 42)    AGGGAGAAGC CCAACTGTTT GAATTTGCAG GACTCCTGCA AGACGAATTA
21acon     (SEQ ID NO: 40)    AGGGAGAAGC CCAACTGTTT GAATTTGCAG GACTCCTGCA AGACGAATTA
21bcon     (SEQ ID NO: 41)    AGGGAGAAGC CCAACTGTTT GAATTTGCAG GACTCCTGCA AGACGAATTA
29brc      (SEQ ID NO: 43)    AGGGAGAAGC CCAACTGTTT GAATTTGCAG GACTCCTGCA AGACGAATTA 1063                                                                      1112
Gdnfr      (SEQ ID NO: 37)    CATCTGCAGA TCTCGCCTTG CGGATTTTTT TACCAACTGC CAGCCAGAGT
Hsgr-21ar  (SEQ ID NO: 44)    CATCTGCAGA TCTCGCCTTG CGGATTTTTT TACCAACTGC CAGCCAGAGT
Hsgr-21br  (SEQ ID NO: 45)    CATCTGCAGA TCTCGCCTTG CGGATTTTTT TACCAACTGC CAGCCAGAGT
Hsgr-29a   (SEQ ID NO: 42)    CATCTGCAGA TCTCGCCTTG CGGATTTTTT TACCAACTGC CAGCCAGAGT
21acon     (SEQ ID NO: 40)    CATCTGCAGA TCTCGCCTTG CGGATTTTTT TACCAACTGC CAGCCAGAGT
21bcon     (SEQ ID NO: 41)    CATCTGCAGA TCTCGCCTTG CGGATTTTTT TACCAACTGC CAGCCAGAGT
29brc      (SEQ ID NO: 43)    CATCTGCAGA TCTCGCCTTG CGGATTTTTT TACCAACTGC CAGCCAGAGT 1113                                                                      1162
Gdnfr      (SEQ ID NO: 37)    CAAGGTCTGT CAGCAGCTGT CTAAAGGAAA ACTACGCTGA CTGCCTCCTC
Hsgr-21ar  (SEQ ID NO: 44)    CAAGGTCTGT CAGCAGCTGT CTAAAGGAAA ACTACGCTGA CTGCCTCCTC
Hsgr-21br  (SEQ ID NO: 45)    CAAGGTCTGT CAGCAGCTGT CTAAAGGAAA ACTACGCTGA CTGCCTCCTC
Hsgr-29a   (SEQ ID NO: 42)    CAAGGTCTGT CAGCAGCTGT CTAAAGGAAA ACTACGCTGA CTGCCTCCTC
21acon     (SEQ ID NO: 40)    CAAGGTCTGT CAGCAGCTGT CTAAAGGAAA ACTACGCTGA CTGCCTCCTC
21bcon     (SEQ ID NO: 41)    CAAGGTCTGT CAGCAGCTGT CTAAAGGAAA ACTACGCTGA CTGCCTCCTC
29brc      (SEQ ID NO: 43)    CAAGGTCTGT CAGCAGCTGT CTAAAGGAAA ACTACGCTGA CTGCCTCCTC
```

FIG. 51

```
                                  1163                                                              1212
           Gdnfr      GCCTACTCGG GGCTTATTGG CACAGTCATG ACCCCCAACT ACATAGACTC    (SEQ ID NO: 37)
           Hsgr-21ar  GCCTACTCGG GGCTTATTGG CACAGTCATG ACCCCCAACT ACATAGACTC    (SEQ ID NO: 44)
           Hsgr-21br  GCCTACTCGG GGCTTATTGG CACAGTCATG ACCCCCAACT ACATAGACTC    (SEQ ID NO: 45)
           Hsgr-29a   GCCTACTCGG GGCTTATTGG CACAGTCATG ACCCCCAACT ACATAGACTC    (SEQ ID NO: 42)
           21acon     GCCTACTCGG GGCTTATTGG CACAGTCATG ACCCCCAACT ACATAGACTC    (SEQ ID NO: 40)
           21bcon     GCCTACTCGG GGCTTATTGG CACAGTCATG ACCCCCAACT ACATAGACTC    (SEQ ID NO: 41)
           29brc      GCCTACTCGG GGCTTATTGG CACAGTCATG ACCCCCAACT ACATAGACTC    (SEQ ID NO: 43)

1213                                                              1262
           Gdnfr      CAGTAGCCTC AGTGTGGCCC CATGGTGTGA CTGCAGCAAC AGTGGGAACG    (SEQ ID NO: 37)
           Hsgr-2                                                  TGGGAACG    (SEQ ID NO: 46)
           Hsgr-21ar  CAGTAGCCTC AGTGTGGCCC CATGGTGTGA CTGCAGCAAC AGTGGGAACG    (SEQ ID NO: 44)
           Hsgr-21br  CAGTAGCCTC AGTGTGGCCC CATGGTGTGA CTGCAGCAAC AGTGGGAACG    (SEQ ID NO: 45)
           Hsgr-29a   CAGTAGCCTC AGTGTGGCCC CATGGTGTGA CTGCAGCAAC AGTGGGAACG    (SEQ ID NO: 42)
           21acon     CAGTAGCCTC AGTGTGGCCC CATGGTGTGA CTGCAGCAAC AGTGGGAACG    (SEQ ID NO: 40)
           21bcon     CAGTAGCCTC AGTGTGGCCC CATGGTGTGA CTGCAGCAAC AGTGGGAACG    (SEQ ID NO: 41)
           29brc      CAGTAGCCTC AGTGTGGCCC CATGGTGTGA CTGCAGCAAC AGTGGGAACG    (SEQ ID NO: 43)
```

FIG. 5J

```
                              1263                                                                          1312
Gdnfr     (SEQ ID NO: 37)          ACCTAGAAGA GTGCTTGAAA TTTTTGAATT TCTTCAAGGA CAATACATGT
Hsgr-2    (SEQ ID NO: 46)          ACCTAGAAGA GTGCTTGAAA TTTTTGAATT TCTTCAAGGA CAATACATGT
Hsgr-9    (SEQ ID NO: 47)                   A GTGCTTGAAA TTTTTGAATT TCTTCAAGGA CAATACATGT
Hsgr-21ar (SEQ ID NO: 44)          ACCTAGAAGA GTGCTTGAAA TTTTTGAATT TCTTCAAGGA CAATACATGT
Hsgr-21br (SEQ ID NO: 45)          ACCTAGAAGA GTGCTTGAAA TTTTTGAATT TCTTCAAGGA CAATACATGT
Hsgr-29a  (SEQ ID NO: 42)          ACCTAGAAGA GTGCTTGAAA TTTTTGAATT TCTTCAAGGA CAATACATGT
21acon    (SEQ ID NO: 40)          ACCTAGAAGA GTGCTTGAAA TTTTTGAATT TCTTCAAGGA CAATACATGT
21bcon    (SEQ ID NO: 41)          ACCTAGAAGA GTGCTTGAAA TTTTTGAATT TCTTCAAGGA CAATACATGT
29brc     (SEQ ID NO: 43)          ACCTAGAAGA GTGCTTGAAA TTTTTGAATT TCTTCAAGGA CAATACATGT 1313                                                                          1362
Gdnfr     (SEQ ID NO: 37)          CTTAAAAATG CAATTCAAGC CTTTGGCAAT GGCTCCGATG TGACCGTGTG
Hsgr-2    (SEQ ID NO: 46)          CTTAAAAATG CAATTCAAGC CTTTGGCAAT GGCTCCGATG TGACCGTGTG
Hsgr-9    (SEQ ID NO: 47)          CTTAAAAATG CAATTCAAGC CTTTGGCAAT GGCTCCGATG TGACCGTGTG
Hsgr-21ar (SEQ ID NO: 44)          CTTAAAAATG CAATTCAAGC CTTTGGCAAT GGCTCCGATG TGACCGTGTG
Hsgr-21br (SEQ ID NO: 45)          CTTAAAAATG CAATTCAAGC CTTTGGCAAT GGCTCCGATG TGACCGTGTG
Hsgr-29a  (SEQ ID NO: 42)          CTTAAAAATG CAATTCAAGC CTTTGGCAAT GGCTCCGATG TGACCGTGTG
21acon    (SEQ ID NO: 40)          CTTAAAAATG CAATTCAAGC CTTTGGCAAT GGCTCCGATG TGACCGTGTG
21bcon    (SEQ ID NO: 41)          CTTAAAAATG CAATTCAAGC CTTTGGCAAT GGCTCCGATG TGACCGTGTG
29brc     (SEQ ID NO: 43)          CTTAAAAATG CAATTCAAGC CTTTGGCAAT GGCTCCGATG TGACCGTGTG
```

FIG. 5K

```
                           1363                                                                        1412
(SEQ ID NO: 37)   Gdnfr    GCAGCCAGCC TTCCCAGTAC AGACCACCAC TGCCaCTACC ACCACTGCCC
(SEQ ID NO: 46)   Hsgr-2   GCAGCCAGCC TTCCCAGTAC AGACCACCAC TGCCACTACC ACCACTGCCC
(SEQ ID NO: 47)   Hsgr-9   GCAGCCAGCC TTCCCAGTAC AGACCACCAC TGCCACTACC ACCACTGCCC
(SEQ ID NO: 44)   Hsgr-21ar GCAGCCAGCC TTCCCAGTAC AGACCACCAC TGCCACTACC ACCACTGCCC
(SEQ ID NO: 45)   Hsgr-21br GCAGCCAGCC TTCCCAGTAC AGACCACCAC TGCCACTACC ACCACTGCCC
(SEQ ID NO: 42)   Hsgr-29a GCAGCCAGCC TTCCCAGTAC AGACCACCAC TGCCGCTACC ACCACTGCCC
(SEQ ID NO: 40)   21acon   GCAGCCAGCC TTCCCAGTAC AGACCACCAC TGCCACTACC ACCACTGCCC
(SEQ ID NO: 41)   21bcon   GCAGCCAGCC TTCCCAGTAC AGACCACCAC TGCCACTACC ACCACTGCCC
(SEQ ID NO: 43)   29brc    GCAGCCAGCC TTCCCAGTAC AGACCACCAC TGCCGCTACC ACCACTGCCC 1413                                                                        1462
(SEQ ID NO: 37)   Gdnfr    TCCGGGTTAA GAACAAGCCC CTGGGGCCAG CAGGGTCTGA GAATGAAATT
(SEQ ID NO: 46)   Hsgr-2   TCCGGGTTAA GAACAAGCCC CTGGGGCCAG CAGGGTCTGA GAATGAAATT
(SEQ ID NO: 47)   Hsgr-9   TCCGGGTTAA GAACAAGCCC CTGGGGCCAG CAGGGTCTGA GAATGAAATT
(SEQ ID NO: 44)   Hsgr-21ar TCCGGGTTAA GAACAAGCCC CTGGGGCCAG CAGGGTCTGA GAATGAAATT
(SEQ ID NO: 45)   Hsgr-21br TCCGGGTTAA GAACAAGCCC CTGGGGCCAG CAGGGTCTGA GAATGAAATT
(SEQ ID NO: 42)   Hsgr-29a TCCGGGTTAA GAACAAGCCC CTGGGGCCAG CAGGGTCTGA GAATGAAATT
(SEQ ID NO: 40)   21acon   TCCGGGTTAA GAACAAGCCC CTGGGGCCAG CAGGGTCTGA GAATGAAATT
(SEQ ID NO: 41)   21bcon   TCCGGGTTAA GAACAAGCCC CTGGGGCCAG CAGGGTCTGA GAATGAAATT
(SEQ ID NO: 43)   29brc    TCCGGGTTAA GAACAAGCCC CTGGGGCCAG CAGGGTCTGA GAATGAAATT
```

FIG. 5L

```
              1463
       Gdnfr  CCCACTCATG TTTTGCCACC GTGTGCAAAT TTACAGGCAC AGAAGCTGAA
      Hsgr-2  CCCACTCATG TTTTGCCACC GTGTGCAAAT TTACAGGCAC AGAAGCTGAA
      Hsgr-9  CCCACTCATG TTTTGCCACC GTGTGCAAAT TTACAGGCAC AGAAGCTGAA
   Hsgr-21ar  CCCACTCATG TTTTGCCACC GTGTGCAAAT TTACAGGCAC AGAAGCTGAA
   Hsgr-21br  CCCACTCATG TTTTGCCACC GTGTGCAAAT TTACAGGCAC AGAAGCTGAA
   Hsgr-29a   CCCACTCATG TTTTGCCACC GTGTGCAAAT TTACAGGCAC AGAAGCTGAA
     21acon   CCCACTCATG TTTTGCCACC GTGTGCAAAT TTACAGGCAC AGAAGCTGAA
     21bcon   CCCACTCATG TTTTGCCACC GTGTGCAAAT TTACAGGCAC AGAAGCTGAA
      29brc   CCCACTCATG TTTTGCCACC GTGTGCAAAT TTACAGGCAC AGAAGCTGAA
                                                                1512

1513
       Gdnfr  ATCCAATGTG TCGGGCAATA CACACCTCTG TATTTCCAAT GGTAATTATG
      Hsgr-2  ATCCAATGTG TCGGGCAATA CACACCTCTG TATTTCCAAT GGTAATTATG
      Hsgr-9  ATCCAATGTG TCGGGCAATA CACACCTCTG TATTTCCAAT GGTAATTATG
   Hsgr-21ar  ATCCAATGTG TCGGGCAATA CACACCTCTG TATTTCCAAT GGTAATTATG
   Hsgr-21br  ATCCAATGTG TCGGGCAATA CACACCTCTG TATTTCCAAT GGTAATTATG
   Hsgr-29a   ATCCAATGTG TCGGGCAATA CACACCTCTG TATTTCCAAT GGTAATTATG
     21acon   ATCCAATGTG TCGGGCAATA CACACCTCTG TATTTCCAAT GGTAATTATG
     21bcon   ATCCAATGTG TCGGGCAATA CACACCTCTG TATTTCCAAT GGTAATTATG
      29brc   ATCCAATGTG TCGGGCAATA CACACCTCTG TATTTCCAAT GGTAATTATG
                                                                1562
```

(SEQ ID NO: 37)
(SEQ ID NO: 46)
(SEQ ID NO: 47)
(SEQ ID NO: 44)
(SEQ ID NO: 45)
(SEQ ID NO: 42)
(SEQ ID NO: 40)
(SEQ ID NO: 41)
(SEQ ID NO: 43)

FIG. 5M

```
                        1563                                                                              1612
Gdnfr       (SEQ ID NO: 37)    AAAAAGAAGG  TCTCGGTGCT  TCCAGCCACA  TAACCACAAA  ATCAATGGCT
Hsgr-2      (SEQ ID NO: 46)    AAAAAGAAGG  TCTCGGTGCT  TCCAGCCACA  TAACCACAAA  ATCAATGGCT
Hsgr-9      (SEQ ID NO: 47)    AAAAAGAAGG  TCTCGGTGCT  TCCAGCCACA  TAACCACAAA  ATCAATGGCT
Hsgr-21ar   (SEQ ID NO: 44)    AAAAAGAAGG  TCTCGGTGCT  TCCAGCCACA  TAACCACAAA  ATCAATGGCT
Hsgr-21br   (SEQ ID NO: 45)    AAAAAGAAGG  TCTCGGTGCT  TCCAGCCACA  TAACCACAAA  ATCAATGGCT
21acon      (SEQ ID NO: 40)    AAAAAGAAGG  TCTCGGTGCT  TCCAGCCACA  TAACCACAAA  ATCAATGGCT
21bcon      (SEQ ID NO: 41)    AAAAAGAAGG  TCTCGGTGCT  TCCAGCCACA  TAACCACAAA  ATCAATGGCT
29brc       (SEQ ID NO: 43)    AAAAAGAAGG  TCTCGGTGCT  TCCAGCCACA  TAACCACAAA  ATCAATGGCT 1613                                                                              1662
Gdnfr       (SEQ ID NO: 37)    GCTCCTCCAA  GCTGTGGTCT  GAGCCCACTG  CTGGTCCTGG  TGGTAACCGC
Hsgr-2      (SEQ ID NO: 46)    GCTCCTCCAA  GCTGTGGTCT  GAGCCCACTG  CTGGTCCTGG  TGGTAACCGC
Hsgr-9      (SEQ ID NO: 47)    GCTCCTCCAA  GCTGTGGTCT  GAGCCCACTG  CTGGTCCTGG  TGGTAACCGC
Hsgr-21ar   (SEQ ID NO: 44)    GCTCCTCCAA  GCTGTGGTCT  GAGCCCACTG  CTGGTCCTGG  TGGTAACCGC
Hsgr-21br   (SEQ ID NO: 45)    GCTCCTCCAA  GCTGTGGTCT  GAGCCCACTG  CTGGTCCTGG  TGGTAACCGC
21acon      (SEQ ID NO: 40)    GCTCCTCCAA  GCTGTGGTCT  GAGCCCACTG  CTGGTCCTGG  TGGTAACCGC
21bcon      (SEQ ID NO: 41)    GCTCCTCCAA  GCTGTGGTCT  GAGCCCACTG  CTGGTCCTGG  TGGTAACCGC
29brc       (SEQ ID NO: 43)    GCTCCTCCAA  GCTGTGGTCT  GAGCCCACTG  CTGGTCCTGG  TGGTAACCGC
```

FIG. 5N

```
                                                                                                      1712
             1663
Gdnfr    TCTGTCCACC CTATTATCTT TAACAGAAAC ATCATAGCTG CATTAAAAAA   (SEQ ID NO: 37)
Hsgr-2   TCTGTCCACC CTATTATCTT TAACAGAAAC ATCATAGCTG CATTAAAAAA   (SEQ ID NO: 46)
Hsgr-9   TCTGTCCACC CTATTATCTT TAACAGAAAC ATCATAGCTG CATTAAAAAA   (SEQ ID NO: 47)
Hsgr-21ar TCTGTCCACC CTATTATCTT TAACAGAAA                         (SEQ ID NO: 44)
Hsgr-21br TCTGTCCACC CTATTATCTT TAACAGAAA                         (SEQ ID NO: 45)
21acon   TCTGTCCACC CTATTATCTT TAACAGAAA                          (SEQ ID NO: 40)
21bcon   TCTGTCCACC CTATTATCTT TAACAGAAA                          (SEQ ID NO: 41)
29brc    TCTGTCCACC CTATTATCTT TAACAGAAAC ATCATAGCTG CATTAAAAAA   (SEQ ID NO: 43)

1713                                                 1762
Gdnfr    ATACAATATG GACATGTAAA AAGACAAAAA CCAAGTTATC TGTTTCCTGT   (SEQ ID NO: 37)
Hsgr-2   ATACAATATG GACATGTAAA AAGACAAAAA CCAAGTTATC TGTTTCCTGT   (SEQ ID NO: 46)
Hsgr-9   ATACAATATG GACATGTAAA AAGACAAAAA CCAAGTTATC TGTTTCCTGT   (SEQ ID NO: 47)
29brc    ATACAATATG GACATGTAAA AAGACAAAAA CCAAGTTATC TGTTTCCTGT   (SEQ ID NO: 43)

1763                                                 1812
Gdnfr    TCTCTTGTAT AGCTGAAATT CCAGTTTAGG AGCTCAGTTG AGAAACAGTT   (SEQ ID NO: 37)
Hsgr-2   TCTCTTGTAT AGCTGAAATT CCAGTTTAGG AGCTCAGTTG AGAAACAGTT   (SEQ ID NO: 46)
Hsgr-9   TCTCTTGTAT AGCTGAAATT CCAGTTTAGG AGCTCAGTTG AGAAACAGTT   (SEQ ID NO: 47)
29brc    TCTCTTGTAT AGCTGAAATT CCAGTTTAGG AGCTCAGTTG AGAAACAGTT   (SEQ ID NO: 43)
```

FIG. 50

```
                                                                                                1862
         1813
Gdnfr   CCATTCAACT GGAACATTTT TTTTTTT.CC TTTTAAGAAA GCTTCTTGTG   (SEQ ID NO: 37)
Hsgr-2  CCATTCAACT GGAACATTTT TTTTTTT.CC TTTTAAGAAA GCTTCTTGTG   (SEQ ID NO: 46)
Hsgr-9  CCATTCAACT GGAACATTTT TTTTTTTCC  TTTTAAGAAA GCTTCTTGTG   (SEQ ID NO: 47)
29brc   CCATTCAACT GGAACATTTT TTTTTTT.CC TTTTAAGAAA GCTTCTTGTG   (SEQ ID NO: 43)

1912
         1863
Gdnfr   ATCCTTcGGG GCTTCTGTGA AAAACCTGAT GCAGTGCTCC ATCCAAACTC   (SEQ ID NO: 37)
Hsgr-2  ATCCTTCGGG GCTTCTGTGA AAAACCTGAT GCAGTGCTCC ATCCAAACTC   (SEQ ID NO: 46)
Hsgr-9  ATCCTTTGGG GCTTCTGTGA AAAACCTGAT GCAGTGCTCC ATCCAAACTC   (SEQ ID NO: 47)
29brc   ATCCTTCGGG GCTTCTGTGA AAAACCTGAT GCAGTGCTCC ATCCAAACTC   (SEQ ID NO: 43)

1962
         1913
Gdnfr   AGAAGGCTTT GGGATATGCT GTATTTTAAA GGGACAGTTT GTAACTTGGG   (SEQ ID NO: 37)
Hsgr-2  AGAAGGCTTT GGGATATGCT GTATTTTAAA GGGACAGTTT GTAACTTGGG   (SEQ ID NO: 46)
Hsgr-9  AGAAGGCTTT GGGATATGCT GTATTTTAAA GGGACAGTTT GTAACTTGGG   (SEQ ID NO: 47)
29brc   AGAAGGCTTT GGGATATGCT GTATTTTAAA GGGACAGTTT GTAACTTGGG   (SEQ ID NO: 43)

2012
         1963
Gdnfr   CTGTAAAGCA AACTGGGGCT GTGTTTTCGA TGATGATGAT cATCATGATc   (SEQ ID NO: 37)
Hsgr-2  CTGTAAAGCA AACTGGGGCT GTGTTTTCGA TGATGATGAT CATCATGATC   (SEQ ID NO: 46)
Hsgr-9  CTGTAAAGCA AACTGGGGCT GTGTTTTCGA TGATGATGAT GATCATGATG   (SEQ ID NO: 47)
29brc   CTGTAAAGCA AACTGGGGCT GTGTTTTCGA TGATGATGAT CATCATGATC   (SEQ ID NO: 43)
```

FIG. 5P

```
                                                                                          2062
Gdnfr   (SEQ ID NO: 37)  2013 ATGAT.......  ............  ............  ............  ......GATTTT
Hsgr-2  (SEQ ID NO: 46)       ATGAT.......  ............  ............  ............  ......GATTTT
Hsgr-9  (SEQ ID NO: 47)       ATGATCATCA    TGATCATGAT    ............  ............  TGATGATTTT
29brc   (SEQ ID NO: 43)       ATGAT.......  ............  ............  GATGATCATC    ATGATCATGA  ......GATTTT 2112
Gdnfr   (SEQ ID NO: 37)  2063 AACAGTTTTA    CTTCTGGCCT    TTCCTAGCTA    GAGAAGGAGT    TAATATTTCT
Hsgr-2  (SEQ ID NO: 46)       AACAGTTTTA    CTTCTGGCCT    TTCCTAGCTA    GAGAAGGAGT    TAATATTTCT
Hsgr-9  (SEQ ID NO: 47)       AACAGTTTTA    CTTCTGGCCT    TTCCTAGCTA    GAGAAGGAGT    TAATATTTCT
29brc   (SEQ ID NO: 43)       AACAGTTTTA    CTTCTGGCCT    TTCCTAGCTA    GAGAAGGAGT    TAATATTTCT 2162
Gdnfr   (SEQ ID NO: 37)  2113 AAGGTAACTC    CCATATCTCC    TTTAATGACA    TTGATTTCTA    ATGATATAAA
Hsgr-2  (SEQ ID NO: 46)       AAGGTAACTC    CCATATCTCC    TTTAATGACA    TTGATTTCTA    ATGATATAAA
Hsgr-9  (SEQ ID NO: 47)       AAGGTAACTC    CCATATCTCC    TTTAATGACA    TTGATTTCTA    ATGATATAAA
29brc   (SEQ ID NO: 43)       AAGGTAACTC    CCATATCTCC    TTTAATGACA    TTGATTTCTA    ATGATATAAA 2212
Gdnfr   (SEQ ID NO: 37)  2163 TTTCAGCCTA    CATTGATGCC    AAGCTTTTTT    GCCACAAAGA    AGATTCTTAC
Hsgr-2  (SEQ ID NO: 46)       TTTCAGCCTA    CATTGATGCC    AAGCTTTTTT    GCCACAAAGA    AGATTCTTAC
Hsgr-9  (SEQ ID NO: 47)       TTTCAGCCTA    CATTGATGCC    AAGCTTTTTT    GCCACAAAGA    AGATTCTTAC
29brc   (SEQ ID NO: 43)       TTTCAGCCTA    CATTGATGCC    AAGCTTTTTT    GCCACAAAGA    AGATTCTTAC
```

FIG. 5Q

```
                              2213                                                                                  2262
Gdnfr    (SEQ ID NO: 37)      CAAGAGTGGG  CTTTGTGTGGAA  ACAGCTGGTA  CTGATGTTCA  CCTTTATATA
Hsgr-2   (SEQ ID NO: 46)      CAAGAGTGGG  CTTTGTGTGGAA  ACAGCTGGTA  CTGATGTTCA  CCTTTATATA
Hsgr-9   (SEQ ID NO: 47)      CAAGAGTGGG  CTTTGTGTGGAA  ACAGCTGGTA  CTGATGTTCA  CCTTTATATA
29brc    (SEQ ID NO: 43)      CAAGAGTGGG  CTTTGTGTGGAA  ACAGCTGGTA  CTGATGTTCA  CCTTTATATA 2263                                                                                  2312
Gdnfr    (SEQ ID NO: 37)      TGTACTAGCA  TTTTCCACGC  TGATGTTTAT  GTACTGTAAA  CAGTTCTGCA
Hsgr-2   (SEQ ID NO: 46)      TGTACTAGCA  TTTTCCACGC  TGATGTTTAT  GTACTGTAAA  CAGTTCTGCA
Hsgr-9   (SEQ ID NO: 47)      TGTACTAGCA  TTTTCCACGC  TGATGTTTAT  GTACTGTAAA  CAGTTCTGCA
29brc    (SEQ ID NO: 43)      TGTACTAGCA  TTTTCCACGC  TGATGTTTAT  GTACTGTAAA  CAGTTCTGCA 2313                                                                                  2362
Gdnfr    (SEQ ID NO: 37)      CTCTTGTACA  AAAGAAAAAA  CACCTGTCAC  ATCCAAATAT  AGTATCTGTC
Hsgr-2   (SEQ ID NO: 46)      CTCTTGTACA  AAAGAAAA
Hsgr-9   (SEQ ID NO: 47)      CTCTTGTACA  AAAGAAAA
29brc    (SEQ ID NO: 43)      CTCTTGTACA  AAAGAAAAAA  CACCTGTCAC  ATCCAAATAT  AGTATCTGTC 2363                                                                                  2412
Gdnfr    (SEQ ID NO: 37)      TTTTCGTCAA  AATAGAGAGT  GGGGAATGAG  TGTGCCGATT  CAATACCTCA
29brc    (SEQ ID NO: 43)      TTTTCGTCAA  AATAGAGAGT  GGGGAATGAG  TGTGCCGATT  CAATACCTCA 2413                                                                                  2462
Gdnfr    (SEQ ID NO: 37)      ATCCCTGAAC  GACACTCTCC  TAATCCTAAG  CCTTACCTGA  GTGAGAAGCC
29brc    (SEQ ID NO: 43)      ATCCCTGAAC  GACACTCTCC  TAATCCTAAG  CCTTACCTGA  GTGAGAAGCC
```

FIG. 5R

```
               2463                                                              2512
(SEQ ID NO: 37) Gdnfr  CTTTACCTAA CAAAAGTCCA ATATAGCTGA AATGTCGCTC TAATACTCTT
(SEQ ID NO: 43) 29brc  CTTTACCTAA CAAAAGTCCA ATATAGCTGA AATGTCGCTC TAATACTCTT 2513                                                              2562
(SEQ ID NO: 37) Gdnfr  TACACATATG AGGTTATATG TAGAAAAAAA TTTTACTACT AAATGATTTC
(SEQ ID NO: 43) 29brc  TACACATATG AGGTTATATG TAGAAAAAAA TTTTACTACT AAATGATTTC 2563                                                              2612
(SEQ ID NO: 37) Gdnfr  AACTATTGGC TTTCTATATT TTGAAAGTAA TGATATTGTC TCATTTTTTT
(SEQ ID NO: 43) 29brc  AACTATTGGC TTTCTATATT TTGAAAGTAA TGATATTGTC TCATTTTTTT 2613                                                              2662
(SEQ ID NO: 37) Gdnfr  ACTGATGGTT TAATACAAAA TACACAGAGC TTGTTTCCCC TCATAAGTAG
(SEQ ID NO: 43) 29brc  ACTGATGGTT TAATACAAAA TACACAGAGC TTGTTTCCCC TCATAAGTAG 2663                                                              2712
(SEQ ID NO: 37) Gdnfr  TGTTCGCTCT GATATGAACT TCACAAATAC AGCTCATCAA AAGCAGACTC
(SEQ ID NO: 43) 29brc  TGTTCGCTCT GATATGAACT TCACAAATAC AGCTCATCAA AAGCAGACTC 2713                                                              2762
(SEQ ID NO: 37) Gdnfr  TGAGAAGCCT CGTGCTGTAG CAGAAAGTTC TGCATCATGT GACTGTGGAC
(SEQ ID NO: 43) 29brc  TGAGAAGCCT CGTGCTGTAG CAGAAAGTTC TGCATCATGT GACTGTGGAC
```

FIG. 5S

```
                 2763                                                                          2812
Gdnfr  AGGCAGGAGG  AAACAGAACA  GACAAGCATT  GTCTTTTGTC  ATTGCTCGAA   (SEQ ID NO: 37)
29brc  AGGCAGGAGG  AAACAGAACA  GACAAGCATT  GTCTTTTGTC  ATTGCTCGAA   (SEQ ID NO: 43)

2813                                                                          2862
Gdnfr  GTGCAAGCGT  GCATACCTGT  GGAGGGAACT  GGTGGCTGCT  TGTAAATGTT   (SEQ ID NO: 37)
29brc  GTGCAAGCGT  GCATACCTGT  GGAGGGAACT  GGTGGCTGCT  TGTAAATGTT   (SEQ ID NO: 43)

2863                                                                          2912
Gdnfr  CTGCAGCATC  TCTTGACACA  CTTGTCATGA  CACAATCCAG  TACCTTGGTT   (SEQ ID NO: 37)
29brc  CTGCAGCATC  TCTTGACACA  CTTGTCATGA  CACAATCCAG  TACCTTGGTT   (SEQ ID NO: 43)

2913                                                                          2962
Gdnfr  TTCAGGTTAT  CTGACAAAGG  CAGCTTTGAT  TGGGACATGG  AGGCATGGGC   (SEQ ID NO: 37)
29brc  TTCAGGTTAT  CTGACAAAGG  CAGCTTTGAT  TGGGACATGG  AGGCATGGGC   (SEQ ID NO: 43)

2963
Gdnfr  AGGCCGGAA                                                     (SEQ ID NO: 37)
29brc  AGGCCGGAA                                                     (SEQ ID NO: 43)
```

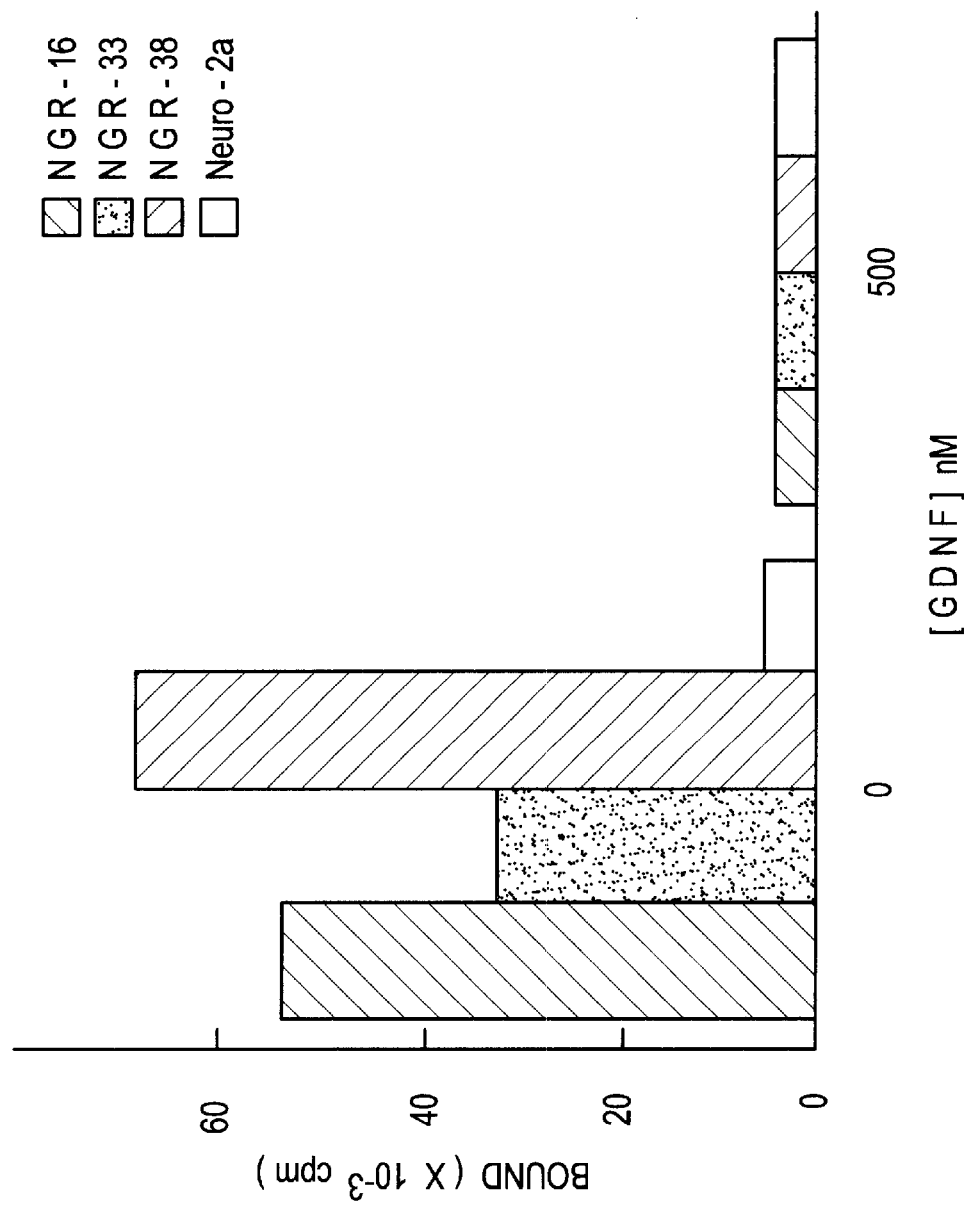

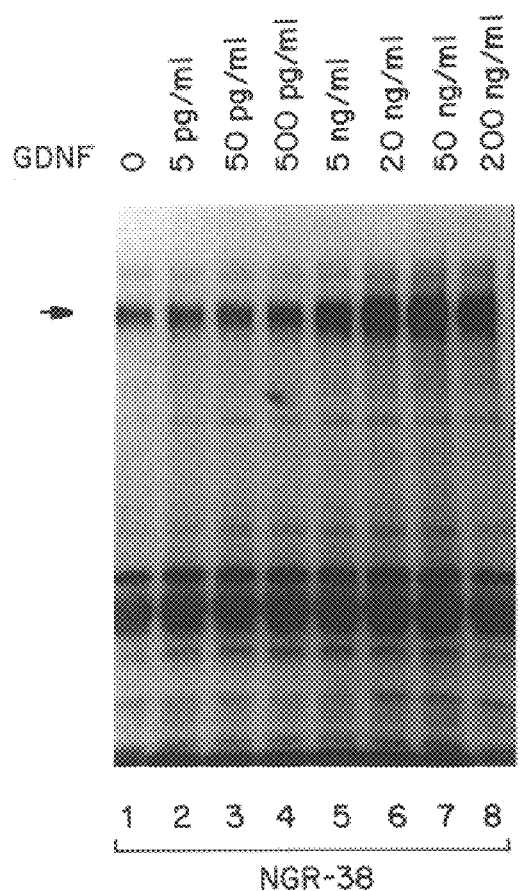
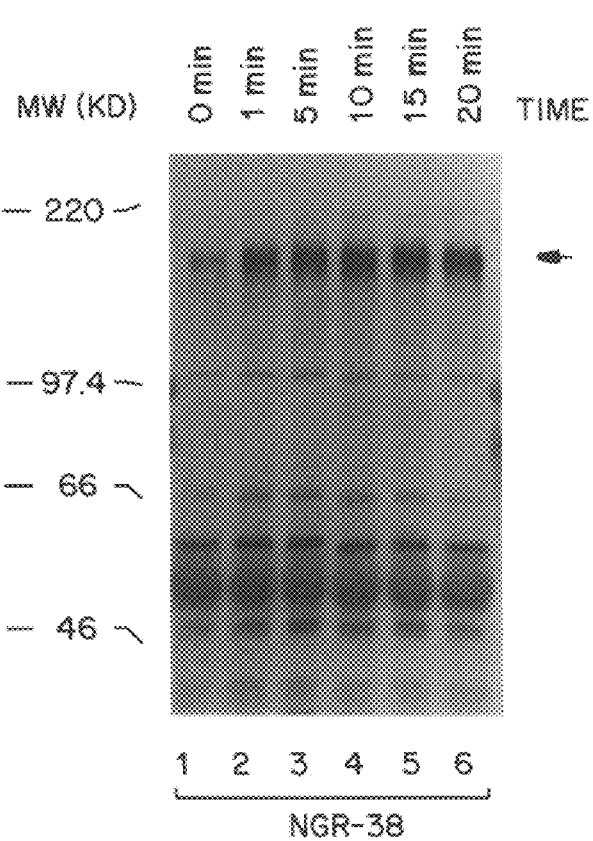

POLYNUCLEOTIDES ENCODING HUMAN GLIAL CELL LINE-DERIVED NEUROTROPHIC FACTOR RECEPTOR POLYPEPTIDES

This application claims the benefit of U.S. Provisional Application No. 60/015,907, filed Apr. 22, 1996, and U.S. Provisional Application No. 60/017,221, filed May 9, 1996.

FIELD OF THE INVENTION

The present invention relates to receptors for glial cell line-derived neurotrophic factor (GDNF) and provides nucleic acid and amino acid sequences encoding GDNF receptor (GDNFR). The present invention also relates to therapeutic techniques for the treatment of GDNF-responsive conditions.

BACKGROUND OF THE INVENTION
Glial Cell Line-Derived Neurotrophic Factor

Glial cell line-derived neurotrophic factor (GDNF) was initially isolated and cloned from rat B49 cells as a potent neurotrophic factor that enhances survival of midbrain dopaminergic neurons (Lin et al., Science, 260, 1130–1132, 1993). Recent studies have indicated that this molecule exhibits a variety of other biological activities, having effects on several types of neurons from both the central and peripheral nervous systems. In the central nervous system (CNS), GDNF has been shown to prevent the axotomy-induced death of mammalian facial and spinal cord motor neurons (Li et al., Proceedings Of The National Academy Of Sciences, U.S.A., 92, 9771–9775, 1995; Oppenheim et al., Nature, 373, 344–346, 1995; Yan et al., Nature, 373, 341–344, 1995; Henderson et al., Science, 266, 1062–1064, 1994; Zurn et al., Neuroreport, 6, 113–118, 1994), and to rescue developing avian motor neurons from natural programmed cell death (Oppenheim et al., 1995 supra). Local administration of GDNF has been shown to protect nigral dopaminergic neurons from axotomy-induced (Kearns and Gash, Brain Research, 672, 104–111, 1995; Beck et al., Nature, 373, 339–341, 1995) or neurotoxin-induced degeneration (Sauer et al., Proceedings Of The National Academy Of Sciences U.S.A., 92, 8935–8939, 1995; Tomac et al., Nature, 373, 335–339, 1995). In addition, local administration of GDNF has been shown to induce sprouting from dopaminergic neurons, increase levels of dopamine, noradrenaline, and serotonin, and improve motor behavior (Tomac et al., 1995 supra).

More recently, GDNF has been reported to be a potential trophic factor for brain noradrenergic neurons and Purkinje cells. Grafting of fibroblasts ectopically expressing GDNF prevented 6-hydroxydopamine-induced degeneration and promoted the phenotype of adult noradrenergic neurons in vivo (Arenas et al., Neuron, 15, 1465–1473, 1995), while exogeneously applied GDNF effectively promoted survival and morphological differentiation of embryonic Purkinje cells in vitro (Mount et al., Proceedings Of The National Academy Of Sciences U.S.A., 92, 9092–9096, 1995). In the peripheral nervous system, GDNF has been shown to promote the survival of neurons in nodose, ciliary, and sympathetic ganglia, as well as small populations of embryonic sensory neurons in dorsal root ganglia (DRG) and trigeminal ganglia (Trupp et al., Journal Of Cell Biology, 130, 137–148, 1995; Ebendal et al., Journal Of Neuroscience Research, 40, 276–284, 1995; Oppenheim et al., 1995 supra; Yan et al., 1995 supra; Henderson et al., 1994 supra). GDNF has also been reported to enhance the expression of vasoactive intestinal peptide and preprotachykinin-A mRNA in cultured superior cervical ganglion (SCG) neurons, and thus effects the phenotype of SCG neurons and induces bundle-like sprouting (Trupp et al., 1995 supra).

Expression of GDNF has been observed in a number of different cell types and structures of the nervous system. In the CNS, GDNF mRNA expression has been observed by reverse transcriptase polymerase chain reaction (RT-PCR) in both developing and adult rat striatum, the major target of nigral dopaminergic innervation, and widely in other regions, including hippocampus, cortex, thalamus, septum, cerebellum, spinal cord, and medulla oblongata (Arenas et al., supra 1995; Poulsen et al., Neuron, 13, 1245–1252, 1994; Springer et al., Experimental Neurology, 127, 167–170, 1994; Stroemberg et al., Experimental Neurology, 124, 401–412, 1993; Schaar et al., Experimental Neurology, 124, 368–371, 1993). In human, GDNF transcripts have also been detected in striatum, with highest level in the caudate and lower levels in the putamen. Detectable levels are also found in hippocampus, cortex, and spinal cord, but not in cerebellum (Schaar et al., Experimental Neurology, 130, 387–393, 1994; Springer et al., 1994 supra). In the periphery, GDNF mRNA expression has been reported in DRG and SCG of postnatal day 1 rats, sciatic nerve, and primary cultures of neonatal Schwann cells (Trupp et al., 1995 supra; Hoffer et al., Neuroscience Letters, 182, 107–111, 1994; Henderson et al., 1994 supra; Springer et al., 1994 supra). In addition, recent studies have shown that GDNF transcripts are also widely expressed in peripheral non-neuronal organs, including postnatal testis and kidney, embryonic whisker pad, stomach, and skin. Expression can be detected at lower levels in embryonic muscle, adrenal gland and limb bud, and in postnatal lung, liver and ovary (Trupp et al., 1995 supra; Henderson et al., 1994 supra). So far, however, the biological significance of the non-neuronal expression of GDNF is not clear.

Detailed descriptions of the preparation and characterization of GDNF protein products may be found in U.S. patent application Ser. No. 08/182,183 filed May 23, 1994 and its parent applications (also see PCT/US92/07888, WO 93/06116 filed Sep. 17, 1992 and European Patent Application No. 92921022.7, Publication No. EP 610 254) the disclosures of which are hereby incorporated by reference. Additional GDNF protein products are described in pending U.S. patent application Ser. No. 08/535,681 filed Sep. 28, 1995, the disclosure of which is hereby incorporated by reference. As used herein, the term "GDNF protein product" includes biologically active synthetic or recombinant GDNF proteins and analogs, as well as chemically modified derivatives thereof. GDNF analogs include deletion variants such as truncated GDNF proteins, as well as insertion and substitution variants of GDNF. Also included are GDNF proteins that are substantially homologous to the human GDNF protein.

GDNF Therapy

GDNF therapy is helpful in the treatment of nerve damage caused by conditions that compromise the survival and/or proper function of one or more types of nerve cells. Such nerve damage may occur from a wide variety of different causes. Nerve damage may occur to one or more types of nerve cells by: (1) physical injury, which causes the degeneration of the axonal processes and/or nerve cell bodies near the site of injury; (2) temporary or permanent cessation of blood flow to parts of the nervous system, as in stroke; (3) intentional or accidental exposure to neurotoxins, such as chemotherapeutic agents (e.g., cisplatinum) for the treatment of cancer or dideoxycytidine (ddC) for the treatment of AIDS; (4) chronic metabolic diseases, such as diabetes or renal dysfunction; or (5) neurodegenerative diseases such as Parkinson's disease, Alzheimer's disease, and amyotrophic lateral sclerosis (ALS), which result from the degeneration of specific neuronal populations.

Several studies indicate that GDNF therapy is particularly helpful in the treatment of neurodegenerative conditions such as the degeneration of the dopaminergic neurons of the substantia nigra in Parkinson's disease. The only current treatments for Parkinson's disease are palliative, aiming at increasing dopamine levels in the striatum. The expected impact of GDNF therapy is not simply to produce an increase in the dopaminergic neurotransmission at the dopaminergic nerve terminals in the striatum (which will result in a relief of the symptoms), but also to slow down, or even stop, the progression of the degenerative processes and to repair the damaged nigrostriatal pathway and restore its function. GDNF may also be used in treating other forms of damage to or improper function of dopaminergic nerve cells in human patients. Such damage or malfunction may occur in schizophrenia and other forms of psychosis. The only current treatments for such conditions are symptomatic and require drugs which act upon dopamine receptors or dopamine uptake sites, consistent with the view that the improper functioning of the dopaminergic neurons which innervate these receptor-bearing neuronal populations may be involved in the disease process.

Receptors

A number of receptors which mediate binding and response to protein factors have been characterized and molecularly cloned, including receptors for insulin, platelet derived growth factor, epidermal growth factor and its relatives, the fibroblast growth factors, various interleukins, hematopoietic growth factors and ciliary neurotrophic factor (U.S. Pat. No. 5,426,177). Study results indicate that some receptors can bind to multiple (related) growth factors, while in other cases the same factor can bind and activate multiple (related) receptors (e.g., Lupu et al., Science, 249:1552–1555, 1990; Dionne et al., EMBO J., 9:2685–2692, 1990; Miki et al., Science, 251:72–75, 1991). Most receptors can broadly be characterized as having an extracellular portion or domain responsible for specifically binding a protein factor, a transmembrane domain which spans the cell membrane, and an intracellular domain that is often involved in initiating signal transduction upon binding of the protein factor to the receptor's extracellular portion. Although many receptors are comprised of a single polypeptide chain, other receptors apparently require two or more separate subunits in order to bind to their protein factor with high-affinity and to allow functional response following binding (e.g., Hempstead et al., Science, 243:373–375, 1989; Hibi et al., Cell, 63:1149–1157, 1990).

The extracellular and intracellular portions of a given receptor may share common structural motifs with the corresponding regions of other receptors, suggesting evolutionary and functional relationships between different receptors. These relationships can often be quite distant and may simply reflect the repeated use of certain general domain structures. For example, a variety of different receptors that bind unrelated factors make use of "immunoglobulin" domains in their extracellular portions, while other receptors utilize "cytokine receptor" domains in their factor-binding regions (e.g., Akira et al., The FASEB J., 4:2860–2867, 1990). A large number of receptors with distinct extracellular binding domains (which thus bind different factors) contain related intracytoplasmic domains encoding tyrosine-specific protein kinases that are activated in response to factor binding (e.g., Ullrich and Schlessinger, Cell, 61:203–212, 1990). The mechanisms by which factor-binding "activates" the signal transduction process is poorly understood, even in the case of receptor tyrosine kinases. For other receptors, in which the intracellular domain encodes a domain of unknown function or in which the binding component associates with a second protein of unknown function (e.g., Hibi et al., Cell, 63:1149–1157, 1990), activation of signal transduction is not well characterized.

The mode of action of GDNF in vivo is not clearly elucidated in the art, in part due to the absence of information on a receptor for GDNF. Two groups have independently found that striatum injected $[^{125}I]$-labeled GDNF can be retrogradely transported by dopaminergic neurons in the substantia nigra (Tomac et al., Proceedings Of The National Academy Of Sciences Of The United States Of America. 92, 8274–8278, 1995; Yan et al., 1995 supra). Retrograde transport of $[^{125}I]$-GDNF by spinal cord motor neurons, DRG sensory neurons and neurons in the B layer of retina ganglia was also been observed. These retrograde transport phenomena can all be specifically inhibited by 100-fold or higher concentrations of unlabeled GDNF, suggesting a saturable, receptor-mediated transport process. In vitro, recombinant GDNF has been shown to enhance the survival and promote dopamine uptake of cultured dopaminergic neurons at very low concentrations. The observed half-maximal effective concentration ($EC_{50}$) of GDNF on these neurons is 0.2 to 1.6 pM (Lin et al., 1993 supra). GDNF has also been shown to support the survival of dissociated motor neurons at low concentrations. The reported $EC_{50}$ of GDNF on motor neurons, in a 5 to 10 fM range, is even lower than that on dopaminergic neurons (Henderson et al., 1994 supra).

Taken together, these observations indicate that receptor (s) for GDNF expressed in these cells have very high ligand binding affinities. Similar to members of the TGF-β family, the widely diversified tissue distribution and varied biological function of GDNF on different populations of cells suggest that different types of receptor(s) for GDNF or receptor complexes may exist. Saturation steady-state and competitive binding of $[^{125}I]$-GDNF to E10 chick sympathetic neurons has shown that these neurons express GDNF binding sites differing from those observed in dopaminergic and motor neurons. The half maximal saturation concentration and the half-maximal inhibition concentration of GDNF on these binding sites is in the range of 1 to 5 nM (Trupp et al., 1995 supra). Similarly, the $EC_{50}$ of GDNF in supporting the survival of sympathetic neurons from P1 rat SCG has also been reported to be in the nanomolar range (Trupp et al., 1995 supra).

To better understand the mechanism by which GDNF activates signal transduction to exert its affects on cells, it would be beneficial to identify the receptor(s) which mediate binding and response to this protein factor. It would also be beneficial for GDNF therapy to identify and make possible the production of accessory molecules which provide for or enhance GDNF signal transduction. Moreover, the identification of a protein receptor for GDNF would provide powerful applications in diagnostic uses, for example, as an aid in determining if individuals would benefit from GDNF protein therapy. Furthermore, the protein receptor for GDNF could be a key component in an assay for identifying additional molecules which bind to the receptor and result in desired biological activity.

SUMMARY OF THE INVENTION

The present invention provides nucleic acid sequences which encode a neurotrophic factor receptor protein having an amino acid sequence as depicted in FIGS. 2 and 4 (SEQ. ID. NOs.: 2 and 4) as well as biologically equivalent analogs. The neurotrophic factor receptor protein and protein products of the present invention are designated herein as glial cell line-derived neurotrophic factor receptor (GDNFR) protein and protein products. The novel GDNFRs are functionally characterized by the ability to bind GDNF specifically and with high affinity, and to act as part of a molecular complex which mediates or enhances the signal transduction affects of GDNF. GDNFR protein products are typically provided as a soluble receptor protein and in a substantially purified form.

In one aspect, the present invention provides for the production of GDNFR protein products by recombinant genetic engineering techniques. In an alternative embodiment, the GDNFR proteins are synthesized by chemical techniques, or a combination of the recombinant and chemical techniques.

In another aspect of the present invention, the GDNFR proteins may be made in glycosylated or non-glycosylated forms. Derivatives of GDNFR protein typically involve attaching the GDNFR protein to a water soluble polymer. For example, the GDNFR protein may be conjugated to one or more polyethylene glycol molecules to decrease the precipitation of the GDNFR protein product in an aqueous environment.

Yet another aspect of the present invention includes the various polynucleotides encoding GDNFR proteins. These nucleic acid sequences are used in the expression of GDNFR in a eukaryotic or prokaryotic host cell, wherein the expression product or a derivative thereof is characterized by the ability to bind to GDNF and thereby form a complex capable of mediating GDNF activity, such as increasing dopamine uptake by dopaminergic cells. The polynucleotides may also be used in cell therapy or gene therapy applications. Suitable nucleic acid sequences include those specifically depicted in the Figures as well as degenerate sequences, naturally occurring allelic variations and modified sequences based on the present invention.

Exemplary nucleic acid sequences include sequences encoding a neurotrophic factor receptor protein comprising an amino acid sequence as depicted in FIGS. 2 and 4 (SEQ ID NOs. 2 and 4) capable of complexing with glial cell line-derived neurotrophic factor (GDNF) and mediating cell response to GDNF, and biologically equivalent analogs thereof. Such sequences include: (a) a sequence set forth in FIG. 1 (SEQ ID NO. 1) comprising nucleotides encoding $Met^1$ through $Ser^{465}$ or FIG. 3 (SEQ ID NO. 3) comprising nucleotides encoding $Met^1$ through $ger^{468}$ encoding a neurotrophic factor receptor (GDNFR) capable of complexing with glial cell line-derived neurotrophic factor (GDNF) and mediating cell response to GDNF; (b) a nucleic acid sequence which (1) hybridizes to a complementary sequence of (a) and (2) encodes an amino acid sequence with GDNFR activity; and (c) a nucleic acid sequence which but for the degeneracy of the genetic code would hybridize to a complementary sequence of (a) and (2) encodes an amino acid sequence with GDNFR activity. Also disclosed herein are vectors such nucleic acid sequences wherein the sequences typically are operatively linked to one or more operational elements capable of effecting the amplification or expression of the nucleic acid sequence. Host cells containing such vectors are also contemplated. Typically, the host cell is selected from mammalian cells and bacterial cells, such as a COS-7 cell or E. coli, respectively.

A further aspect of the present invention involves vectors containing the polynucleotides encoding GDNFR proteins operatively linked to amplification and/or expression control sequences. Both prokaryotic and eukaryotic host cells may be stably transformed or transfected with such vectors to express GDNFR proteins. The present invention further includes the recombinant production of a GDNFR protein wherein such transformed or transfected host cells are grown in a suitable nutrient medium, and the GDNFR expressed by the cells is, optionally, isolated from the host cells and/or the nutrient medium. The present invention further includes the use of polynucleotides encoding GDNFR and vectors containing such polynucleotides in gene therapy or cell therapy.

The host cell may also be selected for its suitability to human implantation, wherein the implanted cell expresses and secretes a neurotrophic factor receptor of the present invention. The host cell also may be enclosed in a semipermeable membrane suitable for human implantation. The host cell may be transformed or transfected ex vivo. An exemplary device for treating nerve damage involves: (a) a semipermeable membrane suitable for implantation; and (b) cells encapsulated within the membrane, wherein the cells express and secrete a neurotrophic factor receptor as disclosed herein. The membrane is selected from a material that is permeable to the neurotrophic factor receptor protein but impermeable to materials detrimental to the encapsulated cells.

Methods for the recombinant production of a neurotrophic factor receptor of the present invention are also disclosed. An exemplary methods involves: (a) culturing a host cell containing a nucleic acid sequence encoding a neurotrophic factor receptor of the present invention, such as an amino acid sequence depicted in FIGS. 2 and 4 (SEQ ID NOs. 2 and 4) capable of completing with glial cell line-derived neurotrophic factor (GDNF) and mediating cell response to GDNF, or biologically equivalent analogs thereof; (b) maintaining said host cell under conditions suitable for the expression of said neurotrophic factor receptor by said host cell; and (c) optionally, isolating said neurotrophic factor receptor expressed by said host cell. The host cell may be a prokaryotic cell or a eukaryotic cell. If bacterial expression is involved, the method may further include the step of refolding the neurotrophic factor receptor.

The present invention includes an isolated and purified protein comprising an amino acid sequence as depicted in FIGS. 2 and 4 (SEQ ID NOs. 2 and 4) capable of complexing with glial cell line-derived neurotrophic factor (GDNF) and mediating cell response to GDNF, and biologically equivalent analogs thereof. Exemplary analogs include, but are not limited to, proteins comprising the amino acid sequence $Ser^{18}$ through $Pro^{446}$, $Asp^{25}$ through $Leu^{447}$ and $Cys^{29}$ through $Cys^{442}$ as depicted in FIG. 2 (SEQ. ID. NO:2) as well as proteins comprising the amino acid sequence $Met^{17}$ through $Pro^{449}$ and $Cys^{29}$ through $Cys^{443}$ as depicted in FIG. 4 (SEQ. ID. NO:4). The proteins of the present invention may be glycosylated or non-glycosylated and may be produced by recombinant technology or chemical synthesis. The present invention further includes nucleic acid sequences encoding a receptor protein comprising such amino acid sequences.

Also disclosed herein are pharmaceutical compositions comprising a protein receptor of the present invention in combination with a pharmaceutically acceptable carrier. A variety of other formulation materials may be used to facilitate manufacture, storage, handling, delivery and/or efficacy.

Another aspect of the present invention includes the therapeutic use of GDNFR genes and proteins. For example, a circulating or soluble GDNFR protein product may be used alone or in conjunction with GDNF in treating disease of or injury to the nervous system by enhancing the activity of transmembrane signaling of GDNF. Thus, the proteins and pharmaceutical compositions of the present invention may be used in treating improperly functioning dopaminergic nerve cells, Parkinson's disease, Alzheimer's disease and amyotrophic lateral sclerosis. Alternatively, a recombinant GDNFR gene may be inserted in the cells of tissues which would benefit from increased sensitivity to GDNF, such as motor neurons in patients suffering from amyotrophic lateral sclerosis. In yet another embodiment, GDNFR may be used to block GDNF activity in cases where GDNF activity is thought to be detrimental. The GDNFR may be used to verify that observed effects of GDNF are due to the GDNFR.

In another aspect of the invention, GDNFR probes may be used to identify cells and tissues which are responsive to GDNF in normal or diseased states. Alternatively, the probes may be used to detect an aberrancy of GDNFR expression in a patient suffering from a GDNF-related disorder.

In a further aspect of the invention, GDNFR probes, including nucleic acid as well as antibody probes, may be used to identify GDNFR-related molecules. For example, the present invention provides for such molecules which form a complex with GDNFR and thereby participate in GDNFR function. As another example, the present invention provides for receptor molecules which are homologous or cross-reactive antigenically, but not identical to GDNFR.

The present invention also provides for the development of both binding and functional assays for GDNF based on the receptor. For example, assay systems for detecting GDNF activity may involve cells which express high levels of GDNFR, and which are therefore extremely sensitive to even very low concentrations of GDNF or GDNF-like molecules. In yet another embodiment, soluble GDNFR may be used to bind or detect the presence of GDNF or GDNF-like molecules.

In addition, the present invention provides for experimental model systems for studying the physiological role of GDNF. Such systems include assays involving anti-GDNF antibodies or oligonucleotide probes as well as animal models, such as transgenic animals which express high levels of GDNFR and therefore are hypersensitive to GDNF or animals derived using embryonic stem cell technology in which the endogenous GDNFR genes were deleted from the genome. An anti-GDNFR antibody will binds a peptide portion of the neurotrophic factor receptor proteins. Antibodies include monoclonal and polyclonal antibodies. Alternatively, immunological tags for which antibodies already exist may be attached to the GDNFR protein to aid in detection. Such tags include but are not limited to Flag (IBI/Eastman Kodak) and myc sequences. Other tag sequences such as polyhistidine have also been used for detection and purification on metal chelating columns.

Additional aspects and advantages of the invention will be apparent to those skilled in the art upon consideration of the following description, which details the practice of the present invention.

BRIEF DESCRIPTION OF THE FIGURES

FIGS. 1A–E depict a nucleic acid sequence (SEQ ID NO:1) encoding human glial cell line-derived neurotrophic factor receptor (GDNFR). The amino acid sequence of the full length GDNFR protein is encoded by nucleic acids 540 to 1934.

FIG. 2 depicts the amino acid sequence (SEQ ID NO:2) of the full length human GDNFR protein.

FIGS. 3A–D depict a nucleic acid sequence (SEQ ID NO:3) encoding rat GDNFR. The amino acid sequence of the full length GDNFR protein is encoded by nucleic acids 302 to 1705.

FIG. 4 depicts the amino acid sequence (SEQ ID NO:4) of the full length rat GDNFR protein FIGS. 5A–K depict the alignment and comparison of portions of GDNPR cDNA sequences produced in various clones as well as the consensus sequence for human GDNFR. SEQ ID NO:37 represents a nucleic acid sequence encoding a GDNF receptor. SEQ ID NO:38 and SEQ ID NO:39 are nucleic acid sequences from clones encoding at least portions of a GDNF receptor. SEQ ID NO:40 and SEQ ID NO:41 represent the consensus nucleotide sequence of SEQ ID NO:38 and SEQ ID NO:39 relative to SEQ ID NO:37, respectively. SEQ ID NOS:42, 43, 44, 45, 46 and 47 represent nucleotide sequences from additional clones encoding at least portions of a GDNF receptor.

FIG. 6 depicts the identification of Neuro-2A derived cell lines expressing GDNFR.

FIGS. 9A–C depict the results of the induction of c-Ret autophosphorylation by GDNF in cells expressing GDNFR.

DETAILED DESCRIPTION OF THE INVENTION

Figure 7A:
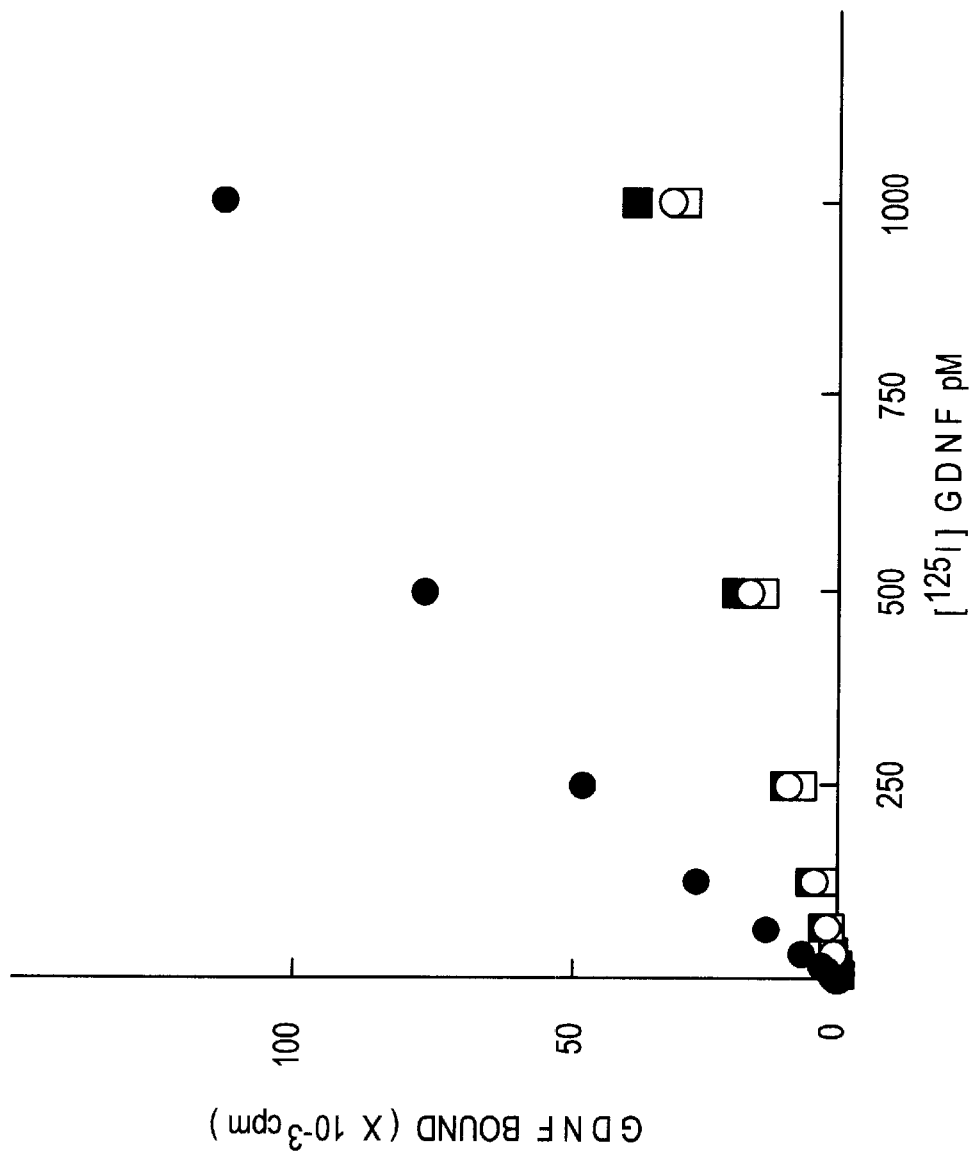
FIGS. 7A and 7B depict the results of the equilibrium binding of [$^{125}$I]GDNF to cells expressing GDNFR.

Glial cell line-derived neurotrophic factor (GDNF) is a potent neurotrophic factor which exhibits a broad spectrum of biological activities on a variety of cell types from both the central and peripheral nervous systems. It is a glycosylated, disulfide-linked dimer which is distantly related (less than 20% homology) to the transforming growth factor-β (TGF-β) superfamily. GDNFs ability to enhance the survival of dopaminergic neurons and other neuron populations demonstrates its therapeutic potential for the treatment of Parkinson's disease as well as other forms of nerve damage or malfunction.

In contrast to the extensive studies on the distribution and bioactivity of GDNF, there have been no reports on the identification of a receptor or receptors which mediate binding of GDNF to a cell and thereby mediate intracellular signaling and a cell response. The present invention is based upon the discovery of a high affinity receptor first found on the surface of cultured retinal cells from postnatal rats. These receptors possess an estimated GDNF binding affinity comparable to that of the receptors found in dopaminergic and motor neurons; midbrain dopaminergic neurons (Lin et al., 1993 supra; Sauer et al., 1995 supra; Kearns and Gash, 1995 supra; Beck et al., 1995 supra; Tomac et al., 1995a supra), facial and spinal cord motor neurons (Li et al., 1995 supra; Oppenheim et al., 1995 supra; Yan et al., 1995 supra; Zurn et al., 1994 supra; Henderson et al., 1994 supra). The receptor molecule has been named GDNF receptor (GDNFR) since it is the first known component of a receptor system for GDNF. The present invention also provides the first description of the expression cloning and characterization of GDNFR protein. Cells modified to express the recombinant receptor bind GDNF with high affinity.

Using a dopamine uptake assay and [$^{125}$I]-GDNF binding on cultured cells, high affinity receptors to GDNF were detected on the surface of rat photoreceptor cells. As further described in the Examples, the study of photoreceptor cells lead to the isolation of a cDNA clone by expression cloning for GDNF receptor. The nucleic acid sequence for GDNFR encodes a protein of 468 amino acids with 31 cysteine residues and three potential N-glycosylation sites. Next, a nucleic acid sequence from the rat cDNA clone was used to isolate its human homolog which was found to be nearly identical to the rat receptor at the amino acid level. The human GDNFR cDNA sequence encodes a protein of 465 amino acids with the positions of all cysteine residues and potential N-glycosylation sites conserved relative to the rat receptor. This high degree of primary sequence conservation indicated an important role for this receptor in the biological function of GDNF.

As discussed above, many receptors have three main domains: an extracellular or cell surface domain responsible for specifically binding a protein factor; a transmembrane domain which spans the cell's membrane; and an intracellular or cytoplasmic domain that is typically involved in initiating signal transduction when a protein factor binds to the extracellular domain. It was determined, however, that GDNFR is unrelated in sequence or structural characteristics to any known protein (such as the consensus sequences found in either receptor kinases or cytokine receptors), lacks a cytoplasmic domain, lacks the C-terminal charged residues characteristic of a transmembrane domain and is anchored to the cell membrane by glycosyl-phosphatidylinositol (GPI) linkage, as described in greater detail below. Although the absence of an intracellular catalytic domain precluded a direct role in transmembrane signaling, the high binding affinity and strong evolutionary sequence conservation further suggested that this receptor was important for GDNF function.

Because GDNFR lacks a cytoplasmic domain, it was thought that this receptor must act in conjunction with one or more accessory molecules which play a role in transmembrane signaling. It was then discovered that transgenic mice which lack the gene for GDNF die and have no kidneys. Transgenic mice which lack the gene for c-ret proto-oncogene (Schuchardt, et al., Nature, 367, 380–383, 1994) were found to have a similar phenotype. The c-ret proto-oncogene encodes a receptor tyrosine kinase (RTK) whose normal function had not yet been determined. All RTKs have a similar topology; they possess in extracellular ligand-binding domain, a tansmembrane domain and a cytoplasmic segment containing the catalytic protein-tyrosine kinase domain. Binding of a ligand leads to the activation of the kinase domain and phosphorylation of specific substrates in the cell that mediate intracellular signaling. The present invention involves the discovery that a soluble form of GDNFR may be used to mediate the binding of GDNF to the c-ret proto-oncogene and thereby elicit a cellular response to GDNF as well as modify its cell-type specificity.

Similar species, called "receptor alpha" components, provide ligand binding specificity but do not have the capacity to transduce signal on their own. Such components are found in the ciliary neurotrophic factor (CNTF) and interleukin-6 (IL-6) receptor systems. Like GDNFR, and in contrast to IL-6 receptor, CNTF receptor binds its ligand with high affinity, has a hydrophobic C-terminus, no cytoplasmic domain, and is anchored to the cell membrane by GPI linkage (Davis et al., 1991). In order to mediate signal transduction, CNTF binds first to CNTF receptor, creating a complex which is able to bind gp 130. This inactive complex then binds to LIF receptor to form the active signaling complex (Davis, et al., Science, 260, 1805–1807, 1993). As with the present invention, CNTF receptor (the ligand specific binding component) must be present for signaling to occur but it need not be membrane bound (Economides et al., Science, 270, 1351–1353, 1995).

As further described below, GDNFR protein may be anchored to a cell surface, or it may be provided in a soluble form, In either case, GDNFR protein forms a ligand complex with GDNF, and the ligand complex binds to cell surface receptor to effectuate intracellular signaling. Thus, a soluble form of GDNFR may be used to potentiate the action of GDNF and/or modify its cell-type specificity.

GDNFR is unrelated to any known receptor. There are no apparent matches in the GenBank and Washington University-Merck databases for related sequences. An expressed sequence tag (EST) found in the Washington University-Merck EST database shows 75% homology to a small portion of the coding region of GDNFR (approximately 340 nucleotides of the 521 nucleotides of sequence generated from the 5' end of the clone). This clone (GenBank accession #H12981) was isolated from an oligo-dT primed human infant brain library and cloned directionally into the Lafmid BA vector (Hillier, L. et al, unpublished data). The 3' end of the #H12981 clone has been sequenced, but it exhibits no homology to any part of the GDNFR. The appearance of homology between this #112981 clone and GDNFR over a short region, which homology then disappears, suggests that the #H12981 clone represents an unspliced transcript, or cloning artifact rather than a bona fide cDNA transcript.

Thus, the present invention enables the cloning of GDNFR protein by providing a method for selecting target cells which express GDNFR. By providing a means of enriching for GDNFR encoding sequences, the present invention further provides for the purification of GDNFR protein and the direct cloning of GDNFR-encoding DNA. The present description of the GDNFR nucleic acid and amino acid sequences provides the information needed to reproduce these entities as well as a variety of GDNFR analogs. With this information, GDNFR protein products may be isolated or generated by any means known to those skilled in the art. A variety of means for the recombinant or synthetic production of GDNFR protein are disclosed.

Figure 2:
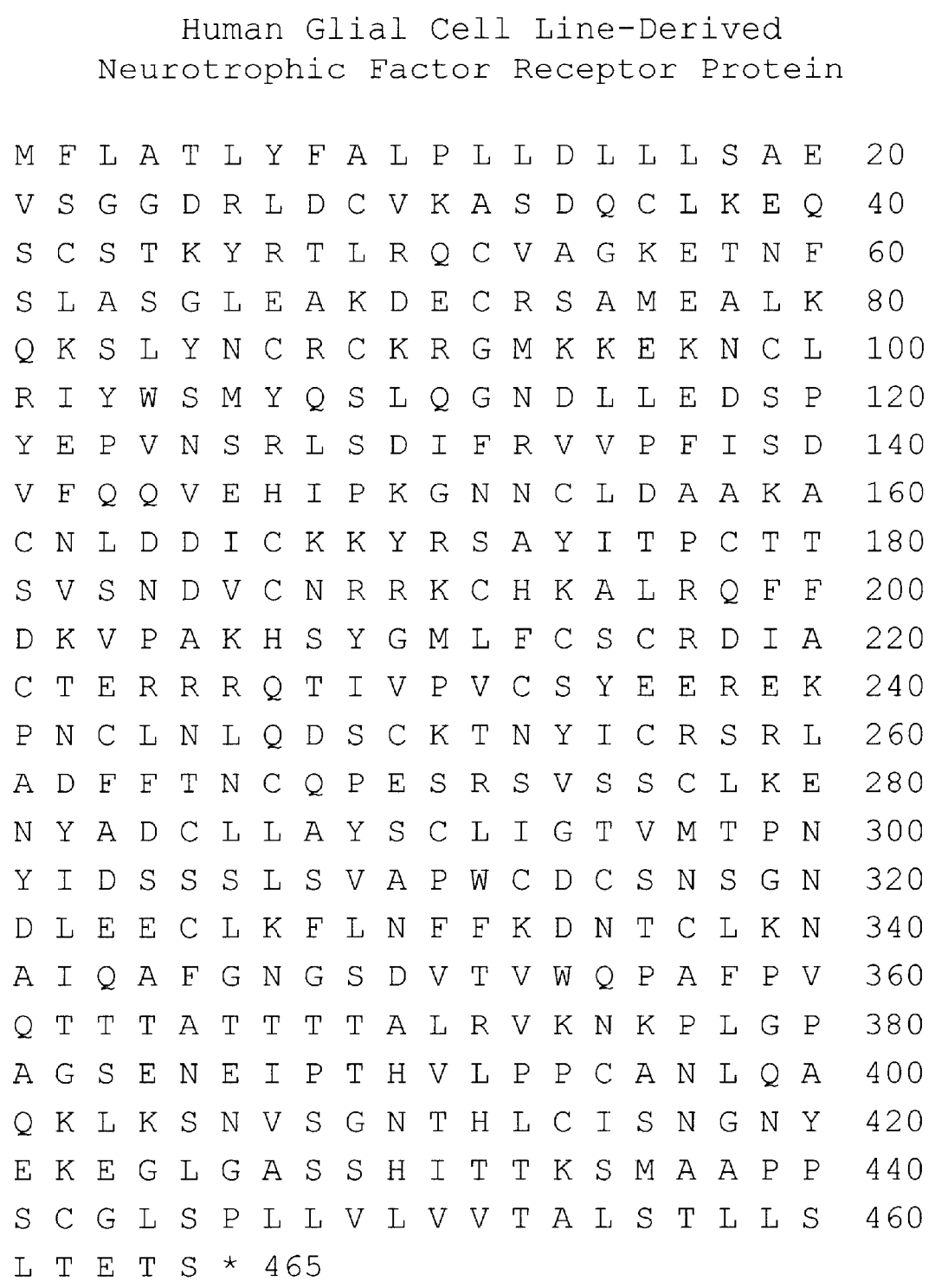

As used herein, the term "GDNFR protein product" includes biologically active purified natural, synthetic or recombinant GDNFR, GDNFR analogs (i.e., GDNFR homologs and variants involving insertion, substitution and deletion variations), and chemically modified derivatives thereof. GDNFR analogs are substantially homologous to the GDNFR amino acid sequences set forth in FIGS. 2 and 4 (SEQ ID NOs:2 and 4).

The term "biologically active", as used herein, means that the GDNFR protein product demonstrates high affinity binding to GDNF and mediates or enhances GDNF-induced signal transduction. Using the present disclosure, it is well within the ability of those of ordinary skill in the art to determine whether a GDNFR polypeptide analog has substantially the same biological activity as the GDNFR protein products set forth in FIGS. 2 and 4.

The term "substantially homologous" amino acid sequence, as used herein, refers to an amino acid sequence sharing a degree of "similarity" or homology to the GDNFR amino acid sequences set forth in FIGS. 2 and 4 such that the homologous sequence has a biological activity or function similar to that described for these GDNFR amino acid sequences. It will be appreciated by those skilled in the art, that a relatively large number of individual or grouped amino acid residues can be changed, positionally exchanged (e.g.s, reverse ordered or reordered) or deleted entirely in an amino acid sequence without affecting the three dimensional configuration or activity of the molecule. Such modifications are well within the ability of one skilled in the art following the present disclosure. The identification and means of providing such modified sequences are described in greater detail below. It is preferable that the degree of homology of a substantially homologous protein (peptide) is equal to or in excess of 70% (i.e., a range of from 70% to 100% homology). Thus, a preferable "substantially homologous" GDNFR amino acid sequence may have a degree of homology greater than or equal to 70% of the amino acid sequences set forth in SEQ ID NOs:2 and 4. More preferably the degree of homology may be equal to or in excess of 85%. Even more preferably it is equal to or in excess of 90%, or most preferably it is equal to or in excess of 95%.

The percentage of homology as described herein is calculated as the percentage of amino acid residues found in one protein sequence which align with identical or similar amino acid residues in the second protein sequence. Thus, in the case of GDNFR homology, the degree of sequence homology may be determined by optimally aligning the amino acid residues of the comparison molecule to those of a reference GDNFR polypeptide, such as depicted in SEQ ID NOs: 2 and 4 or those encoded by the nucleic acid sequences depicted in the Figures, to maximize matches of residues between the two sequences. It will be appreciated by those skilled in the art that such alignment may include appropriate conservative residue substitutions and will disregard truncations and internal deletions or insertions of the comparison sequence by introducing gaps as required; see, for example Dayhoff, Atlas of Protein Sequence and Structure Vol. 5, wherein an average of three or four gaps in a length of 100 amino acids may be introduced to assist in alignment (p. 124, National Biochemical Research Foundation, Washington, D.C., 1972; the disclosure of which is hereby incorporated by reference). Once so aligned, the percentage is determined by the number of aligned residues in the comparison polypeptide divided by the total number of residues in the comparison polypeptide. It is further contemplated that the GDNFR sequences of the present invention may be used to form a portion of a fusion protein or chimeric protein which has, at least in part, GDNFR activity. The alignment and homology of such a protein would be determined using that portion of the fusion protein or chimeric protein which is related to GDNFR activity.

The sources of such substantially homologous GDNFR proteins include the GDNFR proteins of other mammals which are expected to have a high degree of homology to the human GDNFR protein. For example, the degree of homology between the rat and human GDNFR proteins disclosed herein is about 93%. Substantially homologous GDNFR proteins may be isolated from such mammals by virtue of cross-reactivity with antibodies to the GDNFR amino acid sequences of SEQ ID NOs: 2 and 4. Alternatively, they may be expressed by nucleic acid sequences which are isolated through hybridization with the gene or with segments of the gene encoding the GDNFR of SEQ ID NOs 2 and 4 or which hybridize to a complementary sequence of the nucleic acid sequences illustrated in SEQ ID NOs: 2 and 4. Suitable hybridization conditions are described in further detail below.

The novel GDNFR protein products are typically isolated and purified to form GDNFR protein products which are substantially free of unwanted substances that would detract from the use of the present polypeptides for an intended purpose. For example, preferred GDNFR protein products may be substantially free from the presence of other human (e.g., non-GDNFR) proteinaceous materials or pathological agents. Preferably, the GDNFR protein products are about 80% free of other proteins which may be present due to the production technique used in the manufacture of the GDNFR protein product. More preferably, the GDNFR protein products are about 90% free of other proteins, particularly preferably, about 95% free of other proteins, and most preferably about >98% free of other proteins. In addition, the present invention furnishes the unique advantage of providing polynucleotide sequences for the manufacture of homogeneous GDNFR proteins.

A variety of GDNFR variants are contemplated, including addition, deletion and substitution variants. For example, a series of deletion variants may be made by removing one or more amino acid residues from the amino and/or carboxy termini of the GDNFR protein. Using rules for the prediction of signal peptide cleavage as described by von Heijne (von Heijne, Nucleic Acids Research, 14, 4683–4690, 1986), the first amino acid residue of the GDNFR protein which might be involved in GDNF binding is $Ser^{18}$, as depicted in the full length amino acid sequence of human GDNFR in FIG. 2 (SEQ. ID. NO:2). Amino acid residues $Met^1$ through $Ser^{18}$ are in the amino-terminal hydrophobic region that is likely to be part of a signal peptide sequence, and therefore, not be included in the mature form of the receptor protein. Similarly, the last amino acid residue of the GDNFR protein which is likely to be necessary for GDNF binding is $Ser^{446}$. Amino acid residues $Leu^{447}$ through $Ser^{465}$ are in the carboxy-terminal hydrophobic region that is involved in the GPI linkage of the protein to the cell surface. Thus, it is contemplated that any or all of the residues from $Met^1$ through $Ser^{18}$ and/or $Leu^{447}$ through $Ser^{465}$ (as depicted in FIG. 2 (SEQ. ID. NO:2) may be removed from the protein without affecting GDNF binding to the GDNFR protein, thereby leaving a "core" sequence of $Ala^{19}$ through $pro^{446}$. Using known analysis techniques, it is further contemplated that N-terminal truncations may include the removal of one or more amino acid residues up to and including $Gly^{24}$. Thus, GDNFR truncation analogs also may include the deletion of one or more amino acid residues from either or both termini such that an amino acid sequence of $Asp^{25}$ through $pro^{446}$ or $Leu^{447}$ forms the basis for a core molecule. Additional GDNFR analogs are contemplated as involving amino acid residues $Ser^{18}$ through $Pro^{449}$ as depicted in the GDNFR amino acid sequence of FIG. 4 (SEQ. ID. NO:4), i.e., deleting one or more amino acid residues from either or both termini involving the hydrophobic regions depicted as amino acid residues $Met^1$ through $Ser^{18}$ and/or $pro^{449}$ through $Ser^{468}$.

In addition, it is contemplated that one or more amino acid residues may be removed from either or both of the amino and carboxy termini until the first and last cysteine residues in the full length sequence are reached. It is advantageous to retain the cysteine residues for the proper intramolecular binding of the GDNFR protein. As depicted in the full length amino acid sequence of human GDNFR in FIG. 2 (SEQ. ID. NO:2), any or all of amino acid residues from $Met^1$ to $Asp^{28}$ may be removed from the amino terminal without removing the first cysteine residue which appears as $Cys^{29}$. Similarly, any or all of amino acid residues from $Gly^{443}$ to $Ser^{465}$ may be removed from the carboxy terminal without removing the last cysteine residue which appears as $Cys^{442}$. Other GDNFR analogs may be made using amino acid residues $Cys^{29}$ through $Cys^{443}$ as depicted in the GDNFR amino acid sequence of FIG. 4 (SEQ. ID. NO:4), i.e., deleting all or part of the terminal regions depicted as amino acid residues $Met^{1}$ through $Asp^{28}$ and/or $Ser^{444}$ through $Ser^{468}$ It will be appreciated by those skilled in the art that, for the same reasons, it is contemplated that these identified amino acid residues may be replaced, rather than deleted, without affecting the function of the GDNFR protein. Alternatively, these identified amino acid residues may be modified by intra-residue insertions or terminal additions without affecting the function of the GDNFR protein. In yet another embodiment, a combination of one or more deletions, substitutions or additions may be made.

The present GDNFR proteins or nucleic acids may be used for methods of treatment, or for methods of manufacturing medicaments for treatment. Such treatment includes conditions characterized by excessive production of GDNFR protein, wherein the present GDNFRs, particularly in soluble form, may be used to complex to and therefore inactivate such excessive GDNF protein. This treatment may be accomplished by preparing soluble receptor (e.g., use of the GDNF binding domain) or by preparation of a population of cells containing such GDNFR, and transplanting such cells into the individual in need thereof. The present GDNFR protein products may also be used for treatment of those having defective GDNF receptors. For example, one may treat an individual having defective GDNFRs by preparation and delivery of a soluble receptor, or by preparation of a population of cells containing such non-defective GDNFR and transplanting such cells into an individual. Or, an individual may have an inadequate number of GDNF receptors, and cells containing such receptors may be transplanted in order to increase the number of GDNF receptors available to an individual. Such compositions may be used in conjunction with the delivery of GDNF. It is also contemplated GDNFR protein products may be used in the treatment of conditions responsive to the activation of the c-ret receptor tyrosine kinase.

In yet another aspect of the present invention, a further advantage to the novel compositions is the use of GDNFR to stabilize GDNF protein pharmaceutical compositions. In another aspect of the present invention, a GDNFR may be used to screen compounds for antagonist activity.

Other aspects and advantages of the present invention will be apparent to those skilled in the art. For example, additional uses include new assay systems, transgenic animals and antibody production.

Study Models

The present invention provides for assay systems in which GDNF activity or activities similar to GDNF activity resulting from exposure to a peptide or non-peptide compound may be detected by measuring an elicited physiological response in a cell or cell line which expresses the GDNFR molecules of the present invention. A physiological response may comprise any of the biological effects of GDNF, including but not limited to, dopamine uptake, extension of neurites, increased cell survival or growth, as well as the transcriptional activation of certain nucleic acid sequences (e.g. promoter/enhancer elements as well as structural genes), GDNF-related processing, translation, or phosphorylation, and the induction of secondary processes in response to processes directly or indirectly induced by GDNF, to name but a few.

For example, a model system may be created which may be used to study the effects of excess GDNF activity. In such a system, the response of a cell to GDNF may be increased by engineering an increased number of GDNFRs on the cells of the model system relative to cells which have not been so modified. A system may also be developed to selectively provide an increased number of GDNFRs on cells which normally express GDNFRs. In order to ensure expression of GDNFR, the GDNFR gene may be placed under the control of a suitable promoter sequence. It may be desirable to put the GDNFR gene under the control of a constitutive and/or tissue specific promoter (including but not limited to the CNS neuron specific enolase, neurofilament, and tyrosine hydroxylase promoter), an inducible promoter (such as the metallothionein promoter), the UV activated promoter in the human immunodeficiency virus long terminal repeat (Valeri et al., 1988, Nature 333:78–81), or the CMV promoter (as contained in PCMX, infra) or a developmentally regulated promoter.

By increasing the number of cellular GDNFRs, the response to endogenous GDNF may be increased. If the model system contains little or no GDNF, GDNF may be added to the system. It may also be desirable to add additional GDNF to the model system in order to evaluate the effects of excess GDNF activity. Over expressing GDNF (or secreted GDNF) may be one method for studying the effects of elevated levels of GDNF on cells already expressing GDNFR.

GDNFR Therapies

In another aspect, certain conditions may benefit from an increase in GDNF responsiveness. It may, therefore, be beneficial to increase the number or binding affinity of GDNFRs in patients suffering from conditions responsive to GDNF therapy. This could be achieved through gene therapy, whereby selective expression of recombinant GDNFR in appropriate cells is achieved, for example, by using GDNFR genes controlled by tissue specific or inducible promoters or by producing localized infection with replication defective viruses carrying a recombinant GDNFR gene.

It is envisioned that conditions which will benefit from GDNFR or combined GDNF/GDNFR delivery include, but are not limited to, motor neuron disorders including amyotrophic lateral sclerosis, neurological disorders associated with diabetes, Parkinson's disease, Alzheimer's disease, and Huntington's chorea. Additional indications for the use of GDNFR or combined GDNF/GDNFR delivery are described above and further include the treatment of: glaucoma or other diseases and conditions involving retinal ganglion cell degeneration; sensory neuropathy caused by injury to, insults to, or degeneration of, sensory neurons; pathological conditions, such as inherited retinal degenerations and age, disease or injury-related retinopathies, in which photoreceptor degeneration occurs and is responsible for vision loss; and injury or degeneration of inner ear sensory cells, such as hair cells and auditory neurons for preventing and/or treating hearing loss due to variety of causes.

Transgenic Animals

In yet another aspect, a recombinant GDNFR gene may be used to inactivate or "knock out" the endogenous gene (e.g., by homologous recombination) and thereby create a GDNFR deficient cell, tissue, or animal. For example, a recombinant GDNFR gene may be engineered to contain an insertional mutation which inactivates GDNFR. Such a construct, under the control of a suitable promoter, may be introduced into a cell, such as an embryonic stem cell, by any conventional technique including transfection, transduction, injection, etc. Cells containing the construct may then be selected, for example by G418 resistance. Cells which lack an intact GDNFR gene are then identified (e.g., by Southern blotting or Northern blotting or assay of expression). Cells lacking an intact GDNFR gene may then be fused to early embryo cells to generate transgenic animals deficient in GDNFR. A comparison of such an animal with an animal not expressing endogenous GDNF would reveal that either the two phenotypes match completely or that they do not, implying the presence of additional GDNF-like factors or receptors. Such an animal may be used to define specific neuronal populations, or other in vivo processes, normally dependent upon GDNF. Thus, these populations or processes may be expected to be effected if the animal did not express GDNFR, and therefore, could not respond to GDNF.

Diagnostic Applications

According to the present invention, GDNFR probes may be used to identify cells and tissues which are responsive to GDNF in normal or diseased states. The present invention provides for methods for identifying cells which are responsive to GDNF by detecting GDNFR expression in such cells. GDNFR expression may be evidenced by transcription of GDNFR mRNA or production of GDNFR protein. GDNFR expression may be detected using probes which identify GDNFR nucleic acid or protein or by detecting "tag" sequences artificially added to the GDNFR protein.

One variety of probe which may be used to detect GDNFR expression is a nucleic acid probe, which may be used to detect GDNFR-encoding RNA by any method known in the art, including, but not limited to, in situ hybridization, Northern blot analysis, or PCR related techniques. Nucleic acid products of the invention may be labeled with detectable markers (such as radiolabels and non-isotopic labels such as biotin) and employed in hybridization processes to locate the human GDNFR gene position and/or the position of any related gene family in a chromosomal map. They may also be used for identifying human GDNFR gene disorders at the DNA level and used as gene markers for identifying neighboring genes and their disorders. Contemplated herein are kits containing such labeled materials.

Polypeptide products of the invention may be "labeled" by association with a detectable marker substance or label (e.g., a radioactive isotope, a fluorescent or chemiluminescent chemical, an enzyme or other label available to one skilled in the art) to provide reagents useful in detection and quantification of GDNF in solid tissue and fluid samples such as blood or urine. Such products may also be used in detecting cells and tissues which are responsive to GDNF in normal or diseased states.

Another possible assay for detecting the presence of GDNF in a test sample or screening for the presence of a GDNF-like molecule involves contacting the test sample with a GDNFR peptide immobilized on a solid phase, thereby producing GDNFR-bound GDNF. The GDNFR-bound GDNF may optionally be contacted with a detection reagent, such as a labeled antibody specific for GDNF, thereby forming a detectable product. Such assays may be developed in the form of assay devices for analyzing a test sample. In a basic form, such devices include a solid phase containing or coated with GDNFR. A method for analyzing a test sample for the presence of GDNF may involve contacting the sample to an assay reagent comprising GDNFR protein, wherein said GDNFR protein reacts with GDNF present in the test sample and produces a detectable reaction product indicative of the presence of GDNF.

The assay reagents provided herein may also be embodied as part of a kit or article of manufacture. Contemplated is an article of manufacture comprising a packaging material and one or more preparations of the presently provided nucleic acid or amino acid sequences. Such packaging material will comprise a label indicating that the preparation is useful for detecting GDNF, GDNFR or GDNFR defects in a biological sample. As such, the kit may optionally include materials to carry out such testing, such as reagents useful for performing protein analysis, DNA or RNA hybridization analysis, or PCR analysis on blood, urine, or tissue samples.

Anti-GDNFR Antibody

According to the present invention, GDNFR protein, or fragments or derivatives thereof, may be used as an immunogen to generate anti-GDNFR antibodies. To further improve the likelihood of producing an anti-GDNFR immune response, the amino acid sequence of GDNFR may be analyzed in order to identify portions of the molecule which may be associated with increased immunogenicity. For example, the amino acid sequence may be subjected to computer analysis to identify surface epitopes which present computer-generated plots of hydrophilicity, surface probability, flexibility, antigenic index, amphiphilic helix, amphiphilic sheet, and secondary structure of GDNFR. Alternatively, the amino acid sequences of GDNFR from different species could be compared, and relatively non-homologous regions identified; these non-homologous regions would be more likely to be immunogenic across various species.

Also comprehended are polypeptide fragments duplicating only a part of the continuous amino acid sequence or secondary conformations within GDNFR, which fragments may possess one activity of mammalian GDNFR (e.g., immunological activity) and not others (e.g., GDNF protein binding activity). Thus, the production of antibodies can include the production of anti-peptide antibodies. The following exemplary peptides were synthesized using GDNFR sequences:

TABLE 1

| GDNFR Peptides | | |
|---|---|---|
| SJP-6 | H₂N-QSCSTKYRTL-COOH | human GDNFR, AA 40–49 (SEQ ID NO:25) |
| SJP-7 | H₂N-CKRGMKKEKN-COOH | human GDNFR, AA 89–98 (SEQ ID NO:26) |
| SJP-8 | H₂N-LLEDSPYEPV-COOH | human GDNFR, AA 115–124 (SEQ ID NO:27) |
| SJP-9 | H₂N-CSYEERERPN-COOH | rat GDNFR, AA 233–242 (SEQ ID NO:28) |
| SJP-10 | H₂N-PAPPVQTTTATTTT-COOH | rat GDNFR, AA 356–369 (SEQ ID NO:29) |

Peptides SJP-6, 7, and 8 are identical in rat and human GDNFR. Peptides SJP-9 and 10 are derived from the rat sequence and are each one amino acid different from human. Both polyclonal and monoclonal antibodies may be made by methods known in the art using these peptides or other portions of GDNFR.

Monoclonal antibodies directed against GDNFR may be prepared by any known technique which provides for the production of antibody molecules by continuous cell lines in culture. For example, the hybridoma technique originally developed by Kohler and Milstein to produce monoclonal antibodies (Nature, 256:495–497, 1975), as well as the trioma technique, the human B-cell hybridoma technique (Kozbor et al., Immunology Today 4:72, 1983), the EBV-hybridoma technique (Cole et al., in "Monoclonal Antibodies and Cancer Therapy," Alan R. Liss, Inc. pp. 77–96, 1985), and the like, may be used.

Human monoclonal antibodies or chimeric human-mouse (or other species) monoclonal antibodies also may be prepared for therapeutic use and may be made by any of numerous techniques known in the art (e.g., Teng et al., Proc. Natl. Acad. Sci. U.S.A., 80:7308–7312, 1983: Kozbor et al., Immunology Today, 4:72–79, 1983; Olsson et al., Meth. Enzymol., 92:3–16, 1982). Chimeric antibody molecules may be prepared containing a mouse antigen-binding domain with human constant regions (Morrison et al., Proc. Natl. Acad. Sci. U.S.A., 81:6851, 1984; Takeda et al., Nature, 314:452, 1985).

Various procedures known in the art also may be used for the production of polyclonal antibodies. For the production of antibody, various host animals including, but not limited to, rabbits, mice, rats, etc., can be immunized by injection with GDNFR protein, or a fragment or derivative thereof. Various adjuvants may be used to increase the immunological response, depending on the host species selected. Useful adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and human adjuvants such as BCG (Bacille Calmette-Guerin) and *Corynebacterium parvum*.

A molecular clone of an antibody to a GDNFR epitope also may be prepared by known techniques. Recombinant DNA methodology (see e.g., Maniatis et al., Molecular Cloning, A Laboratory Manual, Cold Spring Harbor Laboratory, Cold spring Harbor, N.Y., 1982) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as high performance liquid chromatography, or a combination thereof, etc. The present invention provides for antibody molecules as well as fragments of such antibody molecules. Antibody fragments which contain the idiotype of the molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

Such selective binding molecules may themselves be alternatives to GDNFR protein, and may be formulated as a pharmaceutical composition.

Recombinant Expression of GDNFR Protein

The present invention provides various polynucleodides encoding GDNFR proteins. The expression product or a derivative thereof is characterized by the ability to bind to GDNF specifically and with high affinity so that further interactions with signaling molecules can occur, thereby providing or enhancing GDNF activity such as increasing dopamine uptake by dopaminergic cells. The polynucleotides may also be used in cell therapy or gene therapy applications.

According to the present invention, novel GDNFR protein and DNA sequences coding for all or part of such receptors are provided. Novel nucleic acid sequences of the invention include sequences useful in securing expression in procaryotic or eucaryotic host cells of polypeptide products having at least a part of the primary structural conformation and one or more of the biological properties of recombinant human GDNFR. The nucleic acids may be purified and isolated, go that the desired coding region is useful to produce the present polypeptides. Alternatively, the nucleic acid sequence may be used for diagnostic purposes, as described more fully below. Exemplary DNA sequences of the present invention comprise nucleic acid sequences encoding the GDNFR amino acid sequences depicted in FIGS. 2 and 4 and set forth in SEQ. ID NOs:2 and 4. In addition, DNA sequences disclosed by the present invention specifically comprise: (a) any of the DNA sequences depicted in FIGS. 1 and 3 (and complementary strands); (b) a DNA sequence which hybridizes (under hybridization conditions disclosed in the cDNA library screening section below, or equivalent conditions or more stringent conditions) to the DNA sequence in subpart (a) or to fragments thereof; and (c) a DNA sequence which, but for the degeneracy of the genetic code, would hybridize to the DNA sequence in subpart (a). Specifically comprehended in parts (b) and (c) are genomic DNA sequences encoding allelic variant forms of human GDNFR and/or encoding GDNFR from other mammalian species, and manufactured DNA sequences encoding GDNFR, fragments of GDNFR, and analogs of GDNFR which DNA sequences may incorporate codons facilitating transcription and translation of messenger RNA in microbial hosts. Such manufactured sequences may readily be constructed according to the methods known in the art as well as the methods described herein.

Recombinant expression techniques, conducted in accordance with the descriptions set forth herein or other known methods, may be used to produce these polynucleotides and express the various GDNFR proteins. For example, by inserting a nucleic acid sequence which encodes a GDNFR protein into an appropriate vector, one skilled in the art can readily produce large quantities of the desired nucleotide sequence. The sequences can then be used to generate detection probes or amplification primers. Alternatively, a polynucleotide encoding a GDNFR protein can be inserted into an expression vector. By introducing the expression vector into an appropriate host, the desired GDNFR protein may be produced in large amounts.

As further described herein, there are numerous host/vector systems available for the propagation of nucleic acid sequences and/or the production of GDNFR proteins. These include, but are not limited to, plasmid, viral and insertional vectors, and prokaryotic and eukaryotic hosts. One skilled in the art can adapt a host/vector system which is capable of propagating or expressing heterologous DNA to produce or express the sequences of the present invention.

By means of such recombinant techniques, the GDNFR proteins of the present invention are readily produced in commercial quantities with greater purity. Furthermore, it will be appreciated by those skilled in the art that, in view of the present disclosure, the novel nucleic acid sequences include degenerate nucleic acid sequences encoding the GDNFR proteins specifically set forth in the Figures, sequences encoding variants of GDNFR proteins, and those nucleic acid sequences which hybridize, preferably under stringent hybridization conditions, to complements of these nucleic acid sequences (see, Maniatis et. al., Molecular Cloning (A Laboratory Manual); Cold Spring Harbor Laboratory, pages 387 to 389, 1982.) Exemplary stringent hybridization conditions are hybridization in 4×SSC at 62–67° C., followed by washing in 0.1×SSC at 62–67° C. for approximately an hour. Alternatively, exemplary stringent hybridization conditions are hybridization in 45–55% formamide, 4×SSC at 40–45° C. DNA sequences which hybridize to the complementary sequences for GDNFR protein under relaxed hybridization conditions and which encode a GDNFR protein of the present invention are also included herein. Examples of such relaxed stringency hybridization conditions are 4×SSC at 45–55° C. or hybridization with 30–40% formamide at 40–45° C.

Preparation of Polynucleotides Encoding GDNFR

Based upon the disclosure of the present invention, a nucleic acid sequence encoding a full length GDNFR polypeptide or a fragment thereof may readily be prepared or obtained in a variety of ways, including, without limitation, chemical synthesis, cDNA or genomic library screening, expression library screening, and/or PCR amplification of cDNA. These methods and others useful for preparing nucleic acid sequences are known in the art and are set forth, for example, by Sambrook et al. (Molecular Cloning: A Laboratory Manual, Cold Spring Harbor Laboratory Press, Cold Spring Harbor, N.Y., 1989), by Ausubel et al., eds (Current Protocols in Molecular Biology, Current Protocols Press, 1994), and by Berger and Kimmel (Methods in Enzymology: Guide to Molecular Cloning Techniques, vol. 152, Academic Press, Inc., San Diego, Calif., 1987). Preferred nucleic acid sequences encoding GDNFR are mammalian sequences.

Chemical synthesis of a nucleic acid sequence which encodes a GDNFR protein can also be accomplished using methods known in the art, such as those set forth by Engels et al. (Angew. Chem. Intl. Ed., 28:716–734, 1989). These methods include, inter alia, the phosphotriester, phosphoramidite and H-phosphonate methods of nucleic acid sequence synthesis. A preferred method for such chemical synthesis is polymer-supported synthesis using standard phosphoramidite chemistry. Typically, the DNA encoding the desired polypeptide will be several hundred base pairs (bp) or nucleotides in length. Nucleic acid sequences larger than about 100 nucleotides can be synthesized as several fragments using these methods. The fragments can then be ligated together to form a sequence for the expression of a full length GDNFR polypeptide or a portion thereof.

Alternatively, a suitable nucleic acid sequence may be obtained by screening an appropriate cDNA library (i.e., a library prepared from one or more tissue source(s) believed to express the protein) or a genomic library (a library prepared from total genomic DNA). The source of the cDNA library is typically a tissue that is believed to express GDNFR in reasonable quantities. Typically, the source of the genomic library is any tissue or tissues from a mammalian species believed to harbor a gene encoding GDNFR. The library can be screened for the presence of the GDNFR cDNA/gene using one or more nucleic acid probes (such as oligonucleotides, cDNA or genomic DNA fragments based upon the presently disclosed sequences) that will hybridize selectively with GDNFR cDNA(s) or gene(s) present in the library. The probes typically used for such library screening usually encode a small region of the GDNFR nucleic acid sequence from the same or a similar species as the species from which the library was prepared. Alternatively, the probes may be degenerate, as discussed herein.

Library screening is typically accomplished by annealing the oligonucleotide probe or cDNA to the clones in the library under conditions of stringency that prevent nonspecific binding but permit binding (hybridization) of those clones that have a significant level of homology with the probe or primer. Typical hybridization and washing stringency conditions depend in part on the size (i.e., number of nucleotides in length) of the cDNA or oligonucleotide probe, and whether the probe is degenerate. The probability of obtaining a clone(s) is also considered in designing the hybridization solution (e.g., whether a cDNA or genomic library is being screened; if it is a cDNA library, the probability that the cDNA of interest is present at a high level).

Where DNA fragments (such as cDNAs) are used as probes, typical hybridization conditions include those as set forth in Ausubel et al., eds., supra. After hybridization, the blot containing the library is washed at a suitable stringency, depending on several factors such as probe size, expected homology of probe to clone, type of library being screened, number of clones being screened, and the like. Examples of stringent washing solutions (which are usually low in ionic strength and are used at relatively high temperatures) are as follows. One such stringent wash is 0.015 M NaCl, 0.005 M NaCitrate and 0.1% SDS at 55–65° C. Another such stringent buffer is 1 mM $Na_2EDTA$, 40 mM $NaHPO_4$, pH 7.2, and 1% SDS at about 40–50° C. One other stringent wash is 0.2×SSC and 0.1% SDS at about 50–65° C.

There are also exemplary protocols for stringent washing conditions where oligonucleotide probes are used to screen cDNA or genomic libraries. For example, a first protocol uses 6×SSC with 0.05 percent sodium pyrophosphate at a temperature of between about 35 and 62° C., depending on the length of the probe. For example, 14 base probes are washed at 35–40° C., 17 base probes at 45–50° C., 20 base probes at 52–57° C., and 23 base probes at 57–63° C. The temperature can be increased 2–3° C. where the background non-specific binding appears high. A second protocol uses tetramethylammonium chloride (TMAC) for washing. One such stringent washing solution is 3 M TMAC, 50 mM Tris-HCl, pH 8.0, and 0.2% SDS.

Another suitable method for obtaining a nucleic acid sequence encoding a GDNFR protein is by polymerase chain reaction (PCR). In this method, poly(A)+RNA or total RNA is extracted from a tissue that expresses GDNFR. A cDNA is then prepared from the RNA using the enzyme reverse transcriptase (i.e., RT-PCR). Two primers, typically complementary to two separate regions of the GDNFR cDNA (oligonucleotides), are then added to the cDNA along with a polymerase such as Taq polymerase, and the polymerase amplifies the cDNA region between the two primers.

Where the method of choice for preparing the nucleic acid sequence encoding the desired GDNFR protein requires the use of oligonucleotide primers or probes (e.g., PCR, cDNA or genomic library screening), the oligonucleotide sequences selected as probes or primers should be of adequate length and sufficiently unambiguous so as to minimize the amount of non-specific binding that will occur during library screening or PCR amplification. The actual sequence of the probes or primers is usually based on conserved or highly homologous sequences or regions from the same or a similar gene from another organism, such as the rat nucleic acid sequence involved in the present invention. Optionally, the probes or primers can be fully or partially degenerate, i.e., contain a mixture of probes/primers, all encoding the same amino acid sequence, but using different codons to do so. An alternative to preparing degenerate probes is to place an inosine in some or all of those codon positions that vary by species. The oligonucleotide probes or primers may be prepared by chemical synthesis methods for DNA as described above.

GDNFR proteins based on these nucleic acid sequences encoding GDNFR, as well as mutant or variant sequences thereof, are also contemplated as within the scope of the present invention. Mutant or variant sequences include those sequences containing one or more nucleotide substitutions, deletions, and/or insertions as compared to the wild type sequence and that results in the expression of amino acid sequence variations as compared to the wild type amino acid sequence. In some cases, naturally occurring GDNFR amino acid mutants or variants may exist, due to the existence of natural allelic variation. GDNFR proteins based on such naturally occurring mutants or variants are also within the scope of the present invention. Preparation of synthetic mutant sequences is also well known in the art, and is described for example in Wells et al. (Gene, 34:315, 1985) and in Sambrook et al., supra.

In some cases, it may be desirable to prepare nucleic acid and/or amino acid variants of naturally occurring GDNFR. Nucleic acid variants (wherein one or more nucleotides are designed to differ from the wild-type or naturally occurring GDNFR) may be produced using site directed mutagenesis or PCR amplification where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to recombinantly produce GDNFR. Other preferred variants are those encoding conservative amino acid changes (e.g., wherein the charge or polarity of the naturally occurring amino acid side chain is not altered substantially by substitution with a different amino acid) as compared to wild type, and/or those designed to either generate a novel glycosylation and/or phosphorylation site(s) on GDNFR, or those designed to delete an existing glycosylation and/or phosphorylation site(s) on GDNFR.

Vectors

The cDNA or genomic DNA encoding the desired GDNFR protein is inserted into a vector for further cloning (amplification of the DNA) or for expression. Suitable vectors are commercially available, or the vector may be specially constructed. Possible vectors include, but are not limited to, cosmids, plasmids or modified viruses, but the vector system must be compatible with the selected host cell. Such vectors include, but are not limited to, bacteriophages such as lambda derivatives, or plasmids such as pBR322, pUC, or Bluescript® plasmid derivatives (Stratagene, La Jolla Calif.). The recombinant molecules can be introduced into host cells via transformation, transfection, infection, electroporation, or other known techniques.

For example, the GDNFR-encoding nucleic acid sequence is inserted into a cloning vector which is used to transform, transfect, or infect appropriate host cells so that many copies of the nucleic acid sequence are generated. This can be accomplished by ligating a DNA fragment into a cloning vector which has complementary cohesive termini. If the complementary restriction sites used to fragment the DNA are not present in the cloning vector, the ends of the DNA molecules may be enzymatically modified. It also may prove advantageous to incorporate restriction endonuclease cleavage sites into the oligonucleotide primers used in polymerase chain reaction to facilitate insertion of the resulting nucleic acid sequence into vectors. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and GDNFR-encoding nucleic acid sequence may be modified by homopolymeric tailing. In specific embodiments, transformation of host cells with recombinant DNA molecules that incorporate an isolated GDNFR gene, cDNA, or synthesized DNA sequence enables generation of multiple copies of the gene. Thus, the GDNFR-encoding nucleic acid sequence may be obtained in large quantities by growing transformants, isolating the recombinant DNA molecules from the transformants and, when necessary, retrieving the inserted gene from the isolated recombinant DNA.

The selection or construction of the appropriate vector will depend on 1) whether it is to be used for DNA amplification or for DNA expression, 2) the size of the DNA to be inserted into the vector, and 3) the host cell (e.g., mammalian, insect, yeast, fungal, plant or bacterial cells) to be transformed with the vector. Each vector contains various components depending on its function (amplification of DNA or expression of DNA) and its compatibility with the intended host cell. For DNA expression, the vector components may include, but are not limited to, one or more of the following: a signal sequence, an origin of replication, one or more selection or marker genes, enhancer elements, promoters, a transcription termination sequence, and the like. These components may be obtained from natural sources or synthesized by known procedures. The vectors of the present invention involve a nucleic acid sequence which encodes the GDNFR protein of interest operatively linked to one or more amplification, expression control, regulatory or similar operational elements capable of directing, controlling or otherwise effecting the amplification or expression of the GDNFR-encoding nucleic acid sequence in the selected host cell.

Expression vectors containing GDNFR nucleic acid sequence inserts can be identified by three general approaches: (a) DNA-DNA hybridization; (b) the presence or absence of "marker" gene functions, and (c) the expression of inserted sequences. In the first approach, the presence of a foreign nucleic acid sequence inserted in an expression vector can be detected by DNA-DNA hybridization using probes comprising sequences that are homologous to an inserted GDNFR-encoding nucleic acid sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a foreign nucleic acid sequence into the vector. For example, if a GDNFR-encoding nucleic acid sequence is inserted within the marker gene sequence of the vector, recombinants containing the GDNFR insert can be identified by the absence of the marker gene function. In the third approach, recombinant expression vectors can be identified by detecting the foreign protein product expressed by the recombinant nucleic acid sequence. Such assays can be based on the physical or functional properties of the expressed GDNFR protein product, for example, by binding of the GDNFR protein to GDNF or to an antibody which directly recognizes GDNFR.

Signal Sequence

The signal sequence may be a component of the vector, or it may be a part of GDNFR DNA that is inserted into the vector. The native GDNFR DNA encodes a signal sequence at the amino terminus of the protein that is cleaved during post-translational processing of the protein to form the mature GDNFR protein. Included within the scope of this invention are GDNFR polynucleotides with the native signal sequence as well as GDNFR polynucleotides wherein the native signal sequence is deleted and replaced with a heterologous signal sequence. The heterologous signal sequence selected should be one that is recognized and processed, i.e., cleaved by a signal peptidase, by the host cell. For prokaryotic host cells that do not recognize and process the native GDNFR signal sequence, the signal sequence is substituted by a prokaryotic signal sequence selected, for example, from the group of the alkaline phosphatase, penicillinase, or heat-stable enterotoxin II leaders. For yeast secretion, the native GDNFR signal sequence may be substituted by the yeast invertase, alpha factor, or acid phosphatase leaders. In mammalian cell expression the native signal sequence is satisfactory, although other mammalian signal sequences may be suitable.

Origin of Replication

Expression and cloning vectors generally include a nucleic acid sequence that enables the vector to replicate in one or more selected host cells. In cloning vectors, this sequence is typically one that enables the vector to replicate independently of the host chromosomal DNA, and includes origins of replication or autonomously replicating sequences. Such sequences are well known for a variety of bacteria, yeasts, and viruses. The origin of replication from the plasmid pBR322 is suitable for most Gram-negative bacteria and various origins (e.g., SV40, polyoma, adenovirus, VSV or BPV) are useful for cloning vectors in mammalian cells. Generally, the origin of replication component is not needed for mammalian expression vectors (for example, the SV40 origin is often used only because it contains the early promoter), Selection Gene The expression and cloning vectors may contain a selection gene. This gene encodes a "marker" protein necessary for the survival or growth of the transformed host cells when grown in a selective culture medium. Host cells that were not transformed with the vector will not contain the gelecfion gene, and therefore, they will not survive in the culture medium. Typical selection genes encode proteins that (a) confer resistance to antibiotics or other toxins, e.g., ampicillin, neomycin, methotrexate, or tetracycline; (b) complement auxotrophic deficiencies; or (c) supply critical nutrients not available from the culture medium.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the marker present in the vector. Selection pressure is imposed by culturing the transformed cells under conditions in which the concentration of selection agent in the medium is successively changed, thereby leading to amplification of both the selection gene and the DNA that encodes GDNFR. As a result, increased quantities of GDNFR are synthesized from the amplified DNA.

For example, cells transformed with the DHFR selection gene are first identified by culturing all of the transformants in a culture medium that contains methotrexate, a competitive antagonist of DHFR. An appropriate host cell when wild-type DHFR is used is the Chinese hamster ovary cell line deficient in DHFR activity (see, for example, Urlaub and Chasin, Proc. Natl. Acad. Sci., U.S.A., 77(7): 4216–4220, 1980). The transformed cells are then exposed to increased levels of methotrexate. This leads to the synthesis of multiple copies of the DHFR gene, and, concomitantly, multiple copies of other DNA present in the expression vector, such as the DNA encoding a GDNFR protein.

Promoter

The expression and cloning vectors of the present invention will typically contain a promoter that is recognized by the host organism and operably linked to the nucleic acid sequence encoding the GDNFR protein. Promoters are untranslated sequences located upstream (5') to the start codon of a structural gene (generally within about 100 to 1000 bp) that control the transcription and translation of a particular nucleic acid sequence, such as that encoding GDNFR. Promoters are conventionally grouped into one of two classes, inducible promoters and constitutive promoters. Inducible promoters initiate increased levels of transcription from DNA under their control in response to some change in culture conditions, such as the presence or absence of a nutrient or a change in temperature. A large number of promoters, recognized by a variety of potential host cells, are well known. These promoters are operably linked to the DNA encoding GDNFR by removing the promoter from the source DNA by restriction enzyme digestion and inserting the desired promoter sequence into the vector. The native GDNFR promoter sequence may be used to direct amplification and/or expression of GDNFR DNA. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their nucleotide sequences have been published, thereby enabling one skilled in the art to ligate them to the desired DNA sequence(s), using linkers or adaptors as needed to supply any required restriction sites.

Suitable promoting sequences for use with yeast hosts are also well known in the art. Yeast enhancers are advantageously used with yeast promoters. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40). Other suitable mammalian promoters include heterologous mammalian promoters, e.g., heat-shock promoters and the actin promoter. A promoter for possible use in the production of GDNFR proteins in CHO cells is SRa (see Takebe et al., Mol. Cell. Biol., 8(1): 466–472, 1988). A suitable expression vector is pDSRa2. The pDSRa2 plasmid constructs containing the appropriate GDNFR cDNA may be prepared substantially in accordance with the process described in the co-owned and copending U.S. patent application Ser. No. 501,904 filed Mar. 29, 1990

(also see, European Patent Application No. 90305433, Publication No. EP 398 753, filed May 18, 1990 and WO 90/14363 (1990), the disclosures of which are hereby incorporated by reference.

Additional promoters which may be of interest in controlling GDNFR expression include, but are not limited to: the SV40 early promoter region (Bernoist and Chambon, Nature, 290:304–310, 1981); the CMV promoter; the promoter contained in the 3' long terminal repeat of Rous sarcoma virus (Yamamoto, et al., Cell, 22:787–797, 1980); the herpes thymidine kinase promoter (Wagner et al., Proc. Natl. Acad. Sci. U.S.A., 78:144–1445, 1981); the regulatory sequences of the metallothionine gene (Brinster et al., Nature, 296–39–42, 1982); prokaryotic expression vectors such as the beta-lactamase promoter (Villa-Kamaroff, et al., Proc. Natl. Acad. Sci. U.S.A., 75:3727–3731, 1978); or the tac promoter (DeBoer, et al., Proc. Natl. Acad. Sci. U.S.A., 80:21–25, 1983). Also of interest are the following animal transcriptional control regions, which exhibit tissue specificity and have been utilized in transgenic animals: the elastase I gene control region which is active in pancreatic acinar cells (Swift et al., Cell, 38:639–646, 1984; Ornitz et al., Cold Spring Harbor Symp. Quant. Biol. 50:399–409, 1986; MacDonald, Hepatology, 7:425–515, 1987); the insulin gene control region which is active in pancreatic beta cells (Hanahan, Nature, 315:115–122, 1985); the immunoglobulin gene control region which is active in lymphoid cells (Grosschedl et al., Cell, 38:647–658, 1984; Adames et al., Nature, 318:533–538, 1985; Alexander et al., Mol. Cell. Biol., 7:1436–1444, 1987); the mouse mammary tumor virus control region which is active in testicular, breast, lymphoid and mast cells (Leder et al., Cell, 45:485–495, 1986), albumin gene control region which is active in liver (Pinkert et al., Genes and Devel., 1:268–276, 1987); the alpha-fetoprotein gene control region which is active in liver (Krumlauf et al., Mol. Cell. Biol., 5:1639–1648, 1985; Hammer et al., Science, 235:53–58, 1987); the alpha 1-antitrypsin gene control region which is active in the liver (Kelsey et al., Genes and Devel., 1:161–171, 1987); the beta-globin gene control region which is active in myeloid cells (Mogram et al., Nature, 315:338–340, 1985; Kollias et al., Cell, 46:89–94, 1986); the myelin basic protein gene control region which is active in oligodendrocyte cells in the brain (Readhead et al., Cell, 48.703–712, 1987); the myosin light chain-2 gene control region which is active in skeletal muscle (Sani, Nature, 314:283–286, 1985); and the gonadotropic releasing hormone gene control region which is active in the hypothalamus (Mason et al., Science, 234:1372–1378, 1986).

Enhancer Element

An enhancer sequence may be inserted into the vector to increase the transcription of a DNA sequence encoding a GDNFR protein of the present invention by higher eukaryotes. Enhancers are cis-acting elements of DNA, usually about 10–300 bp in length, that act on the promoter to increase its transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to GDNFR DNA, it is typically located at a site 5' from the promoter.

Transcription Termination

Expression vectors used in eukaryotic host cells (yeast, fungi, insect, plant, animal, human, or nucleated cells from other multicellular organisms) will also contain sequences necessary for terminating transcription and stabilizing the mRNA. Such sequences are commonly available from the 5' and occasionally 3' untranslated regions of eukaryotic DNAs or cDNAs. These regions contain nucleotide segments transcribed as polyadenylated fragments in the untranslated portion of the mRNA encoding GDNFR.

The construction of suitable vectors containing one or more of the above-listed components together with the desired GDNFR-encoding sequence is accomplished by standard ligation techniques. Isolated plasmids or DNA fragments are cleaved, tailored, and religated in the desired order to generate the plasmids required. To confirm that the correct sequences have been constructed, the ligation mixtures may be used to transform E. coli, and successful transformants may be selected by known techniques, such as ampicillin or tetracycline resistance as described above. Plasmids from the transformants may then be prepared, analyzed by restriction endonuclease digestion, and/or sequenced to confirm the presence of the desired construct.

Vectors that provide for the transient expression of DNA encoding GDNFR in mammalian cells may also be used. In general, transient expression involves the use of an expression vector that is able to replicate efficiently in a host cell, such that the host cell accumulates many copies of the expression vector and, in turn, synthesizes high levels of the desired protein encoded by the expression vector. Transient expression systems, comprising a suitable expression vector and a host cell, allow for the convenient positive identification of proteins encoded by cloned DNAs, as well as for the rapid screening of such proteins for desired biological or physiological properties. Thus, transient expression systems are particularly useful in identifying variants of the protein.

Selection and Transformation of Host Cells

Host cells (e.g., bacterial, mammalian, insect, yeast, or plant cells) transformed with nucleic acid sequences for use in expressing a recombinant GDNFR protein are also provided by the present invention. The transformed host cell is cultured under appropriate conditions permitting the expression of the nucleic acid sequence. The selection of suitable host cells and methods for transformation, culture, amplification, screening and product production and purification are well known in the art. See for example, Gething and Sambrook, Nature, 293: 620–625 (1981), or alternatively, Kaufman et al., Mol. Cell. Biol., 5 (7): 1750–1759 (1985) or Howley et al., U.S. Pat. No. 4,419,446. Additional exemplary materials and methods are discussed herein. The transformed host cell is cultured in a suitable medium, and the expressed GDNFR protein is then optionally recovered, isolated and purified from the culture medium (or from the cell, if expressed intracellularly) by an appropriate means known to those skilled in the art.

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycogylated core protein product. Expression in yeast may be used to produce a glycosylated product. Expression in mammalian cells can be used to ensure "native" glycosylation of the heterologous GDNFR protein. Furthermore, different vector/host expression systems may effect processing reactions such as proteolytic cleavages to different extents.

Suitable host cells for cloning or expressing the vectors disclosed herein are prokaryote, yeast, or higher eukaryote cells. Eukaryotic microbes such as filamentous fungi or yeast may be suitable hosts for the expression of GDNFR proteins. *Saccharomyces cerevisiae*, or common baker's yeast, is the most commonly used among lower eukaryotic host microorganisms, but a number of other genera, species, and strains are well known and commonly available.

Host cells to be used for the expression of glycosylated GDNFR protein are also derived from multicellular organisms. Such host cells are capable of complex processing and glycosylation activities. In principle, any higher eukaryotic cell culture might be used, whether such culture involves vertebrate or invertebrate cells, including plant and insect cells. The propagation of vertebrate cells in culture (tissue culture) is a well known procedure. Examples of useful mammalian host cell lines include, but are not limited to, monkey kidney CV1 line transformed by SV40 (COS7), human embryonic kidney line (293 or 293 cells subcloned for growth in suspension culture), baby hamster kidney cells, and Chinese hamster ovary cells. Other suitable mammalian cell lines include but are not limited to, HeLa, mouse L-929 cells, 3T3 lines derived from Swiss, Balb-c or NIH mice, BHK or HaK hamster cell lines.

Suitable host cells also include prokaryotic cells. Prokaryotic host cells include, but are not limited to, bacterial cells, such as Gram-negative or Gram-positive organisms, for example, *E. coli*, Bacilli such as *B. subtilis*, Pseudomonas species such as *P. aeruginosa, Salmonella typhimurium*, or *Serratia marcescans*. For example, the various strains of *E. coli* (e.g., HB101, DH5a, DH10, and MC1061) are well-known as host cells in the field of biotechnology. Various strains of Streptomyces spp. and the like may also be employed. Presently preferred host cells for producing GDNFR proteins are bacterial cells (e.g., *Escherichia coli*) and mammalian cells (such as Chinese hamster ovary cells, COS cells, etc.)

The host cells are transfected and preferably transformed with the above-described expression or cloning vectors and cultured in a conventional nutrient medium. The medium may be modified as appropriate for inducing promoters, selecting transformants, or amplifying the genes encoding the desired sequences. Transfection and transformation are performed using standard techniques which are well known to those skilled in the art and which are selected as appropriate to the host cell involved. For example, for mammalian cells without cell walls, the calcium phosphate precipitation method may be used. Electroporation, micro injection and other known techniques may also be used.

Culturing the Host Cells

Transformed cells used to produce GDNFR proteins of the present invention are cultured in suitable media The media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamicin), trace elements (defined as inorganic compounds usually present at final concentrations in the micromolar range), and glucose or other energy source. Other supplements may also be included, at appropriate concentrations, as will be appreciated by those skilled in the art. Suitable culture conditions, such as temperature, pH, and the like, are also well known to those skilled in the art for use with the selected host cells.

Once the GDNFR protein is produced, it may be isolated and purified by standard methods including chromatography (e.g., ion exchange, affinity, and sizing column chromatography), centrifugation, differential solubility, or by any other standard technique for the purification of proteins. In particular, GDNFR protein may be isolated by binding to an affinity column comprising GDNF or anti-GDNFR antibody bound to a stationary support.

Homologous Recombination

It is further envisioned that GDNFR proteins may be produced by homologous recombination, or with recombinant production methods utilizing control elements introduced into cells already containing DNA encoding GDNFR. For example, homologous recombination methods may be used to modify a cell that contains a normally transcriptionally silent GDNFR gene or under expressed gene and thereby produce a cell which expresses GDNFR. Homologous recombination is a technique originally developed for targeting genes to induce or correct mutations in transcriptionally active genes (Kucherlapati, Prog. in Nucl. Acid Res. and Mol. Biol., 36:301, 1989). The basic technique was developed as a method for introducing specific mutations into specific regions of the mammalian genome (Thomas et al., Cell, 44:419–428, 1986; Thomas and Capecchi, Cell, 51:503–512, 1987; Doetschman et al., Proc. Natl. Acad. Sci., 85:8583–8587, 1988) or to correct specific mutations within defective genes (Doetschman et al., Nature, 330:576–578, 1987). Exemplary homologous recombination techniques are described in U.S. Pat. No. 5,272,071 (EP 91 90 3051, EP Publication No. 505 500; PCT/US90/07642, International Publication No. WO 91/09955) the disclosure of which is hereby incorporated by reference.

Through homologous recombination, the DNA sequence to be inserted into the genome can be directed to a specific region of the gene of interest by attaching it to targeting DNA. The targeting DNA is DNA that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence of DNA, it too is incorporated into the newly synthesized strand as a result of the recombination. As a result of the proofreading function, it is possible for the new sequence of DNA to serve as the template. Thus, the transferred DNA is incorporated into the genome.

If the sequence of a particular gene is known, such as the nucleic acid sequence, the pre-pro sequence or expression control sequence of GDNFR presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be backstitched into the newly synthesized daughter strand of DNA.

Attached to these pieces of targeting DNA are regions of DNA which may interact with the expression of a GDNFR protein. For example, a promoter/enhancer element, a suppresser, or an exogenous transcription modulatory element is inserted in the genome of the intended host cell in proximity and orientation sufficient to influence the transcription of DNA encoding the desired GDNFR protein. The control element does not encode GDNFR, but instead controls a portion of the DNA present in the host cell genome. Thus, the expression of GDNFR proteins may be achieved not by transfection of DNA that encodes the GDNFR gene itself, but rather by the use of targeting DNA (containing regions of homology with the endogenous gene of interest) coupled with DNA regulatory segments that provide the endogenous gene sequence with recognizable signals for transcription of a GDNFR protein.

A. GDNFR Variants

As discussed above, the terms "GDNFR analogs" as used herein include polypeptides in which amino acids have been deleted from ("deletion variants"), inserted into ("addition variants"), or substituted for ("substitution variants") residues within the amino acid sequence of naturally-occurring GDNFR polypeptides including those depicted in FIGS. 2 and 4 (SEQ. ID. NOs.:2 and 4). Such variants are prepared by introducing appropriate nucleotide changes into the DNA encoding the polypeptide or by in vitro chemical synthesis of the desired polypeptide. It will be appreciated by those skilled in the art that many combinations of deletions, insertions, and substitutions can be made to an amino acid sequence such as mature human GDNFR provided that the final molecule possesses GDNFR activity.

Based upon the present description of GDNFR amino acid sequences, one can readily design and manufacture a variety of nucleic acid sequences suitable for use in the recombinant (e.g., microbial) expression of polypeptides having primary conformations which differ from those depicted in the Figures in terms of the identity or location of one or more residues. Mutagenesis techniques for the replacement, insertion or deletion of one or more selected amino acid residues encoded by the nucleic acid sequences depicted in FIGS. 2 and 4 are well known to one skilled in the art (e.g., U.S. Pat. No. 4,518,584, the disclosure of which is hereby incorporated by reference.) There are two principal variables in the construction of substitution variants: the location of the mutation site and the nature of the mutation. In designing GDNFR substitution variants, the selection of the mutation site and nature of the mutation will depend on the GDNFR characteristic(s) to be modified. The sites for mutation can be modified individually or in series, e.g., by (1) substituting first with conservative amino acid modifications and then with more radical selections depending upon the results achieved, (2) deleting the target amino acid residue, or (3) inserting amino acid residues adjacent to the located site. Conservative changes in from 1 to 30 contiguous amino acids are preferred. N-terminal and C-terminal deletion GDNFR protein variants may also be generated by proteolytic enzymes.

For GDNFR deletion variants, deletions generally range from about 1 to 30 contiguous residues, more usually from about 1 to 10 contiguous residues, and typically from about 1 to 5 contiguous residues. N-terminal, C-terminal and internal intrasequence deletions are contemplated. Deletions may be introduced into regions of the molecule which have low homology with non-human GDNFR to modify the activity of GDNFR. Deletions in areas of substantial homology with non-human GDNFR sequences will be more likely to significantly modify GDNFR biological activity. The number of consecutive deletions typically will be selected so as to preserve the tertiary structure of the GDNFR protein product in the affected domain, e.g., cysteine crosslinking. Non-limiting examples of deletion variants include truncated GDNFR protein products lacking N-terminal or C-terminal amino acid residues. For example, one may prepare a soluble receptor by elimination of the peptide region involved in a glycosyl-phosphatidylinositol (GPI) anchorage of GDNFR receptor to the cytoplasmic membrane.

For GDNFR addition variants, amino acid sequence additions typically include N- and/or C-terminal fusions or terminal additions ranging in length from one residue to polypeptides containing a hundred or more residues, as well as internal or medial additions of single or multiple amino acid residues. Polypeptides of the invention may also include an initial methionine amino acid residue (at position-1 with respect to the first amino acid residue of the desired polypeptide). Internal additions may range generally from about 1 to 10 contiguous residues, more typically from about 1 to 5 residues, and usually from about 1 to 3 amino acid residues. Examples of N-terminal addition variants include GDNFR with the inclusion of a heterologous N-terminal signal sequence to the N-terminus of GDNFR to facilitate the secretion of mature GDNFR from recombinant host cells and thereby facilitate harvesting or bioavailability. Such signal sequences generally will be obtained from, and thus be homologous to, the intended host cell species. Additions may also include amino acid sequences derived from the sequence of other neurotrophic factors. For example, it is contemplated that a fusion protein of GDNF and GDNFR may be produced, with or without a linking sequence, thereby forming a single molecule therapeutic entity.

GDNFR substitution variants have one or more amino acid residues of the GDNFR amino acid sequence removed and a different residue(s) inserted in its place. Such substitution variants include allelic variants, which are characterized by naturally-occurring nucleotide sequence changes in the species population that may or may not result in an amino acid change. As with the other variant forms, substitution variants may involve the replacement of single or contiguous amino acid residues at one or more different locations.

Specific mutations of the GDNFR amino acid sequence may involve modifications to a glycosylation site (e.g., serine, threonine, or asparagine). The absence of glycosylation or only partial glycosylation results from amino acid substitution or deletion at any asparagine-linked glycosylation recognition site or at any site of the molecule that is modified by addition of an O-linked carbohydrate. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. A variety of amino acid substitutions or deletions at one or both of the first or third amino acid positions of a glycosylation recognition site (and/or amino acid deletion at the second position) result in non-glycosylation at the modified tripeptide sequence. Thus, the expression of appropriate altered nucleotide sequences produces variants which are not glycosylated at that site. Alternatively, the GDNFR amino acid sequence may be modified to add glycosylation sites.

One method for identifying GDNFR amino acid residues or regions for mutagenesis is called "alanine scanning mutagenesis" as described by Cunningham and Wells (Science, 244: 1081–1085, 1989). In this method, an amino acid residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions may then be refined by introducing additional or alternate residues at the sites of substitution. Thus, the target site for introducing an amino acid sequence variation is determined, alanine scanning or random mutagenesis is conducted on the corresponding target codon or region of the DNA sequence, and the expressed GDNFR variants are screened for the optimal combination of desired activity and degree of activity.

The sites of greatest interest for substitutional mutagenesis include sites where the amino acids found in GDNFR proteins from various species are substantially different in terms of side-chain bulk, charge, and/or hydrophobicity. Other sites of interest are those in which particular residues of GDNFR-like proteins, obtained from various species, are identical. Such positions are generally important for the biological activity of a protein. Initially, these sites are substituted in a relatively conservative manner. Such conservative substitutions are shown in Table 2 under the heading of preferred substitutions. If such substitutions result in a change in biological activity, then more substantial changes (exemplary substitutions) may be introduced, and/or other additions or deletions may be made, and the resulting products are screened for activity.

TABLE 2

Amino Acid Substitutions

| Original Residue | Preferred Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (R) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Conservative modifications to the amino acid sequence (and the corresponding modifications to the encoding nucleic acid sequences) are expected to produce GDNFR protein products having functional and chemical characteristics similar to those of naturally occurring GDNFR. In contrast, substantial modifications in the functional and/or chemical characteristics of GDNFR protein products may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues may be divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for a member from another class. Such substituted residues may be introduced into regions of the human GDNFR protein that are homologous with non-human GDNFR proteins, or into the non-homologous regions of the molecule.

Thus, GDNFR proteins, analogs, or derivatives thereof include, but are not limited to, those biologically active molecules containing, as a primary amino acid sequence, all or part of the amino acid sequences as depicted in FIGS. 2 and 4 (SEQ ID NOs. 2 and 4). The proteins will include altered sequences in which biologically equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. It is also contemplated that the GDNFR proteins, analogs, or fragments or derivatives thereof may be differentially modified during or after translation, e.g., by phosphorylation, glycosylation, crosslinking, acylation, proteolytic cleavage, linkage to an antibody molecule, membrane molecule or other ligand.

B. GDNFR Derivatives

Chemically modified derivatives of GDNFR or GDNFR analogs may be prepared by one of skill in the art based upon the present disclosure. The chemical moieties most suitable for derivatization include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (e.g., by osmotic pump, or, more preferably, by injection or infusion, or, further formulated for oral, pulmonary or other delivery routes), and determining its effectiveness.

Suitable water soluble polymers include, but are not limited to, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. For polyethylene glycol, the preferred molecular weight is between about 2 kDa and about 100 kDa for ease in handling and manufacturing (the term "about" indicating that in preparations of polyethylene glycol, some molecules will weigh more, some less, than the stated molecular weight). Other sizes may be used, depending on the desired therapeutic profile (e.g., the duration of sustained release desired; the effects, if any, on biological activity; the ease in handling; the degree or lack of antigenicity and other known effects of polyethylene glycol on a therapeutic protein or variant).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proporton of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. See for example, EP 0 401 384, the disclosure of which is hereby incorporated by reference (coupling PEG to G-CSF), see also Malik et al., Exp. Hematol., 20: 1028–1035, 1992 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydrl groups may also be used as a reactive group for attaching the polyethylene glycol molecule(s). For therapeutic purposes, attachment at an amino group, such as attachment at the N-terminus or lysine group is preferred. Attachment at residues important for receptor binding should be avoided if receptor binding is desired.

One may specifically desire an N-terminal chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the pKa differences between the e-amino group of the lysine residues and that of the a-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein, Polyethylene glycol propionaldehyde, containing a single reactive aldehyde, may be used.

The present invention contemplates use of derivatives which are prokaryote-expressed GDNFR, or variants thereof, linked to at least one polyethylene glycol molecule, as well as use of GDNFR, or variants thereof, attached to one or more polyethylene glycol molecules via an acyl or alkyl linkage, Pegylation may be carried out by any of the pegylation reactions known in the art. See, for example: Focus on Growth Factors, 3 (2): 4–10, 1992; EP 0 154 316, the disclosure of which is hereby incorporated by reference; EP 0 401 384; and the other publications cited herein that relate to pegylation. The pegylation may be carried out via an acylation reaction or an alkylation reaction with a reactive polyethylene glycol molecule (or an analogous reactive water-soluble polymer).

Pegylation by acylation generally involves reacting an active ester derivative of polyethylene glycol (PEG) with the GDNFR protein or variant. Any known or subsequently discovered reactive PEG molecule may be used to carry out the pegylation of GDNFR protein or variant. A preferred activated PEG ester is PEG esterified to N-hydroxysuccinimide (NHS). As used herein, "acylation" is contemplated to include without limitation the following types of linkages between the therapeutic protein and a water soluble polymer such as PEG: amide, carbamate, urethane, and the like. See Bioconjugate Chem., 5: 133–140, 1994. Reaction conditions may be selected from any of those known in the pegylation art or those subsequently developed, but should avoid conditions such as temperature, solvent, and pH that would inactivate the GDNFR or variant to be modified.

Pegylation by acylation will generally result in a poly-pegylated GDNFR protein or variant. Preferably, the connecting linkage will be an amide. Also preferably, the resulting product will be substantially only (e.g., >95%) mono, di- or tri-pegylated. However, some species with higher degrees of pegylation may be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with the GDNFR protein or variant in the presence of a reducing agent. Pegylation by alkylation can also result in poly-pegylated GDNFR protein or variant. In addition, one can manipulate the reaction conditions to favor pegylation substantially only at the a-amino group of the N-terminus of the GDNFR protein or variant (i.e., a mono-pegylated protein). In either case of monopegylation or polypegylation, the PEG groups are preferably attached to the protein via a —CH2—NH— group. With particular reference to the —CH2— group, this type of linkage is referred to herein as an "alkyl" linkage.

Derivatization via reductive alkylation to produce a monopegylated product exploits differential reactivity of different types of primary amino groups (lysine versus the N-terminal) available for derivatization. The reaction is performed at a pH which allows one to take advantage of the pKa differences between the e-amino groups of the lysine residues and that of the a-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs. In one important aspect, the present invention contemplates use of a substantially homogeneous preparation of monopolymer/GDNFR protein (or variant) conjugate molecules (meaning GDNF protein or variant to which a polymer molecule has been attached substantially only (i.e., >95%) in a single location). More specifically, if polyethylene glycol is used, the present invention also encompasses use of pegylated GDNFR protein or variant lacking possibly antigenic linking groups, and having the polyethylene glycol molecule directly coupled to the GDNFR protein or variant.

Thus, GDNFR protein products according to the present invention include pegylated GDNFR protein or variants, wherein the PEG group(s) is (are) attached via acyl or alkyl groups. As discussed above, such products may be monopegylated or poly-pegylated (e.g., containing 2–6, and preferably 2–5, PEG groups). The PEG groups are generally attached to the protein at the a- or e-amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches may be selected from among water soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1–C10 alkoxy or aryloxy derivatives thereof (see, U.S. Pat. No. 5,252,714). The polymer may be branched or unbranched. For the acylation reactions, the polymer(s) selected should have a single reactive ester group. For the present reductive alkylation, the polymer(s) selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

An exemplary water-soluble polymer for use herein is polyethylene glycol. As used herein, polyethylene glycol is meant to encompass any of the forms of PEG that have been used to derivatize other proteins, such as mono-(C1–C10) alkoxy- or aryloxy-polyethylene glycol.

In general, chemical derivatization may be performed under any suitable condition used to react a biologically active substance with an activated polymer molecule. Methods for preparing a pegylated GDNFR protein product will generally comprise the steps of (a) reacting a GDNFR protein product with polyethylene glycol (such as a reactive ester or aldehyde derivative of PEG) under conditions whereby the protein becomes attached to one or more PEG groups, and (b) obtaining the reaction product(s). In general, the optimal reaction conditions for the acylation reactions will be determined case-by-case based on known parameters and the desired result. For example, the larger the ratio of PEG:protein, the greater the percentage of poly-pegylated product.

Reductive alkylation to produce a substantially homogeneous population of mono-polymer/GDNFR protein product will generally comprise the steps of: (a) reacting a GDNFR protein or variant with a reactive PEG molecule under reductive alkylation conditions, at a pH suitable to permit selective modification of the a-amino group at the amino terminus of said GDNFR protein or variant; and (b) obtaining the reaction product(s).

For a substantially homogeneous population of monopolymer/GDNFR protein product, the reductive alkylation reaction conditions are those which permit the selective attachment of the water soluble polymer moiety to the N-terminus of GDNFR protein or variant. Such reaction conditions generally provide for pKa differences between the lysine amino groups and the a-amino group at the N-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal a-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6.

Another important consideration is the molecular weight of the polymer. In general, the higher the molecular weight of the polymer, the fewer polymer molecules may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa. The preferred average molecular weight is about 5 kDa to about 50 kDa, particularly preferably about 12 kDa to about 25 kDa. The ratio of water-soluble polymer to GDNF protein or variant will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any GDNFR protein or variant having an a-amino group at the amino terminus, and provide for a substantially homogenous preparation of monopolymer/GDNFR protein (or variant) conjugate. The term "monopolymer/GDNFR protein (or variant) conjugate" is used here to mean a composition comprised of a single polymer molecule attached to a molecule of GDNFR protein or GDNFR variant protein. The monopolymer/GDNFR protein (or variant) conjugate typically will have a polymer molecule located at the N-terminus, but not on lysine amino side groups. The preparation will generally be greater than 90% monopolymer/GDNFR protein (or variant) conjugate, and more usually greater than 95% monopolymer/GDNFR protein (or variant) conjugate, with the remainder of observable molecules being unreacted (i.e., protein lacking the polymer moiety). It is also envisioned that the GDNFR protein product may involve the preparation of a pegylated molecule involving a fusion protein or linked GDNFR and GDNF molecules.

For the present reductive alkylation, the reducing agent should be stable in aqueous solution and preferably be able to reduce only the Schiff base formed in the initial process of reductive alkylation. Suitable reducing agents may be selected from sodium borohydride, sodium cyanoborohydride, dimethylamine borane, trimethylamine borane and pyridine borane. A particularly suitable reducing agent is sodium cyanoborohydride. Other reaction parameters, such as solvent, reaction times, temperatures, etc., and means of purification of products, can be determined case-by-case based on the published information relating to derivatization of proteins with water soluble polymers (see the publications cited herein).

C. GDNFR Protein Product Pharmaceutical Compositions

GDNFR protein product pharmaceutical compositions typically include a therapeutically or prophylactically effective amount of GDNFR protein product in admixture with one or more pharmaceutically and physiologically acceptable formulation materials selected for suitability with the mode of administration. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial cerebrospinal fluid, possibly supplemented with other materials common in compositions for parenteral administration. Neutral buffered saline or saline mixed with serum albumin are further exemplary vehicles. The term "pharmaceutically acceptable carrier" or "physiologically acceptable carrier" as used herein refers to a formulation material(s) suitable for accomplishing or enhancing the delivery of the GDNFR protein product as a pharmaceutical composition.

The primary solvent in a vehicle may be either aqueous or non-aqueous in nature. In addition, the vehicle may contain other formulation materials for modifying or maintaining the pH, osmolarity, viscosity, clarity, color, sterility, stability, rate of dissolution, or odor of the formulation. Similarly, the vehicle may contain additional formulation materials for modifying or maintaining the rate of release of GDNFR protein product, or for promoting the absorption or penetration of GDNFR protein product across the blood-brain barrier.

Once the therapeutic pharmaceutical composition has been formulated, it may be stored in sterile vials as a solution, suspension, gel, emulsion, solid, or dehydrated or lyophilized powder. Such formulations may be stored either in a ready to use form or in a form (e.g., lyophilized) requiring reconstitution prior to administration.

The optimal pharmaceutical formulation will be determined by one skilled in the art depending upon the intended route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such compositions may influence the physical state, stability, rate of in vivo release, and rate of in vivo clearance of the present proteins and derivatives.

Effective administration forms, such as (1) slow-release formulations, (2) inhalant mists, or (3) orally active formulations are envisioned. The GDNFR protein product pharmaceutical composition also may be formulated for parenteral administration. Such parenterally administered therapeutic compositions are typically in the form of a pyrogen-free, parenterally acceptable aqueous solution comprising the GDNFR protein product in a pharmaceutically acceptable vehicle. One preferred vehicle is physiological saline. The GDNFR protein product pharmaceutical compositions also may include particulate preparations of polymeric compounds such as polylactic acid, polyglycolic acid, etc. or into liposomes. Hyaluronic acid may also be used, and this may have the effect of promoting sustained duration in the circulation.

A particularly suitable vehicle for parenteral injection is sterile distilled water in which the GDNFR protein product is formulated as a sterile, isotonic solution, properly preserved. Yet another preparation may involve the formulation of the GDNFR protein product with an agent, such as injectable microspheres or liposomes, that provides for the slow or sustained release of the protein which may then be delivered as a depot injection. Other suitable means for the introduction of GDNFR protein product include implantable drug delivery devices which contain the GDNFR protein product.

The preparations of the present invention may include other components, for example parenterally acceptable preservatives, tonicity agents, cosolvents, wetting agents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative. Suitable cosolvents are for example glycerin, propylene glycol and polyethylene glycol. Suitable complexing agents are for example caffeine, polyvinylpyrrolidone, beta-cyclodextrin or hydroxypropyl-beta-cyclodextrin. Suitable surfactants or wetting agents include sorbitan esters, polysorbates such as polysorbate 80, tromethamine, lecithin, cholesterol, tyloxapal and the like. The buffers can be conventional buffers such as borate, citrate, phosphate, bicarbonate, or Tris-HCl.

The formulation components are present in concentration that are acceptable to the site of administration. For example, buffers are used to maintain the composition at physiological pH or at slightly lower pH, typically within a pH range of from about 5 to about 8.

A pharmaceutical composition may be formulated for inhalation. For example, the GDNFR protein product may be formulated as a dry powder for inhalation. GDNFR protein product inhalation solutions may also be formulated in a liquefied propellant for aerosol delivery. In yet another formulation, solutions may be nebulized.

It is also contemplated that certain formulations containing GDNFR protein product are to be administered orally. GDNFR protein product which is administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional formulation materials may be included to facilitate absorption of GDNFR protein product. Diluents, flavorings, low melting point waxes, vegetable oils, lubricants, suspending agents, tablet disintegrating agents, and binders may also be employed.

Another preparation may involve an effective quantity of GDNFR protein product in a mixture with non-toxic excipients which are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional GDNFR protein product formulations will be evident to those skilled in the art, including formulations involving GDNFR protein product in combination with GDNF protein product. Techniques for formulating a variety of other sustained- or controlled-delivery means, such as liposome carriers, bio-erodible microparacles or porous beads and depot injections, are also known to those skilled in the art. See, for example, Supersaxo et al. description of controlled release porous polymeric microparticles for the delivery of pharmaceutical compositions (International Publication No. WO 93/15722; International Application No. PCT/US93/00829) the disclosure of which is hereby incorporated by reference.

D. Administration of GDNFR Protein Product

The GDNFR protein product may be administered parenterally via a variety of routes, including subcutaneous, intramuscular, intravenous, transpulmonary, transdermal, intrathecal and intracerebral delivery. In addition, protein factors that do not readily cross the blood-brain barrier may be given directly intracerebrally or otherwise in association with other elements that will transport them across the barrier. For example, the GDNFR protein product may be administered intracerebroventricularly or into the brain or spinal cord subarachnoid space. GDNFR protein product may also be administered intracerebrally directly into the brain parenchyma. GDNFR protein product may be administered extracerebrally in a form that has been modified chemically or packaged so that it passes the blood-brain barrier, or with one or more agents capable of promoting penetration of GDNFR protein product across the barrier. For example, a conjugate of NGF and monoclonal anti-transferrin receptor antibodies has been shown to be transported to the brain via binding to transferrin receptors.

To achieve the desired level of GDNFR protein product, repeated daily or less frequent injections may be administered, or GDNFR protein product may be infused continuously or periodically from a constant- or programmable-flow implanted pump. Slow-releasing implants containing the neurotrophic factor embedded in a biodegradable polymer matrix can also deliver GDNFR protein product. The frequency of dosing will depend on the pharmacokinetic parameters of the GDNFR protein product as formulated, and the route and site of administration.

Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art and is within the ambit of tasks routinely performed by them. Appropriate dosages may be ascertained through use of appropriate dose-response data.

The final dosage regimen involved in a method for treating a specific injury or condition will be determined by the attending physician. Generally, an effective amount of the present GDNFR polypeptides will be determined by considering various factors which modify the action of drugs, e.g. the age, condition, body weight, sex and diet of the patient, the severity of any infection, time of administration and other clinical factors. See, Remington's Pharmaceutical Sciences, supra, at pages 697–773, herein incorporated by reference. It is contemplated that if GDNFR is used to enhance GDNF action, then the GDNFR dose is selected to be similar to that required for GDNF therapy; if GDNFR is used to antagonize GDNF action, then the GDNFR dose would be several many times the GDNF dose. Dosing may be one or more times daily, or less frequently, and may be in conjunction with other compositions as described herein. It should be noted that the present invention is not limited to the dosages recited herein.

It is envisioned that the continuous administration or sustained delivery of GDNFR protein products may be advantageous for a given treatment. While continuous administration may be accomplished via a mechanical means, such as with an infusion pump, it is contemplated that other modes of continuous or near continuous administration may be practiced. For example, chemical derivatization or encapsulation may result in sustained release forms of the protein which have the effect of continuous presence in the bloodstream, in predictable amounts, based on a determined dosage regimen. Thus, GDNFR protein products include proteins derivatized or otherwise formulated to effectuate such continuous administration. Sustained release forms of the GDNFR protein products will be formulated to provide the desired daily or weekly effective dosage.

It is further contemplated that the GDNFR protein product may be administered in a combined form with GDNF. Alternatively, the GDNFR and GDNF protein products may be administered separately, either sequentially or simultaneously.

GDNFR protein product of the present invention may also be employed, alone or in combination with other growth factors in the treatment of nerve disease. In addition, other factors or other molecules, including chemical compositions, may be employed together with a GDNFR protein product. In the treatment of Parkinson's Disease, it is contemplated that GDNFR protein product be used by itself or in conjunction with the administration of Levodopa, wherein the GDNFR would enhance the activity of endogenous GDNF and thereby enhance the neuronal uptake of the increased concentration of dopamine.

As stated above, it is also contemplated that additional neurotrophic or neuron nurturing factors will be useful or necessary to treat some neuronal cell populations or some types of injury or disease. Other factors that may be used in conjunction with GDNFR or a combination of GDNFR and GDNF include, but are not limited to: mitogens such as insulin, insulin-like growth factors, epidermal growth factor, vasoactive growth factor, pituitary adenylate cyclase activating polypeptide, interferon and somatostatin; neurotrophic factors such as nerve growth factor, brain derived neurotrophic factor, neurotrophin-3, neurotrophin-4/5, neurotrophin-6, insulin-like growth factor, ciliary neurotrophic factor, acidic and basic fibroblast growth factors, fibroblast growth factor-5, transforming growth factor-$\beta$, cocaine-amphetamine regulated transcript (CART); and other growth factors such as epidermal growth factor, leukemia inhibitory factor, interleukins, interferons, and colony stimulating factors; as well as molecules and materials which are the functional equivalents to these factors.

GDNFR Protein Product Cell Therapy and Gene Therapy

GDNFR protein product cell therapy, e.g., intracerebral implantation of cells producing GDNFR protein product, is also contemplated. This embodiment would involve implanting into patients cells capable of synthesizing and secreting a biologically active form of GDNFR protein product. Such GDNFR protein product-producing cells may be cells that are natural producers of GDNFR protein product or may be recombinant cells whose ability to produce GDNFR protein product has been augmented by transformation with a gene encoding the desired GDNFR protein product. Such a modification may be accomplished by means of a vector suitable for delivering the gene as well as promoting its expression and secretion. In order to minimize a potential immunological reaction in patients being administered a GDNFR protein product of a foreign species, it is preferred that the natural cells producing GDNFR protein product be of human origin and produce human GDNFR protein product. Likewise, it is preferred that the recombinant cells producing GDNFR protein product be transformed with an expression vector containing a gene encoding a human GDNFR protein product.

Implanted cells may be encapsulated to avoid infiltration of surrounding tissue. Human or non-human animal cells may be implanted in patients in biocompatible, semipermeable polymeric enclosures or membranes that allow release of GDNFR protein product, but that prevent destruction of the cells by the patient's immune system or by other detrimental factors from the surrounding tissue. Alternatively, the patient's own cells, transformed to produce GDNFR protein product ex vivo, could be implanted directly into the patient without such encapsulation.

Techniques for the encapsulation of living cells are familiar to those of ordinary skill in the art, and the preparation of the encapsulated cells and their implantation in patients may be accomplished without undue experimentation. For example, Baetge et al. (International Publication No. WO 95/05452; International Application No. PCT/US94/09299 the disclosure of which is hereby incorporated by reference) describe biocompatible capsules containing genetically engineered cells for the effective delivery of biologically active molecules. In addition, see U.S. Pat. Nos. 4,892,538, 5,011,472, and 5,106,627, each of which is specifically incorporated herein by reference. A system for encapsulating living cells is described in PCT Application WO 91/10425 of Aebischer et al., specifically incorporated herein by reference. See also, PCT Application WO 91/10470 of Aebischer et al., Winn et al., Exper. Neurol., 113:322–329, 1991, Aebischer et al., Exper. Neurol., 111:269–275, 1991; Tresco et al., ASAIO, 38:17–23, 1992, each of which is specifically incorporated herein by reference.

In vivo and in vitro gene therapy delivery of GDNFR protein product is also envisioned. In vitro gene therapy may be accomplished by introducing the gene coding for GDNFR protein product into targeted cells via local injection of a nucleic acid construct or other appropriate delivery vectors. (Hefti, J. Neurobiol,. 25:1418–1435, 1994). For example, a nucleic acid sequence encoding a GDNFR protein product may be contained in an adeno-associated virus vector for delivery into the targeted cells (e.g., Johnson, International Publication No. WO 95/34670; International Application No. PCT/US95/07178 the disclosure of which is hereby incorporated by reference). Alternative viral vectors include, but are not limited to, retrovirus, adenovirus, herpes simplex virus and papilloma virus vectors. Physical transfer, either in vivo or ex vivo as appropriate, may also be achieved by liposome-mediated transfer, direct injection (naked DNA), receptor-mediated transfer (ligand-DNA complex), electroporation, calcium phosphate precipitation or microparticle bombardment (gene gun).

It is also contemplated that GDNFR protein product gene therapy or cell therapy can further include the delivery of GDNF protein product. For example, the host cell may be modified to express and release both GDNFR protein product and GDNF protein product. Alternatively, the GDNFR and GDNF protein products may be expressed in and released from separate cells. Such cells may be separately introduced into the patient or the cells may be contained in a single implantable device, such as the encapsulating membrane described above.

It should be noted that the GDNFR protein product formulations described herein may be used for veterinary as well as human applications and that the term "patient" should not be construed in a limiting manner. In the case of veterinary applications, the dosage ranges may be determined as described above.

EXAMPLES

Example 1

Identification of Cells Expressing High Affinity GDNF Binding Sites

Expression cloning involved the selection of a source of mRNA which is likely to contain significant levels of the target transcript. Retina photoreceptor cells were identified as responsive to GDNF at very low concentrations, suggesting the existence of a functional, high affinity receptor. To confirm that rat photoreceptor cells did express a high affinity receptor for GDNF, [$^{125}$I]GDNF binding and photographic emulsion analysis were carried out.

Rat Retinal Cell Cultures

The neural retinas of 5-day-old C57B1/6 mouse pups or 3-day-old Sprague-Dawley rat pups (Jackson Laboratories, Bar Harbor, Mass.) were carefully removed and dissected free of the pigment epithelium, cut into 1 mm$^2$ fragments and placed into ice-cold phosphate-buffered saline (PBS). The retinas were then transferred into 10 mL of Hank's balanced salt solution (HBSS) containing 120 units papain and 2000 units DNAase and incubated for 20 minutes at 37° C. on a rotary platform shaker at about 200 rpm. The cells were then dispersed by trituration through fire-polished Pasteur pipettes, sieved through a 20 µm Nitex nylon mesh and centrifuged for five minutes at 200×g. The resulting cell pellet was resuspended into HBSS containing 1% ovalbumin and 500 units DNAase, layered on top of a 4% ovalbumin solution (in HBSS) and centrifuged for 10 minutes at 500×g. The final pellet was resuspended in complete culture medium (see below), adjusted to about 15,000 cells/mL, and seeded in 90 µl aliquots into tissue culture plates coated with polyornithine and laminin as previously described (Louis et al., Journal Of Pharmacology And Experimental Therapeutics, 262, 1274–1283, 1992).

The culture medium consisted of a 1:1 mixture of Dulbecco's Modified Eagle's Medium (DMEM) and F12 medium, and was supplemented with 2.5% heat-inactivated horse serum (Hyclone, Logan, Utah), B27 medium supplement (GIBCO, Grand Island, N.Y.), D-glucose (final concentration: 5mg/mL), L-glutamine (final concentration: 2 mM), 20 mM HEPES, bovine insulin and human transferrin (final concentrations: 2.5 and 0.1 mg/mL, respectively).

Immunocytochemical Identification of Photorecegtors

Photoreceptors were identified by immunostaining for arrestin, a rod-specific antigen. Cultures of photoreceptors were fixed for 30 minutes at room temperature with 4% paraformaldehyde in PBS, pH 7.4, followed by three washes in PBS. The fixed cultures were then incubated in Superblock blocking buffer (Pierce, Rockford, Ill.), containing 1% Nonidet P-40 to increase the penetration of the antibodies.

The anti-arrestin antibodies (polyclonal rabbit antibody against the synthetic peptide sequence of arrestin: Val-Phe-Glu-Glu-Phe-Ala-Arg-Gln-Asn-Leu-Lys-Cys) (SEQ ID NO:35) were then applied at a dilution of between 1:2000 in the same buffer, and the cultures were incubated for one hour at 37° C. on a rotary shaker. After three washes with PBS, the cultures were incubated for one hour at 37° C. with goat-anti-rabbit IgG (Vectastain kit from Vector Laboratories, Burlingame, Calif.) at a 1:500 dilution. After three washes with PBS, the secondary antibodies were then labeled with an avidin-biotin-peroxidase complex diluted at 1:500 (45 minutes at 37° C.). After three more washes with PBS, the labeled cell cultures were reacted for 5–20 minutes in a solution of 0.1 M Tris-HCl, pH 7.4, containing 0.04% 3',3'-diaminobenzidine-(HCl)4, 0.06 percent $NiCl_2$ and 0.02 percent hydrogen peroxide. Based on arrestin-immunoreactivity, about 90% of the cells in the cultures were rod photoreceptors.

The survival of photoreceptors was determined by examination of arrestin-stained cultures with bright-light optics at 200× magnification. The number of arrestin-positive photoreceptors was counted in one diametrical 1×6 mm strip, representing about 20 percent of the total surface area of a 6 mm-well. Viable photoreceptors were characterized as having a regularly-shaped cell body, with a usually short axon-like process. Photoreceptors showing signs of degeneration, such as having irregular, vacuolated perikarya or fragmented neurites, were excluded from the counts (most of the degenerating photoreceptors, however, detached from the culture substratum). Cell numbers were expressed either as cells/6-mm well.

Cultured rat retinal cells enriched for photoreceptors (10,000/6-mm well) were treated with human recombinant GDNF (ten-told serial dilutions ranging from 10 ng/mL to 1 pg/mL). The cultures were fixed after six days and immunostained for arrestin, a rod photoreceptor-specific antigen. In cultures that were not treated with GDNF, the number of photoreceptors declined steadily over time to reach about 25 percent of the initial number after six days in culture. Treatment of the cultures with GDNF resulted in an about two-fold higher number of viable arrestin-positive photoreceptors after six days in culture. The effect of GDNF was maximal at about 200 pg/mL, with an $ED_{50}$ of about 30 pg/mL. In addition to promoting photoreceptor survival, the addition of the GDNF also stimulated the extension of their axon-like process, thereby demonstrating an effect on the morphological development of the photoreceptors (mean neurite length of photoreceptors in GDNF: 68 μm, compared to 27±18 μm in control cultures).

In order to confirm that rat retinal cells express high affinity GDNF receptors, [$^{125}$I]GDNF binding and photographic emulsion analysis were carried out. Post-natal rat photoreceptor cells were seeded on plastic slide flaskettes (Nunc) at a density of 2800 cells/mm2, three to four days before the experiments. The cells were washed once with ice-cold washing buffer (Dulbecco's Modified Eagle's Medium (DMEM) containing 25 mM N-2-hydroxyethylpiperazine-N'-2-ethanesulfonic acid (HEPES), pH 7.5). For competitive binding, the cells were incubated with various concentrations of [$^{125}$I]GDNF in binding buffer (DMEM containing 25 mM HEPES, pH 7.5, and 2 mg/mL of bovine serum albumin (BSA)) in the presence or absence of 500 nM unlabeled GDNF at 4° C. for four hours. Cells were washed four times with ice-cold washing buffer, lysed in 1 M NaOH and the radioactivity associated with the cells was determined in a gamma counter. A significant amount of [$^{125}$I]GDNF bound to the photoreceptor cells even at low ligand concentrations (as low as 30 pM), and this binding was inhibited completely by the presence of excess unlabeled GDNF.

For photographic emulsion detection, cells were incubated with 50 pM of [$^{125}$I]GDNF in binding buffer in the presence or absence of 500 nM unlabeled GDNF at 4° C. for four hours. Cells were washed six times with ice-cold washing buffer, fixed with 2.5% glutaraldehyde and dehydrated sequentially with 50% and 70% ethanol, and dipped in NTB-2 photographic emulsion (Eastman Kodak, Rochester N.Y.). After five days of exposure, the slides were developed and examined. The photographic emulsion analysis demonstrated the association of [$^{125}$I]GDNF to some of the photoreceptor cells, thereby indicating the presence of a receptor for GDNF. This association, however, was efficiently blocked by the addition of unlabeled GDNF.

Example 2

Expression Cloning of a GDNFR from Photoreceptor Cells

Rat photoreceptor cells were selected as a possible source of a high affinity receptor for GDNF based upon their cell surface binding of radiolabeled GDNF and their ability to respond to very low concentrations of the ligand, as described in Example 1. In order to identify the receptor, a size-selected cDNA library of approximately 50,000 independent clones was constructed using a mammalian expression vector (a derivative of pSR, Takebe et al., 1988 supra) and mRNA isolated from cultured post-natal rat photoreceptor cells, by the methods described below. The library was divided into pools of approximately 1,500 to 2,000 independent clones and screened using an established expression cloning approach (Gearing et al., EMBO Journal, 8, 3667–3676, 1989). Plasmid DNA representing each pool of the library was prepared and transfected into COS7 cells grown on plastic microscope slide flaskettes (Nunc, Naperville, Ill.).

The transfected cells were treated with [$^{125}$I]GDNF, fixed with glutaraldehyde, dehydrated, and dipped in photographic emulsion for autoradiography. Following exposure for five days, the slides were developed and examined for the presence of cells covered by silver grains which indicated the binding of [$^{125}$I]GDNF to the cell surface as a result of the cell's expression of a receptor for GDNF. EGF receptor transfected cells treated with [$^{125}$I]EGF were used as a positive control.

One of the 27 pools (F8-11) screened in this manner exhibited 19 positive cells following transfection. Thus, a single cDNA library pool was identified which contained a cDNA clone that expressed GDNFR. This pool was divided into 60 smaller subpools of 100 clones/pool which were rescreened by the same procedure described above. Five of these pools were identified as positive and two of the five pools were further subdivided to yield single clones responsible for the GDNF binding activity. Transfection of plasmid DNA from the single clones into COS7 cells resulted in the binding of [$^{125}$I]GDNF to approximately 15% of the cells. This binding was specifically inhibited by competition with excess unlabeled GDNF.

Construction of Expression cDNA Libraries

Rat retinal cells were harvested from postnatal day 3–7 rats and seeded into culture dishes coated with laminin and polyornithine at a density of approximately 5700 cells/mm$^2$. After 3–4 days in culture, the population was estimated to contain approximately 80% photoreceptor cells. Total RNA was prepared from this culture by standard methods, and Poly A+RNA was purified using a polyA-tract kit (Promega, Madison, Wis.). A cDNA library was constructed from the rat photoreceptor poly A+RNA using the Gibco Superscript Choice System (Gibco/BRL, Gaithersburg, Md.). Two micrograms of poly A+RNA were mixed with 50 ng of random hexamers, heated to 70° C. for 10 minutes and then quick-chilled on ice. First stand synthesis was carried out with 400U Superscript II RT at 37° C. for one hour. Second strand synthesis was performed in the same tube after the addition of dNTPs, 10U of *E. coli* DNA ligase, 40U of *E. coli* DNA polymerase I, and 2U of *E. coli* RNase H. After two hours at 16° C., the cDNA ends were blunted by treatment with 10U of T4 polymerase for an additional five minutes at 16° C. Following isopropanol precipitation, EcoRI cloning sites were added to the cDNA by ligation overnight with 10 µg of unphosphorylated EcoRI adapter oligonucleotides.

The EcoRI adapted cDNA was then phosphorylated and applied to a Sephacryl S-500 HR size fractionation column. Following loading, the column was washed with 100 µl aliquots of TEN buffer (10 mM Tris-HCl pH 7.5, 0.1 mM EDTA, 25 mM NaCl), and 30 µl fractions were collected. Fractions 6 through 8, which contained approximately 34 ng of high molecular weight cDNA, were pooled and precipitated. The recovered EcoRI-adapted cDNA was ligated overnight with 50 ng of EcoRI cut vector pBJ5. Aliquots of the ligation mix containing about 15 ng cDNA each were transformed into competent cells (*E. coli* strain DH10B; GIBCO/BRL, Gaithersburg, Md.) by electroporation. The transformation mixture was titered and then plated on 27 Amp/LB plates at a density of 1500 colonies/plate. Colonies were scraped from each plate and collected into 10 mL of Luria broth (LB) to make 27 pools of 1500 independent clones each. A portion of the cells from each pool was frozen in glycerol and the remainder was used to isolate plasmid DNA using a Qiagen tip-500 kit (Qiagen Inc., Chatsworth, Calif.).

COS Cell Transfection and Photographic Emulsion Analysis

COS7 cells were seeded (220,000 cells/slide) on plastic slide flaskettes (Nunc) coated with ProNectin (10 µg/mL in phosphate buffered saline (PBS)) one day before transfection. For transfection, 700 µl of Opti MEMI (GIBCO/BRL, Gaithersburg, Md.) containing 2 µg cDNA was mixed gently with 35 µl of DEAE Dextran solution (10 mg/mL, Sigma, St. Louis, Mo.) in an Eppendorf tube. Cells were washed twice with PBS and incubated with the transfection mix for 30 minutes at 37° C. in a 5% $CO_2$ atmosphere. Following incubation, 3 mL of DMEM media containing 10% fetal calf serum (FCS) and 80 nM Chloroquine (Sigma, St. Louis, Mo.) were added to each flaskette. Cells were further incubated for 3.5 hours, shocked with 10% dimethylsulfoxide in DMEM at room temperature for two minutes, washed once with PBS, and allowed to grow in DMEM containing 10% FCS. After 48 hours, the transfected COS7 cells were washed once with ice-cold washing buffer (DMEM containing 25 mM HEPES, pH 7.5) and incubated in ice-cold binding buffer (DMEM containing 25 mM HEPES, pH 7.5 and 2 mg/mL BSA) supplemented with 50 pM [$^{125}$I]GDNF at 4° C. for four hours. Cells were washed six times in ice-cold washing buffer, fixed with 2.5% glutaraldehyde at room temperature for five minutes, dehydrated sequentially with 50% and 70% ethanol, and then dipped in NTB-2 photographic emulsion (Eastman Kodak). After 4–5 day exposure at 4° C. in dark, the slides were developed and screened by bright-field and dark-field microscopy.

Subdivision of Positive Pools

A single pool was identified which contained a putative GDNF receptor clone. Clones from this pool were plated on 60 plates at a density of 100 colonies/plate. Cells were scraped from each plate, collected in LB, and allowed to grow for 4–5 hours at 37° C. Frozen stocks and DNA preparations were made from each pool, as before, to generate 60 subpools containing 100 independent clones each. Two of these 60 subpools were identified as positive by the method described above, and clones from those pools were plated at low density to allow isolation of single colonies. Single colonies (384) were picked from each of the two subpools and grown for six hours in 200 µl LB in 96-well plates. In order to select single clones expressing GDNFR, the four 96-well plates were arrayed into a single large matrix consisting of 16 rows and 24 columns. Cells from the wells in each row and in each column were combined to yield a total of 40 mixtures. These mixtures were grown overnight in 10 mL LB/Amp (100 µg/mL), and DNA was prepared using a Qiagen tip-20 kit. When analyzed for putative GDNF receptor clones, three row mixtures and three column mixtures gave positive signals, suggesting nine potentially positive single clones. DNA from each of the potentially positive single clones was prepared and digested with EcoRI and PstI. DNA from three of the nine single clones exhibited identical restriction patterns while the other six were unrelated, suggesting that the three represented the authentic clones containing GDNFR.

Example 3

DNA Sequencing and Sequence Analysis

DNA from positive, single clones was prepared and sequenced using an automated ABI373A DNA sequencer (Perkin/Elmer Applied Biosystems, Santa Clara, Calif.) and dideoxy-dye-terminators, according to manufacturer's instructions. Comparison of GDNF receptor sequence with all available public databases was performed using the FASTA (Pearson and Lipman, Proceedings Of The National Academy Of Sciences U.S.A., 85, 2444–2448, 1988) program algorithm as described in the University of Wisconsin Genetics Computer Group package (Program Manual for the Wisconsin Package, Version 8, September 1994, Genetics Computer Group, Madison, Wis.).

Sequence Characterization of the Rat GDNFR

Plasmid DNA from the clones described in Example 2, above, was prepared and submitted for DNA sequence analysis. Nucleotide sequence analysis of the cloned 2138 bp rat cDNA revealed a single large open reading frame encoding a translation protein of 468 amino acid residues (FIG. 3).

The coding sequence is flanked by a 5'-untranslated region of 301 bp and a 3'-untranslated region of 430 bp that does not contain a potential polyadenylation site. The presence of an in-frame stop codon upstream of the first ATG at base pair 302 and its surrounding nucleotide context indicate that this methionine codon is the most likely translation initiator site (Kozak, Nucleic Acids Research. 15, 8125–8148, 1987).

No polyadenylation signal is found in the 430 nucleotides of 3' untranslated sequence in the rat cDNA clone. This is not surprising, since the Northern blot data shows the shortest mRNA transcripts to be approximately 3.6 kb.

The GDNFR polypeptide sequence has an N-terminal hydrophobic region of approximately 19 residues (methionine-1 to alanine-19, FIG. 3) with the characteristics of a secretory signal peptide (von Heijne, Protein Sequences And Data Analysis. 1, 41–42, 1987; von Heijne, Nucleic Acids Research. 14, 4683–4690, 1986). No internal hydrophobic domain that could serve as a transmembrane domain was found. Instead, a carboxy-terminal hydrophobic region of 21 residues (leucine-448 to serine-468 in FIG. 3) is present and may be involved in a glycosylphosphatidylinositol (GPI) anchorage of the receptor to the cytoplasmic membrane. Except for the presence of three potential N-linked glycosylation sites, no conserved sequence or structural motifs were found. The protein is extremely rich in cysteine (31 of the 468 amino acid residues) but their spacing is not shared with that of cysteine-rich domains found in the extracellular portions of known receptors.

The GDNFR sequence was compared to sequences in available public databases using FASTA. The search did not reveal significant homology to other published sequences. Once the rat cDNA clone was obtained, it was radiolabeled and used to probe a cDNA library prepared from human brain substantia nigra as described below in Example 5.

Example 4

GDNF Binding to Cells Expressing GDNFR

A binding assay was performed in accordance with an assay method previously described by Jing et al. (Journal Of Cell Biology, 110, 283–294, 1990). The assay involved the binding of [$^{125}$I]GDNF to rat photoreceptor cells, COS7 cells or 293T cells which had been transfected to express GDNFR. Recombinant GDNFR expressed on the surface of 293T cells was able to bind GDNF specifically and with an affinity comparable to that observed for GDNF binding sites on rat retinal cells.

Rat photoreceptor cells were prepared as described in Example 1, above, and seeded at a density of $5.7 \times 10^5$ cells/cm$^2$ two to three days before the assay in 24-well Costar tissue culture plates pre-coated with polyornithine and laminin. COS7 cells were seeded at a density of $2.5 \times 10^4$ cells/cm$^2$ one day before the assay and transfected with 10–20 μg of plasmid DNA using the DEAE-dextran-chloroquine method (Aruffo and Seed, Proceedings Of The National Academy Of Sciences U.S.A., 84, 8573–8577, 1987). Cells from each dish were removed and reseeded into 30 wells of 24-well Costar tissue culture plates 24 hours following the transfection, and allowed to grow for an additional 48 hours. Cells were then left on ice for 5 to 10 minutes, washed once with ice-cold washing buffer and incubated with 0.2 mL of binding buffer containing various concentrations of [$^{125}$I]GDNF with or without unlabeled GDNF at 4° C. for four hours. Cells were washed four times with 0.5 mL ice-cold washing buffer and lysed with 0.5 mL of 1 M NaOH. The lysates were counted in a 1470 Wizard Automatic Gamma Counter.

For some binding experiments, transiently transfected 293T cells were used (see below for 293T cell transfection). Two days following transfection, cells were removed from dishes by 2x versine. Cells were pelleted, washed once with ice-cold binding buffer and resuspended in ice-cold binding buffer at a density of $3 \times 10^5$ cells/mL. The cell suspension was divided into aliquots containing $1.5 \times 10^5$ cell/sample. Cells were then pelleted and incubated with various concentrations of [$^{125}$I]GDNF in the presence or absence of 500 nM of unlabeled GDNF at 4° C. for four hours with gentle agitation. Cells were washed four times with ice-cold washing buffer and resuspended in 0.5 mL washing buffer. Two 0.2 mL aliquots of the suspension were counted in a gamma counter to determine the amount of [$^{125}$I]GDNF associated with the cells.

In all assays, nonspecific binding was determined by using duplicate samples, one of which contained 500 nM of unlabeled GDNF. The level of nonspecific binding varied from 10% to 20% of the specific binding measured in the absence of unlabeled GDNF and was subtracted from the specific binding. The assays demonstrated that cells did not bind GDNF unless the cell had been transfected with the GDNFR cDNA clone.

Example 5

Tissue Distribution of GDNFR mRNA

The pattern of expression of GDNFR mRNA in embryonic mouse, adult mouse, rat, and human tissues was examined by Northern blot analysis. The cloned rat GDNFR cDNA was labeled using the Random Primed DNA Labeling Kit (Boehringer Mannheim, Indianapolis, Ind.) according to the manufacturer's procedures. Rat, mouse, and human tissue RNA blots (purchased from Clontech, Palo Alto, Calif.) were hybridized with the probe and washed using the reagents of the ExpressHyb Kit (Clontech) according to the manufacturer's instructions.

Tissue Northern blots prepared from adult rat, mouse, and human tissues indicated that GDNFR mRNA is most highly expressed in liver, brain, and kidney. High mRNA expression was also detected in lung, with lower or non-detectable amounts in spleen, intestine, testis, and skeletal muscle. In blots made from mRNA isolated from mouse embryo, expression was undetectable at embryonic day 7, became apparent at day E11, and was very high by day E17. GDNFR mRNA was expressed in tissue isolated from several sub-regions of adult human brain at relatively equal levels. Expression of GDNFR mRNA in human adult brain showed little specificity for any particular region.

In most tissues, transcripts of two distinct sizes were present. In mouse and human tissues, transcripts of 8.5 and 4.4 kb were found, while in rat the transcripts were 8.5 and 3.6 kb. The relative amounts of the larger and smaller transcripts varied with tissue type, the smaller transcript being predominant in liver and kidney and the larger being more abundant in brain. The binding of GDNF to 293T cells transfected with a GDNFR cDNA clone in the pBKRSV vector was examined by Scatchard analysis. Two classes of binding sites were detected, one with a binding affinity in the low picomolar range and another with an affinity of about 500 pM.

Example 6

Recombinant Human GDNFR

An adult human substantia nigra cDNA library (5'-stretch plus cDNA library, Clontech, Palo Alto, Calif.) cloned in bacteriophage gt10 was screened using the rat GDNFR cDNA clone of Example 1 as a probe. The probe was labeled with [$^{32}$P]-dNTPs using a Random Primed DNA Labeling Kit (Boehringer Mannheim, Indianapolis, Ind.) according to the manufacturer's instructions. Approximately $1.2 \times 10^6$ gt10 phage from the human substantia nigra cDNA library were plated on 15 cm agarose plates and replicated on duplicate nitrocellulose filters. The filters were then screened by hybridization with the radiolabeled probe. The filters were prehybridized in 200 mL of 6×SSC, 1×Denhardts, 0.5% SDS, 50 μg/mL salmon sperm DNA at 55° C. for 3.5 hours. Following the addition of $2 \times 10^8$ cpm of the radiolabeled probe, hybridization was continued for 18 hours. Filters were then washed twice for 30 minutes each in 0.5×SSC, 0.1% SDS at 55° C. and exposed to X-ray film overnight with an intensifying screen.

Five positive plaques were isolated whose cDNA inserts represented portions of the human GDNFR cDNA. In comparison to the nucleic acid sequence of rat GDNFR depicted in FIG. 3 (bp 0 through 2140), the five human GDNFR clones were found to contain the following sequences:

TABLE 3

| Clone 2   | 1247 through 2330 | (SEQ ID NO:21) |
|-----------|-------------------|----------------|
| Clone 9   | 1270 through 2330 | (SEQ ID NO:23) |
| Clone 21-A | −235 through 1692 | (SEQ ID NO:9)  |
| Clone 21-B | −237 through 1692 | (SEQ ID NO:11) |
| Clone 29  | 805 through 2971  | (SEQ ID NO:15) |

An alignment and comparison of the sequences, as depicted in FIG. 5, provided a consensus sequence for human GDNFR. The translation product predicted by the human cDNA sequence consists of 465 amino acids and is 93% identical to rat GDNFR. SEQ ID NO:5 to SEQ ID NO:8 are nucleotide sequences and coding regions for clones shown in FIG. 5. SEQ ID NO:10 represents the amino acid sequence corresponding to SEQ ID NO:9. SEQ ID NO:12 represents the amino acid sequence corresponding to SEQ ID NO:11. SEQ ID NO:13 is a nucleotide sequence of another clone shown in FIG. 5 and SEQ ID NO:14 is the amino acid sequence corresponding to that part of the coding region in SEQ ID NO:13. Similarly, SEQ ID NO:16 represents the amino acid sequence of SEQ ID NO:15, another clone shown in FIG. 5. SEQ ID NOS:17, 19, 21 and 23 are the nucleotide sequence and coding regions of other clones shown in FIG. 5. SEQ ID NOS:18, 20, 22 and 24 represent the coding region from each of these additional clones.

To generate a human cDNA encoding the full length GDNFR, portions of clones 21B and 2 were spliced together at an internal BglII site and subcloned into the mammalian expression vector pBKRSV (Stratagene, La Jolla, Calif.).

Recombinant human GDNFR expression vectors may be prepared for expression in mammalian cells. As indicated above, expression may also be in non-mammalian cells, such as bacterial cells. The nucleic acid sequences disclosed herein may be placed into a commercially available mammalian vector (for example, CEP4, Invitrogen) for expression in mammalian cells, including the commercially available human embryonic kidney cell line, "293". For expression in bacterial cells, one would typically eliminate that portion encoding the leader sequence (e.g., nucleic acids 1–590 of FIG. 1). One may add an additional methionyl at the N-terminus for bacterial expression. Additionally, one may substitute the native leader sequence with a different leader sequence, or other sequence for cleavage for ease of expression.

EXAMPLE 7

Soluble GDNFR Constructs

Soluble human GDNFR protein products were made. The following examples provide four different forms, differing only at the carboxy terminus, indicated by residue numbering as provided in FIG. 2. Two are soluble forms truncated at different points just upstream from the hydrophobic tail and downstream from the last cysteine residue. The other two are the same truncations but with the addition of the "FLAG" sequence, an octapeptide to which a commercial antibody is available (Eastman Kodak). The FLAG sequence is H2N— DYKDDDDK (SEQ ID NO:36)— COOH.

Method

Lambda phage clone #21, containing nearly the entire coding region of human GDNFR, was digested with EcoRI to excise the cDNA insert. This fragment was purified and ligated into EcoRI cut pBKRSV vector (Stratagene, La Jolla, Calif.) to produce the clone 21-B-3/pBKRSV. Primers 1 and 2 as shown below were used in a PCR reaction with the human GDNFR clone 21-B-3/pBKRSV as template. PCR conditions were 94° C., five minutes followed by 25 cycles of 940C, one minute; 55° C., one minute; 72° C., two minutes and a final extension of five minutes at 72° C. This produced a fragment consisting of nucleotides 1265–1868 of the human GDNFR clone plus a termination codon and Hind III restriction site provided by primer 2. This fragment was digested with restriction enzymes Hind III (contained in primer 2) and BglII (position 1304 in human GDNFR), and the resulting 572 nucleotide fragment was isolated by gel electrophoresis. This fragment contained the hGDNFR-coding region from isoleucine-255 to glycine-443. A similar strategy was used with primers 1 and 3 to produce a fragment with BglII and HindIII ends which coded for isoleucine-255 to proline-446. Primers 4 and 5 were designed to produce fragments coding for the same regions of hGDNFR and primers 1 and 3, but with the addition of the Flag peptide coding sequence (IBI/Kodak, New Haven, Conn.). The Flag peptide sequence consists of eight amino acids (H2N-Asp-Tyr-Lys-Asp-Asp-Asp-Asp-Lys (SEQ ID NO:36)—COOH) to which antibodies are commercially available. Primers 1 and 4 or 1 and 5 were used in PCR reactions with the same template as before, and digested with HindIII and BglII as before. This procedure produced fragments coding for isoleucine-255 to glycine-443 and isoleucine-255 to proline-446, but with the addition of the Flag peptide at their carboxy termini.

Primers 1) 5'-CTGTTTGAATTTGCAGGACTC-3' (SEQ ID NO:30)

2) 5'-CTCCTCTCTAAGCTTCTAACCACAGCTTGG AGGAGC-3' (SEQ ID NO:31)

3) 5'-CTCCTCTCTAAGCTTCTATGGGCTCAGACC ACAGCTT-3' (SEQ ID NO:32)

4) 5'-CTCCTCTCTAAGCTTCTACTTGTCATCGTC GTCCTTGTAGTCACCACAGCTTGGA GAGC-3' (SEQ ID NO:33)

5) 5'-CTCCTCTCTAAGCTTCTACTTGTCATCGTCG TCCTTGTAGTCTGGCTCAGACCAC AGCTT-3' (SEQ ID NO:34)

All four fragments, produced as described above, were transferred back into 21B3/pBKRSV. The 21B3/pBKRSV clone was digested with BglII and HindIII, and treated with calf intestinal alkaline phosphatase (CIAP). The large fragment containing the vector and the human GDNFR coding region up to the BglII site was gel purified and extracted from gel. Each of the four BglII/HindIII fragments produced as described above were ligated into this vector resulting in the following constructs in the pBKRSV vector:

TABLE 4

| 1) GDNFR/gly-443/ pBKRSV | hGDNFR terminating at glycine 443, followed by stop codon |
| 2) GDNFR/pro-446/ pBKRSV | hGDNFR terminating at proline 446, foilowed by stop codon |
| 3) GDNFR/gly-443/ Flag/pBKRSV | hGDNFR tenninating at glycine 443 with C-term Flag tag, followed by stop codon |
| 4) GDNFR/pro-446/ Flag/pBKRSV | hGDNFR terminating at proline 446 with C-term Flag tag, followed by stop codon |

Correct construction of all clones was confirmed by DNA sequencing. Inserts from the pBKRSV clones were transferred to other expression vectors using enzyme sites present in the pBKRSV polylinker sequence as described below. Soluble GDNFRs (e.g., sGDNFR/gly and sGDNFR/pro) have also been transferred into vectors for transient expression and into pDSR-2 for stable expression in CHO cells.

pDSRα2+PL Clones

The appropriate pBKRSV clone is digested with XbaI and SalI. The insert is ligated to pDSRα2+PL cut with the same enzymes and treated with CIAP. This construction may be used for stable expression of GDNFR in CHO cells.

DCEP4 Clones

The appropriate pBKRSV clone is digested with SpeI and XhoI. The insert is ligated to pCEP4 (Invitrogen, San Diego, Calif.) digested with NheI (SpeI ends) and XhoI, and treated with CIAP. This construction may be used for transient of expression of GDNFR.

The plasmid construct pDSR-2 is prepared substantially in accordance with the process described in the co-owned and copending U.S. patent application Ser. No. 501,904 filed Mar. 29, 1990 (also see, European Patent Application No. 90305433, Publication No. EP 398 753, filed May 18, 1990 and WO 90/14363 (1990), the disclosures of which are hereby incorporated by reference. It will be appreciated by those skilled in the art that a variety of nucleic acid sequences encoding GDNFR analogs may be used.

Another construct is pDSRα2, a derivative of the plasmid pCD (Okayama & Berg, Mol. Cell Biol. 3: 280–289, 1983) with three main modifications: (i) the SV40 polyadenylation signal has been replaced with the signal from the α-subunit of bovine follicular stimulating hormone, α-bFSH (Goodwin et al., Nucleic Acids Res. 11: 6873–6882, 1983); (ii) a mouse dihydrofolate reductase minigene (Gasser et al., Proc. Natl. Acad. Sci. 79: 6522–6526, 1982) has been inserted downstream from the expression cassette to allow selection and amplification of the transformants; and (iii) a 267 bp fragment containing the "R-element" and part of the "U5" sequences of the long terminal repeat (LTR) of human T-cell leukemia virus type I (HTLV-I) has been cloned and inserted between the SV40 promoter and the splice signals as described previously (Takebe et al., Mol. Cell Biol. 8: 466–472, 1988).

The expression of GDNFR in CHO cells has been verified by the binding of iodinated GDNF to the cell surface. As discussed above, the recombinantly expressed soluble GDNFR protein product may be used to potentiate the activity or cell specificity of GDNF. Soluble GDNFR attached to a detectable label also may be used in diagnostic applications as discussed above.

Example 8

Chemical Crosslinking of GDNF with GDNFR

In order to study its binding properties and molecular characteristics, GDNFR was transiently expressed on the surface of 293T cells by transfection of the rat cDNA clone. Transfection of 293T cells was performed using the Calcium Phosphate Transfection System (GIBCO/BRL, Gaithersburg, Md.) according to the manufacturers instructions. Two days following transfection, cells were removed by 2× versine treatment, washed once with washing buffer, and resuspended in washing buffer at a density of $2 \times 10^6$ cells/mL. A duplicate set of cells were incubated with 0.5 u/mL PI-PLC at 37° C. for 30 minutes before [$^{125}$I]GDNF binding. These cells were washed three times with ice-cold binding buffer and then incubated with 1 to 3 nM of [$^{125}$I]GDNF along with other cells at 4° C. for four hours. Cells were washed four times with ice-cold washing buffer, resuspended in washing buffer supplemented with 1 mM of Bis suberate for crosslinking (BS$^3$ Pierce, Rockford, Ill.) and incubated at room temperature for 30 minutes. Following three washes with TBS, a duplicate group of samples was treated by 0.5 u/mL of PI-PLC at 37° C. for 30 minutes. These cells were pelleted and the supernatants were collected. The cells were then washed with washing buffer and lysed along with all other cells with 2×SDS-PAGE sample buffer. The cell lysates and the collected supernatants were resolved on a 7.5% SDS-PAGE.

The cell suspension was divided into aliquots containing $1.5 \times 10^5$ cell/sample. Cells were then pelleted and incubated with various concentrations of [$^{125}$I]GDNF in the presence or absence of 500 nM of unlabeled GDNF at 4° C. for four hours with gentle agitation. Cells were washed four times with ice-cold washing buffer and resuspended in 0.5 mL washing buffer. Two 0.2 mL aliquots of the suspension were counted in a gamma counter to determine the amount of [$^{125}$I]GDNF associated with the cells.

Although mock transfected 293T cells did not exhibit any GDNF binding capacity, GDNFR transfected cells bound [$^{125}$I]GDNF strongly even at picomolar concentrations. This binding was almost completely inhibited by 500 nM of unlabeled GDNF, indicating a specific binding of native GDNF to the expressed receptors.

GDNFR expressed by the 293T cells can be released from the cells by treatment with phosphatidylinositol-specific phospholipase C (PI-PLC, Boehringer Mannheim, Indianapolis, Ind.). The treatment of transfected cells with PI-PLC prior to ligand binding almost entirely eliminated the GDNF binding capacity of the cell. Additionally, treatment of the transfected cells after cross-linking released the majority of the cross-linked products into the media. These results strongly suggest that GDNFR is anchored to the cell membrane through a GPI linkage.

Crosslinking data further indicated that the molecular weight of GDNFR is approximately 50–65 kD, suggesting that there is a low level of glycosylation. Although the major cross-linked species has a molecular mass consistent with a monomer of the receptor, a minor species with approximately the mass expected for a dimer has been found.

Example 9

GDNF Signaling is Mediated by a Complex of GDNFR and the Ret Receptor Protein Tyrosine Kinase Introduction Mice carrying targeted null mutations in the GDNF gene exhibit various defects in tissues derived from neural crest cells, in the autonomic nervous system, and in trigeminal and spinal cord motor neurons. The most severe defects are the absence of kidneys and complete loss of enteric neurons in digestive tract. The phenotype of GDNF knockout mice is strikingly similar to that of the c-ret knockout animals (Schuchardt et al. 1994), suggesting a possible linkage between the signal transduction pathways of GDNF and c-ret.

The proto-oncogene c-ret was identified using probes derived from an oncogene isolated in gene transfer experiments (Takahashi et al., Cell. 42, 581–588, 1985; Takahashi and Cooper, Mol. Cell. Biol., 7, 1378–1385, 1987). Sequence analysis of the c-ret cDNA revealed a large open reading frame encoding a novel receptor protein tyrosine kinase (PTK). The family of receptor PTKs has been grouped into sub-families according to extracellular domain structure and sequence homology within the intracellular kinase domain (van der Geer et al., 1994). The unique extracellular domain structure of Ret places it outside any other known receptor PTK sub-family; it includes a signal peptide, a cadherin-like motif, and a cysteine-rich region (van Heyningen, Nature, 367, 319–320, 1994; Iwamoto et al., 1993). In situ hybridization and immunohistochemical analysis showed high level expression of ret mRNA and protein in the developing central and peripheral nervous systems and in the excretory system of the mouse embryo (Pachnis et al., 1993; Tsuzuki et al., Oncogene, 10, 191–198, 1995), suggesting a role of the Ret receptor either in the development or in the function of these tissues. A functional ligand of the Ret receptor has not been identified, thereby limiting a further understanding of the molecular mechanism of Ret signaling. Mutations in the c-ret gene are associated with inherited predisposition to cancer in familial medullary thyroid carcinoma (FMTC), and multiple endocrine neoplasia type 2A (MEN2A) and 2B (MEN2B). These diseases are probably caused by "gain of function" mutations that constitutively activate the Ret kinase (Donis-Keller et al., Hum. Molec. Genet. 2, 851–856, 1993; Hofstra et al., Nature. 367, 375–376, 1994; Mulligan et al., Nature. 363, 458–460, 1993; Santoro et al., Science. 267, 381–383, 1995). They confer a predisposition to malignancy specifically in tissues derived from the neural crest, where ret is normally expressed in early development. Another ret-associated genetic disorder, Hirschsprung's disease (HSCR), is characterized by the congenital absence of parasympathetic innervation in the lower intestinal tract (Edery et al., Nature. 367, 378–380, 1994; Romeo et al., 1994). The most likely causes of HSCR are nonsense mutations that result in the production of truncated Ret protein lacking a kinase domain or missense mutations that inactivate the Ret kinase. As noted above, targeted disruption of the c-ret proto-oncogene in mice results in renal agenesis or severe dysgenesis and lack of enteric neurons throughout the digestive tract (Schuchardt et al., 1994). This phenotype closely resembles that of GDNF knockout mice. Taken together, these data suggest that both Ret and GDNF are involved in signal transduction pathways critical to the development of the kidney and the enteric nervous system. How Ret and GDNF are involved, however, was not known.

The isolation and characterization of cDNA for GDNFR by expression cloning, as described above, lead to the expression of GDNFR in the transformed human embryonic kidney cell line 293T. Transformation resulted in the appearance of both high ($K_d$ of approximately 2 pM) and low ($K_d$ of approximately 200 pM) affinity binding sites. The high affinity binding sites could be composed of homodimers or homo-oligomers of GDNFR alone, or of heterodimers or hetero-oligomers of GDNFR with other molecules. As discussed above, because GDNFR lacks a cytoplasmic domain, it must function through one or more accessory molecules in order to play a role in GDNF signal transduction. In this study we confirm that, in the presence of GDNFR, GDNF associates with the Ret protein tyrosine kinase receptor, and quickly induces Ret autophosphorylation.

Results
Neuro-2a Cells Expressing GDNFR Bind GDNF with High Affinity

Neuro-2a is a mouse neuroblastoma cell line that endogenously expresses a high level of Ret protein (Ikeda et al., Oncogene. 5, 1291–1296, 1990; Iwamoto et al., Oncogene. 8, 1087–1091, 1993; Takahashi and Cooper, 1987) but does not express detectable levels of GDNFR mRNA as judged by Northern blot. In order to determine if Ret could associate with GDNF in the presence of GDNFR, a study was performed to examine the binding of [$^{125}$I]GDNF to Neuro-2a cells engineered to express GDNFR. Neuro-2a cells were transfected with a mammalian expression vector containing the rat GDNFR cDNA (such as the expression plasmid described above). Three clonal lines, NGR-16, NGR-33, and NGR-38 were tested for their ability to bind [$^{125}$I]GDNF. The unbound [$^{125}$I]GDNF was removed at the end of the incubation and the amount of radioactivity associated with the cells was determined as described in Experimental Procedures. All three lines were able to bind [$^{125}$I]GDNF specifically while parental Neuro-2a cells exhibited little or no [$^{125}$I]GDNF binding (FIG. 6). Binding could be effectively competed by the addition of 500 nM unlabeled GDNF. These results demonstrate that Ret receptor expressed on Neuro-2a cells is unable to bind GDNF in the absence of GDNFR and are consistent with the previous observation that GDNFR is not expressed at appreciable levels in Neuro-2a cells.

Figure 7B:
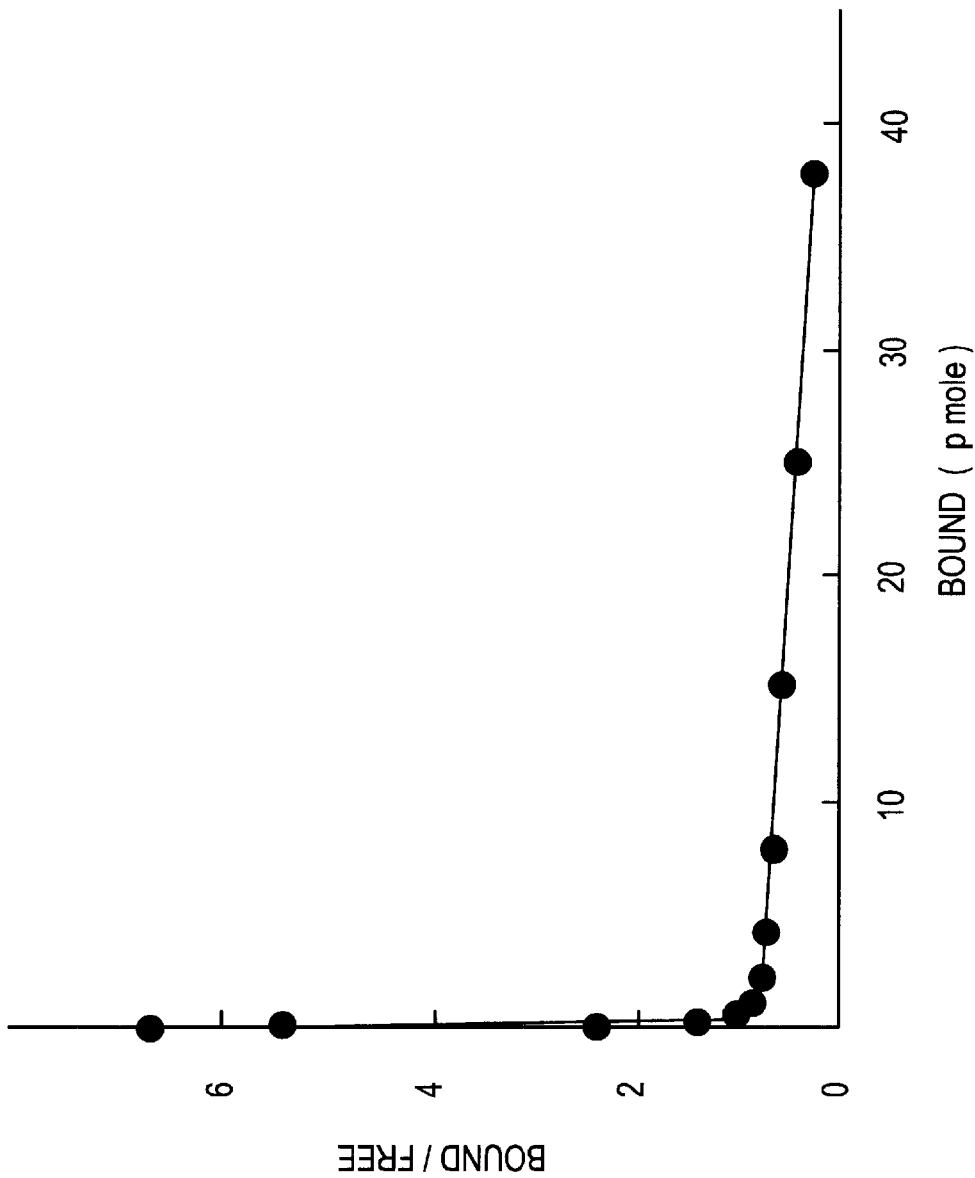

Equilibrium binding of [$^{125}$I]GDNF to NGR-38 cells was examined over a wide range of ligand concentrations (0.5 pM to 1 nM of [$^{125}$I]GDNF in the presence or absence of 500 nM of unlabeled GDNF) (see FIG. 7A). Following incubation, unbound [$^{125}$I]GDNF was removed and the radioactivity associated with the cells was determined as described in Experimental Procedures. Results are depicted in FIG. 7: (A) Equilibrium binding of [$^{125}$I]GDNF to NGR-38 cells (circles) and Neuro-2a cells (squares) in the presence (open circles and open squares) or absence (filled circles and filled squares) of unlabeled GDNF; (B) Scatchard analysis of [$^{125}$I]GDNF binding to NGR-38 cells. Neuro-2a cells exhibited little binding even at a concentration of 1 nM [$^{125}$I]GDNF, and this binding was not affected by the addition of excess unlabeled GDNF. Binding to NGR-38 cells was analyzed by Scatchard plot as shown in FIG. 7B. Two classes of binding sites were detected, one with $K_d$=1.5±0.5 pM and the other with $K_d$=332±53 pM. These dissociation constants are very similar to the values obtained for the high and low affinity binding sites in 293T cells transiently expressing GDNFR, as described above.

GDNF Associates with Ret in Neuro-2a Cells Expressing GDNFR

Figure 8:
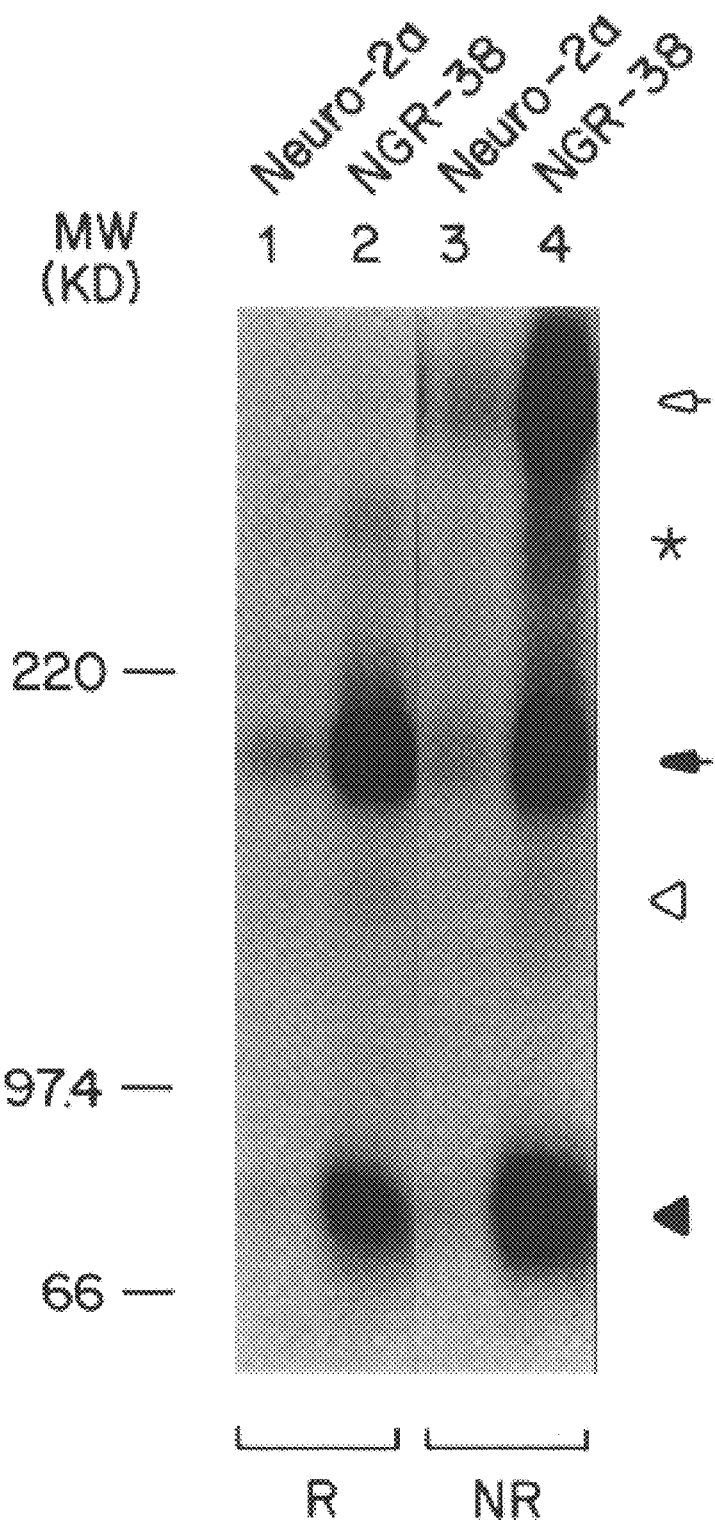
FIG. 8 depicts the results of the chemical cross-linking of [$^{125}$I]GDNF to GDNFR and Ret Expressed in cells expressing GDNFR.

In order to determine if the Ret receptor PTK could associate with GDNF in cells expressing GDNFR, a cross-linking experiment was carried out using NGR-38 and parental Neuro-2a cells. NGR-38 cells were incubated with [$^{125}$I]GDNF, treated with cross-linking reagent, then lysed either directly in SDS-PAGE sample buffer or in Triton X-100 lysis buffer and further immunoprecipitated with anti-Ret antibody as described in the Experimental Procedures. The immunoprecipitates were analyzed by SDS-PAGE in the absence (NR) or presence (R) of -mercaptoethanol. Lysates were treated with Ret specific antibody, immunoprecipitated, and analyzed by SDS-PAGE under reducing conditions (see FIG. 8, bands are marked as follows: ~75 kD, solid triangle; ~150 kD, open triangle; ~185 kD, solid arrow; ~250 kD, asterisk; ~400 kD, open arrow). The most prominent cross-linked species were at ~75 kD, and ~185 kD, with less intense bands of ~150 kD and ~250 kD. A very faint band of ~400 kD was also visible (FIG. 8, lane 2). When immunoprecipitates were analyzed by non-reducing SDS-PAGE, the ~75 kD, ~150 and ~185 kD bands were present at about the same intensity as in the reducing gel, but the amount of the ~400 kD band increased dramatically (FIG. 8, lane 4). Also becoming more prominent was the band at ~250 kD.

Under both reducing and non-reducing conditions, bands of similar molecular weight but of greatly reduced intensity were observed when parental Neuro-2a cells were used instead of NGR-38 (FIG. 8, lanes 1 and 3). The ~75 kD and ~150 kD species are likely to represent cross-linked complexes of GDNF and GDNFR, since species with identical molecular weights are produced by cross-linking in 293T cells that do not express Ret. Furthermore, since the molecular weight of Ret is 170 kD, any complex including Ret must be of at least this size.

The fact that these complexes are immunoprecipitated by anti-Ret antibody indicates they are products of an association between Ret and the GDNF/GDNFR complex which was disrupted under the conditions of the gel analysis. It is envisioned that the broad band at ~185 kD probably consists of one molecule of Ret (170 kD) cross-linked with one molecule of monomeric recombinant GDNF (15 kD), although some dimeric GDNF may be included. The presence of Ret in this species was confirmed by a separate experiment in which a band of the same molecular weight was observed when unlabeled GDNF was cross-linked to NGR-38 cells and the products examined by Western blot with anti-Ret antibody (data not shown).

The ~400 kD band was not reliably identified, partly due to the difficulty in estimating its molecular weight. The fact that it is prominent only under non-reducing conditions indicates that it is a disulfide-linked dimer of one or more of the species observed under reducing conditions. The most likely explanation is that it represents a dimer of the 185 kD species, although it may be a mixture of high molecular weight complexes consisting of two Ret, one or two GDNFR, and one or two GDNF molecules. The exact identity of the ~250 kD band has not yet been determined. One possibility is that it represents cross-linked heterodimers of the ~75 kD (GDNF+GDNFR) and ~185 kD (GDNF+Ret) complexes.

GDNF Stimulates Autophosphorylation of Ret in Neuro-2a Cells Expressing GDNFR

Figure 9A:
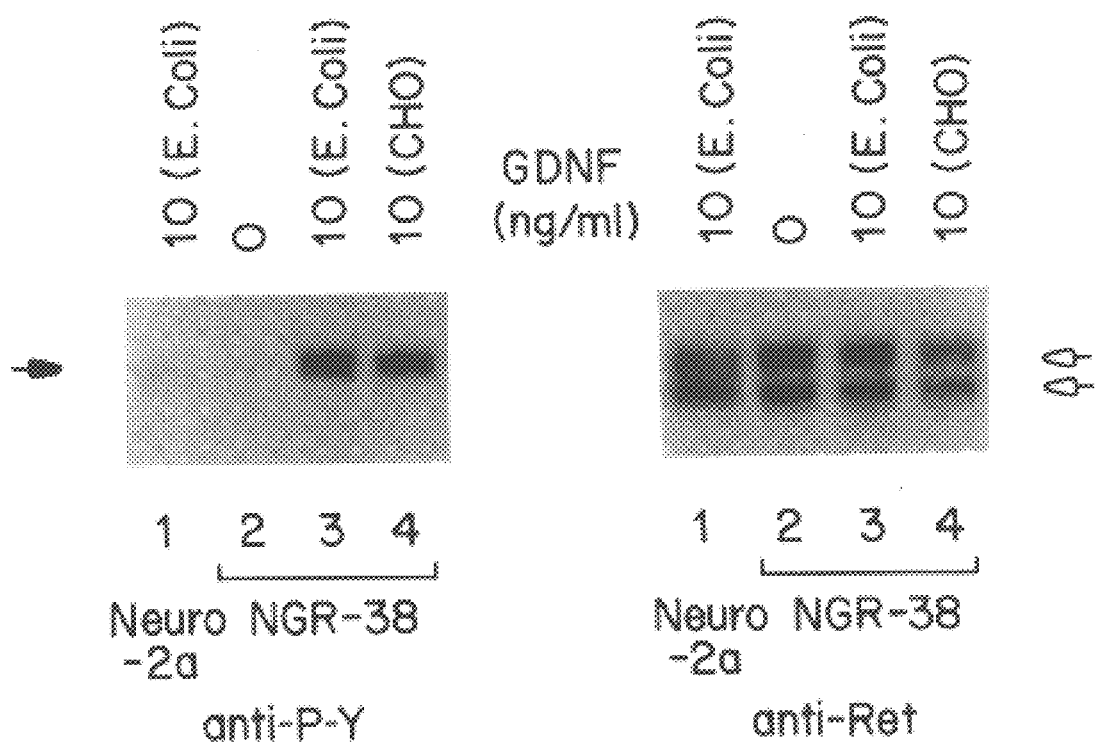

The ability of the Ret protein tyrosine kinase receptor to associate with GDNF in the presence of GDNFR led to the study of GDNF stimulation of the autophosphorylation of Ret. NGR-38 cells were treated with GDNF, lysed, and the lysates immunoprecipitated with anti-Ret antibody. The immunoprecipitates were analyzed by Western blot using an anti-phosphotyrosine antibody as described in the Experimental Procedures. When NGR-38 cells (FIG. 9A, lanes 2–4) were treated with purified recombinant GDNF produced in either mammalian (CHO cells; FIG. 9A, lanes 4) or *E. coli* cells (FIG. 9A, lanes 1, 3), a strong band was observed at 170 kD, indicating autophosphorylation of tyrosine residues on the mature form of Ret. A much weaker corresponding band was observed in GDNF-treated Neuro-2a cells (FIG. 9A, lane 1). No phosphorylation was observed on the alternatively glycosylated 150 kD precursor form of Ret (FIG. 9A). The induction of Ret autophosphorylation by GDNF was dosage dependent. The dose response and kinetics of GDNF-induced Ret tyrosine phosphorylation in NGR-38 cells are shown in panels B and C. In all panels, the tyrosine phosphorylated 170 kD Ret bands are indicated by solid arrows. The amount of Ret protein loaded in each lane as determined by reprobing of the immunoblot with anti-Ret antibody (Santa Cruz, C-19, Cat. #sc-167) is shown on the right side of panel A. The band at ~150 kD represents an alternately glycosylated immature form of Ret that does not autophosphorylate. As shown in FIG. 9B, stimulation of Ret autophosphorylation in NGR-38 cells could be detected with 50 pg/mL of GDNF and the response was saturated at 20–50 ng/mL GDNF. The stimulation of Ret autophosphorylation by purified recombinant GDNF in NGR-38 cells over times of 0–20 minutes following treatment is shown in FIG. 9C. Increased levels of Ret autophosphorylation could be observed within one minute of GDNF treatment and was maximal at 10 minutes following treatment (FIG. 9C).

GDNF and Soluble GDNFR Induce Ret Autophosphorylation in Neuro-2A Cells

Figure 10A:
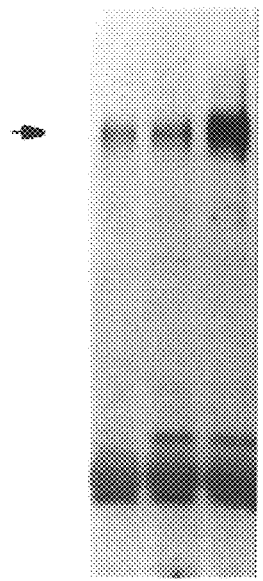
FIGS. 10A–B depict the results of the induction of c-Ret autophosphorylation by GDNF and soluble GDNFR.

As discussed above, GDNFR is anchored to the cytoplasmic membrane through a GPI linkage and can be released by treatment with phosphatidylinositol-specific phospholipase C (PI-PLC). When NGR-38 cells were incubated with PI-PLC, GDNF-induced receptor autophosphorylation of Ret in these cells was abolished (FIG. 10A; PI-PLC treated (lane 1) or untreated (lanes 2 and 3) NGR-38 cells were incubated with (lanes 1 and 3) or without (lane 2) GDNF and analyzed for Ret autophosphorylation by immunoblotting as described in the Experimental Procedures).

Figure 10B:
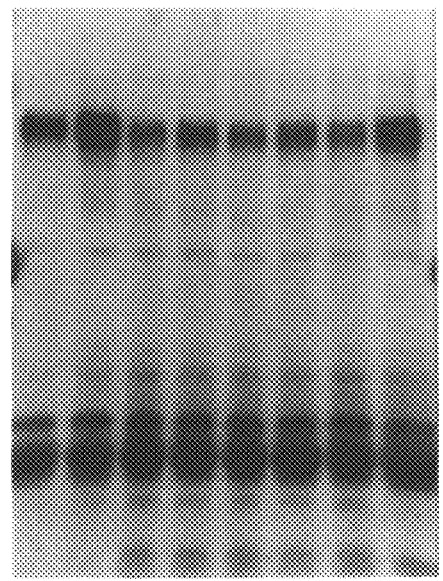

FIG. 10B depicts parental Neuro-2a cells treated with (lanes 2,4,6,8) or without (lanes 1,3,5,7) GDNF in the presence (lanes 5–8) or absence (lanes 1–4) of PI-PLC/CM obtained from Neuro-2a or NGR-38 cells, as analyzed for Ret autophosphorylation by immunoblotting as described in the Experimental Procedures. NGR-38 cells treated with GDNF were used as a positive control. In both panels A and B, the autophosphorylated 170 kD Ret bands are marked by solid arrows. When conditioned medium containing soluble GDNFR released by PI-PLC treatment (PI-PLC/CM) of NGR-38 cells was added to parental Neuro-2a cells along with GDNF, autophosphorylation of the Ret receptor comparable to that obtained with GDNF treatment of NGR-38 cells was observed (FIG. 10B, lanes 2 and 8). Only background levels of Ret autophosphorylation were observed when no GDNF was added, or when conditioned media derived from PI-PLC treatment of Neur-2a cells was tested (FIG. 10B, lanes 3–7).

Figure 11:
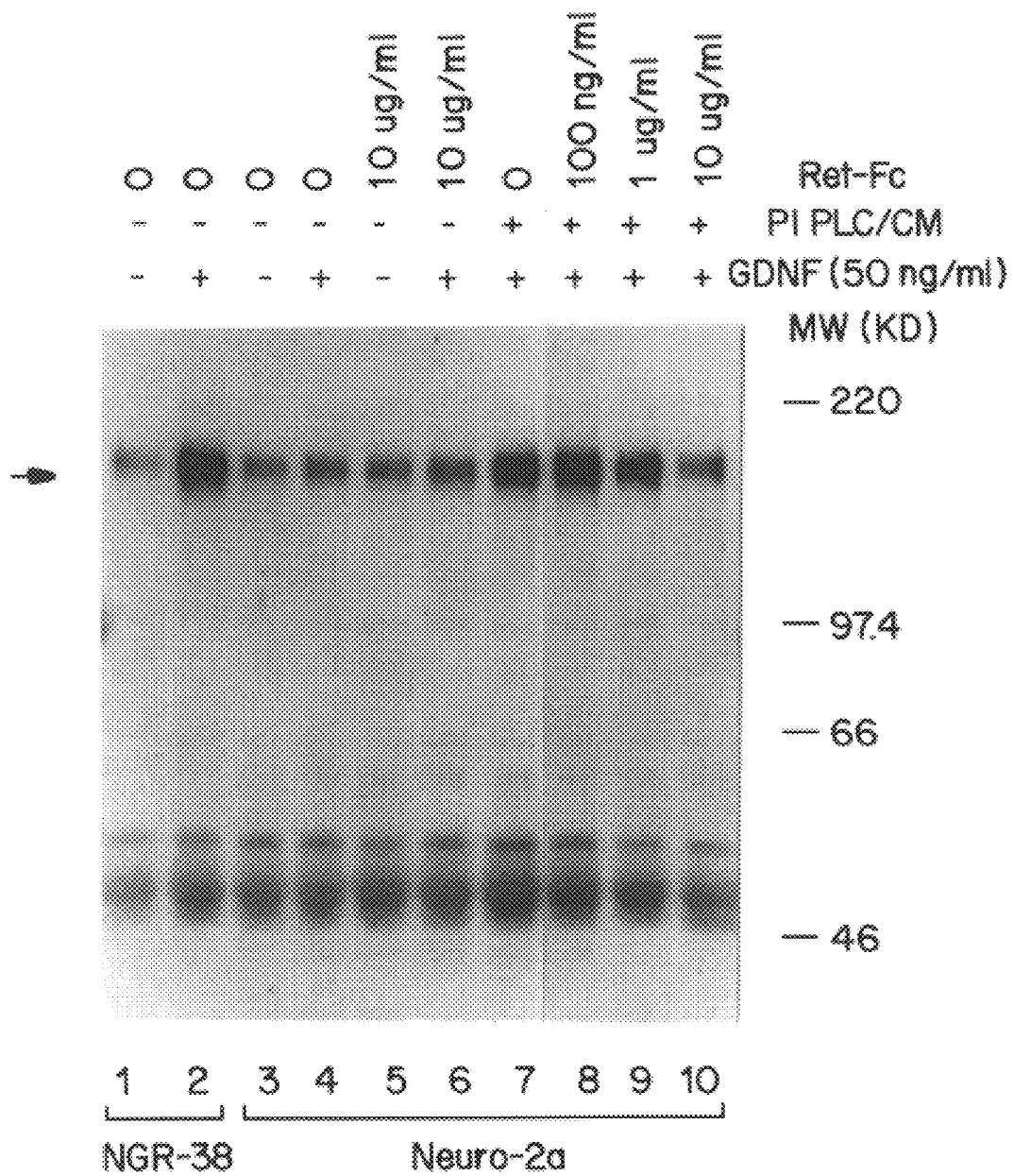
FIG. 11 depicts the results of the blocking of c-Ret autophosphorylation by a Ret-Fc fusion protein.

Ret-Fc Fusion Protein Blocks Ret Phosphorylation Induced by GDNF and Soluble GDNFR To confirm that Ret phosphorylation induced by GDNF in the presence of GDNFR is the result of receptor autophosphorylation, a study was performed to determine whether a Ret extrrcellular domain/Immunoglobulin Fc (Ret-Fc) fusion protein could block Ret activation. Because of the technical difficulty of blocking the large number of GDNF alpha receptors expressed on NGR-38 cells, Ret phosphorylation assays were performed using Neuro-2a as the target cell and culture media removed from NGR-38 cells treated with PI-PLC as a source of GDNFR. Cells were treated with mixtures including various combinations of GDNF (50 ng/mL), media containing soluble GDNFR (e.g., PI-PLC/CM derived from NGR-38 cells), and different concentrations of Ret-Fc fusion protein either alone or in various combinations as indicated in FIG. 11. Neuro-2a cells were treated with GDNF, media containing soluble GDNFR, Ret-Fc, or the pre-incubated mixtures. The cells were then lysed, and the lysates were analyzed for c-Ret autophosphorylation by immunoprecipitation using anti-Ret antibody as described in the Experimental Procedures. The immunoprecipitates were analyzed by Western blot using an anti-phosphotyrosine antibody.

The pre-incubated mixture of GDNF and media containing soluble GDNFR induced tyrosine phosphorylation of Ret receptors expressed in Neuro-2a at a level comparable to GDNF-treated NGR-38 control cells (FIG. 11, lanes 7 and 2). The position of the autophosphorylated 170 kD Ret bands are marked by a solid arrow. When Ret-Fc fusion protein was included in the pre-incubated GDNF/GDNFR mixture, Ret phosphorylation was inhibited in a dose dependent manner (FIG. 11, lanes 8–10). This indicated that Ret phosphorylation is a result of a GDNF/Ret interaction mediated by GDNFR. In untreated Neuro-2a cells or in cells treated with any combination of GDNF or Ret-Fc fusion protein in the absence of GDNFR, only background levels of Ret phosphorylation were observed (FIG. 11, lanes 3–6).

GDNF Induces Autophosphorylation of c-RET Expressed in Embryonic Motor Neurons

Figure 12:
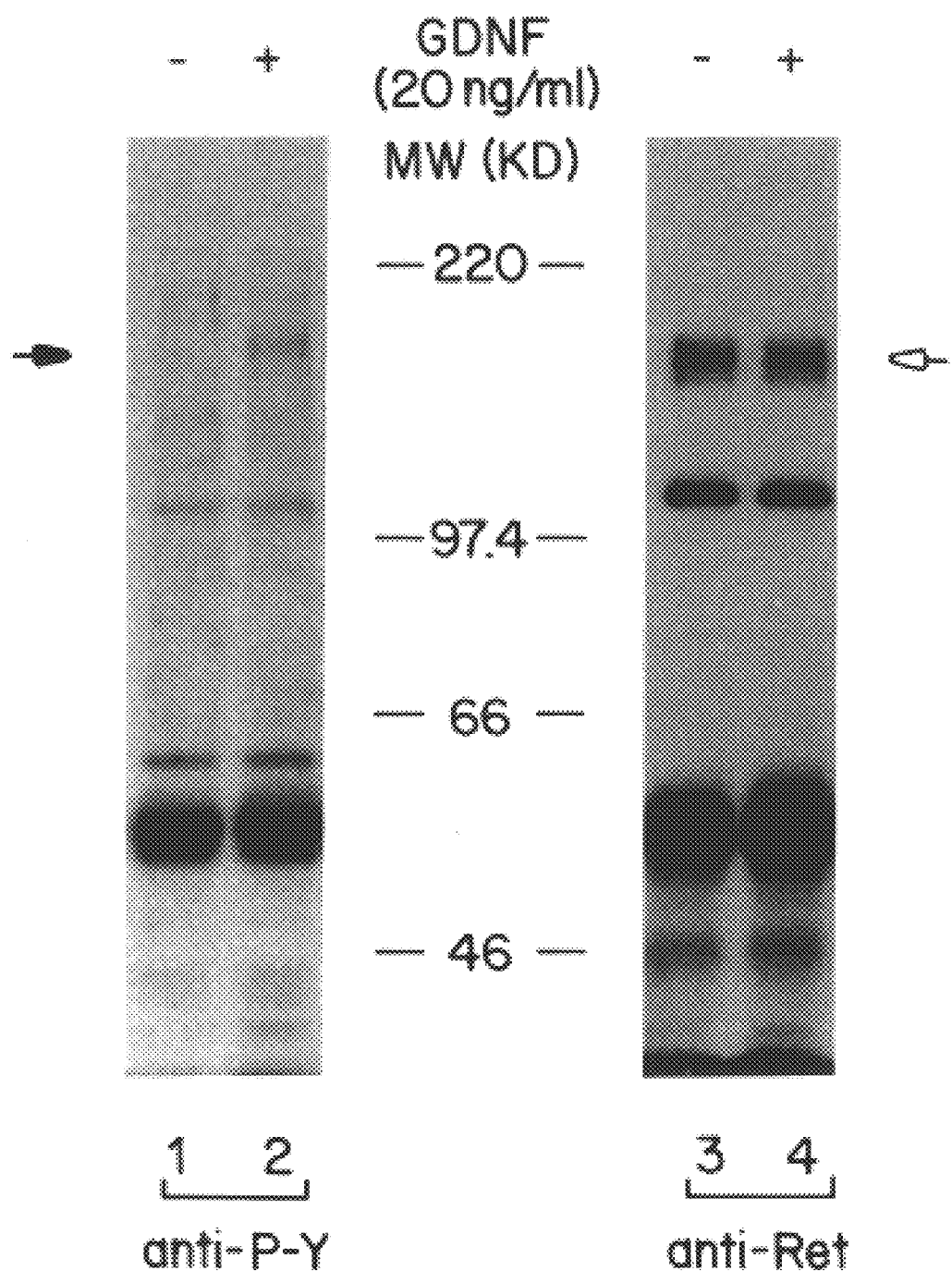
FIG. 12 depicts the results of the induction of c-Ret autophosphorylation by GDNF in motor neurons.

Spinal cord motor neurons are one of the major targets of GDNF action in vivo (Henderson et al., Science. 266, 1062–1064, 1994; Li et al., Proceedings Of The National Academy Of Sciences, U.S.A. 92, 9771–9775, 1995; Oppenheim et al., Nature. 373, 344–346, 1995; Yan et al., Nature. 373, 341–344, 1995; Zurn et al., Neuroreport. 6, 113–118, 1995). To test the ability of GDNF to induce Ret autophoshoxylation in these cells, embryonic rat spinal cord motor neurons were treated with (lanes 2 and 4) or without (lanes 1 and 3) 20 ng/mL GDNF followed by lysis of the cells, immunoprecipitation with anti-Ret antibody, and analysis by Western blotting with anti-phosphotyrosine antibody as described in the Experimental Procedures. In lysates of cells treated with GDNF, a band of tyrosine phosphorylated protein with a molecular mass of ~170 kD was observed (FIG. 12, lane 2). No such signal was observed with cells treated with binding buffer alone (FIG. 12, lane 1). When the same Western blot filter was stripped and re-probed with anti-Ret antibody (i.e., the amount of c-Ret protein loaded in each lane was determined by reprobing the immunoblot with the anti-Ret antibody), bands with the same molecular mass and similar intensities appeared in both samples (FIG. 12, lanes 3 and 4). The phosphotyrosine band in GDNF-treated cells co-migrates with the Ret protein band, indicating GDNF stimulated autophosphorylation of Ret. The autophosphorylated Ret bands (lanes 1 and 2) and the corresponding protein bands (lanes 3 and 4) were marked by a solid arrow.

Discussion

Polypeptide growth factors elicit biological effects through binding to their cognate cell surface receptors. Receptors can be grouped into several classes based on their structure and mechanism of action. These classifications include the protein tyrosine kinases (PTKs), the serine/threonine kinases, and the cytokine receptors. Receptor PTK signaling is initiated by a direct interaction with ligand, which induces receptor dimerization or oligomerization that in turn leads to receptor autophosphorylation. The activated receptor then recruits and phosphorylates intracellular substrates, initiating a cascade of events which culminates in a biological response (Schlessinger and Ullrich, Neuron 9, 383–391, 1992). In contrast, signal transduction by serine/threonine kinase or cytokine receptors often involves formation of multi-component receptor complexes in which the ligand binding and signal transducing components are distinct. Examples are the TGF-receptor complex, a serine/threonine kinase receptor consisting of separate binding (Type II) and signaling (Type I) components and the CNTF family. CNTF, interleukin-6 (IL-6) and leukocyte inhibitory factor (LIF) share the common signaling components, gp130 and/or LIFR, in their respective receptor complexes. While the ligand specificity of these complexes is determined by a specific binding subunit to each individual ligand, signal transduction requires association of the initial complex of ligand and ligand binding subunit with other receptor subunits which cannot bind ligand directly (Ip et al., Cell. 69, 1121–1132, 1992). In the CNTF receptor complex, the ligand binding component is CNTF receptor (CNTFR), which like GDNFR, is a GPI-anchored membrane protein. The present invention involves the description of the first example of a receptor PTK whose autophosphorylation is dependent upon association with a separate ligand-specific binding component.

The present study confirms that GDNFR, a GPI-linked membrane protein that binds to GDNF with high affinity, is required for the efficient association of GDNF with the Ret receptor PTK. In the absence of GDNFR, GDNF is unable to bind to Ret or stimulate Ret receptor autophosphorylation. In the presence of GDNFR, GDNF associates with Ret and rapidly induces Ret autophosphorylation in a dose-dependent manner. GDNFR is able to function in either membrane bound or soluble forms (FIG. 11), as discussed above. GDNF concentrations of 50 pg/mL (1.7 pM) are able activate the Ret tyrosine kinase in cells expressing GDNFR. This is consistent with the dissociation constant (1.5 pM) found for the high affinity GDNF binding sites on NGR-38 cells. The rapid induction of Ret phosphorylation by GDNF (detectable one minute after treatment) and the ability of Ret-Fc to block autophosphorylation suggest that Ret is being activated directly rather than as a downstream consequence of the phosphorylation of some other receptor.

Cross-linking studies support the hypothesis that efficient association of Ret with GDNF depends on GDNFR. Cross-linking of GDNF to Ret in NGR-38 cells which express high levels of GDNFR is robust, but in parental Neuro-2a cells cross-linked products are barely detectable. Although conclusive identification of all the cross-linked complexes is difficult, the data clearly demonstrates an association of Ret with GDNF that is dependent on the presence of GDNFR, and demonstrates that GDNFR is included in some of the cross-linked products. The reason for the presence of minor cross-linked species in Neuro-2a cells is not clear. While the expression of GDNFR mRNA in Neuro-2a cells could not be detected by Northern blot, it is possible that GDNFR is expressed at very low levels in these cells.

The fact that Ret can be activated by GDNF in cultured rat embryonic spinal cord motor neurons further demonstrates the biological relevance of the Ret/GDNF interaction. These cells are a primary target of GDNF in vivo, and have been shown to respond to low doses of GDNF in vitro (Henderson et al., 1994). Stimulation of Ret phosphorylation was abolished when the motor neuron cells were pre-treated with PI-PLC (data not shown), suggesting that the activation of Ret by GDNF requires GDNFR.

Figure 13:
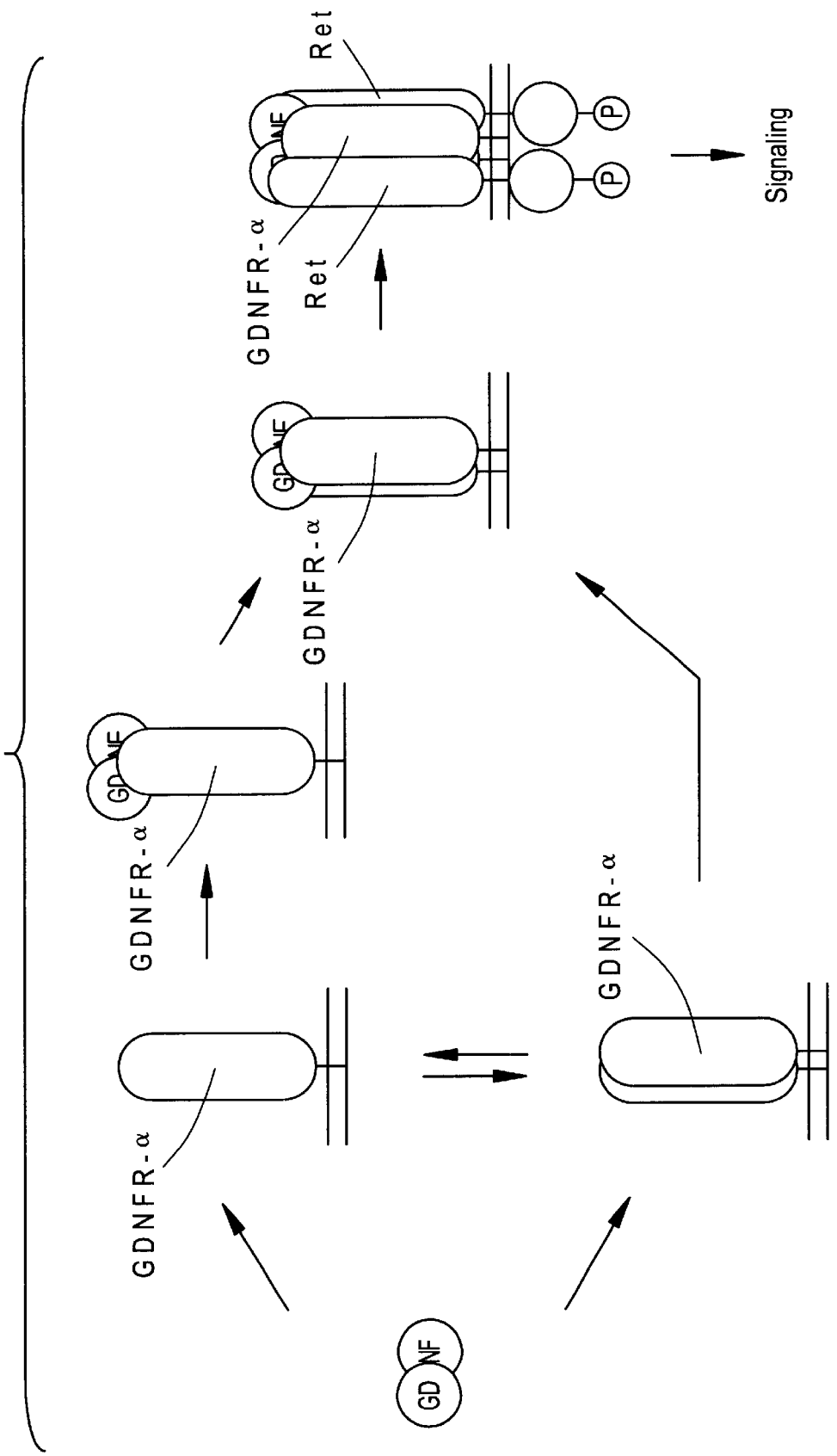
FIG. 13 depicts a model for GDNF signaling mediated by GDNFR and Ret.

Although binding of ligand to the receptor extracellular domain is the first step in the activation of other known receptor PTKs, the present data has shown that this is not the case for GDNF and Ret. FIG. 13 depicts a model for the binding of GDNF to GDNFR and Ret, and the consequent activation of the Ret PTK in response to GDNF. The initial event in this process is the binding of disulfide-linked dimeric GDNF to GDNFR in either monomeric or dimeric form. Although there is currently no direct evidence for the existence of dimeric GDNFR, when 293T cells were transfected with GDNFR cDNA, two classes of binding sites appeared. The simplest explanation for this observation is the existence of monomeric and dimeric GDNFR, each with its own ligand binding affinity. This is consistent with the finding that GDNF binding affinities are apparently unaffected by the presence of Ret. Since the present experiments do not address the question of whether dimeric GDNFR is in equilibrium with its monomer in the absence of GDNF or if dimerization is induced by GDNF binding, these possibilities are presented as alternate pathways. The complex consisting of dimeric GDNFR and dimeric GDNF can bind two molecules of Ret, forming the active signaling complex. As for other PTKs, close contact between the intracellular catalytic domains of two Ret molecules is likely to result in receptor autophosphorylation. This notion that Ret functions by this mechanism is supported by the fact that the MEN2A mutation which causes steady state dimerization of Ret results in constituitive activation of the Ret kinase (Santoro et al., 1995).

Motor neurons have been reported to respond to GDNF with an $ED_{50}$ of as low as 5 fM (Henderson et al., 1994). Although it is difficult to compare binding affinity with the $ED_{50}$ for a biological response, it is possible that very high affinity GDNF binding sites exist on these cells. Other cells, such as embryonic chick sympathetic neurons, have been reported to bind GDNF with a Kd of 1–5 nM (Trupp et al., Journal Of Cell Biology. 130, 137–148, 1995). It is unlikely that GDNFR is involved in a receptor complex for such low affinity sites, but a weak direct interaction between GDNF and Ret may be present.

Expression of c-ret has been observed during embryogenesis in many cell lineages of the developing central and peripheral nervous systems, including cells of the enteric nervous system (Pachnis, et al., Development, 119, 1005–1017, 1993; Tsuzuki et al., 1995). Outside the nervous system, c-ret expression has been detected in the Wolffian duct, ureteric bud epithelium and collecting ducts of the kidney (Pachnis, et al., supra; Tsuzuki et al., 1995). Ret expression has also been detected in all neuroblastoma cell lines derived from the neural crest (Ikeda et al., 1990) and from surgically resected neuroblastomas (Nagao et al., 1990; Takahashi & Cooper, 1987). GDNF expression has been observed in both CNS and PNS, as well as in non-neuronal tissues during embryonic development. The levels of GDNF expression found in many non-neuronal tissues were higher than in the nervous system (Choi-Lundberg and Bohn, Brain Res. Dev. Brain Res. 85, 80–88, 1995). Although expression of GDNFR has not been extensively studied, primary Northern blot analysis detected the presence of high levels of the GDNFR mRNA in the liver, brain, and kidney of adult rat and mouse. The similarity of the expression patterns of ret, GDNF, and GDNFR in developing nervous system and kidney is consistent with their combined action during development Mammalian kidney development has been postulated to result from reciprocal interactions between the metanephron and the developing ureter, a branch developed from the caudal part of the Wolffian duct (Saxen, Organogenesis of the kidney. Development and Cell Biology series, Cambridge University Press, Cambridge, England, 1987). While the expression of Ret has been found at the ureteric bud but not in the surrounding mesenchyme in developing embryos, the expression of GDNF was detected in the undifferentiated but not adult metanephric cap of the kidney. These observations suggest that an interaction between GDNF and Ret is responsible for initiating the development of the ureteric structure. Further support for this hypothesis is provided by targeted disruptions of the GDNF and ret genes, which result in very similar phenotypic defects in kidney (Schuchardt et al., Nature. 367, 380–383, 1994; Sanchez, in press). Another major phenotypic defect observed in both GDNF (−/−) and ret (−/−) knockout animals is a complete loss of the enteric neurons throughout the digestive tract. Hirschsprung's disease, a genetic disorder characterized by the congenital absence of parasympathetic innervation in the lower intestinal tract, has also been linked to "loss-of-function" mutations in ret (Romeo et al., Nature. 367, 377–378, 1994. Edery et al., 1994). A later report (Angrist et al., Hum. Mol.Genet. 4, 821–830, 1995) indicated that, contrary to earlier observations, some Hirschsprung's patients do not carry mutations in ret. It is now envisioned that such patients may carry mutations in GDNF, GDNFR or some other critical component of this signaling pathway.

Experimental Procedures

[$^{125}$I]GDNF Binding to Neuro-2a Cells Expressing GDNFR

Neuro-2a cells (ATCC #CCL 131) were transfected with an expression plasmid, as described above, using the Calcium Phosphate Transfection System (GIBCO/BRL) according to the manufacturer's directions. Transfected cells were selected for expression of the plasmid by growth in 400 μg/mL G418 antibiotic (Sigma). G418 resistant clones were expanded and assayed for GDNFR expression by binding to [$^{125}$I]GDNF (Amersham, Inc., custom iodination, catalog #IMQ1057). Cells from each clone were seeded at a density of $3 \times 10^4$ cells/cm$^2$ in duplicate wells of 24-well tissue culture plates (Becton Dickinson) pre-coated with polyornithine. Cells were washed once with ice-cold washing buffer (DMEM containing 25 mM HEPES, pH 7.5) and were then incubated with 50 pM [$^{125}$I]GDNF in binding buffer (washing buffer plus 0.2% BSA) at 4° C. for four hours either in the presence or absence of 500 mM unlabeled GDNF. Cells were then washed four times with ice-cold washing buffer, lysed in 1 M NaOH, and the cell-associated radiolabel quantitated in a 1470 Wizard Automated Gamma Counter (Wallac Inc.). The amount of GDNFR expressed by individual clones was estimated by the ratio of [$^{125}$I]GDNF bound to cells in the absence and presence of unlabeled GDNF. Three clones were chosen as representatives of high, moderate, and low level expressors of GDNFR for use in binding experiments. The ratios [$^{125}$I]GDNF bound in the absence and presence of unlabeled GDNF for these clones were: NGR-38) 16:1, NGR-16) 12.8:1, and NGR-33) 8:1. Equilibrium binding of [$^{125}$I]GDNF to NGR-38 cells was carried out as described above except that concentrations of labeled GDNF ranged from 0.5 pM to 1 nM. In all assays, nonspecific binding as estimated by the amount of radiolabel binding to cells in the presence of 500 nM unlabeled GDNF was subtracted from binding in the absence of unlabeled GDNF. Binding data was analyzed by Scatchard plot.

Chemical Cross-Linking

Neuro-2a or NGR-38 cells were washed once with phosphate-buffered saline (PBS, pH 7.1), then treated for four hours at 4° C. with 1 or 3 nM [$^{125}$I]GDNF in binding buffer in the presence or absence of 500 nM unlabeled GDNF. Following binding, cells were washed four times with ice-cold washing buffer and incubated at room temperature for 45 minutes with 1 mM bis suberate (BS$^3$, Pierce) in washing buffer. The cross-linking reaction was quenched by washing the cells three times with Tris-buffered saline (TBS, pH 7.5). The cells were then either lysed directly in SDS-PAGE sample buffer (80 mM Tris HCl [pH 6.8], 10% glycerol, 1% SDS, 0.025% bromophenol blue) or in Triton X-100 lysis buffer (50 mM Hepes, pH 7.5, 1% Triton X-100, 50 mM NaCl, 50 mM NaF, 10 mM sodium pyrophosphate, 1% aprotinin (Sigma, Cat.#A-6279), 1 mM PMSF (Sigma, Cat.#P-7626), 0.5 mM Na$_3$VO$_4$ (Fisher Cat.#S454–50). The lysates were clarified by centrifugation, incubated with 5 μg/mL of anti-Ret antibody (Santa Cruz Antibody, C-19, Cat. #SC-167), and the resulting immunocomplexes were collected by precipitation with protein A-Sepharose CL-4B (Pharmacia). The immunoprecipitates were washed three times with the lysis buffer, once with 0.5% NP-40 containing 50 mM NaCl and 20 mM Tris-Cl, pH 7.5, and were then resuspended in SDS-PAGE sample buffer. Both the whole cell lysates and the immunoprecipitates were fractionated by 7.5% SDS-PAGE with a ratio of Bis:Acrylamide at 1:200.

Western Blot Analysis

The autophosphorylation of Ret receptor was examined by Western blot analysis. Briefly, cells were seeded 24 hours prior to the assay in 6-well tissue culture dishes at a density of $1.5 \times 10^6$ cells/well. Cells were washed once with binding buffer and treated with various concentrations of different reagents (including GDNF, PI-PLC, PI-PLC/CM, and Ret-Fc fusion protein), either alone or in combination, in binding buffer for various periods of times. Treated cells and untreated controls were lysed in Triton X-100 lysis buffer and immunoprecipitated with the anti-Ret antibody (Santa Cruz, C-19, Cat. #SC-167) and protein-A Sepharose as described above. Immunoprecipitates were fractionated by SDS-PAGE and transferred to nitrocellulose membranes as described by Harlow and Lane (Antibodies: A Laboratory Manual. Cold Spring Harbor Laboratory: Cold Spring Harbor, N.Y., 1988). The membranes were pre-blocked with 5% BSA (Sigma) and the level of tyrosine phosphorylation of the receptor was determined by blotting the membrane with an anti-phosphotyrosine monoclonal antibody 4G10 (UBI, Cat. #05-321) at room temperature for two hours. The amount of protein included in each lane was determined by stripping and re-probing the same membrane with the anti-Ret antibody. Finally, the membrane was treated with chemiluminescence reagents (ECL, Amersham) following the manufacturer's instructions and exposed to X-ray films (Hyperfilm-ELC, Amersham).

Treatment of Cells with PI-PLC and Generation of PI-PLC Treated Conditioned Media In order to release GPI-linked GDNFR from the cell surface, cells were washed once with washing buffer, then incubated with 1 U/mL phosphatidylinositol specific phospholipase C (PI-PLC, Boehringer Mannheim, Cat. #1143069) in binding buffer at 37° C. for 45 minutes. The cells were then washed three times with washing buffer and further processed for Ret autophosphorylation assay or cross-linking. For generation of PI-PLC treated conditioned media (PI-PLC/CM), $8 \times 10^6$ cells were removed from tissue culture dishes by treating the cells with PBS containing 2 mM of DTA at 37° C. for 5 to 10 minutes. Cells were washed once with washing buffer, resuspended in 1 mL of binding buffer containing 1 U/mL of PI-PLC, and incubated at 37° C. for 45 minutes. The cells were pelleted, and the PI-PLC/CM was collected.

Preparation of the Ret-Fc Fusion Protein

A cDNA encompassing the entire coding region of c-Ret was isolated from a day 17 rat placenta cDNA library using an oligonucleotide probe corresponding to the first 20 amino acids of the mouse c-Ret (Iwamoto et al., 1993; van Heyningen, 1994). The region coding for the extracellular domain of the Ret receptor (ending with the last amino acid, R636) was fused in-frame with the DNA coding for the Fc region of human IgG (IgG1) and subcloned into the expression vector pDSR2 as previously described (Bartley et al., Nature. 368, 558–560, 1994). The ret-Fc/pDSRa2 plasmid was transfected into Chinese hamster ovary (CHO) cells and the recombinant Ret-Fc fusion protein was purified by affinity chromatography using a $Ni^{++}$ column (Qiagen).

Preparation of Embryonic Rat Spinal Cord Motor Neuron Cultures

Enriched embryonic rat spinal cord motor neuron cultures were prepared from entire spinal cords of E15 Sprague-Dawley rat fetuses 24 hours before the experiments. The spinal cords were dissected, and the meninges and dorsal root ganglia (DRGs) were removed. The spinal cords were cut into smaller fragments and digested with papain in L15 medium (Papain Kit, Worthington). The motor neurons, which are larger than other types of cells included in the dissociated cell suspension, were enriched using a 6.8% Metrizamide gradient (Camu and Henderson, J Neuroscience. 44, 59–70, 1992). Enriched motor neurons residing at the interface between the metrizamide cushion and the cell suspension were collected, washed, and seeded in tissue culture dishes pre-coated with poly-L-omithine and laminin at a density of $\sim 9 \times 10^4$ cells/cm$^2$ and were cultured at 37° C.

Various references are cited herein, the disclosures of which are incorporated by reference in their entireties.

While the present invention has been described in terms of preferred embodiments and exemplary nucleic acid and amino acid sequences, it is understood that variations and modifications will occur to those skilled in the art. Therefore, it is intended that the appended claims cover all such equivalent variations which come within the scope of the invention as claimed.

References

Angrist, M., Bolk, S., Thiel, B., Puffenberger, E. G., Hofstra, R. M., Buys, C. H., Cass, D. T., and Chakravarti, A. (1995). Mutation analysis of the RET receptor tyrosine kinase in Hirschsprung disease. Hum. Mol.Genet.4, 821–830.

Arenas, E., Trupp, M., Akerud, P., and Ibanez, C. F. (1995). GDNF Prevents degeneration and promotes the phenotype of brain noradrenergic neurons in vivo. Neuron 15, 1465–1473.

Aruffo, A. and Seed, B. (1987). Molecular cloning of a CD28 cDNA by a high-efficiency COS cell expression system. Proceedings Of The National Academy Of Sciences Of The United States Of America. 84, 8573–8577.

Bartley, T. D., Hunt, R. W., Welcher, A. A., Boyle, W. J., Parker, V. P., Lindberg, R. A., Lu, H. S., Colombero, A. M., Elliott, R. L., Guthrie, B. A., Holst, P. L., Skrine, J. D., Toso, R. J., Zhang, M., Fernandez, E., Trail, G., Varnum, B., Yarden, Y., Hunter, T., and Fox, G. M. (1994). B61 is a Ligand for the ECK Receptor protein-tyrosine kinase. Nature. 368, 558–560.

Beck, K. D., Valverde, J., Alexi, T., Poulsen, K., Moffat, B., Vandlen, R. A., Rosenthal, A., and Hefti, F. (1995). Mesencephalic dopaminergic neurons protected by GDNF from axotomy-induced degeneration in the adult brain. Nature. 373, 339–341.

Camu, W. and Henderson, C. (1992). Purification of embryonic rat motoneurons by panning on a monoclonal antibody to the low-affinity NGF receptor. J Neuroscience. 44, 59–70.

Choi-Lundberg, D. L. and Bohn, M. C. (1995). Ontogeny and distribution of glial cell line-derived neurotrophic factor (GDNF) mRNA in rat. Brain Res. Dev. Brain Res. 85, 80–88.

Davis, S., Aldrich, T. H., Valenzuela, D. M., Wong, V. V., Furth, M. E., Squinto, S. P., and Yancopoulos, G. D. (1991). The receptor for ciliary neurotrophic factor. Science. 253, 59–63.

Donis-Keller, H., Dou, S., Chi, D., Carlson, K., Toshima, K., Lairmore, T., Howe, J., Moley, J., Goodfellow, P. and Wells, S. (1993). Mutations in the ret proto-oncogene are associated with MEN 2A and FMTC. Hum. Molec. Genet. 2, 851–856.

Ebendal, T., Tomac, A., Hoffer, B. J., and Olson, L. (1995). Glial cell line-derived neurotrophic factor stimulates fiber formation and survival in cultured neurons from peripheral autonomic ganglia. Journal Of Neuroscience Research. 40, 276–284.

Economides, A. N., Ravetch, J. V., Yancopoulos, G. D., and Stahl, N. (1995). Designer cytokines: targeting actions to cells of choice. Science 270, 1351–1353.

Edery, P., Lyonnet, S., Mulligan, L., Pelet, A., Dow, E., Abel, L., Holder, S., Nihoul-Fekete, C., Ponder, B. and Munnich, A. (1994). Mutations of the ret proto-oncogene in Hirschsprug's disease. Nature. 367, 378–380.

Gearing, D. P., King, J. A., Gough, N. M., and Nicola, N. A. (1989). Expression cloning of a receptor for human granulocyte-macrophage colony-stimulating factor. EMBO Journal 8, 3667–3676.

Henderson, C. E., Phillips, H. S., Pollock, R. A., Davies, A. M., Lemeulle, C., Armanini, M., Simpson, L. C., Moffet, B., Vandlen, R. A., Koliatsos, V. E., and et al (1994). GDNF: a potent survival factor for motoneurons present in peripheral nerve and muscle. Science. 266, 1062–1064.

Hoffer, B. J., Hoffman, A., Bowenkamp, K., Huettl, P., Hudson, J., Martin, D., Lin, L. F., and Gerhardt, G. A. (1994). Glial cell line-derived neurotrophic factor reverses toxin-induced injury to midbrain dopaminergic neurons in vivo. Neuroscience Letters. 182, 107–111.

Hofstra, R., Landsvater, R., Ceccherini, I., Stulp, R., Stelwagen, T., Luo, Y., Pasini, B., Hoppener, J., van Amstel, H., Romeo, G., Lips, C. and Buys, C. (1994). A mutation in the ret protooncogene associated with multipleendocrine neoplasia type 2B and sporadic medullary thyroid carcinoma. Nature. 367, 375–376.

Ikeda, I., Ishizaka, Y., Tahira, T., Suzuki, T., Onda, M., Sugimura, T., and Nagao, M. (1990). Specific expression of the ret proto-oncogene in human neuroblastoma cell lines. Oncogene. 5, 1291–1296.

Ip, N.Y., Nye, S. H., Boulton, T. G., Davis, S., Yasukawa, K., Kishimoto, T., Anderson, D. J., and et al (1992). CNTF and LIF act on neuronal cells via shared signaling pathways that involve the IL-6 signal transducing receptor component gp130. Cell. 69, 1121–1132.

Iwamoto, T., Taniguchi, M., Asia, N., Ohkusu, K., Nakashima, I. and Takahashi, M. (1993). cDNA cloning of mouse ret proto-oncogene and its sequence similarity to the cadherin superfamily. Oncogene. 8, 1087–1091.

Jing, S. Q., Spencer, T., Miller, K., Hopkins, C., and Trowbridge, I. S. (1990). Role of the human transferrin receptor cytoplasmic domain in endocytosis: localization of a specific signal sequence for internalization. Journal Of Cell Biology. 110, 283–294.

Kearns, C. M. and Gash, D. M. (1995). GDNF protects nigral dopamine neurons against 6-hydroxydopamine in vivo. Brain Research. 672, 104–111.

Kozak, M. (1987). An analysis of 5'-noncoding sequences from 699 vertebrate messenger RNAs. Nucleic Acids Research. 15, 8125–8148.

Li, L., Wu, W., Lin, L. F., Lei, M., Oppenheim, R. W., and Houenou, L. J. (1995). Rescue of adult mouse motoneurons from injury-induced cell death by glial cell line-derived neurotrophic factor. Proceedings Of The National Academy Of Sciences Of The United States Of America. 92, 9771–9775.

Lin, L-F. H., Doherty, D. H., Lile, J. D., Bektesh, S., and Collins, F. (1993). GDNF: a glial cell line-derived neurotrophic factor for midbrain dopaminergic neurons. Science. 260, 1130–1132.

Louis, J. C., Magal, E., and Varon, S. (1992). Receptor-mediated toxicity of norepinephrine on cultured catecholaminergic neurons of the rat brain stem. Journal Of Pharmacology And Experimental Therapeutics. 262, 1274–1283.

Mount, H. T., Dean, D. O., Alberch, J., Dreyfus, C. F., and Black, I. B. (1995). Glial cell line-derived neurotrophic factor promotes the survival and morphologic differentiation of Purkinje cells. Proceedings Of The National Academy Of Sciences Of The United States Of America. 92, 9092–9096.

Mulligan, L., Kwok, J., Healey, C., Elsdon, M., Eng, C., Gardner, E., Love, D., Mole, S., Moore, J., Papi, L., Ponder, M., Telenius, H., Tunnacliffe, A. and Ponder, A. (1993). Germ-line mutations of the ret proto-oncongene in mutiple endocrine neoplasia type 2A. Nature. 363, 458–460.

Oppenheim, R. W., Houenou, L. J., Johnson, J. E., Lin, L. F., Li, L., Lo, A. C., Newsome, A. L., Prevette, D. M., and Wang, S. (1995). Developing motor neurons rescued from programmed and axotomy-induced cell death by GDNF. Nature. 373, 344–346.

Pachnis, V., Mankoo, B., and Costantini, F. (1993). Expression of the c-ret proto-oncogene during mouse embryogenesis. Development, 119, 1005–1017.

Pearson, W. R. and Lipman, D. J. (1988). Improved tools for biological sequence comparison. Proceedings Of The National Academy Of Sciences Of The United States Of America. 85, 2444–2448.

Poulsen, K. T., Armanini, M. P., Klein, R. D., Hynes, M. A., Phillips, H. S., and Rosenthal, A. (1994). TGF beta 2 and TGF beta 3 are potent survival factors for midbrain dopaminergic neurons. Neuron. 13, 1245–1252.

Romeo, G., Patrizia, R, Luo, Y., Barone, V., Seri, M., Ceccherini, I., Pasini, B., Bocciardi, R., Lerone, M., Kaariainen, H. and Maartucciello, G. (1994). Point mutations affecting the tyrosine kinase domain of the ret proto-oncogene in Hirschsprung's disease. Nature. 367, 377–378.

Santoro, M., Carlomagno, F., Romeo, A., Bottaro, D., Dathan, N., Grieco, M., Fusco, A., Vecchio, G., Matoskova, B., Kraus, M. and Di Fiore, P. (1995). Activation of ret as a dominant transforming gene by germline mutations of MEN2A and MEN2B. Science. 267, 381–383.

Sauer, H., Rosenblad, C., and Bjoerklund, A. (1995). Glial cell line-derived neurotrophic factor but not transforming growth factor beta 3 prevents delayed degeneration of nigral dopaminergic neurons following striatal 6-hydroxydopamine lesion. Proceedings Of The National Academy Of Sciences Of The United States Of America. 92, 8935–8939.

Saxen, L. (1987). Organogenesis of the kidney. Development and Cell Biology series, Cambridge University Press, Cambridge, England.

Schaar, D. G., Sieber, B. A., Dreyfus, C. F., and Black, I. B. (1993). Regional and cell-specific expression of GDNF in rat brain. Experimental Neurology. 124, 368–371.

Schaar, D. G., Sieber, B. A., Sherwood, A. C., Dean, D., Mendoza, G., Ramakrishnan, L., Dreyfus, C. F., and Black, I. B. (1994). Multiple astrocyte transcripts encode nigral trophic factors in rat and human. Experimental Neurology. 130, 387–393.

Schlessinger, J. and Ulhrich, A. (1992). Growth factor signaling by receptor tyrosine kinases. Neuron 9, 383–391.

Schuchardt, A., D'Agati, V., Larsson-Blomberg, L., Costantini, F. and Pachnis, V. (1994). Defects in the kidney and enteric nervous system of mice lacking the tyrosine kinase receptor ret. Nature. 367, 380–383.

Segarini, P. R., Ziman, J. M., Kane, C. J., and Dasch, J. R. (1992). Two novel patterns of transforming growth factor beta (TGF-beta) binding to cell surface proteins are dependent upon the binding of TGF-beta 1 and indicate a mechanism of positive cooperativity. Journal Of Biological Chemistry. 267, 1048–1053.

Springer, J. E., Mu, X., Bergmann, L. W., and Trojanowski, J. Q. (1994). Expression of GDNF mRNA in rat and human nervous tissue. Experimental Neurology. 127, 167–170.

Stroemberg, I., Bjoerklund, L., Johansson, M., Tomac, A., Collins, F., Olson, L., Hoffer, B., and Humpel, C. (1993). Glial cell line-derived neurotrophic factor is expressed in the developing but not adult striatum and stimulates developing dopamine neurons in vivo. Experimental Neurology. 124, 401–412.

Takahashi, M., Ritz, J. and Cooper, G. (1985). Activation of a novel human tranforming gene, ret, by DNA rearrangement. Cell. 42, 581–588.

Takahashi, M. and Cooper, G. (1987). Ret transforming gene encodes a fusion protein homologous to tyrosine kinases. Mol. Cell. Biol., 7, 1378–1385.

Takebe, Y., Seiki, M., Fujisawa, J., Hoy, P., Yokota, K., Arai, K., Yoshida, M., and Arai, N. (1988). SRa promoter: an efficient and versatile mammalian cDNA expression system composed of the simian virus 40 early promoter and the R-U5 segment of human T-cell leukemia virus type 1 long terminal repeat. Mol. Cell. Biol. 8, 466–472.

Tomac, A., Lindqvist, E., Lin, L. F., Ogren, S. O., Young, D., Hoffer, B. J., and Olson, L. (1995a). Protection and repair of the nigrostriatal dopaminergic system by GDNF in vivo. Nature. 373, 335–339.

Tomac, A., Widenfalk, J., Lin, L. F., Kohno, T., Ebendal, T., Hoffer, B. J., and Olson, L. (1995b). Retrograde axonal transport of glial cell line-derived neurotrophic factor in the adult nigrostriatal system suggests a trophic role in the adult. Proceedings Of The National Academy Of Sciences Of The United States Of America. 92, 8274–8278.

Trupp, M., Ryden, M., Joernvall, H., Funakoshi, H., Timmusk, T., Arenas, E., and Ibanez, C. F. (1995). Peripheral expression and biological activities of GDNF, a new neurotrophic factor for avian and mammalian peripheral neurons. Journal Of Cell Biology. 130, 137–148.

Tsuzuki, T., Takahashi, M., Asai, N., Iwashita, T., Matsuyama, M. and Asai, J. (1995). Spatial and temporal expression of the ret proto-oncongene product in embryonic, infant and adult rat tissues. Oncogene, 10, 191–198.

Ulhrich, A and Schlessinger, J. (1990). Signal transduction by receptors with tyrosine kinase activity. Cell, 61, 203–211.

van der Geer, P., Hunter, T., and Lindberg, R. A. (1994). Receptor protein-tyrosine kinases and their signal transduction pathways. 10, 251–337.

van Heyningen, V. (1994). One gene-four syndromes. Nature, 367, 319–320.

von Heijne, G. (1986). A new method for predicting signal sequence cleavage sites. Nucleic Acids Research. 14,4683–4690.

Yan, Q., Matheson, C., and Lopez, O. T. (1995). In vivo neurotrophic effects of GDNF on neonatal and adult facial motor neurons. Nature. 373, 341–344.

Zurn, A. D., Baetge, E. E., Hammang, J. P., Tan, S. A., and Aebischer, P. (1994). Glial cell line-derived neurotrophic factor (GDNF), a new neurotrophic factor for motoneurones. Neuroreport. 6, 113–118.

What is claimed is:

1. An isolated polynucleic acid molecule encoding a neurotrophic factor receptor protein comprising an amino acid sequence selected from the group consisting of
   (a) an amino acid sequence of FIG. 2 (SEQ ID NO: 2)
   (b) an amino acid sequence comprising $Ser^{18}$ through $pro^{446}$ of FIG. 2 (SEQ ID NO:2)
   (c) amino acid sequence comprising $Asp^{25}$ through $Leu^{447}$ of FIG. 2 (SEQ ID NO:2), and
   (d) amino add sequence comprising $Cys^{29}$ through $Cys^{442}$ of FIG. 2 (SEQ ID NO:2).

2. An isolated polynucleic acid molecule encoding a neurotrophic factor receptor protein comprising the amino acid sequence as depicted in FIG. 2 (SEQ ID NO: 2).

3. A vector comprising a polynucleic acid molecule of claim 1 or 2 operatively linked to one or more operational elements effecting the amplification or expression of said polynucleic acid sequence.

4. A vector comprising a polynucleic acid molecule encoding a neurotrophic factor receptor protein comprising an amino acid sequence selected from the group consisting of
   (a) an amino add sequence of FIG. 2 (SEQ ID NO:2),
   (b) an amino acid sequence comprising $Ser^{18}$ through $Pro^{446}$ of FIG. 2 (SEQ ID NO:2),
   (c) amino acid sequence comprising $Asp^{25}$ through $Leu^{447}$ of FIG. 2 (SEQ ID NO:2), and
   (d) amino acid sequence comprising $Cys^{29}$ through $Cys^{442}$ of FIG. 2 (SEQ ID NO:2) operatively linked to one or more operational elements effecting the amplification or expression of said polynucleic acid molecule.

5. An isolated host cell containing a vector of claim 3.

6. A host cell of claim 5 wherein said cell is transformed or transfected ex vivo.

7. An isolated host cell containing a vector of claim 4.

8. A host cell of claim 7 wherein said cell is selected from the group consisting of a mammalian cell and a bacterial cell.

9. A host cell of claim 5 which is a COS-7 cell or *E. coli*.

10. A method for the production of a neurotrophic factor receptor protein comprising the steps of:
    (a) culturing a host cell, containing a polynucleic acid molecule encoding a neurotrophic factor receptor protein comprising an amino acid sequence selected from the group consisting of
        (i) an amino add sequence of FIG. 2 (SEQ ID NO: 2),
        (ii) an amino acid sequence comprising $Ser^{18}$ through $pro^{446}$ of FIG. 2 (SEQ ID NO:2),
        (iii) amino acid sequence comprising $Asp^{25}$ through $Leu^{447}$ of FIG. 2 (SEQ ID NO:2), and
        (iv) amino acid sequence comprising $Cys^{29}$ through $Cys^{442}$ of FIG. 2 (SEQ ID NO:2) under conditions suitable for the expression of said neurotrophic factor receptor protein by said host cell; and
    (b) optionally, isolating said neurotrophic factor receptor protein expressed by said host cell.

11. A method for the production of a neurotrophic factor receptor protein comprising the steps of:
    (a) culturing a host cell, containing a polynucleic acid molecule encoding a neurotrophic factor receptor protein a neurotrophic factor receptor protein comprising the amino acid sequence as depicted in FIG. 2 (SEQ ID NO:2) under conditions suitable for the expression of said neurotrophic factor receptor protein by said host cell; and
    (b) optionally, isolating said neurotrophic factor receptor protein expressed by said host cell.

* * * * *

SEQUENCE LISTING

```
<160> NUMBER OF SEQ ID NOS: 47

<210> SEQ ID NO 1
<211> LENGTH: 2568
<212> TYPE: DNA
<213> ORGANISM: HUMAN
<220> FEATURE:
<221> NAME/KEY: CDS
<222> LOCATION: (540)..(1934)
<223> OTHER INFORMATION:
<221> NAME/KEY: misc_feature
<222> LOCATION: (2078)..(2078)
<223> OTHER INFORMATION: N in position 2078 indicates a position of
      divergence between different receptor clones
<221> NAME/KEY: misc_feature
<222> LOCATION: (2107)..(2107)
<223> OTHER INFORMATION: N in position 2107 indicates a position of
      divergence between different receptor clones
<221> NAME/KEY: misc_feature
<222> LOCATION: (2241)..(2241)
<223> OTHER INFORMATION: N in position 2241 indicates a position of
      divergence between different receptor clones
<221> NAME/KEY: misc_feature
<222> LOCATION: (2250)..(2250)
<223> OTHER INFORMATION: N in position 2250  indicates a position of
      divergence between different receptor clones
<221> NAME/KEY: misc_feature
<222> LOCATION: (2256)..(2294)
<223> OTHER INFORMATION: N in positions 2256 to 2294  indicates
      positions of divergence between different receptor clones

<400> SEQUENCE: 1
```

-continued

```
aatctggcct cggaacacgc cattctccgc gccgcttcca ataaccacta acatccctaa      60
cgagcatccg agccgagggc tctgctcgga aatcgtcctg gcccaactcg gcccttcgag     120
ctctcgaaga ttaccgcatc tattttttt ttctttttt tcttttccta gcgcagataa      180
agtgagcccg gaaagggaag gaggggggcgg ggacaccatt gccctgaaag aataaataag    240
taaataaaca aactggctcc tcgccgcagc tggacgcggt cggttgagtc caggttgggt    300
cggacctgaa cccctaaaag cggaaccgcc tcccgccctc gccatccggg agctgagtcg    360
ccggcggcgg tggctgctgc cagacccgga gtttcctctt tcactggatg gagctgaact    420
ttgggcggcc agagcagcac agctgtccgg ggatcgctgc acgctgagct ccctcggcaa    480
gacccagcgg cggctcggga ttttttgggg ggggcgggga ccagccccgc gccggcacc    539
```

| | | | | | | | | | | | | | | | | |
|---|---|---|---|---|---|---|---|---|---|---|---|---|---|---|---|---|
| atg | ttc | ctg | gcg | acc | ctg | tac | ttc | gcg | ctg | ccg | ctc | ttg | gac | ttg | ctc | 587 |
| Met | Phe | Leu | Ala | Thr | Leu | Tyr | Phe | Ala | Leu | Pro | Leu | Leu | Asp | Leu | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctg | tcg | gcc | gaa | gtg | agc | ggc | gga | gac | cgc | ctg | gat | tgc | gtg | aaa | gcc | 635 |
| Leu | Ser | Ala | Glu | Val | Ser | Gly | Gly | Asp | Arg | Leu | Asp | Cys | Val | Lys | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| agt | gat | cag | tgc | ctg | aag | gag | cag | agc | tgc | agc | acc | aag | tac | cgc | acg | 683 |
| Ser | Asp | Gln | Cys | Leu | Lys | Glu | Gln | Ser | Cys | Ser | Thr | Lys | Tyr | Arg | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| cta | agg | cag | tgc | gtg | gcg | ggc | aag | gag | acc | aac | ttc | agc | ctg | gca | tcc | 731 |
| Leu | Arg | Gln | Cys | Val | Ala | Gly | Lys | Glu | Thr | Asn | Phe | Ser | Leu | Ala | Ser | |
| | 50 | | | | | 55 | | | | | 60 | | | | | |

| | | | | | | | | | | | | | | | | |
|---|---|---|---|---|---|---|---|---|---|---|---|---|---|---|---|---|
| ggc | ctg | gag | gcc | aag | gat | gag | tgc | cgc | agc | gcc | atg | gag | gcc | ctg | aag | 779 |
| Gly | Leu | Glu | Ala | Lys | Asp | Glu | Cys | Arg | Ser | Ala | Met | Glu | Ala | Leu | Lys | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| cag | aag | tcg | ctc | tac | aac | tgc | cgc | tgc | aag | cgg | ggt | atg | aag | aag | gag | 827 |
| Gln | Lys | Ser | Leu | Tyr | Asn | Cys | Arg | Cys | Lys | Arg | Gly | Met | Lys | Lys | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| aag | aac | tgc | ctg | cgc | att | tac | tgg | agc | atg | tac | cag | agc | ctg | cag | gga | 875 |
| Lys | Asn | Cys | Leu | Arg | Ile | Tyr | Trp | Ser | Met | Tyr | Gln | Ser | Leu | Gln | Gly | |
| | | | | 100 | | | | | 105 | | | | | 110 | | |

| | | | | | | | | | | | | | | | | |
|---|---|---|---|---|---|---|---|---|---|---|---|---|---|---|---|---|
| aat | gat | ctg | ctg | gag | gat | tcc | cca | tat | gaa | cca | gtt | aac | agc | aga | ttg | 923 |
| Asn | Asp | Leu | Leu | Glu | Asp | Ser | Pro | Tyr | Glu | Pro | Val | Asn | Ser | Arg | Leu | |
| | | | 115 | | | | | 120 | | | | | 125 | | | |

| | | | | | | | | | | | | | | | | |
|---|---|---|---|---|---|---|---|---|---|---|---|---|---|---|---|---|
| tca | gat | ata | ttc | cgg | gtg | gtc | cca | ttc | ata | tca | gat | gtt | ttt | cag | caa | 971 |
| Ser | Asp | Ile | Phe | Arg | Val | Val | Pro | Phe | Ile | Ser | Asp | Val | Phe | Gln | Gln | |
| | 130 | | | | | 135 | | | | | 140 | | | | | |

| | | | | | | | | | | | | | | | | |
|---|---|---|---|---|---|---|---|---|---|---|---|---|---|---|---|---|
| gtg | gag | cac | att | ccc | aaa | ggg | aac | aac | tgc | ctg | gat | gca | gcg | aag | gcc | 1019 |
| Val | Glu | His | Ile | Pro | Lys | Gly | Asn | Asn | Cys | Leu | Asp | Ala | Ala | Lys | Ala | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| tgc | aac | ctc | gac | gac | att | tgc | aag | aag | tac | agg | tcg | gcg | tac | atc | acc | 1067 |
| Cys | Asn | Leu | Asp | Asp | Ile | Cys | Lys | Lys | Tyr | Arg | Ser | Ala | Tyr | Ile | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| ccg | tgc | acc | acc | agc | gtg | tcc | aac | gat | gtc | tgc | aac | cgc | cgc | aag | tgc | 1115 |
| Pro | Cys | Thr | Thr | Ser | Val | Ser | Asn | Asp | Val | Cys | Asn | Arg | Arg | Lys | Cys | |
| | | | 180 | | | | | 185 | | | | | 190 | | | |

| | | | | | | | | | | | | | | | | |
|---|---|---|---|---|---|---|---|---|---|---|---|---|---|---|---|---|
| cac | aag | gcc | ctc | cgg | cag | ttc | ttt | gac | aag | gtc | ccg | gcc | aag | cac | agc | 1163 |
| His | Lys | Ala | Leu | Arg | Gln | Phe | Phe | Asp | Lys | Val | Pro | Ala | Lys | His | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| tac | gga | atg | ctc | ttc | tgc | tcc | tgc | cgg | gac | atc | gcc | tgc | aca | gag | cgg | 1211 |
| Tyr | Gly | Met | Leu | Phe | Cys | Ser | Cys | Arg | Asp | Ile | Ala | Cys | Thr | Glu | Arg | |
| | | 210 | | | | | 215 | | | | | 220 | | | | |

| | | | | | | | | | | | | | | | | |
|---|---|---|---|---|---|---|---|---|---|---|---|---|---|---|---|---|
| agg | cga | cag | acc | atc | gtg | cct | gtg | tgc | tcc | tat | gaa | gag | agg | gag | aag | 1259 |
| Arg | Arg | Gln | Thr | Ile | Val | Pro | Val | Cys | Ser | Tyr | Glu | Glu | Arg | Glu | Lys | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| ccc | aac | tgt | ttg | aat | ttg | cag | gac | tcc | tgc | aag | acg | aat | tac | atc | tgc | 1307 |

```
Pro Asn Cys Leu Asn Leu Gln Asp Ser Cys Lys Thr Asn Tyr Ile Cys
                245                 250                 255 aga tct cgc ctt gcg gat ttt ttt acc aac tgc cag cca gag tca agg    1355
Arg Ser Arg Leu Ala Asp Phe Phe Thr Asn Cys Gln Pro Glu Ser Arg
        260                 265                 270 tct gtc agc agc tgt cta aag gaa aac tac gct gac tgc ctc ctc gcc    1403
Ser Val Ser Ser Cys Leu Lys Glu Asn Tyr Ala Asp Cys Leu Leu Ala
            275                 280                 285 tac tcg ggg ctt att ggc aca gtc atg acc ccc aac tac ata gac tcc    1451
Tyr Ser Gly Leu Ile Gly Thr Val Met Thr Pro Asn Tyr Ile Asp Ser
        290                 295                 300 agt agc ctc agt gtg gcc cca tgg tgt gac tgc agc aac agt ggg aac    1499
Ser Ser Leu Ser Val Ala Pro Trp Cys Asp Cys Ser Asn Ser Gly Asn
305                 310                 315                 320 gac cta gaa gag tgc ttg aaa ttt ttg aat ttc ttc aag gac aat aca    1547
Asp Leu Glu Glu Cys Leu Lys Phe Leu Asn Phe Phe Lys Asp Asn Thr
                325                 330                 335 tgt ctt aaa aat gca att caa gcc ttt ggc aat ggc tcc gat gtg acc    1595
Cys Leu Lys Asn Ala Ile Gln Ala Phe Gly Asn Gly Ser Asp Val Thr
            340                 345                 350 gtg tgg cag cca gcc ttc cca gta cag acc acc act gcc act acc acc    1643
Val Trp Gln Pro Ala Phe Pro Val Gln Thr Thr Thr Ala Thr Thr Thr
        355                 360                 365 act gcc ctc cgg gtt aag aac aag ccc ctg ggg cca gca ggg tct gag    1691
Thr Ala Leu Arg Val Lys Asn Lys Pro Leu Gly Pro Ala Gly Ser Glu
370                 375                 380 aat gaa att ccc act cat gtt ttg cca ccg tgt gca aat tta cag gca    1739
Asn Glu Ile Pro Thr His Val Leu Pro Pro Cys Ala Asn Leu Gln Ala
385                 390                 395                 400 cag aag ctg aaa tcc aat gtg tcg ggc aat aca cac ctc tgt att tcc    1787
Gln Lys Leu Lys Ser Asn Val Ser Gly Asn Thr His Leu Cys Ile Ser
            405                 410                 415 aat ggt aat tat gaa aaa gaa ggt ctc ggt gct tcc agc cac ata acc    1835
Asn Gly Asn Tyr Glu Lys Glu Gly Leu Gly Ala Ser Ser His Ile Thr
        420                 425                 430 aca aaa tca atg gct gct cct cca agc tgt ggt ctg agc cca ctg ctg    1883
Thr Lys Ser Met Ala Ala Pro Pro Ser Cys Gly Leu Ser Pro Leu Leu
            435                 440                 445 gtc ctg gtg gta acc gct ctg tcc acc cta tta tct tta aca gaa aca    1931
Val Leu Val Val Thr Ala Leu Ser Thr Leu Leu Ser Leu Thr Glu Thr
        450                 455                 460 tca tagctgcatt aaaaaaatac aatatggaca gtaaaaaga caaaaccaa           1984
Ser
465 gttatctgtt tcctgttctc ttgtatagct gaaattccag tttaggagct cagttgagaa  2044 acagttccat tcaactggaa catttttttt tttnccttttt aagaaagctt cttgtgatcc 2104 ttngggcttt ctgtgaaaaa cctgatgcag tgctccatcc aaactcagaa ggctttggga  2164 tatgctgtat tttaaaggga cagtttgtaa cttgggctgt aaagcaaact ggggctgtgt  2224 tttcgatgat gatgatnatc atgatnatga tnnnnnnnnn nnnnnnnnnn nnnnnnnnnn  2284 nnnnnnnnnn gattttaaca gttttacttc tggcctttcc tagctagaga aggagttaat  2344 atttctaagg taactcccat atctccttta atgacattga tttctaatga tataaatttc  2404 agcctacatt gatgccaagc ttttttgcca caaagaagat tcttaccaag agtgggcttt  2464 gtggaaacag ctggtactga tgttcacctt tatatatgta ctagcatttt ccacgctgat  2524 gtttatgtac tgtaaacagt tctgcactct tgtacaaaag aaaa                  2568
```

<210> SEQ ID NO 2
<211> LENGTH: 465
<212> TYPE: PRT
<213> ORGANISM: HUMAN
<220> FEATURE:
<221> NAME/KEY: misc_feature
<222> LOCATION: (2078)..(2078)
<223> OTHER INFORMATION: N in position 2078 indicates a position of
      divergence between different receptor clones
<221> NAME/KEY: misc_feature
<222> LOCATION: (2107)..(2107)
<223> OTHER INFORMATION: N in position 2107 indicates a position of
      divergence between different receptor clones
<221> NAME/KEY: misc_feature
<222> LOCATION: (2241)..(2241)
<223> OTHER INFORMATION: N in position 2241 indicates a position of
      divergence between different receptor clones
<221> NAME/KEY: misc_feature
<222> LOCATION: (2250)..(2250)
<223> OTHER INFORMATION: N in position 2250  indicates a position of
      divergence between different receptor clones
<221> NAME/KEY: misc_feature
<222> LOCATION: (2256)..(2294)
<223> OTHER INFORMATION: N in positions 2256 to 2294  indicates
      positions of divergence between different receptor clones

<400> SEQUENCE: 2

Met Phe Leu Ala Thr Leu Tyr Phe Ala Leu Pro Leu Leu Asp Leu Leu
1               5                   10                  15

Leu Ser Ala Glu Val Ser Gly Gly Asp Arg Leu Asp Cys Val Lys Ala
            20                  25                  30

Ser Asp Gln Cys Leu Lys Glu Gln Ser Cys Ser Thr Lys Tyr Arg Thr
        35                  40                  45

Leu Arg Gln Cys Val Ala Gly Lys Glu Thr Asn Phe Ser Leu Ala Ser
    50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125

Ser Asp Ile Phe Arg Val Val Pro Phe Ile Ser Asp Val Phe Gln Gln
    130                 135                 140

Val Glu His Ile Pro Lys Gly Asn Asn Cys Leu Asp Ala Ala Lys Ala
145                 150                 155                 160

Cys Asn Leu Asp Asp Ile Cys Lys Lys Tyr Arg Ser Ala Tyr Ile Thr
                165                 170                 175

Pro Cys Thr Thr Ser Val Ser Asn Asp Val Cys Asn Arg Arg Lys Cys
            180                 185                 190

His Lys Ala Leu Arg Gln Phe Phe Asp Lys Val Pro Ala Lys His Ser
        195                 200                 205

Tyr Gly Met Leu Phe Cys Ser Cys Arg Asp Ile Ala Cys Thr Glu Arg
    210                 215                 220

Arg Arg Gln Thr Ile Val Pro Val Cys Ser Tyr Glu Glu Arg Glu Lys
225                 230                 235                 240

Pro Asn Cys Leu Asn Leu Gln Asp Ser Cys Lys Thr Asn Tyr Ile Cys
                245                 250                 255

Arg Ser Arg Leu Ala Asp Phe Phe Thr Asn Cys Gln Pro Glu Ser Arg
            260                 265                 270

```
Ser Val Ser Ser Cys Leu Lys Glu Asn Tyr Ala Asp Cys Leu Leu Ala
        275                 280                 285
Tyr Ser Gly Leu Ile Gly Thr Val Met Thr Pro Asn Tyr Ile Asp Ser
        290                 295                 300
Ser Ser Leu Ser Val Ala Pro Trp Cys Asp Cys Ser Asn Ser Gly Asn
305                 310                 315                 320
Asp Leu Glu Glu Cys Leu Lys Phe Leu Asn Phe Lys Asp Asn Thr
                325                 330                 335
Cys Leu Lys Asn Ala Ile Gln Ala Phe Gly Asn Gly Ser Asp Val Thr
                340                 345                 350
Val Trp Gln Pro Ala Phe Pro Val Gln Thr Thr Thr Ala Thr Thr Thr
        355                 360                 365
Thr Ala Leu Arg Val Lys Asn Lys Pro Leu Gly Pro Ala Gly Ser Glu
    370                 375                 380
Asn Glu Ile Pro Thr His Val Leu Pro Pro Cys Ala Asn Leu Gln Ala
385                 390                 395                 400
Gln Lys Leu Lys Ser Asn Val Ser Gly Asn Thr His Leu Cys Ile Ser
                405                 410                 415
Asn Gly Asn Tyr Glu Lys Glu Gly Leu Gly Ala Ser Ser His Ile Thr
                420                 425                 430
Thr Lys Ser Met Ala Ala Pro Pro Ser Cys Gly Leu Ser Pro Leu Leu
            435                 440                 445
Val Leu Val Val Thr Ala Leu Ser Thr Leu Leu Ser Leu Thr Glu Thr
        450                 455                 460
Ser
465

<210> SEQ ID NO 3
<211> LENGTH: 2138
<212> TYPE: DNA
<213> ORGANISM: RAT
<220> FEATURE:
<221> NAME/KEY: CDS
<222> LOCATION: (302)..(1705)
<223> OTHER INFORMATION:

<400> SEQUENCE: 3
agctcgctct cccggggcag tggtgtggat gcaccggagt tcgggcgctg ggcaagttgg      60
gtcggaactg aaccctgaa  agcgggtccg cctcccgccc tcgcgcccgc ccggatctga     120
gtcgctggcg gcggtgggcg gcagagcgac ggggagtctg ctctcaccct ggatggagct     180
gaactttgag tggccagagg agcgcagtcg cccgggatc  gctgcacgct gagctctctc     240
cccgagaccg gcggcggct  ttggattttg gggggcggg  gaccagctgc gcggcggcac     300 c atg ttc cta gcc act ctg tac ttc gcg ctg cca ctc ctg gat ttg ctg     349
  Met Phe Leu Ala Thr Leu Tyr Phe Ala Leu Pro Leu Leu Asp Leu Leu
  1               5                   10                  15 atg tcc gcc gag gtg agt ggt gga gac cgt ctg gac tgt gtg aaa gcc     397
Met Ser Ala Glu Val Ser Gly Gly Asp Arg Leu Asp Cys Val Lys Ala
            20                  25                  30 agc gat cag tgc ctg aag gaa cag agc tgc agc acc aag tac cgc aca     445
Ser Asp Gln Cys Leu Lys Glu Gln Ser Cys Ser Thr Lys Tyr Arg Thr
        35                  40                  45 cta agg cag tgc gtg gcg ggc aag gaa acc aac ttc agc ctg aca tcc     493
Leu Arg Gln Cys Val Ala Gly Lys Glu Thr Asn Phe Ser Leu Thr Ser
    50                  55                  60 ggc ctt gag gcc aag gat gag tgc cgt agc gcc atg gag gcc ttg aag     541
```

```
                                                              -continued

Gly Leu Glu Ala Lys Asp Glu Cys Arg Ser Ala Met Glu Ala Leu Lys
65                  70                  75                  80 cag aag tct ctg tac aac tgc cgc tgc aag cgg ggc atg aag aaa gag      589
Gln Lys Ser Leu Tyr Asn Cys Arg Cys Lys Arg Gly Met Lys Lys Glu
                85                  90                  95 aag aat tgt ctg cgt atc tac tgg agc atg tac cag agc ctg cag gga      637
Lys Asn Cys Leu Arg Ile Tyr Trp Ser Met Tyr Gln Ser Leu Gln Gly
            100                 105                 110 aat gac ctc ctg gaa gat tcc ccg tat gag ccg gtt aac agc agg ttg      685
Asn Asp Leu Leu Glu Asp Ser Pro Tyr Glu Pro Val Asn Ser Arg Leu
        115                 120                 125 tca gat ata ttc cgg gca gtc ccg ttc ata tca gat gtt ttc cag caa      733
Ser Asp Ile Phe Arg Ala Val Pro Phe Ile Ser Asp Val Phe Gln Gln
    130                 135                 140 gtg gaa cac att tcc aaa ggg aac aac tgc ctg gac gca gcc aag gcc      781
Val Glu His Ile Ser Lys Gly Asn Asn Cys Leu Asp Ala Ala Lys Ala
145                 150                 155                 160 tgc aac ctg gac gac acc tgt aag aag tac agg tcg gcc tac atc acc      829
Cys Asn Leu Asp Asp Thr Cys Lys Lys Tyr Arg Ser Ala Tyr Ile Thr
                165                 170                 175 ccc tgc acc acc agc atg tcc aac gag gtc tgc aac cgc cgt aag tgc      877
Pro Cys Thr Thr Ser Met Ser Asn Glu Val Cys Asn Arg Arg Lys Cys
            180                 185                 190 cac aag gcc ctc agg cag ttc ttc gac aag gtt ccg gcc aag cac agc      925
His Lys Ala Leu Arg Gln Phe Phe Asp Lys Val Pro Ala Lys His Ser
        195                 200                 205 tac ggg atg ctc ttc tgc tcc tgc cgg gac atc gcc tgc acc gag cgg      973
Tyr Gly Met Leu Phe Cys Ser Cys Arg Asp Ile Ala Cys Thr Glu Arg
    210                 215                 220 cgg cga cag act atc gtc ccc gtg tgc tcc tat gaa gaa cga gag agg     1021
Arg Arg Gln Thr Ile Val Pro Val Cys Ser Tyr Glu Glu Arg Glu Arg
225                 230                 235                 240 ccc aac tgc ctg agt ctg caa gac tcc tgc aag acc aat tac atc tgc     1069
Pro Asn Cys Leu Ser Leu Gln Asp Ser Cys Lys Thr Asn Tyr Ile Cys
                245                 250                 255 aga tct cgc ctt gca gat ttt ttt acc aac tgc cag cca gag tca agg     1117
Arg Ser Arg Leu Ala Asp Phe Phe Thr Asn Cys Gln Pro Glu Ser Arg
            260                 265                 270 tct gtc agc aac tgt ctt aag gag aac tac gca gac tgc ctc ctg gcc     1165
Ser Val Ser Asn Cys Leu Lys Glu Asn Tyr Ala Asp Cys Leu Leu Ala
        275                 280                 285 tac tcg gga ctg att ggc aca gtc atg act ccc aac tac gta gac tcc     1213
Tyr Ser Gly Leu Ile Gly Thr Val Met Thr Pro Asn Tyr Val Asp Ser
    290                 295                 300 agc agc ctc agc gtg gca cca tgg tgt gac tgc agc aac agc ggc aat     1261
Ser Ser Leu Ser Val Ala Pro Trp Cys Asp Cys Ser Asn Ser Gly Asn
305                 310                 315                 320 gac ctg gaa gac tgc ttg aaa ttt ctg aat ttt ttt aag gac aat act     1309
Asp Leu Glu Asp Cys Leu Lys Phe Leu Asn Phe Phe Lys Asp Asn Thr
                325                 330                 335 tgt ctc aaa aat gca att caa gcc ttt ggc aat ggc tca gat gtg acc     1357
Cys Leu Lys Asn Ala Ile Gln Ala Phe Gly Asn Gly Ser Asp Val Thr
            340                 345                 350 atg tgg cag cca gcc cct cca gtc cag acc acc act gcc acc act acc     1405
Met Trp Gln Pro Ala Pro Pro Val Gln Thr Thr Thr Ala Thr Thr Thr
        355                 360                 365 act gcc ttc cgg gtc aag aac aag cct ctg ggg cca gca ggg tct gag     1453
Thr Ala Phe Arg Val Lys Asn Lys Pro Leu Gly Pro Ala Gly Ser Glu
    370                 375                 380
```

```
aat gag atc ccc aca cac gtt tta cca ccc tgt gcg aat ttg cag gct      1501
Asn Glu Ile Pro Thr His Val Leu Pro Pro Cys Ala Asn Leu Gln Ala
385                 390                 395                 400 cag aag ctg aaa tcc aat gtg tcg ggt agc aca cac ctc tgt ctt tct      1549
Gln Lys Leu Lys Ser Asn Val Ser Gly Ser Thr His Leu Cys Leu Ser
            405                 410                 415 gat agt gat ttc gga aag gat ggt ctc gct ggt gcc tcc agc cac ata      1597
Asp Ser Asp Phe Gly Lys Asp Gly Leu Ala Gly Ala Ser Ser His Ile
        420                 425                 430 acc aca aaa tca atg gct gct cct ccc agc tgc agt ctg agc tca ctg      1645
Thr Thr Lys Ser Met Ala Ala Pro Pro Ser Cys Ser Leu Ser Ser Leu
    435                 440                 445 ccg gtg ctg atg ctc acc gcc ctt gct gcc ctg tta tct gta tcg ttg      1693
Pro Val Leu Met Leu Thr Ala Leu Ala Ala Leu Leu Ser Val Ser Leu
450                 455                 460 gca gaa acg tcg tagctgcatc cgggaaaaca gtatgaaaag acaaaagaga          1745
Ala Glu Thr Ser
465 accaagtatt ctgtccctgt cctcttgtat atctgaaaat ccagttttaa aagctccgtt    1805 gagaagcagt ttcacccaac tggaactctt tccttgtttt taagaaagct tgtggccctc   1865 agggcttct gttgaagaac tgctacaggg ctaattccaa acccataagg ctctggggcg    1925 tggtgcggct taaggggacc atttgcacca tgtaaagcaa gctggctta tcatgtgttt    1985 gatggtgagg atggtagtgg tgatgatgat ggtaattta acagcttgaa ccctgttctc    2045 tctactggtt aggaacagga gatactattg ataaagattc ttccatgtct tactcagcag   2105 cattgccttc tgaagacagg cccgcagccg tcg                                2138

<210> SEQ ID NO 4
<211> LENGTH: 468
<212> TYPE: PRT
<213> ORGANISM: RAT

<400> SEQUENCE: 4

Met Phe Leu Ala Thr Leu Tyr Phe Ala Leu Pro Leu Leu Asp Leu Leu
1               5                   10                  15

Met Ser Ala Glu Val Ser Gly Gly Asp Arg Leu Asp Cys Val Lys Ala
            20                  25                  30

Ser Asp Gln Cys Leu Lys Glu Gln Ser Cys Ser Thr Lys Tyr Arg Thr
        35                  40                  45

Leu Arg Gln Cys Val Ala Gly Lys Glu Thr Asn Phe Ser Leu Thr Ser
    50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125

Ser Asp Ile Phe Arg Ala Val Pro Phe Ile Ser Asp Val Phe Gln Gln
    130                 135                 140

Val Glu His Ile Ser Lys Gly Asn Asn Cys Leu Asp Ala Ala Lys Ala
145                 150                 155                 160

Cys Asn Leu Asp Asp Thr Cys Lys Lys Tyr Arg Ser Ala Tyr Ile Thr
                165                 170                 175
```

-continued

```
Pro Cys Thr Thr Ser Met Ser Asn Glu Val Cys Asn Arg Arg Lys Cys
            180                 185                 190

His Lys Ala Leu Arg Gln Phe Phe Asp Lys Val Pro Ala Lys His Ser
            195                 200                 205

Tyr Gly Met Leu Phe Cys Ser Cys Arg Asp Ile Ala Cys Thr Glu Arg
            210                 215                 220

Arg Arg Gln Thr Ile Val Pro Val Cys Ser Tyr Glu Glu Arg Glu Arg
225                 230                 235                 240

Pro Asn Cys Leu Ser Leu Gln Asp Ser Cys Lys Thr Asn Tyr Ile Cys
                245                 250                 255

Arg Ser Arg Leu Ala Asp Phe Phe Thr Asn Cys Gln Pro Glu Ser Arg
            260                 265                 270

Ser Val Ser Asn Cys Leu Lys Glu Asn Tyr Ala Asp Cys Leu Leu Ala
            275                 280                 285

Tyr Ser Gly Leu Ile Gly Thr Val Met Thr Pro Asn Tyr Val Asp Ser
            290                 295                 300

Ser Ser Leu Ser Val Ala Pro Trp Cys Asp Cys Ser Asn Ser Gly Asn
305                 310                 315                 320

Asp Leu Glu Asp Cys Leu Lys Phe Leu Asn Phe Phe Lys Asp Asn Thr
                325                 330                 335

Cys Leu Lys Asn Ala Ile Gln Ala Phe Gly Asn Gly Ser Asp Val Thr
            340                 345                 350

Met Trp Gln Pro Ala Pro Val Gln Thr Thr Thr Ala Thr Thr Thr Thr
            355                 360                 365

Thr Ala Phe Arg Val Lys Asn Lys Pro Leu Gly Pro Ala Gly Ser Glu
            370                 375                 380

Asn Glu Ile Pro Thr His Val Leu Pro Pro Cys Ala Asn Leu Gln Ala
385                 390                 395                 400

Gln Lys Leu Lys Ser Asn Val Ser Gly Ser Thr His Leu Cys Leu Ser
                405                 410                 415

Asp Ser Asp Phe Gly Lys Asp Gly Leu Ala Gly Ala Ser Ser His Ile
            420                 425                 430

Thr Thr Lys Ser Met Ala Ala Pro Pro Ser Cys Ser Leu Ser Ser Leu
            435                 440                 445

Pro Val Leu Met Leu Thr Ala Leu Ala Ala Leu Leu Ser Val Ser Leu
            450                 455                 460

Ala Glu Thr Ser
465

<210> SEQ ID NO 5
<211> LENGTH: 3209
<212> TYPE: DNA
<213> ORGANISM: HUMAN
<220> FEATURE:
<221> NAME/KEY: CDS
<222> LOCATION: (540)..(1937)
<223> OTHER INFORMATION:
<221> NAME/KEY: misc_feature
<222> LOCATION: (1)..(510)
<223> OTHER INFORMATION: note="1 to 510 is -237 to 272 of Fig 5
    Hsgr-21bf"
<221> NAME/KEY: misc_feature
<222> LOCATION: (1)..(539)
<223> OTHER INFORMATION: note="1 to 539 is -237 to 301 of Fig 5 Gdnfr"
<221> NAME/KEY: misc_feature
<222> LOCATION: (2078)..(2078)
<223> OTHER INFORMATION: N in position 2078 indicates a position of
    divergence between dif
    ferent receptor clones
<221> NAME/KEY: misc_feature
```

```
<222> LOCATION: (2256)..(2294)
<223> OTHER INFORMATION: N in positions 2256 to 2294 indicates
      positions of divergence between different receptor clones
<221> NAME/KEY: misc_feature
<222> LOCATION: (1091)..(1091)
<223> OTHER INFORMATION: N in position 1091 indicates any nucleic acid

<400> SEQUENCE: 5
aatctggcct cggaacacgc cattctccgc gccgcttcca ataaccacta acatccctaa      60
cgagcatccg agccgagggc tctgctcgga aatcgtcctg gcccaactcg gcccttcgag    120
ctctcgaaga ttaccgcatc tatttttttt ttctttttttt tcttttccta gcgcagataa    180
agtgagcccg gaaagggaag gaggggggcgg ggacaccatt gccctgaaag aataaataag    240
taaataaaca aactggctcc tcgccgcagc tggacgcggt cggttgagtc caggttgggt    300
cggacctgaa cccctaaaag cggaaccgcc tcccgccctc gccatcccgg agctgagtcg    360
ccggcggcgg tggctgctgc cagacccgga gtttcctctt tcactggatg gagctgaact    420
ttgggcggcc agagcagcac agctgtccgg ggatcgctgc acgctgagct ccctcggcaa    480
gacccagcgg cggctcggga tttttttggg ggggcgggga ccagccccgc gccggcacc     539 atg ttc ctg gcg acc ctg tac ttc gcg ctg ccg ctc ttg gac ttg ctc    587
Met Phe Leu Ala Thr Leu Tyr Phe Ala Leu Pro Leu Leu Asp Leu Leu
1               5                   10                  15 ctg tcg gcc gaa gtg agc ggc gga gac cgc ctg gat tgc gtg aaa gcc    635
Leu Ser Ala Glu Val Ser Gly Gly Asp Arg Leu Asp Cys Val Lys Ala
            20                  25                  30 agt gat cag tgc ctg aag gag cag agc tgc agc acc aag tac cgc acg    683
Ser Asp Gln Cys Leu Lys Glu Gln Ser Cys Ser Thr Lys Tyr Arg Thr
        35                  40                  45 cta agg cag tgc gtg gcg ggc aag gag acc aac ttc agc ctg gca tcc    731
Leu Arg Gln Cys Val Ala Gly Lys Glu Thr Asn Phe Ser Leu Ala Ser
    50                  55                  60 ggc ctg gag gcc aag gat gag tgc cgc agc gcc atg gag gcc ctg aag    779
Gly Leu Glu Ala Lys Asp Glu Cys Arg Ser Ala Met Glu Ala Leu Lys
65                  70                  75                  80 cag aag tcg ctc tac aac tgc cgc tgc aag cgg ggt atg aag aag gag    827
Gln Lys Ser Leu Tyr Asn Cys Arg Cys Lys Arg Gly Met Lys Lys Glu
                85                  90                  95 aag aac tgc ctg cgc att tac tgg agc atg tac cag agc ctg cag gga    875
Lys Asn Cys Leu Arg Ile Tyr Trp Ser Met Tyr Gln Ser Leu Gln Gly
            100                 105                 110 aat gat ctg ctg gag gat tcc cca tat gaa cca gtt aac agc aga ttg    923
Asn Asp Leu Leu Glu Asp Ser Pro Tyr Glu Pro Val Asn Ser Arg Leu
        115                 120                 125 tca gat ata ttc cgg gtg gtc cca ttc ata tca gat gtt ttt cag caa    971
Ser Asp Ile Phe Arg Val Val Pro Phe Ile Ser Asp Val Phe Gln Gln
    130                 135                 140 gtg gag cac att ccc aaa ggg aac aac tgc ctg gat gca gcg aag gcc   1019
Val Glu His Ile Pro Lys Gly Asn Asn Cys Leu Asp Ala Ala Lys Ala
145                 150                 155                 160 tgc aac ctc gac gac att tgc aag aag tac agg tcg gcg tac atc acc   1067
Cys Asn Leu Asp Asp Ile Cys Lys Lys Tyr Arg Ser Ala Tyr Ile Thr
                165                 170                 175 ccg tgc acc acc agc gtg tcc aan gat gtc tgc aac cgc cgc aag tgc   1115
Pro Cys Thr Thr Ser Val Ser Xaa Asp Val Cys Asn Arg Arg Lys Cys
            180                 185                 190 cac aag gcc ctc cgg cag ttc ttt gac aag gtc ccg gcc aag cac agc   1163
His Lys Ala Leu Arg Gln Phe Phe Asp Lys Val Pro Ala Lys His Ser
        195                 200                 205
```

-continued

| | |
|---|---|
| tac gga atg ctc ttc tgc tcc tgc cgg gac atc gcc tgc aca gag cgg<br>Tyr Gly Met Leu Phe Cys Ser Cys Arg Asp Ile Ala Cys Thr Glu Arg<br>     210                    215               220 | 1211 |
| agg cga cag acc atc gtg cct gtg tgc tcc tat gaa gag agg gag aag<br>Arg Arg Gln Thr Ile Val Pro Val Cys Ser Tyr Glu Glu Arg Glu Lys<br>225                    230               235               240 | 1259 |
| ccc aac tgt ttg aat ttg cag gac tcc tgc aag acg aat tac atc tgc<br>Pro Asn Cys Leu Asn Leu Gln Asp Ser Cys Lys Thr Asn Tyr Ile Cys<br>               245               250               255 | 1307 |
| aga tct cgc ctt gcg gat ttt ttt acc aac tgc cag cca gag tca agg<br>Arg Ser Arg Leu Ala Asp Phe Phe Thr Asn Cys Gln Pro Glu Ser Arg<br>     260                   265               270 | 1355 |
| tct gtc agc agc tgt cta aag gaa aac tac gct gac tgc ctc ctc gcc<br>Ser Val Ser Ser Cys Leu Lys Glu Asn Tyr Ala Asp Cys Leu Leu Ala<br>         275                 280               285 | 1403 |
| tac tcg ggg ctt att ggc aca gtc atg acc ccc aac tac ata gac tcc<br>Tyr Ser Gly Leu Ile Gly Thr Val Met Thr Pro Asn Tyr Ile Asp Ser<br>              290               295               300 | 1451 |
| agt agc ctc agt gtg gcc cca tgg tgt gac tgc agc aac agt ggg aac<br>Ser Ser Leu Ser Val Ala Pro Trp Cys Asp Cys Ser Asn Ser Gly Asn<br>305                  310               315               320 | 1499 |
| gac cta gaa gag tgc ttg aaa ttt ttg aat ttc ttc aag gac aat aca<br>Asp Leu Glu Glu Cys Leu Lys Phe Leu Asn Phe Phe Lys Asp Asn Thr<br>               325               330               335 | 1547 |
| tgt ctt aaa aat gca att caa gcc ttt ggc aat ggc tcc gat gtg acc<br>Cys Leu Lys Asn Ala Ile Gln Ala Phe Gly Asn Gly Ser Asp Val Thr<br>     340                   345               350 | 1595 |
| gtg tgg cag cca gcc ttc cca gta cag acc acc act gcc act acc acc<br>Val Trp Gln Pro Ala Phe Pro Val Gln Thr Thr Thr Ala Thr Thr Thr<br>         355                 360               365 | 1643 |
| act gcc ctc cgg gtt aag aac aag ccc ctg ggg cca gca ggg tct gag<br>Thr Ala Leu Arg Val Lys Asn Lys Pro Leu Gly Pro Ala Gly Ser Glu<br>             370               375               380 | 1691 |
| aat gaa att ccc act cat gtt ttg cca ccg tgt gca aat tta cag gca<br>Asn Glu Ile Pro Thr His Val Leu Pro Pro Cys Ala Asn Leu Gln Ala<br>385                  390               395               400 | 1739 |
| cag aag ctg aaa tcc aat gtg tcg ggc aat aca cac ctc tgt att tcc<br>Gln Lys Leu Lys Ser Asn Val Ser Gly Asn Thr His Leu Cys Ile Ser<br>               405               410               415 | 1787 |
| aat ggt aat tat gaa aaa gaa ggt ctc ggt gct tcc agc cac ata acc<br>Asn Gly Asn Tyr Glu Lys Glu Gly Leu Gly Ala Ser Ser His Ile Thr<br>     420                   425               430 | 1835 |
| aca aaa tca atg gct gct cct cca agc tgt ggt ctg agc cca ctg ctg<br>Thr Lys Ser Met Ala Ala Pro Pro Ser Cys Gly Leu Ser Pro Leu Leu<br>         435                 440               445 | 1883 |
| gtc ctg gtg gta acc gct ctg tcc acc cta tta tct tta aca gaa aca<br>Val Leu Val Val Thr Ala Leu Ser Thr Leu Leu Ser Leu Thr Glu Thr<br>     450                   455               460 | 1931 |
| tca tag ctgcattaaa aaatacaat atggacatgt aaaaagacaa aaaccaagtt<br>Ser<br>465 | 1987 |
| atctgtttcc tgttctcttg tatagctgaa attccagttt aggagctcag ttgagaaaca | 2047 |
| gttccattca actggaacat tttttttttt nccttttaag aaagcttctt gtgatccttc | 2107 |
| ggggcttctg tgaaaaacct gatgcagtgc tccatccaaa ctcagaaggc tttgggatat | 2167 |
| gctgtatttt aaaggacag tttgtaactt gggctgtaaa gcaaactggg gctgtgtttt | 2227 |
| cgatgatgat gatcatcatg atcatgatnn nnnnnnnnn nnnnnnnnnn nnnnnnnnnn | 2287 |
| nnnnnnngat ttaacagtt ttacttctgg cctttcctag ctagagaagg agttaatatt | 2347 |

-continued

```
tctaaggtaa ctcccatatc tcctttaatg acattgattt ctaatgatat aaatttcagc    2407
ctacattgat gccaagcttt tttgccacaa agaagattct taccaagagt gggctttgtg    2467
gaaacagctg gtactgatgt tcacctttat atatgtacta gcattttcca cgctgatgtt    2527
tatgtactgt aaacagttct gcactcttgt acaaaagaaa aaacacctgt cacatccaaa    2587
tatagtatct gtcttttcgt caaaatagag agtggggaat gagtgtgccg attcaatacc    2647
tcaatccctg aacgacactc tcctaatcct aagccttacc tgagtgagaa gcccttacc     2707 taacaaaagt ccaatatagc tgaaatgtcg ctctaatact ctttacacat atgaggttat    2767
atgtagaaaa aaattttact actaaatgat ttcaactatt ggctttctat attttgaaag    2827
taatgatatt gtctcattt tttactgatg gtttaataca aaatacacag agcttgtttc     2887
ccctcataag tagtgttcgc tctgatatga acttcacaaa tacagctcat caaaagcaga    2947
ctctgagaag cctcgtgctg tagcagaaag ttctgcatca tgtgactgtg gacaggcagg    3007
aggaaacaga acagacaagc attgtctttt gtcattgctc gaagtgcaag cgtgcatacc    3067
tgtggaggga actggtggct gcttgtaaat gttctgcagc atctcttgac acacttgtca    3127
tgacacaatc cagtaccttg gttttcaggt tatctgacaa aggcagcttt gattgggaca    3187
tggaggcatg ggcaggccgg aa                                            3209
```

<210> SEQ ID NO 6
<211> LENGTH: 465
<212> TYPE: PRT
<213> ORGANISM: HUMAN
<220> FEATURE:
<221> NAME/KEY: misc_feature
<222> LOCATION: (184)..(184)
<223> OTHER INFORMATION: The 'Xaa' at location 184 stands for Lys, or
    Asn.
<221> NAME/KEY: misc_feature
<222> LOCATION: (1)..(510)
<223> OTHER INFORMATION: note="1 to 510 is -237 to 272 of Fig 5
    Hsgr-21bf"
<221> NAME/KEY: misc_feature
<222> LOCATION: (1)..(539)
<223> OTHER INFORMATION: note="1 to 539 is -237 to 301 of Fig 5 Gdnfr"
<221> NAME/KEY: misc_feature
<222> LOCATION: (2078)..(2078)
<223> OTHER INFORMATION: N in position 2078 indicates a position of
    divergence between different receptor clones
<221> NAME/KEY: misc_feature
<222> LOCATION: (2256)..(2294)
<223> OTHER INFORMATION: N in positions 2256 to 2294 indicates
    positions of divergence between different receptor clones
<221> NAME/KEY: misc_feature
<222> LOCATION: (1091)..(1091)
<223> OTHER INFORMATION: N in position 1091 indicates any nucleic acid

<400> SEQUENCE: 6

```
Met Phe Leu Ala Thr Leu Tyr Phe Ala Leu Pro Leu Leu Asp Leu Leu
 1               5                  10                  15

Leu Ser Ala Glu Val Ser Gly Gly Asp Arg Leu Asp Cys Val Lys Ala
                20                  25                  30

Ser Asp Gln Cys Leu Lys Glu Gln Ser Cys Ser Thr Lys Tyr Arg Thr
            35                  40                  45

Leu Arg Gln Cys Val Ala Gly Lys Glu Thr Asn Phe Ser Leu Ala Ser
        50                  55                  60

Gly Leu Glu Ala Lys Asp Glu Cys Arg Ser Ala Met Glu Ala Leu Lys
    65                  70                  75                  80

Gln Lys Ser Leu Tyr Asn Cys Arg Cys Lys Arg Gly Met Lys Lys Glu
                85                  90                  95
```

```
Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
            115                 120                 125

Ser Asp Ile Phe Arg Val Val Pro Phe Ile Ser Asp Val Phe Gln Gln
            130                 135                 140

Val Glu His Ile Pro Lys Gly Asn Asn Cys Leu Asp Ala Ala Lys Ala
145                 150                 155                 160

Cys Asn Leu Asp Asp Ile Cys Lys Lys Tyr Arg Ser Ala Tyr Ile Thr
                165                 170                 175

Pro Cys Thr Thr Ser Val Ser Xaa Asp Val Cys Asn Arg Arg Lys Cys
            180                 185                 190

His Lys Ala Leu Arg Gln Phe Phe Asp Lys Val Pro Ala Lys His Ser
            195                 200                 205

Tyr Gly Met Leu Phe Cys Ser Cys Arg Asp Ile Ala Cys Thr Glu Arg
            210                 215                 220

Arg Arg Gln Thr Ile Val Pro Val Cys Ser Tyr Glu Glu Arg Glu Lys
225                 230                 235                 240

Pro Asn Cys Leu Asn Leu Gln Asp Ser Cys Lys Thr Asn Tyr Ile Cys
            245                 250                 255

Arg Ser Arg Leu Ala Asp Phe Phe Thr Asn Cys Gln Pro Glu Ser Arg
            260                 265                 270

Ser Val Ser Ser Cys Leu Lys Glu Asn Tyr Ala Asp Cys Leu Leu Ala
            275                 280                 285

Tyr Ser Gly Leu Ile Gly Thr Val Met Thr Pro Asn Tyr Ile Asp Ser
            290                 295                 300

Ser Ser Leu Ser Val Ala Pro Trp Cys Asp Cys Ser Asn Ser Gly Asn
305                 310                 315                 320

Asp Leu Glu Glu Cys Leu Lys Phe Leu Asn Phe Phe Lys Asp Asn Thr
                325                 330                 335

Cys Leu Lys Asn Ala Ile Gln Ala Phe Gly Asn Gly Ser Asp Val Thr
            340                 345                 350

Val Trp Gln Pro Ala Phe Pro Val Gln Thr Thr Thr Ala Thr Thr Thr
            355                 360                 365

Thr Ala Leu Arg Val Lys Asn Lys Pro Leu Gly Pro Ala Gly Ser Glu
            370                 375                 380

Asn Glu Ile Pro Thr His Val Leu Pro Pro Cys Ala Asn Leu Gln Ala
385                 390                 395                 400

Gln Lys Leu Lys Ser Asn Val Ser Gly Asn Thr His Leu Cys Ile Ser
            405                 410                 415

Asn Gly Asn Tyr Glu Lys Glu Gly Leu Gly Ala Ser Ser His Ile Thr
            420                 425                 430

Thr Lys Ser Met Ala Ala Pro Pro Ser Cys Gly Leu Ser Pro Leu Leu
            435                 440                 445

Val Leu Val Val Thr Ala Leu Ser Thr Leu Leu Ser Leu Thr Glu Thr
            450                 455                 460

Ser
465

<210> SEQ ID NO 7
<211> LENGTH: 508
<212> TYPE: DNA
<213> ORGANISM: HUMAN
<220> FEATURE:
```

```
<221> NAME/KEY: misc_feature
<222> LOCATION: (1)..(508)
<223> OTHER INFORMATION: Note="1 to 508 is -235 to 272 of Figure 5
      Hsgr-21af"

<400> SEQUENCE: 7
tctggcctcg gaacacgcca ttctccgcgc cgcttccaat aaccactaac atccctaacg      60
agcatccgag ccgagggctc tgctcggaaa tcgtcctggc ccaactcggc ccttcgagct    120
ctcgaagatt accgcatcta tttttttttt cttttttttc ttttcctagc gcagataaag    180
tgagcccgga aagggaagga gggggcgggg acaccattgc cctgaaagaa taaataagta    240
aataaacaaa ctggctcctc gccgcagctg gacgcggtcg gttgagtcca ggttgggtcg    300
gacctgaacc cctaaaagcg gaaccgcctc ccgccctcgc catcccggag ctgagtcgcc    360
ggcggcggtg gctgctgcca gacccggagt ttcctctttc actggatgga gctgaacttt    420
gggcggccag agcagcacag ctgtccgggg atcgctgcac gctgagctcc ctcggcaaga    480
cccagcggcg gctcgggatt ttttttggg                                      508

<210> SEQ ID NO 8
<211> LENGTH: 510
<212> TYPE: DNA
<213> ORGANISM: HUMAN
<220> FEATURE:
<221> NAME/KEY: misc_feature
<222> LOCATION: (1)..(510)
<223> OTHER INFORMATION: Note="1 to 510 is -237 to 272 of Figure 5
      Hsgr-21bf"

<400> SEQUENCE: 8
aatctggcct cggaacacgc cattctccgc gccgcttcca ataaccacta acatccctaa     60
cgagcatccg agccgagggc tctgctcgga aatcgtcctg gcccaactcg gcccttcgag    120
ctctcgaaga ttaccgcatc tattttttttt tcttttttt tcttttccta gcgcagataa    180
agtgagcccg gaaagggaag gagggggcgg ggacaccatt gccctgaaag aataaataag    240
taaataaaca aactggctcc tcgccgcagc tggacgcggt cggttgagtc caggttgggt    300
cggacctgaa cccctaaaag cggaaccgcc tcccgccctc gccatcccgg agctgagtcg    360
ccggcggcgg tggctgctgc cagacccgga gtttcctctt tcactggatg gagctgaact    420
ttgggcggcc agagcagcac agctgtccgg ggatcgctgc acgctgagct ccctcggcaa    480
gacccagcgg cggctcggga ttttttttggg                                    510

<210> SEQ ID NO 9
<211> LENGTH: 1927
<212> TYPE: DNA
<213> ORGANISM: HUMAN
<220> FEATURE:
<221> NAME/KEY: CDS
<222> LOCATION: (538)..(1926)
<223> OTHER INFORMATION:
<221> NAME/KEY: misc_feature
<222> LOCATION: (1)..(537)
<223> OTHER INFORMATION: Note= "1 to 537 is -235 to 301 of Figure 5
      21acon"
<221> NAME/KEY: misc_feature
<222> LOCATION: (550)..(550)
<223> OTHER INFORMATION: N in position 550 indicates any nucleic acid

<400> SEQUENCE: 9
tctggcctcg gaacacgcca ttctccgcgc cgcttccaat aaccactaac atccctaacg      60
agcatccgag ccgagggctc tgctcggaaa tcgtcctggc ccaactcggc ccttcgagct    120
```

```
ctcgaagatt accgcatcta tttttttttt ctttttttttc ttttcctagc gcagataaag      180
tgagcccgga aagggaagga gggggcgggg acaccattgc cctgaaagaa taaataagta      240
aataaacaaa ctggctcctc gccgcagctg gacgcggtcg gttgagtcca ggttgggtcg      300
gacctgaacc cctaaaagcg gaaccgcctc ccgccctcgc catcccggag ctgagtcgcc      360
ggcggcggtg gctgctgcca gacccggagt ttcctctttc actggatgga gctgaacttt      420
gggcggccag agcagcacag ctgtccgggg atcgctgcac gctgagctcc ctcggcaaga      480
cccagcggcg gctcgggatt tttttggggg ggcggggacc agccccgcgc cggcacc         537
```

| | | | | | | | | | | | | | | | | |
|---|---|---|---|---|---|---|---|---|---|---|---|---|---|---|---|---|
| atg | ttc | ctg | gcg | ncc | ctg | tac | ttc | gcg | ctg | ccg | ctc | ttg | gac | ttg | ctc | 585 |
| Met | Phe | Leu | Ala | Xaa | Leu | Tyr | Phe | Ala | Leu | Pro | Leu | Leu | Asp | Leu | Leu | |
| 1 | | | | 5 | | | | | 10 | | | | | 15 | | |
| ctg | tcg | gcc | gaa | gtg | agc | ggc | gga | gac | cgc | ctg | gat | tgc | gtg | aaa | gcc | 633 |
| Leu | Ser | Ala | Glu | Val | Ser | Gly | Gly | Asp | Arg | Leu | Asp | Cys | Val | Lys | Ala | |
| | | | 20 | | | | | 25 | | | | | 30 | | | |
| agt | gat | cag | tgc | ctg | aag | gag | cag | agc | tgc | agc | acc | aag | tac | cgc | acg | 681 |
| Ser | Asp | Gln | Cys | Leu | Lys | Glu | Gln | Ser | Cys | Ser | Thr | Lys | Tyr | Arg | Thr | |
| | | 35 | | | | | 40 | | | | | 45 | | | | |
| cta | agg | cag | tgc | gtg | gcg | ggc | aag | gag | acc | aac | ttc | agc | ctg | gca | tcc | 729 |
| Leu | Arg | Gln | Cys | Val | Ala | Gly | Lys | Glu | Thr | Asn | Phe | Ser | Leu | Ala | Ser | |
| | 50 | | | | | 55 | | | | | 60 | | | | | |
| ggc | ctg | gag | gcc | aag | gat | gag | tgc | cgc | agc | gcc | atg | gag | gcc | ctg | aag | 777 |
| Gly | Leu | Glu | Ala | Lys | Asp | Glu | Cys | Arg | Ser | Ala | Met | Glu | Ala | Leu | Lys | |
| 65 | | | | | 70 | | | | | 75 | | | | | 80 | |
| cag | aag | tcg | ctc | tac | aac | tgc | cgc | tgc | aag | cgg | ggt | atg | aag | aag | gag | 825 |
| Gln | Lys | Ser | Leu | Tyr | Asn | Cys | Arg | Cys | Lys | Arg | Gly | Met | Lys | Lys | Glu | |
| | | | | 85 | | | | | 90 | | | | | 95 | | |
| aag | aac | tgc | ctg | cgc | att | tac | tgg | agc | atg | tac | cag | agc | ctg | cag | gga | 873 |
| Lys | Asn | Cys | Leu | Arg | Ile | Tyr | Trp | Ser | Met | Tyr | Gln | Ser | Leu | Gln | Gly | |
| | | | 100 | | | | | 105 | | | | | 110 | | | |
| aat | gat | ctg | ctg | gag | gat | tcc | cca | tat | gaa | cca | gtt | aac | agc | aga | ttg | 921 |
| Asn | Asp | Leu | Leu | Glu | Asp | Ser | Pro | Tyr | Glu | Pro | Val | Asn | Ser | Arg | Leu | |
| | | | 115 | | | | | 120 | | | | | 125 | | | |
| tca | gat | ata | ttc | cgg | gtg | gtc | cca | ttc | ata | tca | gat | gtt | ttt | cag | caa | 969 |
| Ser | Asp | Ile | Phe | Arg | Val | Val | Pro | Phe | Ile | Ser | Asp | Val | Phe | Gln | Gln | |
| | 130 | | | | | 135 | | | | | 140 | | | | | |
| gtg | gag | cac | att | ccc | aaa | ggg | aac | aac | tgc | ctg | gat | gca | gcg | aag | gcc | 1017 |
| Val | Glu | His | Ile | Pro | Lys | Gly | Asn | Asn | Cys | Leu | Asp | Ala | Ala | Lys | Ala | |
| 145 | | | | | 150 | | | | | 155 | | | | | 160 | |
| tgc | aac | ctc | gac | gac | att | tgc | aag | aag | tac | agg | tcg | gcg | tac | atc | acc | 1065 |
| Cys | Asn | Leu | Asp | Asp | Ile | Cys | Lys | Lys | Tyr | Arg | Ser | Ala | Tyr | Ile | Thr | |
| | | | | 165 | | | | | 170 | | | | | 175 | | |
| ccg | tgc | acc | acc | agc | gtg | tcc | aac | gat | gtc | tgc | aac | cgc | cgc | aag | tgc | 1113 |
| Pro | Cys | Thr | Thr | Ser | Val | Ser | Asn | Asp | Val | Cys | Asn | Arg | Arg | Lys | Cys | |
| | | | 180 | | | | | 185 | | | | | 190 | | | |
| cac | aag | gcc | ctc | cgg | cag | ttc | ttt | gac | aag | gtc | ccg | gcc | aag | cac | agc | 1161 |
| His | Lys | Ala | Leu | Arg | Gln | Phe | Phe | Asp | Lys | Val | Pro | Ala | Lys | His | Ser | |
| | | | 195 | | | | | 200 | | | | | 205 | | | |
| tac | gga | atg | ctc | ttc | tgc | tcc | tgc | cgg | gac | atc | gcc | tgc | aca | gag | cgg | 1209 |
| Tyr | Gly | Met | Leu | Phe | Cys | Ser | Cys | Arg | Asp | Ile | Ala | Cys | Thr | Glu | Arg | |
| | | 210 | | | | | 215 | | | | | 220 | | | | |
| agg | cga | cag | acc | atc | gtg | cct | gtg | tgc | tcc | tat | gaa | gag | agg | gag | aag | 1257 |
| Arg | Arg | Gln | Thr | Ile | Val | Pro | Val | Cys | Ser | Tyr | Glu | Glu | Arg | Glu | Lys | |
| 225 | | | | | 230 | | | | | 235 | | | | | 240 | |
| ccc | aac | tgt | ttg | aat | ttg | cag | gac | tcc | tgc | aag | acg | aat | tac | atc | tgc | 1305 |
| Pro | Asn | Cys | Leu | Asn | Leu | Gln | Asp | Ser | Cys | Lys | Thr | Asn | Tyr | Ile | Cys | |
| | | | 245 | | | | | 250 | | | | | 255 | | | |
| aga | tct | cgc | ctt | gcg | gat | ttt | ttt | acc | aac | tgc | cag | cca | gag | tca | agg | 1353 |

```
                                                                    -continued Arg Ser Arg Leu Ala Asp Phe Phe Thr Asn Cys Gln Pro Glu Ser Arg
            260                 265                 270 tct gtc agc agc tgt cta aag gaa aac tac gct gac tgc ctc ctc gcc    1401
Ser Val Ser Ser Cys Leu Lys Glu Asn Tyr Ala Asp Cys Leu Leu Ala
        275                 280                 285 tac tcg ggg ctt att ggc aca gtc atg acc ccc aac tac ata gac tcc    1449
Tyr Ser Gly Leu Ile Gly Thr Val Met Thr Pro Asn Tyr Ile Asp Ser
    290                 295                 300 agt agc ctc agt gtg gcc cca tgg tgt gac tgc agc aac agt ggg aac    1497
Ser Ser Leu Ser Val Ala Pro Trp Cys Asp Cys Ser Asn Ser Gly Asn
305                 310                 315                 320 gac cta gaa gag tgc ttg aaa ttt ttg aat ttc ttc aag gac aat aca    1545
Asp Leu Glu Glu Cys Leu Lys Phe Leu Asn Phe Phe Lys Asp Asn Thr
                325                 330                 335 tgt ctt aaa aat gca att caa gcc ttt ggc aat ggc tcc gat gtg acc    1593
Cys Leu Lys Asn Ala Ile Gln Ala Phe Gly Asn Gly Ser Asp Val Thr
            340                 345                 350 gtg tgg cag cca gcc ttc cca gta cag acc acc act gcc act acc acc    1641
Val Trp Gln Pro Ala Phe Pro Val Gln Thr Thr Thr Ala Thr Thr Thr
        355                 360                 365 act gcc ctc cgg gtt aag aac aag ccc ctg ggg cca gca ggg tct gag    1689
Thr Ala Leu Arg Val Lys Asn Lys Pro Leu Gly Pro Ala Gly Ser Glu
    370                 375                 380 aat gaa att ccc act cat gtt ttg cca ccg tgt gca aat tta cag gca    1737
Asn Glu Ile Pro Thr His Val Leu Pro Pro Cys Ala Asn Leu Gln Ala
385                 390                 395                 400 cag aag ctg aaa tcc aat gtg tcg ggc aat aca cac ctc tgt att tcc    1785
Gln Lys Leu Lys Ser Asn Val Ser Gly Asn Thr His Leu Cys Ile Ser
                405                 410                 415 aat ggt aat tat gaa aaa gaa ggt ctc ggt gct tcc agc cac ata acc    1833
Asn Gly Asn Tyr Glu Lys Glu Gly Leu Gly Ala Ser Ser His Ile Thr
            420                 425                 430 aca aaa tca atg gct gct cct cca agc tgt ggt ctc agc cca ctg ctg    1881
Thr Lys Ser Met Ala Ala Pro Pro Ser Cys Gly Leu Ser Pro Leu Leu
        435                 440                 445 gtc ctg gtg gta acc gct ctg tcc acc cta tta tct tta aca gaa a      1927
Val Leu Val Val Thr Ala Leu Ser Thr Leu Leu Ser Leu Thr Glu
    450                 455                 460

<210> SEQ ID NO 10
<211> LENGTH: 463
<212> TYPE: PRT
<213> ORGANISM: HUMAN
<220> FEATURE:
<221> NAME/KEY: misc_feature
<222> LOCATION: (5)..(5)
<223> OTHER INFORMATION: The 'Xaa' at location 5 stands for Thr, Ala,
      Pro, or Ser.
<221> NAME/KEY: misc_feature
<222> LOCATION: (1)..(537)
<223> OTHER INFORMATION: Note= "1 to 537 is -235 to 301 of Figure 5
      21acon"
<221> NAME/KEY: misc_feature
<222> LOCATION: (550)..(550)
<223> OTHER INFORMATION: N in position 550 indicates any nucleic acid

<400> SEQUENCE: 10

Met Phe Leu Ala Xaa Leu Tyr Phe Ala Leu Pro Leu Leu Asp Leu Leu
1               5                   10                  15

Leu Ser Ala Glu Val Ser Gly Gly Asp Arg Leu Asp Cys Val Lys Ala
                20                  25                  30

Ser Asp Gln Cys Leu Lys Glu Gln Ser Cys Ser Thr Lys Tyr Arg Thr
            35                  40                  45
```

```
Leu Arg Gln Cys Val Ala Gly Lys Glu Thr Asn Phe Ser Leu Ala Ser
    50                  55                  60
Gly Leu Glu Ala Lys Asp Glu Cys Arg Ser Ala Met Glu Ala Leu Lys
 65                  70                  75                  80
Gln Lys Ser Leu Tyr Asn Cys Arg Cys Lys Arg Gly Met Lys Lys Glu
                 85                  90                  95
Lys Asn Cys Leu Arg Ile Tyr Trp Ser Met Tyr Gln Ser Leu Gln Gly
                100                 105                 110
Asn Asp Leu Leu Glu Asp Ser Pro Tyr Glu Pro Val Asn Ser Arg Leu
            115                 120                 125
Ser Asp Ile Phe Arg Val Val Pro Phe Ile Ser Asp Val Phe Gln Gln
    130                 135                 140
Val Glu His Ile Pro Lys Gly Asn Asn Cys Leu Asp Ala Ala Lys Ala
145                 150                 155                 160
Cys Asn Leu Asp Asp Ile Cys Lys Lys Tyr Arg Ser Ala Tyr Ile Thr
                165                 170                 175
Pro Cys Thr Thr Ser Val Ser Asn Asp Val Cys Asn Arg Arg Lys Cys
                180                 185                 190
His Lys Ala Leu Arg Gln Phe Phe Asp Lys Val Pro Ala Lys His Ser
            195                 200                 205
Tyr Gly Met Leu Phe Cys Ser Cys Arg Asp Ile Ala Cys Thr Glu Arg
    210                 215                 220
Arg Arg Gln Thr Ile Val Pro Val Cys Ser Tyr Glu Glu Arg Glu Lys
225                 230                 235                 240
Pro Asn Cys Leu Asn Leu Gln Asp Ser Cys Lys Thr Asn Tyr Ile Cys
                245                 250                 255
Arg Ser Arg Leu Ala Asp Phe Phe Thr Asn Cys Gln Pro Glu Ser Arg
                260                 265                 270
Ser Val Ser Ser Cys Leu Lys Glu Asn Tyr Ala Asp Cys Leu Leu Ala
            275                 280                 285
Tyr Ser Gly Leu Ile Gly Thr Val Met Thr Pro Asn Tyr Ile Asp Ser
    290                 295                 300
Ser Ser Leu Ser Val Ala Pro Trp Cys Asp Cys Ser Asn Ser Gly Asn
305                 310                 315                 320
Asp Leu Glu Glu Cys Leu Lys Phe Leu Asn Phe Phe Lys Asp Asn Thr
                325                 330                 335
Cys Leu Lys Asn Ala Ile Gln Ala Phe Gly Asn Gly Ser Asp Val Thr
                340                 345                 350
Val Trp Gln Pro Ala Phe Pro Val Gln Thr Thr Ala Thr Thr Thr
            355                 360                 365
Thr Ala Leu Arg Val Lys Asn Lys Pro Leu Gly Pro Ala Gly Ser Glu
    370                 375                 380
Asn Glu Ile Pro Thr His Val Leu Pro Pro Cys Ala Asn Leu Gln Ala
385                 390                 395                 400
Gln Lys Leu Lys Ser Asn Val Ser Gly Asn Thr His Leu Cys Ile Ser
                405                 410                 415
Asn Gly Asn Tyr Glu Lys Glu Gly Leu Gly Ala Ser Ser His Ile Thr
                420                 425                 430
Thr Lys Ser Met Ala Ala Pro Pro Ser Cys Gly Leu Ser Pro Leu Leu
            435                 440                 445
Val Leu Val Val Thr Ala Leu Ser Thr Leu Leu Ser Leu Thr Glu
    450                 455                 460
```

-continued

```
<210> SEQ ID NO 11
<211> LENGTH: 1929
<212> TYPE: DNA
<213> ORGANISM: HUMAN
<220> FEATURE:
<221> NAME/KEY: CDS
<222> LOCATION: (540)..(1928)
<223> OTHER INFORMATION:
<221> NAME/KEY: misc_feature
<222> LOCATION: (1)..(539)
<223> OTHER INFORMATION: Note= "1 to 539 is -237 to 301 of Figure 5
      21bcon"

<400> SEQUENCE: 11
aatctggcct cggaacacgc cattctccgc gccgcttcca ataaccacta acatccctaa      60
cgagcatccg agccgagggc tctgctcgga aatcgtcctg gcccaactcg gcccttcgag     120
ctctcgaaga ttaccgcatc tattttttt ttcttttttt tcttttccta gcgcagataa      180
agtgagcccg gaaagggaag gaggggcgg ggacaccatt gccctgaaag aataaataag     240
taaataaaca aactggctcc tcgccgcagc tggacgcggt cggttgagtc caggttgggt     300
cggacctgaa cccctaaaag cggaaccgcc tcccgccctc gccatcccgg agctgagtcg     360 ccggcgcgg tggctgctgc cagacccgga gtttcctctt tcactggatg gagctgaact     420
ttgggcggcc agagcagcac agctgtccgg ggatcgctgc acgctgagct ccctcggcaa     480
gacccagcgg cggctcggga tttttttggg ggggcgggga ccagccccgc gccggcacc     539
```

| | | | | | | | | | | | | | | | | |
|---|---|---|---|---|---|---|---|---|---|---|---|---|---|---|---|---|
| atg | ttc | ctg | gcg | acc | ctg | tac | ttc | gcg | ctg | ccg | ctc | ttg | gac | ttg | ctc | 587 |
| Met | Phe | Leu | Ala | Thr | Leu | Tyr | Phe | Ala | Leu | Pro | Leu | Leu | Asp | Leu | Leu | |
| 1 | | | | 5 | | | | | 10 | | | | | 15 | | |

| ctg | tcg | gcc | gaa | gtg | agc | ggc | gga | gac | cgc | ctg | gat | tgc | gtg | aaa | gcc | 635 |
|---|---|---|---|---|---|---|---|---|---|---|---|---|---|---|---|---|
| Leu | Ser | Ala | Glu | Val | Ser | Gly | Gly | Asp | Arg | Leu | Asp | Cys | Val | Lys | Ala | |
| | | | 20 | | | | | 25 | | | | | 30 | | | |

| agt | gat | cag | tgc | ctg | aag | gag | cag | agc | tgc | agc | acc | aag | tac | cgc | acg | 683 |
|---|---|---|---|---|---|---|---|---|---|---|---|---|---|---|---|---|
| Ser | Asp | Gln | Cys | Leu | Lys | Glu | Gln | Ser | Cys | Ser | Thr | Lys | Tyr | Arg | Thr | |
| | | 35 | | | | | 40 | | | | | 45 | | | | |

| cta | agg | cag | tgc | gtg | gcg | ggc | aag | gag | acc | aac | ttc | agc | ctg | gca | tcc | 731 |
|---|---|---|---|---|---|---|---|---|---|---|---|---|---|---|---|---|
| Leu | Arg | Gln | Cys | Val | Ala | Gly | Lys | Glu | Thr | Asn | Phe | Ser | Leu | Ala | Ser | |
| 50 | | | | | 55 | | | | | 60 | | | | | | |

| ggc | ctg | gag | gcc | aag | gat | gag | tgc | cgc | agc | gcc | atg | gag | gcc | ctg | aag | 779 |
|---|---|---|---|---|---|---|---|---|---|---|---|---|---|---|---|---|
| Gly | Leu | Glu | Ala | Lys | Asp | Glu | Cys | Arg | Ser | Ala | Met | Glu | Ala | Leu | Lys | |
| 65 | | | | | 70 | | | | | 75 | | | | | 80 | |

| cag | aag | tcg | ctc | tac | aac | tgc | cgc | tgc | aag | cgg | ggt | atg | aag | aag | gag | 827 |
|---|---|---|---|---|---|---|---|---|---|---|---|---|---|---|---|---|
| Gln | Lys | Ser | Leu | Tyr | Asn | Cys | Arg | Cys | Lys | Arg | Gly | Met | Lys | Lys | Glu | |
| | | | | 85 | | | | | 90 | | | | | 95 | | |

| aag | aac | tgc | ctg | cgc | att | tac | tgg | agc | atg | tac | cag | agc | ctg | cag | gga | 875 |
|---|---|---|---|---|---|---|---|---|---|---|---|---|---|---|---|---|
| Lys | Asn | Cys | Leu | Arg | Ile | Tyr | Trp | Ser | Met | Tyr | Gln | Ser | Leu | Gln | Gly | |
| | | | 100 | | | | | 105 | | | | | 110 | | | |

| aat | gat | ctg | ctg | gag | gat | tcc | cca | tat | gaa | cca | gtt | aac | agc | aga | ttg | 923 |
|---|---|---|---|---|---|---|---|---|---|---|---|---|---|---|---|---|
| Asn | Asp | Leu | Leu | Glu | Asp | Ser | Pro | Tyr | Glu | Pro | Val | Asn | Ser | Arg | Leu | |
| | | 115 | | | | | 120 | | | | | 125 | | | | |

| tca | gat | ata | ttc | cgg | gtg | gtc | cca | ttc | ata | tca | gat | gtt | ttt | cag | caa | 971 |
|---|---|---|---|---|---|---|---|---|---|---|---|---|---|---|---|---|
| Ser | Asp | Ile | Phe | Arg | Val | Val | Pro | Phe | Ile | Ser | Asp | Val | Phe | Gln | Gln | |
| | 130 | | | | | 135 | | | | | 140 | | | | | |

| gtg | gag | cac | att | ccc | aaa | ggg | aac | aac | tgc | ctg | gat | gca | gcg | aag | gcc | 1019 |
|---|---|---|---|---|---|---|---|---|---|---|---|---|---|---|---|---|
| Val | Glu | His | Ile | Pro | Lys | Gly | Asn | Asn | Cys | Leu | Asp | Ala | Ala | Lys | Ala | |
| 145 | | | | | 150 | | | | | 155 | | | | | 160 | |

| tgc | aac | ctc | gac | gac | att | tgc | aag | aag | tac | agg | tcg | gcg | tac | atc | acc | 1067 |
|---|---|---|---|---|---|---|---|---|---|---|---|---|---|---|---|---|
| Cys | Asn | Leu | Asp | Asp | Ile | Cys | Lys | Lys | Tyr | Arg | Ser | Ala | Tyr | Ile | Thr | |
| | | | | 165 | | | | | 170 | | | | | 175 | | |

| ccg | tgc | acc | acc | agc | gtg | tcc | aac | gat | gtc | tgc | aac | cgc | cgc | aag | tgc | 1115 |
|---|---|---|---|---|---|---|---|---|---|---|---|---|---|---|---|---|

```
Pro Cys Thr Thr Ser Val Ser Asn Asp Val Cys Asn Arg Arg Lys Cys
            180                 185                 190 cac aag gcc ctc cgg cag ttc ttt gac aag gtc ccg gcc aag cac agc     1163
His Lys Ala Leu Arg Gln Phe Phe Asp Lys Val Pro Ala Lys His Ser
            195                 200                 205 tac gga atg ctc ttc tgc tcc tgc cgg gac atc gcc tgc aca gag cgg     1211
Tyr Gly Met Leu Phe Cys Ser Cys Arg Asp Ile Ala Cys Thr Glu Arg
            210                 215                 220 agg cga cag acc atc gtg cct gtg tgc tcc tat gaa gag agg gag aag     1259
Arg Arg Gln Thr Ile Val Pro Val Cys Ser Tyr Glu Glu Arg Glu Lys
225                 230                 235                 240 ccc aac tgt ttg aat ttg cag gac tcc tgc aag acg aat tac atc tgc     1307
Pro Asn Cys Leu Asn Leu Gln Asp Ser Cys Lys Thr Asn Tyr Ile Cys
                245                 250                 255 aga tct cgc ctt gcg gat ttt ttt acc aac tgc cag cca gag tca agg     1355
Arg Ser Arg Leu Ala Asp Phe Phe Thr Asn Cys Gln Pro Glu Ser Arg
                260                 265                 270 tct gtc agc agc tgt cta aag gaa aac tac gct gac tgc ctc ctc gcc     1403
Ser Val Ser Ser Cys Leu Lys Glu Asn Tyr Ala Asp Cys Leu Leu Ala
                275                 280                 285 tac tcg ggg ctt att ggc aca gtc atg acc ccc aac tac ata gac tcc     1451
Tyr Ser Gly Leu Ile Gly Thr Val Met Thr Pro Asn Tyr Ile Asp Ser
            290                 295                 300 agt agc ctc agt gtg gcc cca tgg tgt gac tgc agc aac agt ggg aac     1499
Ser Ser Leu Ser Val Ala Pro Trp Cys Asp Cys Ser Asn Ser Gly Asn
305                 310                 315                 320 gac cta gaa gag tgc ttg aaa ttt ttg aat ttc ttc aag gac aat aca     1547
Asp Leu Glu Glu Cys Leu Lys Phe Leu Asn Phe Phe Lys Asp Asn Thr
                325                 330                 335 tgt ctt aaa aat gca att caa gcc ttt ggc aat ggc tcc gat gtg acc     1595
Cys Leu Lys Asn Ala Ile Gln Ala Phe Gly Asn Gly Ser Asp Val Thr
                340                 345                 350 gtg tgg cag cca gcc ttc cca gta cag acc acc act gcc act acc acc     1643
Val Trp Gln Pro Ala Phe Pro Val Gln Thr Thr Thr Ala Thr Thr Thr
            355                 360                 365 act gcc ctc cgg gtt aag aac aag ccc ctg ggg cca gca ggg tct gag     1691
Thr Ala Leu Arg Val Lys Asn Lys Pro Leu Gly Pro Ala Gly Ser Glu
370                 375                 380 aat gaa att ccc act cat gtt ttg cca ccg tgt gca aat tta cag gca     1739
Asn Glu Ile Pro Thr His Val Leu Pro Pro Cys Ala Asn Leu Gln Ala
385                 390                 395                 400 cag aag ctg aaa tcc aat gtg tcg ggc aat aca cac ctc tgt att tcc     1787
Gln Lys Leu Lys Ser Asn Val Ser Gly Asn Thr His Leu Cys Ile Ser
                405                 410                 415 aat ggt aat tat gaa aaa gaa ggt ctc ggt gct tcc agc cac ata acc     1835
Asn Gly Asn Tyr Glu Lys Glu Gly Leu Gly Ala Ser Ser His Ile Thr
            420                 425                 430 aca aaa tca atg gct gct cct cca agc tgt ggt ctg agc cca ctg ctg     1883
Thr Lys Ser Met Ala Ala Pro Pro Ser Cys Gly Leu Ser Pro Leu Leu
                435                 440                 445 gtc ctg gtg gta acc gct ctg tcc acc cta tta tct tta aca gaa a      1929
Val Leu Val Val Thr Ala Leu Ser Thr Leu Leu Ser Leu Thr Glu
            450                 455                 460

<210> SEQ ID NO 12
<211> LENGTH: 463
<212> TYPE: PRT
<213> ORGANISM: HUMAN
<220> FEATURE:
<221> NAME/KEY: misc_feature
<222> LOCATION: (1)..(539)
```

-continued

<223> OTHER INFORMATION: Note= "1 to 539 is -237 to 301 of Figure 5 21bcon"

<400> SEQUENCE: 12

```
Met Phe Leu Ala Thr Leu Tyr Phe Ala Leu Pro Leu Leu Asp Leu Leu
1               5                   10                  15

Leu Ser Ala Glu Val Ser Gly Gly Asp Arg Leu Asp Cys Val Lys Ala
            20                  25                  30

Ser Asp Gln Cys Leu Lys Glu Gln Ser Cys Ser Thr Lys Tyr Arg Thr
        35                  40                  45

Leu Arg Gln Cys Val Ala Gly Lys Glu Thr Asn Phe Ser Leu Ala Ser
    50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125

Ser Asp Ile Phe Arg Val Val Pro Phe Ile Ser Asp Val Phe Gln Gln
    130                 135                 140

Val Glu His Ile Pro Lys Gly Asn Asn Cys Leu Asp Ala Ala Lys Ala
145                 150                 155                 160

Cys Asn Leu Asp Asp Ile Cys Lys Lys Tyr Arg Ser Ala Tyr Ile Thr
                165                 170                 175

Pro Cys Thr Thr Ser Val Ser Asn Asp Val Cys Asn Arg Arg Lys Cys
            180                 185                 190

His Lys Ala Leu Arg Gln Phe Phe Asp Lys Val Pro Ala Lys His Ser
        195                 200                 205

Tyr Gly Met Leu Phe Cys Ser Cys Arg Asp Ile Ala Cys Thr Glu Arg
    210                 215                 220

Arg Arg Gln Thr Ile Val Pro Val Cys Ser Tyr Glu Glu Arg Glu Lys
225                 230                 235                 240

Pro Asn Cys Leu Asn Leu Gln Asp Ser Cys Lys Thr Asn Tyr Ile Cys
                245                 250                 255

Arg Ser Arg Leu Ala Asp Phe Phe Thr Asn Cys Gln Pro Glu Ser Arg
            260                 265                 270

Ser Val Ser Ser Cys Leu Lys Glu Asn Tyr Ala Asp Cys Leu Leu Ala
        275                 280                 285

Tyr Ser Gly Leu Ile Gly Thr Val Met Thr Pro Asn Tyr Ile Asp Ser
    290                 295                 300

Ser Ser Leu Ser Val Ala Pro Trp Cys Asp Cys Ser Asn Ser Gly Asn
305                 310                 315                 320

Asp Leu Glu Glu Cys Leu Lys Phe Leu Asn Phe Phe Lys Asp Asn Thr
                325                 330                 335

Cys Leu Lys Asn Ala Ile Gln Ala Phe Gly Asn Gly Ser Asp Val Thr
            340                 345                 350

Val Trp Gln Pro Ala Phe Pro Val Gln Thr Thr Thr Ala Thr Thr Thr
        355                 360                 365

Thr Ala Leu Arg Val Lys Asn Lys Pro Leu Gly Pro Ala Gly Ser Glu
    370                 375                 380

Asn Glu Ile Pro Thr His Val Leu Pro Pro Cys Ala Asn Leu Gln Ala
385                 390                 395                 400
```

```
Gln Lys Leu Lys Ser Asn Val Ser Gly Asn Thr His Leu Cys Ile Ser
            405                 410                 415

Asn Gly Asn Tyr Glu Lys Glu Gly Leu Gly Ala Ser Ser His Ile Thr
            420                 425                 430

Thr Lys Ser Met Ala Ala Pro Pro Ser Cys Gly Leu Ser Pro Leu Leu
        435                 440                 445

Val Leu Val Thr Ala Leu Ser Thr Leu Leu Ser Leu Thr Glu
    450                 455                 460

<210> SEQ ID NO 13
<211> LENGTH: 699
<212> TYPE: DNA
<213> ORGANISM: HUMAN
<220> FEATURE:
<221> NAME/KEY: CDS
<222> LOCATION: (2)..(697)
<223> OTHER INFORMATION:
<221> NAME/KEY: misc_feature
<222> LOCATION: (1)..(699)
<223> OTHER INFORMATION: Note= "1 to 699 is 814 to 1512 of Figure 5
      Hsgr-29a"

<400> SEQUENCE: 13 g tcg gcg tac atc acc ccg tgc acc acc agc gtg tcc aat gat gtc tgc    49
  Ser Ala Tyr Ile Thr Pro Cys Thr Thr Ser Val Ser Asn Asp Val Cys
  1               5                   10                  15 aac cgc cgc aag tgc cac aag gcc ctc cgg cag ttc ttt gac aag gtc      97
Asn Arg Arg Lys Cys His Lys Ala Leu Arg Gln Phe Phe Asp Lys Val
                20                  25                  30 ccg gcc aag cac agc tac gga atg ctc ttc tgc tcc tgc cgg gac atc     145
Pro Ala Lys His Ser Tyr Gly Met Leu Phe Cys Ser Cys Arg Asp Ile
            35                  40                  45 gcc tgc aca gag cgg agg cga cag acc atc gtg cct gtg tgc tcc tat     193
Ala Cys Thr Glu Arg Arg Arg Gln Thr Ile Val Pro Val Cys Ser Tyr
        50                  55                  60 gaa gag agg gag aag ccc aac tgt ttg aat ttg cag gac tcc tgc aag     241
Glu Glu Arg Glu Lys Pro Asn Cys Leu Asn Leu Gln Asp Ser Cys Lys
65                  70                  75                  80 acg aat tac atc tgc aga tct cgc ctt gcg gat ttt ttt acc aac tgc     289
Thr Asn Tyr Ile Cys Arg Ser Arg Leu Ala Asp Phe Phe Thr Asn Cys
                85                  90                  95 cag cca gag tca agg tct gtc agc agc tgt cta aag gaa aac tac gct     337
Gln Pro Glu Ser Arg Ser Val Ser Ser Cys Leu Lys Glu Asn Tyr Ala
                100                 105                 110 gac tgc ctc ctc gcc tac tcg ggg ctt att ggc aca gtc atg acc ccc     385
Asp Cys Leu Leu Ala Tyr Ser Gly Leu Ile Gly Thr Val Met Thr Pro
            115                 120                 125 aac tac ata gac tcc agt agc ctc agt gtg gcc cca tgg tgt gac tgc     433
Asn Tyr Ile Asp Ser Ser Ser Leu Ser Val Ala Pro Trp Cys Asp Cys
    130                 135                 140 agc aac agt ggg aac gac cta gaa gag tgc ttg aaa ttt ttg aat ttc     481
Ser Asn Ser Gly Asn Asp Leu Glu Glu Cys Leu Lys Phe Leu Asn Phe
145                 150                 155                 160 ttc aag gac aat aca tgt ctt aaa aat gca att caa gcc ttt ggc aat     529
Phe Lys Asp Asn Thr Cys Leu Lys Asn Ala Ile Gln Ala Phe Gly Asn
                165                 170                 175 ggc tcc gat gtg acc gtg tgg cag cca gcc ttc cca gta cag acc acc     577
Gly Ser Asp Val Thr Val Trp Gln Pro Ala Phe Pro Val Gln Thr Thr
            180                 185                 190 act gcc gct acc acc act gcc ctc cgg gtt aag aac aag ccc ctg ggg     625
Thr Ala Ala Thr Thr Thr Ala Leu Arg Val Lys Asn Lys Pro Leu Gly
```

```
cca gca ggg tct gag aat gaa att ccc act cat gtt ttg cca ccg tgt    673
Pro Ala Gly Ser Glu Asn Glu Ile Pro Thr His Val Leu Pro Pro Cys
    210                 215                 220 gca aat tta cag gca cag aag ctg aa                                  699
Ala Asn Leu Gln Ala Gln Lys Leu
225                 230
```

<210> SEQ ID NO 14
<211> LENGTH: 232
<212> TYPE: PRT
<213> ORGANISM: HUMAN
<220> FEATURE:
<221> NAME/KEY: misc_feature
<222> LOCATION: (1)..(699)
<223> OTHER INFORMATION: Note= "1 to 699 is 814 to 1512 of Figure 5 Hsgr-29a"

<400> SEQUENCE: 14

```
Ser Ala Tyr Ile Thr Pro Cys Thr Thr Ser Val Ser Asn Asp Val Cys
1               5                   10                  15

Asn Arg Arg Lys Cys His Lys Ala Leu Arg Gln Phe Phe Asp Lys Val
            20                  25                  30

Pro Ala Lys His Ser Tyr Gly Met Leu Phe Cys Ser Cys Arg Asp Ile
        35                  40                  45

Ala Cys Thr Glu Arg Arg Gln Thr Ile Val Pro Val Cys Ser Tyr
    50                  55                  60

Glu Glu Arg Glu Lys Pro Asn Cys Leu Asn Leu Gln Asp Ser Cys Lys
65                  70                  75                  80

Thr Asn Tyr Ile Cys Arg Ser Arg Leu Ala Asp Phe Phe Thr Asn Cys
                85                  90                  95

Gln Pro Glu Ser Arg Ser Val Ser Ser Cys Leu Lys Glu Asn Tyr Ala
            100                 105                 110

Asp Cys Leu Leu Ala Tyr Ser Gly Leu Ile Gly Thr Val Met Thr Pro
        115                 120                 125

Asn Tyr Ile Asp Ser Ser Ser Leu Ser Val Ala Pro Trp Cys Asp Cys
    130                 135                 140

Ser Asn Ser Gly Asn Asp Leu Glu Glu Cys Leu Lys Phe Leu Asn Phe
145                 150                 155                 160

Phe Lys Asp Asn Thr Cys Leu Lys Asn Ala Ile Gln Ala Phe Gly Asn
                165                 170                 175

Gly Ser Asp Val Thr Val Trp Gln Pro Ala Phe Pro Val Gln Thr Thr
            180                 185                 190

Thr Ala Ala Thr Thr Thr Ala Leu Arg Val Lys Asn Lys Pro Leu Gly
        195                 200                 205

Pro Ala Gly Ser Glu Asn Glu Ile Pro Thr His Val Leu Pro Pro Cys
    210                 215                 220

Ala Asn Leu Gln Ala Gln Lys Leu
225                 230
```

<210> SEQ ID NO 15
<211> LENGTH: 2157
<212> TYPE: DNA
<213> ORGANISM: HUMAN
<220> FEATURE:
<221> NAME/KEY: CDS
<222> LOCATION: (2)..(886)
<223> OTHER INFORMATION:
<221> NAME/KEY: misc_feature
<222> LOCATION: (1)..(2157)

<223> OTHER INFORMATION: Note= "1 to 2157 is 814 to 2971 of Figure 5 29brc"
<221> NAME/KEY: misc_feature
<222> LOCATION: (1204)..(1242)
<223> OTHER INFORMATION: N in positions 1204 to 1242 indicates positions of divergence between different receptor clones.

<400> SEQUENCE: 15

```
g tcg gcg tac atc acc ccg tgc acc acc agc gtg tcc aat gat gtc tgc          49
  Ser Ala Tyr Ile Thr Pro Cys Thr Thr Ser Val Ser Asn Asp Val Cys
  1               5                   10                  15 aac cgc cgc aag tgc cac aag gcc ctc cgg cag ttc ttt gac aag gtc            97
Asn Arg Arg Lys Cys His Lys Ala Leu Arg Gln Phe Phe Asp Lys Val
             20                  25                  30 ccg gcc aag cac agc tac gga atg ctc ttc tgc tcc tgc cgg gac atc          145
Pro Ala Lys His Ser Tyr Gly Met Leu Phe Cys Ser Cys Arg Asp Ile
         35                  40                  45 gcc tgc aca gag cgg agg cga cag acc atc gtg cct gtg tgc tcc tat          193
Ala Cys Thr Glu Arg Arg Arg Gln Thr Ile Val Pro Val Cys Ser Tyr
     50                  55                  60 gaa gag agg gag aag ccc aac tgt ttg aat ttg cag gac tcc tgc aag          241
Glu Glu Arg Glu Lys Pro Asn Cys Leu Asn Leu Gln Asp Ser Cys Lys
65                  70                  75                  80 acg aat tac atc tgc aga tct cgc ctt gcg gat ttt ttt acc aac tgc          289
Thr Asn Tyr Ile Cys Arg Ser Arg Leu Ala Asp Phe Phe Thr Asn Cys
                 85                  90                  95 cag cca gag tca agg tct gtc agc agc tgt cta aag gaa aac tac gct          337
Gln Pro Glu Ser Arg Ser Val Ser Ser Cys Leu Lys Glu Asn Tyr Ala
             100                 105                 110 gac tgc ctc ctc gcc tac tcg ggg ctt att ggc aca gtc atg acc ccc          385
Asp Cys Leu Leu Ala Tyr Ser Gly Leu Ile Gly Thr Val Met Thr Pro
         115                 120                 125 aac tac ata gac tcc agt agc ctc agt gtg gcc cca tgg tgt gac tgc          433
Asn Tyr Ile Asp Ser Ser Ser Leu Ser Val Ala Pro Trp Cys Asp Cys
     130                 135                 140 agc aac agt ggg aac gac cta gaa gag tgc ttg aaa ttt ttg aat ttc          481
Ser Asn Ser Gly Asn Asp Leu Glu Glu Cys Leu Lys Phe Leu Asn Phe
145                 150                 155                 160 ttc aag gac aat aca tgt ctt aaa aat gca att caa gcc ttt ggc aat          529
Phe Lys Asp Asn Thr Cys Leu Lys Asn Ala Ile Gln Ala Phe Gly Asn
                 165                 170                 175 ggc tcc gat gtg acc gtg tgg cag cca gcc ttc cca gta cag acc acc          577
Gly Ser Asp Val Thr Val Trp Gln Pro Ala Phe Pro Val Gln Thr Thr
             180                 185                 190 act gcc gct acc acc act gcc ctc cgg gtt aag aac aag ccc ctg ggg          625
Thr Ala Ala Thr Thr Thr Ala Leu Arg Val Lys Asn Lys Pro Leu Gly
         195                 200                 205 cca gca ggg tct gag aat gaa att ccc act cat gtt ttg cca ccg tgt          673
Pro Ala Gly Ser Glu Asn Glu Ile Pro Thr His Val Leu Pro Pro Cys
     210                 215                 220 gca aat tta cag gca cag aag ctg aaa tcc aat gtg tcg ggc aat aca          721
Ala Asn Leu Gln Ala Gln Lys Leu Lys Ser Asn Val Ser Gly Asn Thr
225                 230                 235                 240 cac ctc tgt att tcc aat ggt aat tat gaa aaa gaa ggt ctc ggt gct          769
His Leu Cys Ile Ser Asn Gly Asn Tyr Glu Lys Glu Gly Leu Gly Ala
                 245                 250                 255 tcc agc cac ata acc aca aaa tca atg gct gct cct cca agc tgt ggt          817
Ser Ser His Ile Thr Thr Lys Ser Met Ala Ala Pro Pro Ser Cys Gly
             260                 265                 270 ctg agc cca ctg ctg gtc ctg gtg gta acc gct ctg tcc acc cta tta          865
Leu Ser Pro Leu Leu Val Leu Val Val Thr Ala Leu Ser Thr Leu Leu
```

```
                275              280              285
tct tta aca gaa aca tca tag ctgcattaaa aaaatacaat atggacatgt          916
Ser Leu Thr Glu Thr Ser
            290 aaaaagacaa aaaccaagtt atctgtttcc tgttctcttg tatagctgaa attccagttt      976 aggagctcag ttgagaaaca gttccattca actggaacat ttttttttttt ccttttaaga   1036 aagcttcttg tgatccttcg gggcttctgt gaaaaacctg atgcagtgct ccatccaaac    1096 tcagaaggct ttgggatatg ctgtatttta agggacagtt tgtaacttg ggctgtaaag     1156 caaactgggg ctgtgttttc gatgatgatg atcatcatga tcatgatnnn nnnnnnnnn     1216 nnnnnnnnnn nnnnnnnnnn nnnnngatt ttaacagttt tacttctggc ctttcctagc      1276 tagagaagga gttaatattt ctaaggtaac tcccatatct cctttaatga cattgatttc    1336 taatgatata aatttcagcc tacattgatg ccaagctttt ttgccacaaa gaagattctt    1396 accaagagtg ggctttgtgg aaacagctgg tactgatgtt cacctttata tatgtactag    1456 cattttccac gctgatgttt atgtactgta aacagttctg cactcttgta caaaagaaaa    1516 aacacctgtc acatccaaat atagtatctg tcttttcgtc aaaatagaga gtggggaatg    1576 agtgtgccga ttcaatacct caatccctga acgacactct cctaatccta agccttacct   1636 gagtgagaag ccctttacct aacaaaagtc aatatagct gaaatgtcgc tctaatactc     1696 tttacacata tgaggttata tgtagaaaaa aattttacta ctaaatgatt tcaactattg    1756 gctttctata ttttgaaagt aatgatattg tctcatttt ttactgatgg tttaatacaa     1816 aatacacaga gcttgtttcc cctcataagt agtgttcgct ctgatatgaa cttcacaaat    1876 acagctcatc aaaagcagac tctgagaagc ctcgtgctgt agcagaaagt tctgcatcat    1936 gtgactgtgg acaggcagga ggaaacagaa cagacaagca ttgtcttttg tcattgctcg    1996 aagtgcaagc gtgcatacct gtggagggaa ctggtggctg cttgtaaatg ttctgcagca    2056 tctcttgaca cacttgtcat gacacaatcc agtaccttgg ttttcaggtt atctgacaaa    2116 ggcagctttg attgggacat ggaggcatgg gcaggccgga a                       2157
```

<210> SEQ ID NO 16
<211> LENGTH: 294
<212> TYPE: PRT
<213> ORGANISM: HUMAN
<220> FEATURE:
<221> NAME/KEY: misc_feature
<222> LOCATION: (1)..(2157)
<223> OTHER INFORMATION: Note= "1 to 2157 is 814 to 2971 of Figure 5 29brc"
<221> NAME/KEY: misc_feature
<222> LOCATION: (1204)..(1242)
<223> OTHER INFORMATION: N in positions 1204 to 1242 indicates positions of divergence between different receptor clones.

<400> SEQUENCE: 16

```
Ser Ala Tyr Ile Thr Pro Cys Thr Thr Ser Val Ser Asn Asp Val Cys
1               5                   10                  15

Asn Arg Arg Lys Cys His Lys Ala Leu Arg Gln Phe Phe Asp Lys Val
            20                  25                  30

Pro Ala Lys His Ser Tyr Gly Met Leu Phe Cys Ser Cys Arg Asp Ile
        35                  40                  45

Ala Cys Thr Glu Arg Arg Arg Gln Thr Ile Val Pro Val Cys Ser Tyr
    50                  55                  60

Glu Glu Arg Glu Lys Pro Asn Cys Leu Asn Leu Gln Asp Ser Cys Lys
65                  70                  75                  80
```

```
Thr Asn Tyr Ile Cys Arg Ser Arg Leu Ala Asp Phe Phe Thr Asn Cys
                85                  90                  95

Gln Pro Glu Ser Arg Ser Val Ser Ser Cys Leu Lys Glu Asn Tyr Ala
            100                 105                 110

Asp Cys Leu Leu Ala Tyr Ser Gly Leu Ile Gly Thr Val Met Thr Pro
        115                 120                 125

Asn Tyr Ile Asp Ser Ser Ser Leu Ser Val Ala Pro Trp Cys Asp Cys
    130                 135                 140

Ser Asn Ser Gly Asn Asp Leu Glu Glu Cys Leu Lys Phe Leu Asn Phe
145                 150                 155                 160

Phe Lys Asp Asn Thr Cys Leu Lys Asn Ala Ile Gln Ala Phe Gly Asn
                165                 170                 175

Gly Ser Asp Val Thr Val Trp Gln Pro Ala Phe Pro Val Gln Thr Thr
            180                 185                 190

Thr Ala Ala Thr Thr Thr Ala Leu Arg Val Lys Asn Lys Pro Leu Gly
        195                 200                 205

Pro Ala Gly Ser Glu Asn Glu Ile Pro Thr His Val Leu Pro Pro Cys
    210                 215                 220

Ala Asn Leu Gln Ala Gln Lys Leu Lys Ser Asn Val Ser Gly Asn Thr
225                 230                 235                 240

His Leu Cys Ile Ser Asn Gly Asn Tyr Glu Lys Gly Leu Gly Ala
                245                 250                 255

Ser Ser His Ile Thr Thr Lys Ser Met Ala Ala Pro Ser Cys Gly
                260                 265                 270

Leu Ser Pro Leu Leu Val Leu Val Thr Ala Leu Ser Thr Leu Leu
            275                 280                 285

Ser Leu Thr Glu Thr Ser
        290

<210> SEQ ID NO 17
<211> LENGTH: 659
<212> TYPE: DNA
<213> ORGANISM: HUMAN
<220> FEATURE:
<221> NAME/KEY: CDS
<222> LOCATION: (2)..(658)
<223> OTHER INFORMATION:
<221> NAME/KEY: misc_feature
<222> LOCATION: (1)..(659)
<223> OTHER INFORMATION: Note= "1 to 659 is 1033 to 1691 of Figure 5
      Hsgr-21ar"

<400> SEQUENCE: 17 g aat ttg cag gac tcc tgc aag acg aat tac atc tgc aga tct cgc ctt      49
  Asn Leu Gln Asp Ser Cys Lys Thr Asn Tyr Ile Cys Arg Ser Arg Leu
  1               5                  10                  15 gcg gat ttt ttt acc aac tgc cag cca gag tca agg tct gtc agc agc      97
Ala Asp Phe Phe Thr Asn Cys Gln Pro Glu Ser Arg Ser Val Ser Ser
            20                  25                  30 tgt cta aag gaa aac tac gct gac tgc ctc ctc gcc tac tcg ggg ctt     145
Cys Leu Lys Glu Asn Tyr Ala Asp Cys Leu Leu Ala Tyr Ser Gly Leu
        35                  40                  45 att ggc aca gtc atg acc ccc aac tac ata gac tcc agt agc ctc agt     193
Ile Gly Thr Val Met Thr Pro Asn Tyr Ile Asp Ser Ser Ser Leu Ser
    50                  55                  60 gtg gcc cca tgg tgt gac tgc agc aac agt ggg aac gac cta gaa gag     241
Val Ala Pro Trp Cys Asp Cys Ser Asn Ser Gly Asn Asp Leu Glu Glu
65                  70                  75                  80
```

-continued

```
tgc ttg aaa ttt ttg aat ttc ttc aag gac aat aca tgt ctt aaa aat      289
Cys Leu Lys Phe Leu Asn Phe Phe Lys Asp Asn Thr Cys Leu Lys Asn
         85                  90                  95 gca att caa gcc ttt ggc aat ggc tcc gat gtg acc gtg tgg cag cca      337
Ala Ile Gln Ala Phe Gly Asn Gly Ser Asp Val Thr Val Trp Gln Pro
            100                 105                 110 gcc ttc cca gta cag acc acc act gcc act acc acc act gcc ctc cgg      385
Ala Phe Pro Val Gln Thr Thr Thr Ala Thr Thr Thr Thr Ala Leu Arg
                115                 120                 125 gtt aag aac aag ccc ctg ggg cca gca ggg tct gag aat gaa att ccc      433
Val Lys Asn Lys Pro Leu Gly Pro Ala Gly Ser Glu Asn Glu Ile Pro
    130                 135                 140 act cat gtt ttg cca ccg tgt gca aat tta cag gca cag aag ctg aaa      481
Thr His Val Leu Pro Pro Cys Ala Asn Leu Gln Ala Gln Lys Leu Lys
145                 150                 155                 160 tcc aat gtg tcg ggc aat aca cac ctc tgt att tcc aat ggt aat tat      529
Ser Asn Val Ser Gly Asn Thr His Leu Cys Ile Ser Asn Gly Asn Tyr
                165                 170                 175 gaa aaa gaa ggt ctc ggt gct tcc agc cac ata acc aca aaa tca atg      577
Glu Lys Glu Gly Leu Gly Ala Ser Ser His Ile Thr Thr Lys Ser Met
            180                 185                 190 gct gct cct cca agc tgt ggt ctg agc cca ctg ctg gtc ctg gtg gta      625
Ala Ala Pro Pro Ser Cys Gly Leu Ser Pro Leu Leu Val Leu Val Val
        195                 200                 205 acc gct ctg tcc acc cta tta tct tta aca gaa a                        659
Thr Ala Leu Ser Thr Leu Leu Ser Leu Thr Glu
    210                 215
```

<210> SEQ ID NO 18
<211> LENGTH: 219
<212> TYPE: PRT
<213> ORGANISM: HUMAN
<220> FEATURE:
<221> NAME/KEY: misc_feature
<222> LOCATION: (1)..(659)
<223> OTHER INFORMATION: Note= "1 to 659 is 1033 to 1691 of Figure 5 Hsgr-21ar"

<400> SEQUENCE: 18

```
Asn Leu Gln Asp Ser Cys Lys Thr Asn Tyr Ile Cys Arg Ser Arg Leu
1               5                   10                  15

Ala Asp Phe Phe Thr Asn Cys Gln Pro Glu Ser Arg Ser Val Ser Ser
            20                  25                  30

Cys Leu Lys Glu Asn Tyr Ala Asp Cys Leu Leu Ala Tyr Ser Gly Leu
        35                  40                  45

Ile Gly Thr Val Met Thr Pro Asn Tyr Ile Asp Ser Ser Ser Leu Ser
    50                  55                  60

Val Ala Pro Trp Cys Asp Cys Ser Asn Ser Gly Asn Asp Leu Glu Glu
65                  70                  75                  80

Cys Leu Lys Phe Leu Asn Phe Phe Lys Asp Asn Thr Cys Leu Lys Asn
                85                  90                  95

Ala Ile Gln Ala Phe Gly Asn Gly Ser Asp Val Thr Val Trp Gln Pro
            100                 105                 110

Ala Phe Pro Val Gln Thr Thr Thr Ala Thr Thr Thr Thr Ala Leu Arg
        115                 120                 125

Val Lys Asn Lys Pro Leu Gly Pro Ala Gly Ser Glu Asn Glu Ile Pro
    130                 135                 140

Thr His Val Leu Pro Pro Cys Ala Asn Leu Gln Ala Gln Lys Leu Lys
145                 150                 155                 160
```

```
Ser Asn Val Ser Gly Asn Thr His Leu Cys Ile Ser Asn Gly Asn Tyr
                165                 170                 175

Glu Lys Glu Gly Leu Gly Ala Ser Ser His Ile Thr Thr Lys Ser Met
            180                 185                 190

Ala Ala Pro Ser Cys Gly Leu Ser Pro Leu Leu Val Leu Val Val
        195                 200                 205

Thr Ala Leu Ser Thr Leu Leu Ser Leu Thr Glu
    210                 215

<210> SEQ ID NO 19
<211> LENGTH: 630
<212> TYPE: DNA
<213> ORGANISM: HUMAN
<220> FEATURE:
<221> NAME/KEY: CDS
<222> LOCATION: (3)..(629)
<223> OTHER INFORMATION:
<221> NAME/KEY: misc_feature
<222> LOCATION: (1)..(630)
<223> OTHER INFORMATION: Note= "1 to 630 is 1062 to 1691 of Figure 5
      Hsgr-21br"

<400> SEQUENCE: 19 ac atc tgc aga tct cgc ctt gcg gat ttt ttt acc aac tgc cag cca        47
   Ile Cys Arg Ser Arg Leu Ala Asp Phe Phe Thr Asn Cys Gln Pro
   1               5                  10                  15 gag tca agg tct gtc agc agc tgt cta aag gaa aac tac gct gac tgc       95
Glu Ser Arg Ser Val Ser Ser Cys Leu Lys Glu Asn Tyr Ala Asp Cys
            20                  25                  30 ctc ctc gcc tac tcg ggg ctt att ggc aca gtc atg acc ccc aac tac      143
Leu Leu Ala Tyr Ser Gly Leu Ile Gly Thr Val Met Thr Pro Asn Tyr
        35                  40                  45 ata gac tcc agt agc ctc agt gtg gcc cca tgg tgt gac tgc agc aac      191
Ile Asp Ser Ser Ser Leu Ser Val Ala Pro Trp Cys Asp Cys Ser Asn
    50                  55                  60 agt ggg aac gac cta gaa gag tgc ttg aaa ttt ttg aat ttc ttc aag      239
Ser Gly Asn Asp Leu Glu Glu Cys Leu Lys Phe Leu Asn Phe Phe Lys
65                  70                  75 gac aat aca tgt ctt aaa aat gca att caa gcc ttt ggc aat ggc tcc      287
Asp Asn Thr Cys Leu Lys Asn Ala Ile Gln Ala Phe Gly Asn Gly Ser
80                  85                  90                  95 gat gtg acc gtg tgg cag cca gcc ttc cca gta cag acc acc act gcc      335
Asp Val Thr Val Trp Gln Pro Ala Phe Pro Val Gln Thr Thr Thr Ala
                100                 105                 110 act acc acc act gcc ctc cgg gtt aag aac aag ccc ctg ggg cca gca      383
Thr Thr Thr Thr Ala Leu Arg Val Lys Asn Lys Pro Leu Gly Pro Ala
            115                 120                 125 ggg tct gag aat gaa att ccc act cat gtt ttg cca ccg tgt gca aat      431
Gly Ser Glu Asn Glu Ile Pro Thr His Val Leu Pro Pro Cys Ala Asn
        130                 135                 140 tta cag gca cag aag ctg aaa tcc aat gtg tcg ggc aat aca cac ctc      479
Leu Gln Ala Gln Lys Leu Lys Ser Asn Val Ser Gly Asn Thr His Leu
145                 150                 155 tgt att tcc aat ggt aat tat gaa aaa gaa ggt ctc ggt gct tcc agc      527
Cys Ile Ser Asn Gly Asn Tyr Glu Lys Glu Gly Leu Gly Ala Ser Ser
160                 165                 170                 175 cac ata acc aca aaa tca atg gct gct cct cca agc tgt ggt ctg agc      575
His Ile Thr Thr Lys Ser Met Ala Ala Pro Pro Ser Cys Gly Leu Ser
                180                 185                 190 cca ctg ctg gtc ctg gtg gta acc gct ctg tcc acc cta tta tct tta      623
Pro Leu Leu Val Leu Val Val Thr Ala Leu Ser Thr Leu Leu Ser Leu
            195                 200                 205
```

```
aca gaa a                                                              630
Thr Glu <210> SEQ ID NO 20
<211> LENGTH: 209
<212> TYPE: PRT
<213> ORGANISM: HUMAN
<220> FEATURE:
<221> NAME/KEY: misc_feature
<222> LOCATION: (1)..(630)
<223> OTHER INFORMATION: Note= "1 to 630 is 1062 to 1691 of Figure 5
      Hsgr-21br"

<400> SEQUENCE: 20

Ile Cys Arg Ser Arg Leu Ala Asp Phe Phe Thr Asn Cys Gln Pro Glu
1               5                   10                  15

Ser Arg Ser Val Ser Ser Cys Leu Lys Glu Asn Tyr Ala Asp Cys Leu
            20                  25                  30

Leu Ala Tyr Ser Gly Leu Ile Gly Thr Val Met Thr Pro Asn Tyr Ile
        35                  40                  45

Asp Ser Ser Ser Leu Ser Val Ala Pro Trp Cys Asp Cys Ser Asn Ser
    50                  55                  60

Gly Asn Asp Leu Glu Glu Cys Leu Lys Phe Leu Asn Phe Phe Lys Asp
65                  70                  75                  80

Asn Thr Cys Leu Lys Asn Ala Ile Gln Ala Phe Gly Asn Gly Ser Asp
                85                  90                  95

Val Thr Val Trp Gln Pro Ala Phe Pro Val Gln Thr Thr Thr Ala Thr
            100                 105                 110

Thr Thr Thr Ala Leu Arg Val Lys Asn Lys Pro Leu Gly Pro Ala Gly
        115                 120                 125

Ser Glu Asn Glu Ile Pro Thr His Val Leu Pro Pro Cys Ala Asn Leu
    130                 135                 140

Gln Ala Gln Lys Leu Lys Ser Asn Val Ser Gly Asn Thr His Leu Cys
145                 150                 155                 160

Ile Ser Asn Gly Asn Tyr Glu Lys Glu Gly Leu Gly Ala Ser Ser His
                165                 170                 175

Ile Thr Thr Lys Ser Met Ala Pro Pro Ser Cys Gly Leu Ser Pro
            180                 185                 190

Leu Leu Val Leu Val Val Thr Ala Leu Ser Thr Leu Leu Ser Leu Thr
        195                 200                 205

Glu

<210> SEQ ID NO 21
<211> LENGTH: 1075
<212> TYPE: DNA
<213> ORGANISM: HUMAN
<220> FEATURE:
<221> NAME/KEY: CDS
<222> LOCATION: (2)..(445)
<223> OTHER INFORMATION:
<221> NAME/KEY: misc_feature
<222> LOCATION: (1)..(1075)
<223> OTHER INFORMATION: Note= "1 to 1075 is 1255 to 2330 of Figure 5
      Hsgr-2"
<221> NAME/KEY: misc_feature
<222> LOCATION: (763)..(801)
<223> OTHER INFORMATION: N in position 763 to 801 indicates positions of
      divergence between different receptor clones.

<400> SEQUENCE: 21 t ggg aac gac cta gaa gag tgc ttg aaa ttt ttg aat ttc ttc aag gac    49
```

```
    Gly Asn Asp Leu Glu Glu Cys Leu Lys Phe Leu Asn Phe Phe Lys Asp
    1               5                   10                  15 aat aca tgt ctt aaa aat gca att caa gcc ttt ggc aat ggc tcc gat       97
Asn Thr Cys Leu Lys Asn Ala Ile Gln Ala Phe Gly Asn Gly Ser Asp
            20                  25                  30 gtg acc gtg tgg cag cca gcc ttc cca gta cag acc acc act gcc act       145
Val Thr Val Trp Gln Pro Ala Phe Pro Val Gln Thr Thr Thr Ala Thr
        35                  40                  45 acc acc act gcc ctc cgg gtt aag aac aag ccc ctg ggg cca gca ggg       193
Thr Thr Thr Ala Leu Arg Val Lys Asn Lys Pro Leu Gly Pro Ala Gly
50                  55                  60 tct gag aat gaa att ccc act cat gtt ttg cca ccg tgt gca aat tta       241
Ser Glu Asn Glu Ile Pro Thr His Val Leu Pro Pro Cys Ala Asn Leu
65                  70                  75                  80 cag gca cag aag ctg aaa tcc aat gtg tcg ggc aat aca cac ctc tgt       289
Gln Ala Gln Lys Leu Lys Ser Asn Val Ser Gly Asn Thr His Leu Cys
                85                  90                  95 att tcc aat ggt aat tat gaa aaa gaa ggt ctc ggt gct tcc agc cac       337
Ile Ser Asn Gly Asn Tyr Glu Lys Glu Gly Leu Gly Ala Ser Ser His
            100                 105                 110 ata acc aca aaa tca atg gct gct cct cca agc tgt ggt ctg agc cca       385
Ile Thr Thr Lys Ser Met Ala Ala Pro Pro Ser Cys Gly Leu Ser Pro
        115                 120                 125 ctg ctg gtc ctg gtg gta acc gct ctg tcc acc cta tta tct tta aca       433
Leu Leu Val Leu Val Val Thr Ala Leu Ser Thr Leu Leu Ser Leu Thr
    130                 135                 140 gaa aca tca tag ctgcattaaa aaaatacaat atggacatgt aaaaagacaa          485
Glu Thr Ser
145 aaaccaagtt atctgtttcc tgttctcttg tatagctgaa attccagttt aggagctcag    545 ttgagaaaca gttccattca actggaacat tttttttttt ccttttaaga aagcttcttg    605 tgatccttcg gggcttctgt gaaaaacctg atgcagtgct ccatccaaac tcagaaggct    665 ttgggatatg ctgtatttta aagggacagt ttgtaacttg ggctgtaaag caaactgggg    725 ctgtgttttc gatgatgatg atcatcatga tcatgatnnn nnnnnnnnnn nnnnnnnnnn    785 nnnnnnnnnn nnnnnngatt ttaacagttt tacttctggc ctttcctagc tagagaagga    845 gttaatattt ctaaggtaac tcccatatct cctttaatga cattgatttc taatgatata    905 aatttcagcc tacattgatg ccaagctttt ttgccacaaa gaagattctt accaagagtg    965 ggctttgtgg aaacagctgg tactgatgtt cacctttata tatgtactag cattttccac    1025 gctgatgttt atgtactgta aacagttctg cactcttgta caaaagaaaa               1075
```

<210> SEQ ID NO 22
<211> LENGTH: 147
<212> TYPE: PRT
<213> ORGANISM: HUMAN
<220> FEATURE:
<221> NAME/KEY: misc_feature
<222> LOCATION: (1)..(1075)
<223> OTHER INFORMATION: Note= "1 to 1075 is 1255 to 2330 of Figure 5
      Hsgr-2"
<221> NAME/KEY: misc_feature
<222> LOCATION: (763)..(801)
<223> OTHER INFORMATION: N in position 763 to 801 indicates positions
      of divergence between different receptor clones.

<400> SEQUENCE: 22

Gly Asn Asp Leu Glu Glu Cys Leu Lys Phe Leu Asn Phe Phe Lys Asp
1               5                   10                  15

-continued

```
Asn Thr Cys Leu Lys Asn Ala Ile Gln Ala Phe Gly Asn Gly Ser Asp
             20                  25                  30

Val Thr Val Trp Gln Pro Ala Phe Pro Val Gln Thr Thr Ala Thr
         35                  40                  45

Thr Thr Thr Ala Leu Arg Val Lys Asn Lys Pro Leu Gly Pro Ala Gly
     50                  55                  60

Ser Glu Asn Glu Ile Pro Thr His Val Leu Pro Pro Cys Ala Asn Leu
65                  70                  75                  80

Gln Ala Gln Lys Leu Lys Ser Asn Val Ser Gly Asn Thr His Leu Cys
                 85                  90                  95

Ile Ser Asn Gly Asn Tyr Glu Lys Glu Gly Leu Gly Ala Ser Ser His
                100                 105                 110

Ile Thr Thr Lys Ser Met Ala Ala Pro Pro Ser Cys Gly Leu Ser Pro
            115                 120                 125

Leu Leu Val Leu Val Val Thr Ala Leu Ser Thr Leu Leu Ser Leu Thr
        130                 135                 140

Glu Thr Ser
145

<210> SEQ ID NO 23
<211> LENGTH: 1059
<212> TYPE: DNA
<213> ORGANISM: HUMAN
<220> FEATURE:
<221> NAME/KEY: CDS
<222> LOCATION: (3)..(428)
<223> OTHER INFORMATION:
<221> NAME/KEY: misc_feature
<222> LOCATION: (1)..(1059)
<223> OTHER INFORMATION: Note= "1 to 1059 is 1272 to 2330 of Figure 5
      Hsgr-9"

<400> SEQUENCE: 23 ag tgc ttg aaa ttt ttg aat ttc ttc aag gac aat aca tgt ctt aaa      47
   Cys Leu Lys Phe Leu Asn Phe Phe Lys Asp Asn Thr Cys Leu Lys
    1               5                  10                  15 aat gca att caa gcc ttt ggc aat ggc tcc gat gtg acc gtg tgg cag     95
Asn Ala Ile Gln Ala Phe Gly Asn Gly Ser Asp Val Thr Val Trp Gln
                 20                  25                  30 cca gcc ttc cca gta cag acc act gcc act acc acc act gcc ctc        143
Pro Ala Phe Pro Val Gln Thr Thr Ala Thr Thr Thr Thr Ala Leu
             35                  40                  45 cgg gtt aag aac aag ccc ctg ggg cca gca ggg tct gag aat gaa att    191
Arg Val Lys Asn Lys Pro Leu Gly Pro Ala Gly Ser Glu Asn Glu Ile
         50                  55                  60 ccc act cat gtt ttg cca ccg tgt gca aat tta cag gca cag aag ctg    239
Pro Thr His Val Leu Pro Pro Cys Ala Asn Leu Gln Ala Gln Lys Leu
65                  70                  75 aaa tcc aat gtg tcg ggc aat aca cac ctc tgt att tcc aat ggt aat    287
Lys Ser Asn Val Ser Gly Asn Thr His Leu Cys Ile Ser Asn Gly Asn
80                  85                  90                  95 tat gaa aaa gaa ggt ctc ggt gct tcc agc cac ata acc aca aaa tca    335
Tyr Glu Lys Glu Gly Leu Gly Ala Ser Ser His Ile Thr Thr Lys Ser
                100                 105                 110 atg gct gct cct cca agc tgt ggt ctg agc cca ctg ctg gtc ctg gtg    383
Met Ala Ala Pro Pro Ser Cys Gly Leu Ser Pro Leu Leu Val Leu Val
            115                 120                 125 gta acc gct ctg tcc acc cta tta tct tta aca gaa aca tca tag        428
Val Thr Ala Leu Ser Thr Leu Leu Ser Leu Thr Glu Thr Ser
        130                 135                 140
```

-continued

```
ctgcattaaa aaaatacaat atggacatgt aaaaagacaa aaaccaagtt atctgtttcc      488
tgttctcttg tatagctgaa attccagttt aggagctcag ttgagaaaca gttccattca      548
actggaacat tttttttttt tccttttaag aaagcttctt gtgatccttt ggggcttctg      608
tgaaaaacct gatgcagtgc tccatccaaa ctcagaaggc tttgggatat gctgtatttt      668
aaagggacag tttgtaactt gggctgtaaa gcaaactggg gctgtgtttt cgatgatgat      728
gatgatcatg atgatgatca tcatgatcat gatgatgatc atcatgatca tgatgatgat      788
tttaacagtt ttacttctgg cctttcctag ctagagaagg agttaatatt tctaaggtaa      848
ctcccatatc tcctttaatg acattgattt ctaatgatat aaatttcagc ctacattgat      908
gccaagcttt tttgccacaa agaagattct taccaagagt gggctttgtg gaaacagctg      968
gtactgatgt tcacctttat atatgtacta gcattttcca cgctgatgtt tatgtactgt      1028
aaacagttct gcactcttgt acaaaagaaa a                                    1059
```

<210> SEQ ID NO 24
<211> LENGTH: 141
<212> TYPE: PRT
<213> ORGANISM: HUMAN
<220> FEATURE:
<221> NAME/KEY: misc_feature
<222> LOCATION: (1)..(1059)
<223> OTHER INFORMATION: Note= "1 to 1059 is 1272 to 2330 of Figure 5 Hsgr-9"

<400> SEQUENCE: 24

```
Cys Leu Lys Phe Leu Asn Phe Phe Lys Asp Asn Thr Cys Leu Lys Asn
1               5                   10                  15

Ala Ile Gln Ala Phe Gly Asn Gly Ser Asp Val Thr Val Trp Gln Pro
            20                  25                  30

Ala Phe Pro Val Gln Thr Thr Thr Ala Thr Thr Thr Ala Leu Arg
        35                  40                  45

Val Lys Asn Lys Pro Leu Gly Pro Ala Gly Ser Glu Asn Glu Ile Pro
    50                  55                  60

Thr His Val Leu Pro Pro Cys Ala Asn Leu Gln Ala Gln Lys Leu Lys
65                  70                  75                  80

Ser Asn Val Ser Gly Asn Thr His Leu Cys Ile Ser Asn Gly Asn Tyr
                85                  90                  95

Glu Lys Glu Gly Leu Gly Ala Ser Ser His Ile Thr Thr Lys Ser Met
            100                 105                 110

Ala Ala Pro Pro Ser Cys Gly Leu Ser Pro Leu Leu Val Leu Val Val
        115                 120                 125

Thr Ala Leu Ser Thr Leu Leu Ser Leu Thr Glu Thr Ser
    130                 135                 140
```

<210> SEQ ID NO 25
<211> LENGTH: 10
<212> TYPE: PRT
<213> ORGANISM: HUMAN

<400> SEQUENCE: 25

```
Gln Ser Cys Ser Thr Lys Tyr Arg Thr Leu
1               5                   10
```

<210> SEQ ID NO 26
<211> LENGTH: 10
<212> TYPE: PRT
<213> ORGANISM: HUMAN

-continued

```
<400> SEQUENCE: 26

Cys Lys Arg Gly Met Lys Lys Glu Lys Asn
1               5                   10

<210> SEQ ID NO 27
<211> LENGTH: 10
<212> TYPE: PRT
<213> ORGANISM: HUMAN

<400> SEQUENCE: 27

Leu Leu Glu Asp Ser Pro Tyr Glu Pro Val
1               5                   10

<210> SEQ ID NO 28
<211> LENGTH: 10
<212> TYPE: PRT
<213> ORGANISM: RAT

<400> SEQUENCE: 28

Cys Ser Tyr Glu Glu Arg Glu Arg Pro Asn
1               5                   10

<210> SEQ ID NO 29
<211> LENGTH: 14
<212> TYPE: PRT
<213> ORGANISM: RAT

<400> SEQUENCE: 29

Pro Ala Pro Pro Val Gln Thr Thr Thr Ala Thr Thr Thr Thr
1               5                   10

<210> SEQ ID NO 30
<211> LENGTH: 21
<212> TYPE: DNA
<213> ORGANISM: HUMAN

<400> SEQUENCE: 30
ctgtttgaat ttgcaggact c                                          21

<210> SEQ ID NO 31
<211> LENGTH: 36
<212> TYPE: DNA
<213> ORGANISM: HUMAN

<400> SEQUENCE: 31
ctcctctcta agcttctaac cacagcttgg aggagc                          36

<210> SEQ ID NO 32
<211> LENGTH: 37
<212> TYPE: DNA
<213> ORGANISM: HUMAN

<400> SEQUENCE: 32
ctcctctcta agcttctatg ggctcagacc acagctt                         37

<210> SEQ ID NO 33
<211> LENGTH: 60
<212> TYPE: DNA
<213> ORGANISM: HUMAN

<400> SEQUENCE: 33
ctcctctcta agcttctact tgtcatcgtc gtccttgtag tcaccacagc ttggaggagc  60
```

-continued

<210> SEQ ID NO 34
<211> LENGTH: 60
<212> TYPE: DNA
<213> ORGANISM: HUMAN

<400> SEQUENCE: 34
ctcctctcta agcttctact tgtcatcgtc gtccttgtag tctggctcag accacagctt    60

<210> SEQ ID NO 35
<211> LENGTH: 12
<212> TYPE: PRT
<213> ORGANISM: Unknown
<220> FEATURE:
<223> OTHER INFORMATION: Synthetic peptide sequence of arrestin

<400> SEQUENCE: 35

Val Phe Glu Glu Phe Ala Arg Gln Asn Leu Lys Cys
1               5                   10

<210> SEQ ID NO 36
<211> LENGTH: 8
<212> TYPE: PRT
<213> ORGANISM: Unknown
<220> FEATURE:
<223> OTHER INFORMATION: FLAG peptide sequence

<400> SEQUENCE: 36

Asp Tyr Lys Asp Asp Asp Asp Lys
1               5

<210> SEQ ID NO 37
<211> LENGTH: 3209
<212> TYPE: DNA
<213> ORGANISM: HUMAN
<220> FEATURE:
<221> NAME/KEY: misc_feature
<222> LOCATION: (1091)..(1091)
<223> OTHER INFORMATION: N in position 1091 indicates any nucleic acid.
<221> NAME/KEY: misc_feature
<222> LOCATION: (2078)..(2078)
<223> OTHER INFORMATION: N in position 2078 indicates a position of
      divergence between different receptor clones.
<221> NAME/KEY: misc_feature
<222> LOCATION: (2256)..(2294)
<223> OTHER INFORMATION: N in positions 2256 to 2294 indicates positions
      of divergence between different receptor clones.

<400> SEQUENCE: 37
aatctggcct cggaacacgc cattctccgc gccgcttcca ataaccacta acatccctaa    60
cgagcatccg agccgagggc tctgctcgga aatcgtcctg gcccaactcg gcccttcgag   120
ctctcgaaga ttaccgcatc tattttttt tctttttttt tcttttccta gcgcagataa    180
agtgagcccg gaaagggaag gagggggcgg ggacaccatt gccctgaaag aataaataag   240
taaataaaca aactggctcc tcgccgcagc tggacgcggt cggttgagtc caggttgggt   300
cggacctgaa cccctaaaag cggaaccgcc tcccgccctc gccatcccgg agctgagtcg   360
ccggcggcgg tggctgctgc cagacccgga gtttcctctt tcactggatg gagctgaact   420
ttgggcggcc agagcagcac agctgtccgg ggatcgctgc acgctgagct ccctcggcaa   480
gacccagcgg cggtcgggga ttttttggg ggggcgggga ccagccccgc gccggcacca   540
tgttcctggc gaccctgtac ttcgcgctgc cgctcttgga cttgctcctg tcggccgaag   600
tgagcggcgg agaccgcctg gattgcgtga agccagtga tcagtgcctg aaggagcaga   660
gctgcagcac caagtaccgc acgctaaggc agtgcgtggc gggcaaggag accaacttca   720

-continued

| | |
|---|---|
| gcctggcatc cggcctggag gccaaggatg agtgccgcag cgccatggag gccctgaagc | 780 |
| agaagtcgct ctacaactgc cgctgcaagc ggggtatgaa gaaggagaag aactgcctgc | 840 |
| gcatttactg gagcatgtac cagagcctgc agggaaatga tctgctggag gattccccat | 900 |
| atgaaccagt taacagcaga ttgtcagata tattccgggt ggtcccattc atatcagatg | 960 |
| tttttcagca agtggagcac attcccaaag gaacaactg cctggatgca gcgaaggcct | 1020 |
| gcaacctcga cgacatttgc aagaagtaca ggtcggcgta catcaccccg tgcaccacca | 1080 |
| gcgtgtccaa ngatgtctgc aaccgccgca agtgccacaa ggccctccgg cagttctttg | 1140 |
| acaaggtccc ggccaagcac agctacggaa tgctcttctg ctcctgccgg gacatcgcct | 1200 |
| gcacagagcg gaggcgacag accatcgtgc ctgtgtgctc ctatgaagag agggagaagc | 1260 |
| ccaactgttt gaatttgcag gactcctgca agacgaatta catctgcaga tctcgccttg | 1320 |
| cggatttttt taccaactgc cagccagagt caaggtctgt cagcagctgt ctaaaggaaa | 1380 |
| actacgctga ctgcctcctc gcctactcgg ggcttattgg cacagtcatg accccaact | 1440 |
| acatagactc cagtagcctc agtgtggccc catggtgtga ctgcagcaac agtgggaacg | 1500 |
| acctagaaga gtgcttgaaa ttttttgaatt tcttcaagga caatacatgt cttaaaaatg | 1560 |
| caattcaagc ctttggcaat ggctccgatg tgaccgtgtg gcagccagcc ttcccagtac | 1620 |
| agaccaccac tgccactacc accactgccc tccgggttaa gaacaagccc ctggggccag | 1680 |
| cagggtctga gaatgaaatt cccactcatg ttttgccacc gtgtgcaaat ttacaggcac | 1740 |
| agaagctgaa atccaatgtg tcgggcaata cacacctctg tatttccaat ggtaattatg | 1800 |
| aaaaagaagg tctcggtgct tccagccaca taaccacaaa atcaatggct gctcctccaa | 1860 |
| gctgtggtct gagcccactg ctggtcctgg tggtaaccgc tctgtccacc ctattatctt | 1920 |
| taacagaaac atcatagctg cattaaaaaa atacaatatg gacatgtaaa aagacaaaaa | 1980 |
| ccaagttatc tgtttcctgt tctcttgtat agctgaaatt ccagtttagg agctcagttg | 2040 |
| agaaacagtt ccattcaact ggaacatttt tttttttncc ttttaagaaa gcttcttgtg | 2100 |
| atccttcggg gcttctgtga aaacctgat gcagtgctcc atccaaactc agaaggcttt | 2160 |
| gggatatgct gtattttaaa gggacagttt gtaacttggg ctgtaaagca aactggggct | 2220 |
| gtgttttcga tgatgatgat catcatgatc atgatnnnnn nnnnnnnnnn nnnnnnnnnn | 2280 |
| nnnnnnnnnn nnnngattt aacagtttta cttctggcct ttcctagcta gagaaggagt | 2340 |
| taatatttct aagtaactc ccatatctcc tttaatgaca ttgatttcta atgatataaa | 2400 |
| tttcagccta cattgatgcc aagcttttt gccacaaaga agattcttac caagagtggg | 2460 |
| ctttgtggaa acagctggta ctgatgttca cctttatata tgtactagca ttttccacgc | 2520 |
| tgatgtttat gtactgtaaa cagttctgca ctcttgtaca aagaaaaaa cacctgtcac | 2580 |
| atccaaatat agtatctgtc ttttcgtcaa aatagagagt ggggaatgag tgtgccgatt | 2640 |
| caatacctca atccctgaac gacactctcc taatcctaag ccttacctga gtgagaagcc | 2700 |
| ctttacctaa caaagtcca atatagctga atgtcgctc taatactctt tacacatatg | 2760 |
| aggttatatg tagaaaaaaa ttttactact aaatgatttc aactattggc tttctatatt | 2820 |
| ttgaaagtaa tgatattgtc tcatttttt actgatggtt taatacaaaa tacacagagc | 2880 |
| ttgtttcccc tcataagtag tgttcgctct gatatgaact tcacaaatac agctcatcaa | 2940 |
| aagcagactc tgagaagcct cgtgctgtag cagaaagttc tgcatcatgt gactgtggac | 3000 |
| aggcaggagg aaacagaaca gacaagcatt gtcttttgtc attgctcgaa gtgcaagcgt | 3060 |
| gcatacctgt ggagggaact ggtggctgct tgtaaatgtt ctgcagcatc tcttgacaca | 3120 |

```
cttgtcatga cacaatccag taccttggtt ttcaggttat ctgacaaagg cagctttgat    3180
tgggacatgg aggcatgggc aggccggaa                                     3209
```

<210> SEQ ID NO 38
<211> LENGTH: 508
<212> TYPE: DNA
<213> ORGANISM: HUMAN

<400> SEQUENCE: 38

```
tctggcctcg gaacacgcca ttctccgcgc cgcttccaat aaccactaac atccctaacg     60
agcatccgag ccgagggctc tgctcggaaa tcgtcctggc ccaactcggc ccttcgagct    120
ctcgaagatt accgcatcta tttttttttt ctttttttc ttttcctagc gcagataaag    180
tgagcccgga aagggaagga gggggcgggg acaccattgc cctgaaagaa taaataagta    240
aataaacaaa ctggctcctc gccgcagctg gacgcggtcg gttgagtcca ggttgggtcg    300
gacctgaacc cctaaaagcg gaaccgcctc cgccctcgc catcccggag ctgagtcgcc    360
ggcggcggtg gctgctgcca gacccggagt tcctcttttc actggatgga gctgaacttt    420
gggcggccag agcagcacag ctgtccgggg atcgctgcac gctgagctcc ctcggcaaga    480
cccagcggcg gctcgggatt tttttggg                                      508
```

<210> SEQ ID NO 39
<211> LENGTH: 510
<212> TYPE: DNA
<213> ORGANISM: HUMAN

<400> SEQUENCE: 39

```
aatctggcct cggaacacgc cattctccgc gccgcttcca ataaccacta acatccctaa     60
cgagcatccg agccgagggc tctgctcgga aatcgtcctg gcccaactcg gcccttcgag    120
ctctcgaaga ttaccgcatc tatttttttt ttcttttttt tcttttccta gcgcagataa    180
agtgagcccg gaaagggaag gagggggcgg ggacaccatt gccctgaaag aataaataag    240
taaataaaca aactggctcc tcgccgcagc tggacgcggt cggttgagtc caggttgggt    300
cggacctgaa cccctaaaag cggaaccgcc tccgccctc gccatcccgg agctgagtcg    360
ccggcggcgg tggctgctgc cagacccgga gtttcctctt tcactggatg gagctgaact    420
ttgggcggcc agagcagcac agctgtccgg ggatcgctgc acgctgagct ccctcggcaa    480
gacccagcgg cggctcggga ttttttttggg                                   510
```

<210> SEQ ID NO 40
<211> LENGTH: 1927
<212> TYPE: DNA
<213> ORGANISM: HUMAN
<220> FEATURE:
<221> NAME/KEY: misc_feature
<222> LOCATION: (550)..(550)
<223> OTHER INFORMATION: N in position 550 indicates any nucleic acid

<400> SEQUENCE: 40

```
tctggcctcg gaacacgcca ttctccgcgc cgcttccaat aaccactaac atccctaacg     60
agcatccgag ccgagggctc tgctcggaaa tcgtcctggc ccaactcggc ccttcgagct    120
ctcgaagatt accgcatcta tttttttttt ctttttttc ttttcctagc gcagataaag    180
tgagcccgga aagggaagga gggggcgggg acaccattgc cctgaaagaa taaataagta    240
aataaacaaa ctggctcctc gccgcagctg gacgcggtcg gttgagtcca ggttgggtcg    300
```

-continued

```
gacctgaacc cctaaaagcg gaaccgcctc ccgccctcgc catcccggag ctgagtcgcc      360
ggcggcggtg gctgctgcca gacccggagt ttcctctttc actggatgga gctgaacttt      420
gggcggccag agcagcacag ctgtccgggg atcgctgcac gctgagctcc ctcggcaaga      480
cccagcggcg gctcgggatt tttttggggg gcgggggacc agccccgcgc ggcaccatg       540 ttcctggcgn ccctgtactt cgcgctgccg ctcttggact tgctcctgtc ggccgaagtg      600
agcggcggag accgcctgga ttgcgtgaaa gccagtgatc agtgcctgaa ggagcagagc      660
tgcagcacca agtaccgcac gctaaggcag tgcgtggcgg gcaaggagac caacttcagc      720
ctggcatccg gcctggaggc caaggatgag tgccgcagcg ccatggaggc cctgaagcag      780
aagtcgctct acaactgccg ctgcaagcgg ggtatgaaga aggagaagaa ctgcctgcgc      840
atttactgga gcatgtacca gagcctgcag ggaaatgatc tgctggagga ttccccatat      900
gaaccagtta acagcagatt gtcagatata ttccgggtgg tcccattcat atcagatgtt      960
tttcagcaag tggagcacat tcccaaaggg aacaactgcc tggatgcagc gaaggcctgc     1020
aacctcgacg catttgcaa gaagtacagg tcggcgtaca tcaccccgtg caccaccagc      1080
gtgtccaacg atgtctgcaa ccgccgcaag tgccacaagg ccctccggca gttctttgac     1140
aaggtcccgg ccaagcacag ctacggaatg ctcttctgct cctgccggga catcgcctgc     1200
acagagcgga ggcgacagac catcgtgcct gtgtgctcct atgaagagag ggagaagccc     1260
aactgtttga atttgcagga ctcctgcaag acgaattaca tctgcagatc tcgccttgcg     1320
gattttttta ccaactgcca gccagagtca aggtctgtca gcagctgtct aaaggaaaac     1380
tacgctgact gcctcctcgc ctactcgggg cttattggca cagtcatgac ccccaactac     1440
atagactcca gtagcctcag tgtggcccca tggtgtgact gcagcaacag tgggaacgac     1500
ctagaagagt gcttgaaatt tttgaatttc ttcaaggaca atacatgtct aaaaatgca      1560 attcaagcct ttggcaatgg ctccgatgtg accgtgtggc agccagcctt cccagtacag     1620
accaccactg ccactaccac cactgccctc cgggttaaga acaagcccct ggggccagca     1680
gggtctgaga atgaaattcc cactcatgtt ttgccaccgt gtgcaaattt acaggcacag     1740
aagctgaaat ccaatgtgtc gggcaataca cacctctgta tttccaatgg taattatgaa     1800
aaagaaggtc tcggtgcttc cagccacata accacaaaat caatggctgc tcctccaagc     1860
tgtggtctga gcccactgct ggtcctggtg gtaaccgctc tgtccaccct attatcttta     1920
acagaaa                                                              1927
```

<210> SEQ ID NO 41
<211> LENGTH: 1929
<212> TYPE: DNA
<213> ORGANISM: HUMAN

<400> SEQUENCE: 41

```
aatctggcct cggaacacgc cattctccgc gccgcttcca ataaccacta acatccctaa       60
cgagcatccg agccgagggc tctgctcgga atcgtcctg gcccaactcg gcccttcgag      120
ctctcgaaga ttaccgcatc tattttttt ttcttttttt tcttttccta gcgcagataa       180
agtgagcccg gaaagggaag gagggggcgg ggacaccatt gccctgaaag aataaataag      240
taaataaaca aactggctcc tcgccgcagc tggacgcggt cggttgagtc caggttgggt      300
cggacctgaa cccctaaaag cggaaccgcc tcccgccctc gccatcccgg agctgagtcg      360
ccggcggcgg tggctgctgc cagacccgga gtttcctctt tcactggatg gagctgaact      420
ttgggcggcc agagcagcac agctgtccgg ggatcgctgc acgctgagct ccctcggcaa      480
```

```
gacccagcgg cggctcggga ttttttttggg ggggcgggga ccagccccgc gccggcacca      540
tgttcctggc gaccctgtac ttcgcgctgc cgctcttgga cttgctcctg tcggccgaag      600
tgagcggcgg agaccgcctg gattgcgtga agccagtga tcagtgcctg aaggagcaga      660
gctgcagcac caagtaccgc acgctaaggc agtgcgtggc gggcaaggag accaacttca      720
gcctggcatc cggcctggag gccaaggatg agtgccgcag cgccatggag gccctgaagc      780
agaagtcgct ctacaactgc cgctgcaagc ggggtatgaa gaaggagaag aactgcctgc      840
gcatttactg gagcatgtac cagagcctgc agggaaatga tctgctggag gattccccat      900
atgaaccagt taacagcaga ttgtcagata tattccgggt ggtcccattc atatcagatg      960
tttttcagca agtggagcac attcccaaag gaacaactg cctggatgca gcgaaggcct     1020
gcaacctcga cgacattgc aagaagtaca ggtcggcgta catcaccccg tgcaccacca     1080
gcgtgtccaa cgatgtctgc aaccgccgca agtgccacaa ggcctccgg cagttcttg      1140 acaaggtccc ggccaagcac agctacggaa tgctcttctg ctcctgccgg gacatcgcct     1200
gcacagagcg gaggcgacag accatcgtgc ctgtgtgctc ctatgaagag agggagaagc     1260
ccaactgttt gaatttgcag gactcctgca agacgaatta catctgcaga tctcgccttg     1320 cggattttt taccaactgc cagccagagt caaggtctgt cagcagctgt ctaaaggaaa     1380
actacgctga ctgcctcctc gcctactcgg ggcttattgg cacagtcatg acccccaact     1440
acatagactc cagtagcctc agtgtggccc atggtgtga ctgcagcaac agtgggaacg     1500
acctagaaga gtgcttgaaa ttttgaatt tcttcaagga aatacatgt cttaaaaatg     1560 caattcaagc ctttgcaat ggctccgatg tgaccgtgtg gcagccagcc ttcccagtac     1620
agaccaccac tgccactacc accactgccc tccgggttaa gaacaagccc ctggggccag     1680
cagggtctga gaatgaaatt cccactcatg ttttgccacc gtgtgcaaat ttacaggcac     1740
agaagctgaa atccaatgtg tcgggcaata cacacctctg tattccaat ggtaattag      1800 aaaaagaagg tctcggtgct ccagccaca taaccacaaa atcaatggct gctcctccaa     1860
gctgtggtct gagcccactg ctggtcctgg tggtaaccgc tctgtccacc ctatattctt     1920
taacagaaa                                                            1929
```

```
<210> SEQ ID NO 42
<211> LENGTH: 699
<212> TYPE: DNA
<213> ORGANISM: HUMAN

<400> SEQUENCE: 42
gtcggcgtac atcaccccgt gcaccaccag cgtgtccaat gatgtctgca accgccgcaa       60
gtgccacaag gccctccggc agttctttga caaggtcccg gccaagcaca gctacggaat      120
gctcttctgc tcctgccggg acatcgcctg cacagagcg aggcgacaga ccatcgtgcc      180
tgtgtgctcc tatgaagaga gggagaagcc caactgtttg aatttgcagg actcctgcaa      240
gacgaattac atctgcagat ctcgccttgc ggattttt ccaactgcc agccagagtc       300 aaggtctgtc agcagctgtc taaaggaaaa ctacgctgac tgcctcctcg cctactcggg      360
gcttattggc acagtcatga ccccaacta catagactcc agtagcctca gtgtggcccc      420
atggtgtgac tgcagcaaca gtgggaacga cctagaagag tgcttgaaat tttgaattt      480 cttcaaggac aatacatgtc ttaaaaatgc aattcaagcc tttggcaatg gctccgatgt      540
gaccgtgtgg cagccagcct tcccagtaca gaccaccact gccgctacca ccactgccct      600
```

-continued

| | |
|---|---|
| ccgggttaag aacaagcccc tggggccagc agggtctgag aatgaaattc ccactcatgt | 660 |
| tttgccaccg tgtgcaaatt tacaggcaca gaagctgaa | 699 |

<210> SEQ ID NO 43
<211> LENGTH: 2158
<212> TYPE: DNA
<213> ORGANISM: HUMAN
<220> FEATURE:
<221> NAME/KEY: misc_feature
<222> LOCATION: (1027)..(1027)
<223> OTHER INFORMATION: N in position 1027 indicates a position of
      divergence between different receptor clones.
<221> NAME/KEY: misc_feature
<222> LOCATION: (1205)..(1243)
<223> OTHER INFORMATION: N in positions 1205 to 1243 indicates
      positions of divergence between different receptor clones.

<400> SEQUENCE: 43

| | |
|---|---|
| gtcggcgtac atcaccccgt gcaccaccag cgtgtccaat gatgtctgca accgccgcaa | 60 |
| gtgccacaag gccctccggc agttctttga caaggtcccg gccaagcaca gctacggaat | 120 |
| gctcttctgc tcctgccggg acatcgcctg cacagagcgg aggcgacaga ccatcgtgcc | 180 |
| tgtgtgctcc tatgaagaga gggagaagcc caactgtttg aatttgcagg actcctgcaa | 240 |
| gacgaattac atctgcagat ctcgccttgc ggattttttt accaactgcc agccagagtc | 300 |
| aaggtctgtc agcagctgtc taaaggaaaa ctacgctgac tgcctcctcg cctactcggg | 360 |
| gcttattggc acagtcatga cccccaacta catagactcc agtagcctca gtgtggcccc | 420 |
| atggtgtgac tgcagcaaca gtgggaacga cctagaagag tgcttgaaat ttttgaattt | 480 |
| cttcaaggac aatacatgtc ttaaaaatgc aattcaagcc tttggcaatg gctccgatgt | 540 |
| gaccgtgtgg cagccagcct tcccagtaca gaccaccact gccgctacca ccactgccct | 600 |
| ccgggttaag aacaagcccc tggggccagc agggtctgag aatgaaattc ccactcatgt | 660 |
| tttgccaccg tgtgcaaatt tacaggcaca gaagctgaaa tccaatgtgt cgggcaatac | 720 |
| acacctctgt atttccaatg gtaattatga aaagaaggt ctcggtgctt ccagccacat | 780 |
| aaccacaaaa tcaatggctg ctcctccaag ctgtggtctg agcccactgc tggtcctggt | 840 |
| ggtaaccgct ctgtccaccc tattatcttt aacagaaaca tcatagctgc attaaaaaaa | 900 |
| tacaatatgg acatgtaaaa agacaaaaac caagttatct gtttcctgtt ctcttgtata | 960 |
| gctgaaattc cagtttagga gctcagttga gaaacagttc cattcaactg gaacattttt | 1020 |
| ttttttncct tttaagaaag cttcttgtga tccttcgggg cttctgtgaa aaacctgatg | 1080 |
| cagtgctcca tccaaactca gaaggctttg ggatatgctg tattttaaag ggacagtttg | 1140 |
| taacttgggc tgtaaagcaa actggggctg tgttttcgat gatgatgatc atcatgatca | 1200 |
| tgatnnnnnn nnnnnnnnnn nnnnnnnnnn nnnnnnnnnn nnngatttta acagttttac | 1260 |
| ttctggcctt tcctagctag agaaggagtt aatatttcta aggtaactcc catatctcct | 1320 |
| ttaatgacat tgatttctaa tgatataaat ttcagcctac attgatgcca agcttttttg | 1380 |
| ccacaaagaa gattcttacc aagagtgggc tttgtgaaaa cagctggtac tgatgttcac | 1440 |
| ctttatatat gtactagcat tttccacgct gatgtttatg tactgtaaac agttctgcac | 1500 |
| tcttgtacaa aagaaaaaac acctgtcaca tccaaatata gtatctgtct tttcgtcaaa | 1560 |
| atagagagtg gggaatgagt gtgccgattc aatacctcaa tccctgaacg acactctcct | 1620 |
| aatcctaagc cttacctgag tgagaagccc tttacctaac aaaagtccaa tatagctgaa | 1680 |
| atgtcgctct aatactcttt acacatatga ggttatatgt agaaaaaaat tttactacta | 1740 |

| | | | | |
|---|---|---|---|---|
| aatgatttca | actattggct | ttctatattt | tgaaagtaat | gatattgtct | cattttttta | 1800 |
| ctgatggttt | aatacaaaat | acacagagct | tgtttcccct | cataagtagt | gttcgctctg | 1860 |
| atatgaactt | cacaaataca | gctcatcaaa | agcagactct | gagaagcctc | gtgctgtagc | 1920 |
| agaaagttct | gcatcatgtg | actgtggaca | ggcaggagga | aacagaacag | acaagcattg | 1980 |
| tcttttgtca | ttgctcgaag | tgcaagcgtg | catacctgtg | gagggaactg | gtggctgctt | 2040 |
| gtaaatgttc | tgcagcatct | cttgacacac | ttgtcatgac | acaatccagt | accttggttt | 2100 |
| tcaggttatc | tgacaaaggc | agctttgatt | gggacatgga | ggcatgggca | ggccggaa | 2158 |

<210> SEQ ID NO 44
<211> LENGTH: 659
<212> TYPE: DNA
<213> ORGANISM: HUMAN

<400> SEQUENCE: 44

| | | | | | |
|---|---|---|---|---|---|---|
| gaatttgcag | gactcctgca | agacgaatta | catctgcaga | tctcgccttg | cggattttt | 60 |
| taccaactgc | cagccagagt | caaggtctgt | cagcagctgt | ctaaaggaaa | actacgctga | 120 |
| ctgcctcctc | gcctactcgg | ggcttattgg | cacagtcatg | accccaact | acatagactc | 180 |
| cagtagcctc | agtgtggccc | catggtgtga | ctgcagcaac | agtgggaacg | acctagaaga | 240 |
| gtgcttgaaa | ttttgaatt | tcttcaagga | caatacatgt | cttaaaaatg | caattcaagc | 300 |
| ctttggcaat | ggctccgatg | tgaccgtgtg | cagccagcc | ttcccagtac | agaccaccac | 360 |
| tgccactacc | accactgccc | tccgggttaa | gaacaagccc | ctggggccag | cagggtctga | 420 |
| gaatgaaatt | cccactcatg | ttttgccacc | gtgtgcaaat | ttacaggcac | agaagctgaa | 480 |
| atccaatgtg | tcgggcaata | cacacctctg | tatttccaat | ggtaattatg | aaaaagaagg | 540 |
| tctcggtgct | tccagccaca | taaccacaaa | atcaatggct | gctcctccaa | gctgtggtct | 600 |
| gagcccactg | ctggtcctgg | tggtaaccgc | tctgtccacc | ctattatctt | taacagaaa | 659 |

<210> SEQ ID NO 45
<211> LENGTH: 630
<212> TYPE: DNA
<213> ORGANISM: HUMAN

<400> SEQUENCE: 45

| | | | | | |
|---|---|---|---|---|---|---|
| acatctgcag | atctcgcctt | gcggattttt | ttaccaactg | ccagccagag | tcaaggtctg | 60 |
| tcagcagctg | tctaaaggaa | aactacgctg | actgcctcct | cgcctactcg | ggcttattg | 120 |
| gcacagtcat | gaccccaac | tacatagact | ccagtagcct | cagtgtggcc | ccatggtgtg | 180 |
| actgcagcaa | cagtgggaac | gacctagaag | agtgcttgaa | attttgaat | tcttcaagg | 240 |
| acaatacatg | tcttaaaaat | gcaattcaag | cctttggcaa | tggctccgat | gtgaccgtgt | 300 |
| ggcagccagc | cttcccagta | cagaccacca | ctgccactac | caccactgcc | tccgggtta | 360 |
| agaacaagcc | cctggggcca | gcagggtctg | agaatgaaat | tcccactcat | gttttgccac | 420 |
| cgtgtgcaaa | tttacaggca | cagaagctga | atccaatgt | gtcgggcaat | acacacctct | 480 |
| gtatttccaa | tggtaattat | gaaaagaag | gtctcggtgc | ttccagccac | ataaccacaa | 540 |
| aatcaatggc | tgctcctcca | agctgtggtc | tgagcccact | gctggtcctg | gtggtaaccg | 600 |
| ctctgtccac | cctattatct | ttaacagaaa | | | | 630 |

<210> SEQ ID NO 46
<211> LENGTH: 1076
<212> TYPE: DNA
<213> ORGANISM: HUMAN

<220> FEATURE:
<221> NAME/KEY: misc_feature
<222> LOCATION: (586)..(586)
<223> OTHER INFORMATION: N in position 586 indicates a position of
      divergence between different receptor clones.
<221> NAME/KEY: misc_feature
<222> LOCATION: (764)..(802)
<223> OTHER INFORMATION: N in positions 764 to 802  indicates positions
      of divergence between different receptor clones.

<400> SEQUENCE: 46

| | | | | |
|---|---|---|---|---|
| tgggaacgac | ctagaagagt | gcttgaaatt | tttgaatttc | ttcaaggaca atacatgtct | 60 |
| taaaaatgca | attcaagcct | ttggcaatgg | ctccgatgtg | accgtgtggc agccagcctt | 120 |
| cccagtacag | accaccactg | ccactaccac | cactgccctc | cgggttaaga acaagccct | 180 |
| ggggccagca | gggtctgaga | atgaaattcc | cactcatgtt | ttgccaccgt gtgcaaattt | 240 |
| acaggcacag | aagctgaaat | ccaatgtgtc | gggcaataca | cacctctgta tttccaatgg | 300 |
| taattatgaa | aagaaggtc | tcggtgcttc | cagccacata | accacaaaat caatggctgc | 360 |
| tcctccaagc | tgtggtctga | gcccactgct | ggtcctggtg | gtaaccgctc tgtccaccct | 420 |
| attatcttta | acagaaacat | catagctgca | ttaaaaaaat | acaatatgga catgtaaaaa | 480 |
| gacaaaaacc | aagttatctg | tttcctgttc | tcttgtatag | ctgaaattcc agtttaggag | 540 |
| ctcagttgag | aaacagttcc | attcaactgg | aacattttt | tttttnccttt ttaagaaagc | 600 |
| ttcttgtgat | ccttcgggc | ttctgtgaaa | aacctgatgc | agtgctccat ccaaactcag | 660 |
| aaggctttgg | gatatgctgt | attttaaagg | acagtttgt | aacttgggct gtaaagcaaa | 720 |
| ctggggctgt | gttttcgatg | atgatgatca | tcatgatcat | gatnnnnnnn nnnnnnnnn | 780 |
| nnnnnnnnnn | nnnnnnnnnn | nngattttaa | cagttttact | tctggccttt cctagctaga | 840 |
| gaaggagtta | atatttctaa | ggtaactccc | atatctcctt | taatgacatt gatttctaat | 900 |
| gatataaatt | tcagcctaca | ttgatgccaa | gcttttttgc | cacaaagaag attcttacca | 960 |
| agagtgggct | ttgtggaaac | agctggtact | gatgttcacc | tttatatatg tactagcatt | 1020 |
| ttccacgctg | atgtttatgt | actgtaaaca | gttctgcact | cttgtacaaa agaaaa | 1076 |

<210> SEQ ID NO 47
<211> LENGTH: 1059
<212> TYPE: DNA
<213> ORGANISM: HUMAN

<400> SEQUENCE: 47

| | | | | |
|---|---|---|---|---|
| agtgcttgaa | atttttgaat | tcttcaagg | acaatacatg | tcttaaaaat gcaattcaag | 60 |
| cctttggcaa | tggctccgat | gtgaccgtgt | ggcagccagc | cttcccagta cagaccacca | 120 |
| ctgccactac | caccactgcc | ctccgggtta | agaacaagcc | cctggggcca gcagggtctg | 180 |
| agaatgaaat | tcccactcat | gttttgccac | cgtgtgcaaa | tttacaggca cagaagctga | 240 |
| aatccaatgt | gtcgggcaat | acacacctct | gtatttccaa | tggtaattat gaaaaagaag | 300 |
| gtctcggtgc | ttcagccac | ataaccacaa | aatcaatggc | tgctcctcca agctgtggtc | 360 |
| tgagcccact | gctggtcctg | gtggtaaccg | ctctgtccac | cctattatct ttaacagaaa | 420 |
| catcatagct | gcattaaaaa | aatacaatat | ggacatgtaa | aaagacaaaa accaagttat | 480 |
| ctgtttcctg | ttctcttgta | tagctgaaat | tccagtttag | gagctcagtt gagaaacagt | 540 |
| tccattcaac | tggaacattt | tttttttttc | cttttaagaa | agcttcttgt gatcctttgg | 600 |
| ggcttctgtg | aaaaacctga | tgcagtgctc | catccaaact | cagaaggctt tgggatatgc | 660 |
| tgtattttaa | agggacagtt | tgtaacttgg | gctgtaaagc | aaactggggc tgtgttttcg | 720 |

```
atgatgatga tgatcatgat gatgatcatc atgatcatga tgatgatcat catgatcatg    780
atgatgattt taacagtttt acttctggcc tttcctagct agagaaggag ttaatatttc    840 taagtaact  cccatatctc ctttaatgac attgatttct aatgatataa atttcagcct    900
acattgatgc caagcttttt tgccacaaag aagattctta ccaagagtgg gctttgtgga    960
aacagctggt actgatgttc acctttatat atgtactagc attttccacg ctgatgttta   1020
tgtactgtaa acagttctgc actcttgtac aaaagaaaa                          1059
```